United States Patent
O'Connor et al.

(10) Patent No.: US 11,427,842 B2
(45) Date of Patent: Aug. 30, 2022

(54) METHOD AND MEANS FOR MANUFACTURING TERPENE INDOLE ALKALOIDS

(71) Applicant: John Innes Centre, Norwich (GB)

(72) Inventors: Sarah O'Connor, Norwich (GB); Lorenzo Caputi, Norwich (GB); Richard Payne, Broadstairs (GB); Jakob Franke, Hannover (DE); Scott Farrow, Norfolk (GB)

(73) Assignee: John Innes Centre, Norwich (GB)

( * ) Notice: Subject to any disclaimer, the term of this patent is extended or adjusted under 35 U.S.C. 154(b) by 0 days.

(21) Appl. No.: 16/981,486

(22) PCT Filed: Mar. 15, 2019

(86) PCT No.: PCT/GB2019/050746
§ 371 (c)(1),
(2) Date: Sep. 16, 2020

(87) PCT Pub. No.: WO2019/175607
PCT Pub. Date: Sep. 19, 2019

(65) Prior Publication Data
US 2021/0269836 A1    Sep. 2, 2021

(30) Foreign Application Priority Data

Mar. 16, 2018   (GB) .................................... 1804289

(51) Int. Cl.
| | |
|---|---|
| C12P 17/18 | (2006.01) |
| C12N 15/82 | (2006.01) |
| C12R 1/19 | (2006.01) |
| C12R 1/865 | (2006.01) |

(52) U.S. Cl.
CPC ........ *C12P 17/182* (2013.01); *C12N 15/8243* (2013.01); *C12R 2001/19* (2021.05); *C12R 2001/865* (2021.05); *C12Y 103/01* (2013.01)

(58) Field of Classification Search
None
See application file for complete search history.

(56) References Cited

U.S. PATENT DOCUMENTS

2016/0340704 A1* 11/2016 Martin ................. C12N 9/1007

FOREIGN PATENT DOCUMENTS

| WO | WO 2015/164960 A1 | 11/2015 |
| WO | WO 2017/152273 A1 | 9/2017 |

OTHER PUBLICATIONS

International Search Report and Written Opinion dated Jun. 7, 2019 issued in PCT/GB2019/050746.
GB Search Report dated Nov. 18, 2018 issued in GB 1804289.5.
Qu et al., "Solution of the multistep pathway for assembly of corynanthean, strychnos, iboga, and aspidosperma monoterpenoid indole alkaloids from 19E-geissoschizine", PNAS, 2018.
El-Sayed et al., "Alkaloid accumulation in Catharanthus roseus cell suspension cultures fed with stemmadenine", Biotechnology Letters (May 1, 2004), vol. 26, No. 10, pp. 793-798.
Edge et al., "A tabersonine 3-reductase Catharanthus roseus mutant accumulates vindoline pathway intermediates", Planta (Sep. 11, 2017), pp. 155-169.
Salim et al., "Virus-induced gene silencing identifies Catharanthus roseus 7-deoxyloganic acid-7-hydroxylase, a step in iridoid and monoterpene indole alkaloid biosynthesis", The Plant Journal (Oct. 23, 2013), vol. 76, No. 5, pp. 754-765.
Qu et al., "Completion of the seven-step pathway from tabersonine to the anticancer drug precursor vindoline and its assembly in yeast", Proceedings of the National Academy of Sciences of the United States of America, vol. 112, No. 19, Apr. 27, 2015, pp. 6224-6229.
Caputi et al., "Missing enzymes in the biosynthesis of the anticancer drug vinblastine in Madagascar periwinkle", Science (Jun. 15, 2018), vol. 360, No. 6394, pp. 1235-1239.
Qureshi et al., "Biosynthesis of indole alkaloids: sequential precursor formation and biological conversion in Vinca rosea", Chemical Communications (1968), issue 16, available from https://pubs.rsc.org/en/Content/ArticleLanding/1968/C 1/c 19680000948!div Abstract [ accessed Nov. 26, 2018].
Stavrinides et al., "Structural Investigation of heteroyohimbine alkaloid synthesis reveals active site elements that control stereoselectivity", available from https://www.nature.com/articles/ncomms 12116 [ accessed Nov. 26, 2018], Nature Communications 7 Article No. 12116, 2016.
Scott, A.I., et al., "Regio- and Stereospecific Models for the Biosynthesis of the Indole Alkaloids. The Corynanthe/Strychnos-Iboga Relationship", Journal of the American Chemical Society, Received Aug. 3, 1972, Nov. 15, 1972, pp. 8263-8264, 94:23.
Campanella, J.J., et al., "MatGAT: An application that generates similarity/identity matrices using protein or DNA sequences", BMC Bioinformatics, Published Jul. 10, 2003, Received May 9, 2003, Accepted Jul. 10, 2003, 4 pages, 4:29.
Needleman, S.B., et al., "A General Method Applicable to the Search for Similarities in the Amino Acid Sequence of Two Proteins", J. Mol. Biol. (1970), Received Jul. 21, 1969, pp. 443-453, 48.

(Continued)

*Primary Examiner* — Christian L Fronda
(74) *Attorney, Agent, or Firm* — Scully, Scott, Murphy & Presser, P.C.

(57) ABSTRACT

The complex chemistry underlying the extensive transformations involved in terpene indole alkaloid synthesis makes identification of the biosynthetic genes challenging. The present invention relates to methods for producing a terpene indole alkaloid derivative, comprising the steps of: (1) providing a terpene indole alkaloid; and (2) providing a first enzyme termed "Precondylocarpine Acetate Synthase" (PAS) or a functional variant or homologue thereof; and/or a second enzyme termed "Dehydroprecondylocarpine Acetate Synthase" (DPAS) or a functional variant or homologue thereof, and optionally providing further identified enzymes involved in this pathway. The invention also encompasses related kits, enzymes, expression vectors, host cells and plants.

22 Claims, 74 Drawing Sheets

Specification includes a Sequence Listing.

(56) References Cited

OTHER PUBLICATIONS

Altschul, S.F., et al., "Basic Local Alignment Search Tool", J. Mol. Biol. (1990), Received Feb. 26, 1990, accepted May 15, 1990, pp. 403-410, 215.

Larkin, M.A., et al., "Clustal W and Clustal X version 2.0", Bioinformatics Applications Note, 2007, Received on Jun. 27, 2007, revised on Aug. 3, 2007, accepted on Aug. 3, 2007, Advance Access publication Sep. 10, 2007, pp. 2947-2948, vol. 23, No. 21.

Kruskal, J.B., "An Overview of Sequence Comparison", Time warps, string edits and macromolecules: the theory and practice of sequence comparison, Sankoff & Kruskal (eds), 1983, pp. 1-44, Chapter 1.

Beatty, J.W., et al., "Synthesis of (−)-Pseudotabersonine, (−)-Pseudovincadifformine, and (+)-Coronaridine Enabled by Photoredox Catalysis in Flow", J. Am. Chem. Soc. 2014, Received Jun. 19, 2014, Published Jul. 8, 2014, pp. 10270-10273, 136.

Zhang, Y., et al., "Enantioselective synthesis of Iboga alkaloids and vinblastine via rearrangements of quaternary ammoniums", Chem. Sci., 2016, 7, Received Feb. 29, 2016, Accepted May 13, 2016, pp. 5530-5536.

Szantay, C., et al., "Synthesis of Vinca Alkaloids and Related Compounds XLVIIII Synthesis 0F (+)-Catharanthine and (+)-Allocatharanthine", Tetrahedron, 1990, Received in UK Nov. 10, 1989, pp. 1711-1732, vol. 46, No. 5.

Geu-Flores, F., et al., "An alternative route to cyclic terpenes by reductive cyclization in iridoid biosynthesis", Nature, Dec. 6, 2012, pp. 138-144, vol. 492.

Lindbo, J.A., et al., "TRBO: A High-Efficiency Tobacco Mosaic Virus RNA-Based Overexpression Vector", Plant Physiology, Dec. 2007, pp. 1232-1240, vol. 145.

Grover, R.K., et al., "Spectral Assignments and Reference Data", Magnetic Resonance in Chemistry Magn. Reson. Chem. 2002, Received Oct. 26, 2001, revised Mar. 8, 2002, accepted Mar. 12, 2002, pp. 474-476, 40.

Feng, T., et al., "Melodinines A-G, Monoterpenoid Indole Alkaloids from Melodinus henryi", Journal of Natural Products, 2010, pp. 22-26, vol. 73, No. 1.

Yamauchi, T., et al., "Alkaloids From Leaves and Bark of Alstonia Scholaris in the Philippines", Phytochemistry 1990, Received Feb. 12, 1990, pp. 3321-3325, vol. 29, No. 10.

Martin, C.L., et al., "Total Synthesis of (+)-Condylocarpine, (+)-Isocondylocarpine, and (+)Tubotaiwine", Org Lett., Jan. 7, 2011, 10 pages, 13(1).

O'Connor, S.E., et al., "Chemistry and biology of monoterpene indole alkaloid biosynthesis", Received in Cambridge, UK Sep. 6, 2005, First published as an Advance Article on the web May 26, 2006, Nat. Prod. Rep., 2006, pp. 532-547, 23.

Daniel, B., et al., "The family of berberine bridge enzyme-like enzymes: A treasure-trove of oxidative reactions", Archives of Biochemistry and Biophysics (2017), Received May 4, 2017, Received in revised form Jun. 29, 2017, Accepted Jun. 30, 2017, Available online Jul. 1, 2017, pp. 88-103, 632.

\* cited by examiner

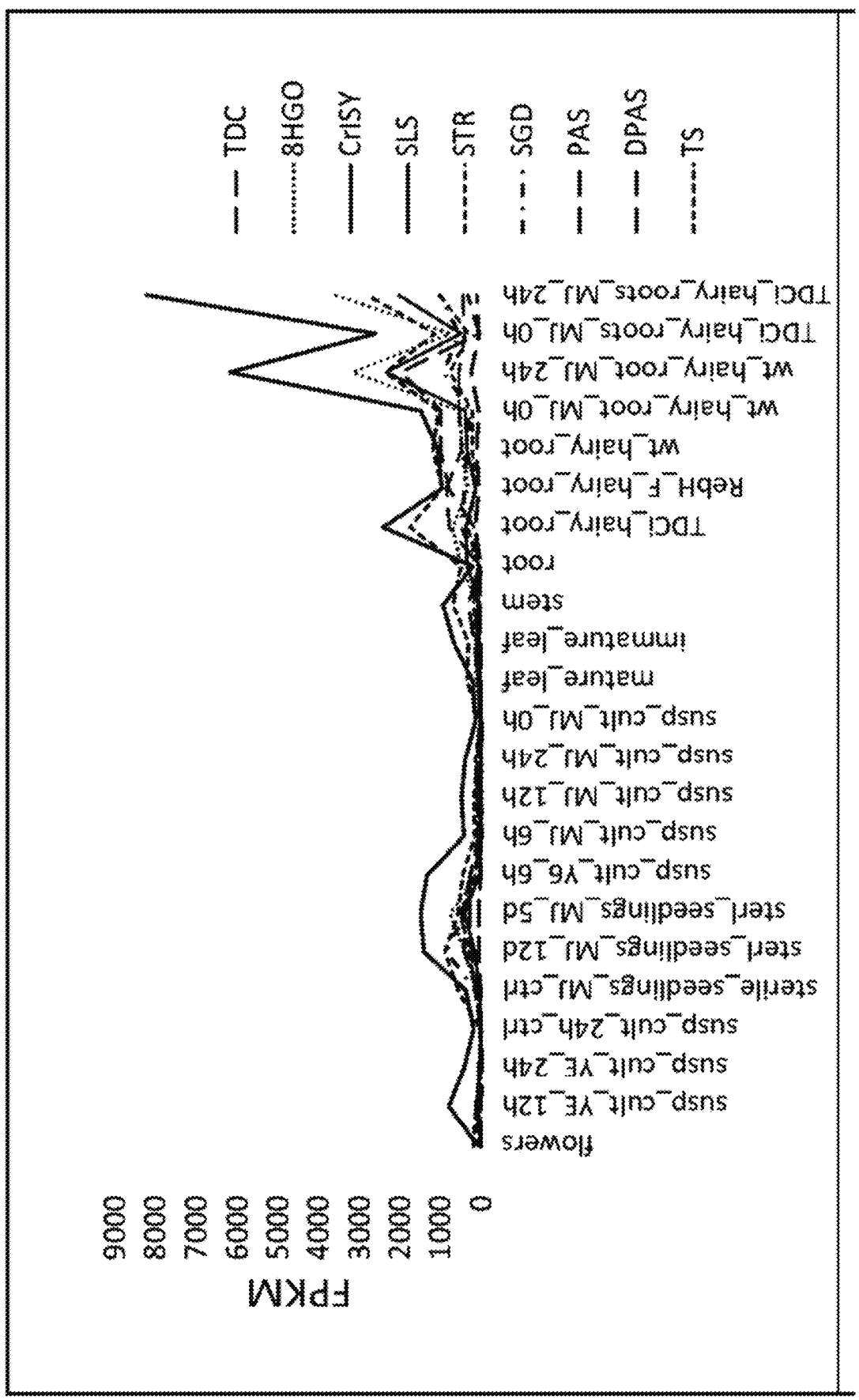

Fig. 1C

| Gene ID | S1 | S2 | S3 | S4 | S5 | S6 | S7 | S8 | S9 | S10 | S11 | Annotation |
|---|---|---|---|---|---|---|---|---|---|---|---|---|
| 6808 cra_locus_15921_iso_3_len_1532_ver_3 | 9.4 | 6.93 | 4.09 | 12.71 | 24.16 | 14.49 | 9.56 | 3.34 | 4.32 | 5.3 | 1.84 | Taxadien-5-alpha-ol O-acetyltransferase |
| 9306 cra_locus_19388_iso_1_len_1432_ver_3 | 4.37 | 3.63 | 3.12 | 7.55 | 6.95 | 15.03 | 3.58 | 1.57 | 4.23 | 1.13 | 0.77 | Taxadien-5-alpha-ol O-acetyltransferase |
| 12052 cra_locus_24127_iso_1_len_1371_ver_3 | 1 | 1 | 1 | 2.33 | 2.43 | 1.82 | 1 | 1 | 1 | 1 | 1 | Minovincinine 19-hydroxy-O-acetyltransferase |
| 20668 cra_locus_5019_iso_5_len_2123_ver_3 | 4.17 | 2.71 | 3.01 | 46.31 | 95.75 | 78.47 | 3.64 | 53.7 | 13.02 | 3.38 | 31.6 | Minovincinine 19-hydroxy-O-acetyltransferase |
| 18041 cra_locus_3992_iso_10_len_1473_ver_3 | 1 | 1 | 1 | 31.79 | 57.14 | 21.85 | 1 | 1 | 1 | 1 | 1 | Minovincinine 19-hydroxy-O-acetyltransferase |
| 4236 cra_locus_1300_iso_1_len_1426_ver_3 | 1 | 1 | 8.9 | 7.7 | 9.95 | 9.92 | 1 | 1 | 1 | 1 | 1 | Vinorine synthase |
| 27122 cra_locus_6962_iso_3_len_1689_ver_3 | 24.42 | 14.78 | 1.73 | 81.43 | 142.41 | 87.73 | 109.76 | 21.55 | 27.04 | 8.7 | 2.09 | Vinorine synthase |
| 31104 cra_locus_8750_iso_1_len_1492_ver_3 | 3.05 | 1.56 | 8.54 | 19.37 | 11.26 | 3.38 | 5.28 | 1.69 | 4.5 | 36.9 | 1 | Vinorine synthase |

| | S12 | S13 | S14 | S15 | S16 | S17 | S18 | S19 | S20 | S21 | S22 |
|---|---|---|---|---|---|---|---|---|---|---|---|
| | 2.16 | 6.61 | 25.65 | 10.56 | 41.28 | 42.27 | 24.36 | 22.14 | 45.79 | 28.51 | 50.52 |
| | 1.16 | 2.71 | 5.37 | 7.7 | 15.05 | 6.45 | 14.05 | 11.81 | 8.4 | 11.73 | 9.01 |
| | 1 | 1 | 1.57 | 1 | 1 | 23.94 | 28.31 | 32.71 | 9.15 | 43.46 | 7.85 |
| | 20.67 | 26.86 | 22.07 | 17.92 | 40.74 | 95.95 | 139.51 | 104.31 | 271.24 | 43.86 | 350.79 |
| | 1 | 1.09 | 57.19 | 1 | 51.29 | 62.67 | 48.69 | 34.03 | 73.53 | 63.25 | 1 |
| | 1 | 1 | 1.38 | 1 | 22.07 | 2.13 | 14.74 | 4.95 | 22.71 | 10.56 | 1 |
| | 41.29 | 74.08 | 83.76 | 41.63 | 187.13 | 141.57 | 138.26 | 137.67 | 220.24 | 132.98 | 297.51 |
| | 2.27 | 2.19 | 7.57 | 1.18 | 22.97 | 7.2 | 36.97 | 33.81 | 78.13 | 17.64 | 91.16 |

Fig. 2A
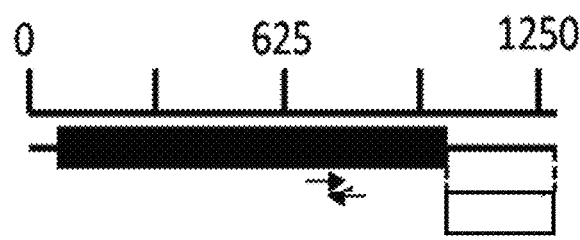
Fig. 2B
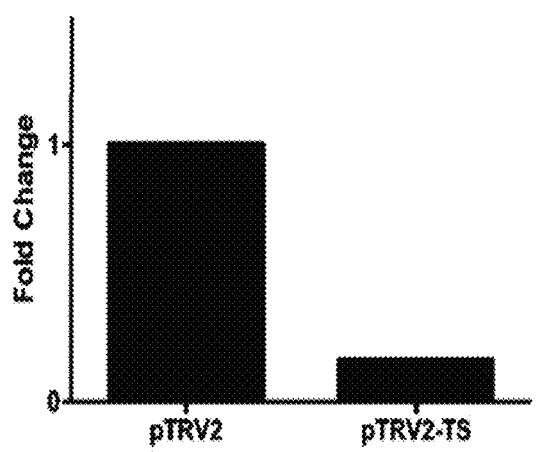
Fig. 2C
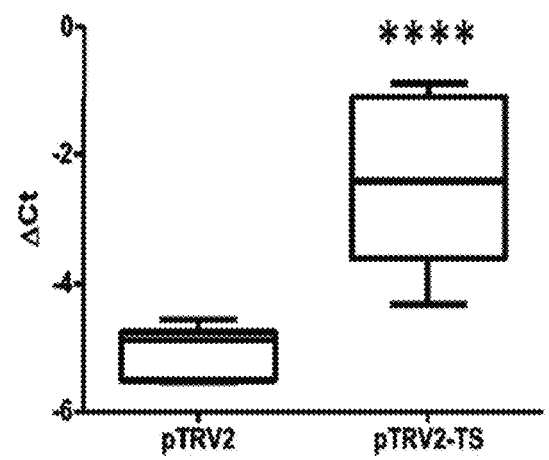
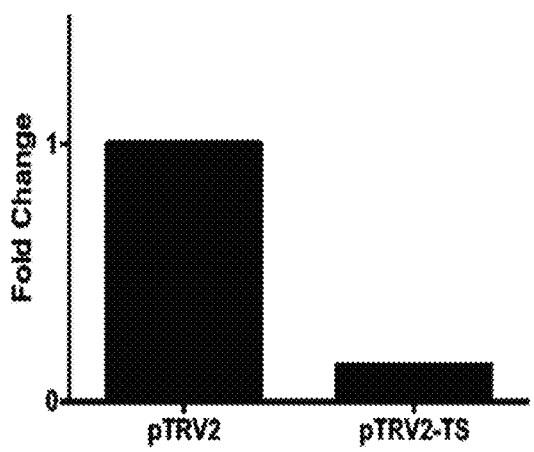
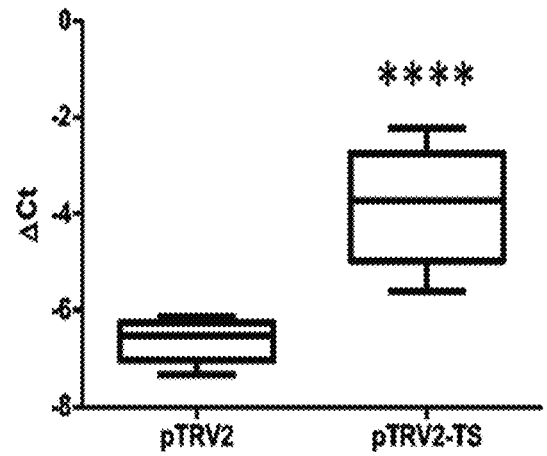

Fig. 3A
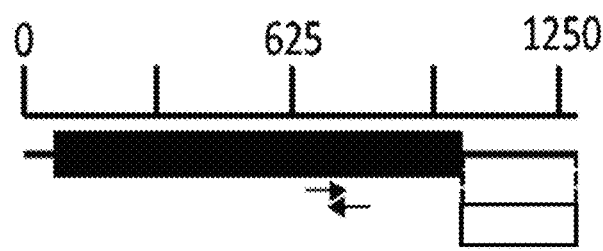
Fig. 3B
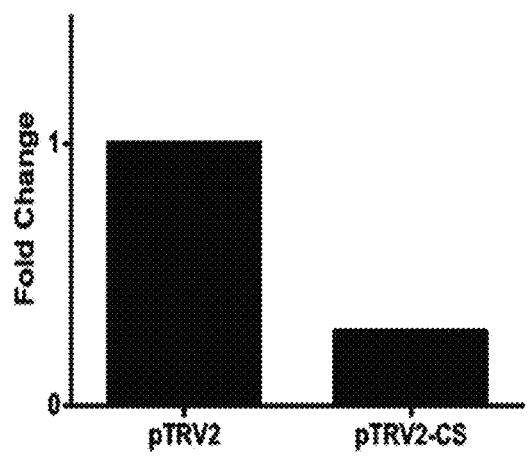
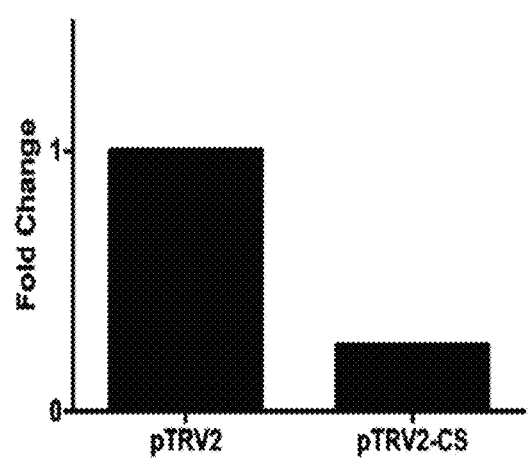
Fig. 3C
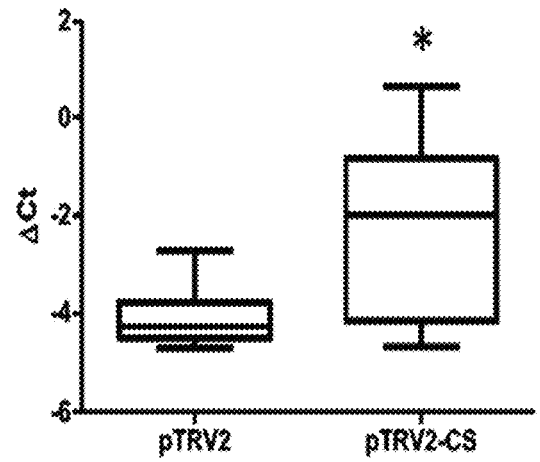
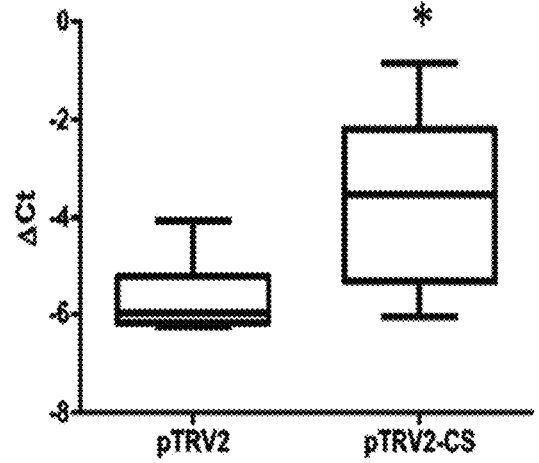

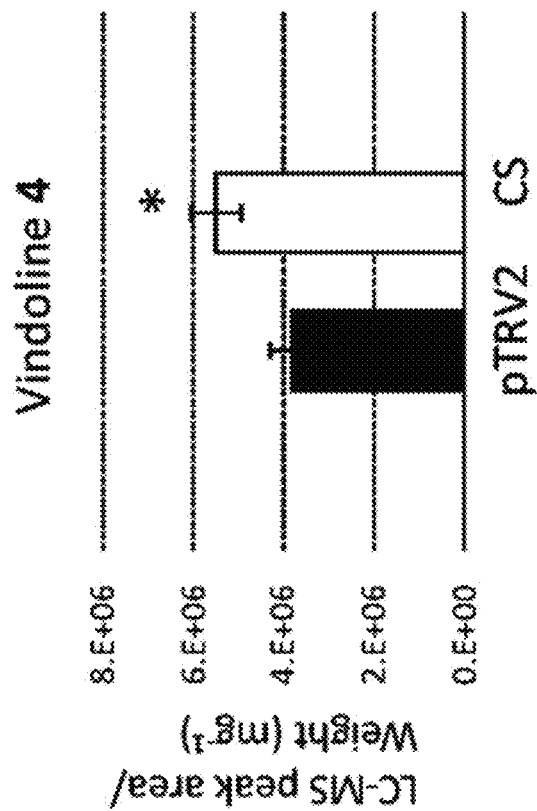
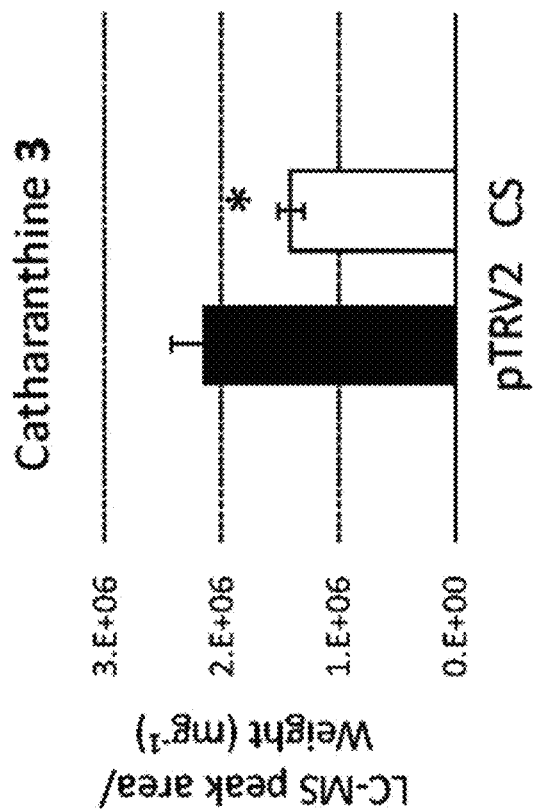

HMBC

HMBC

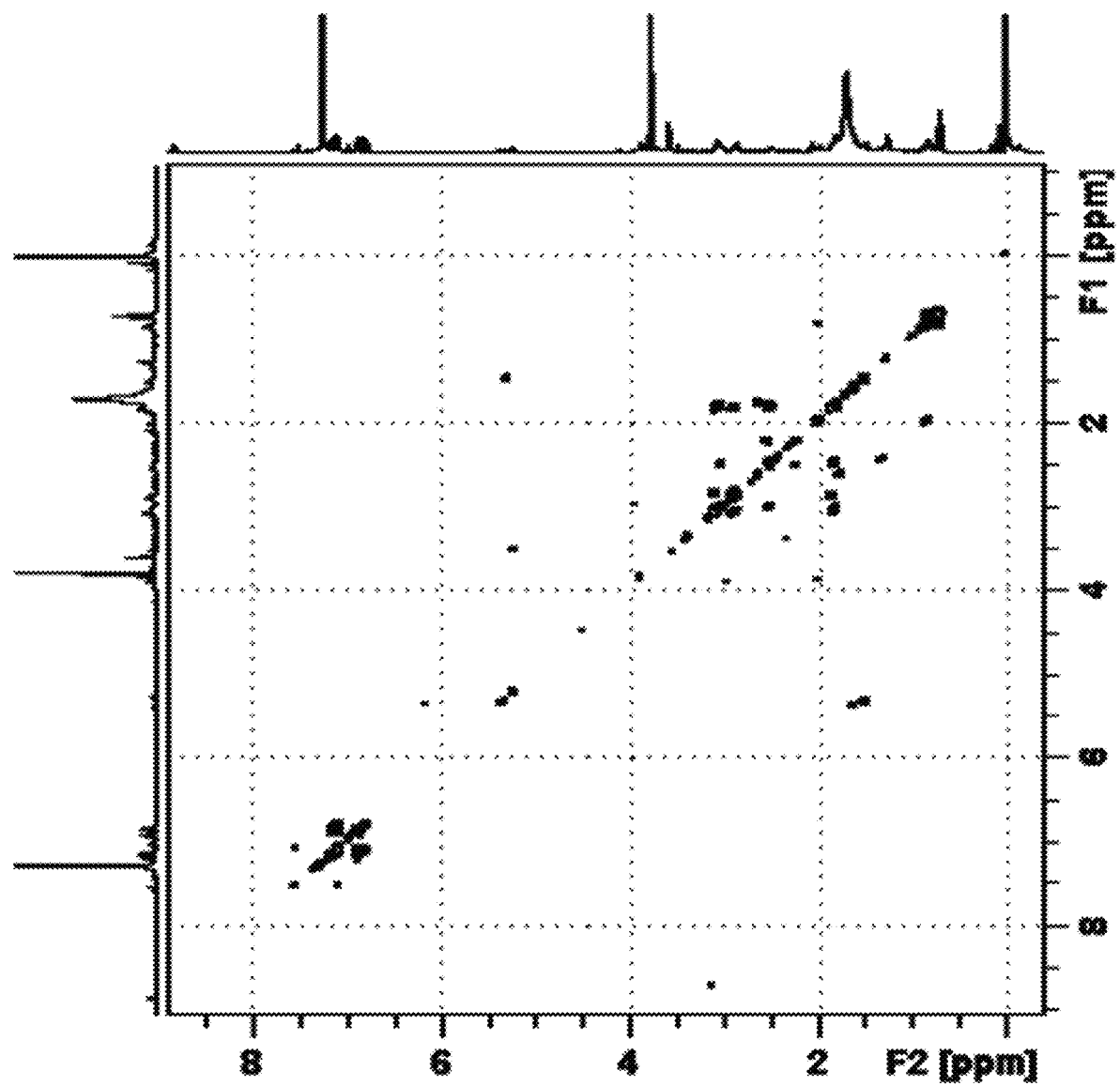

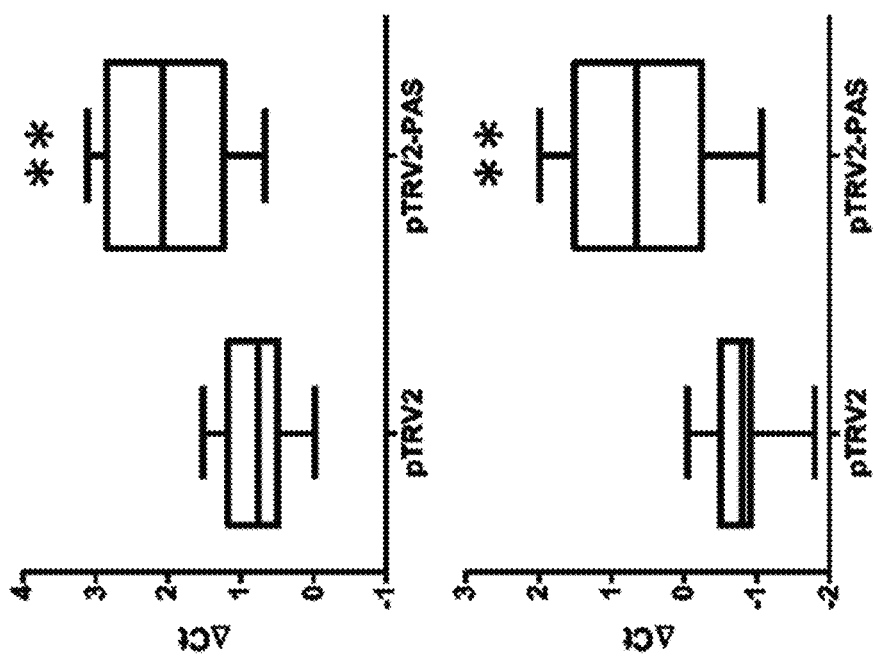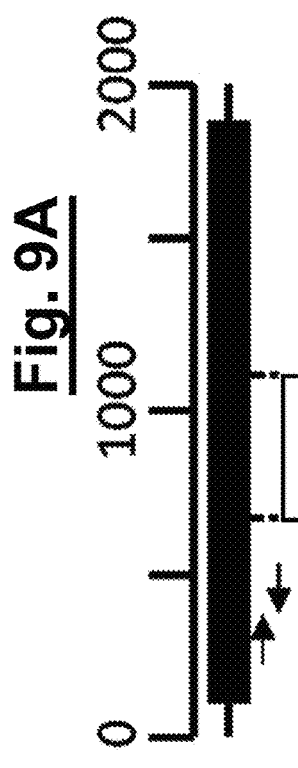

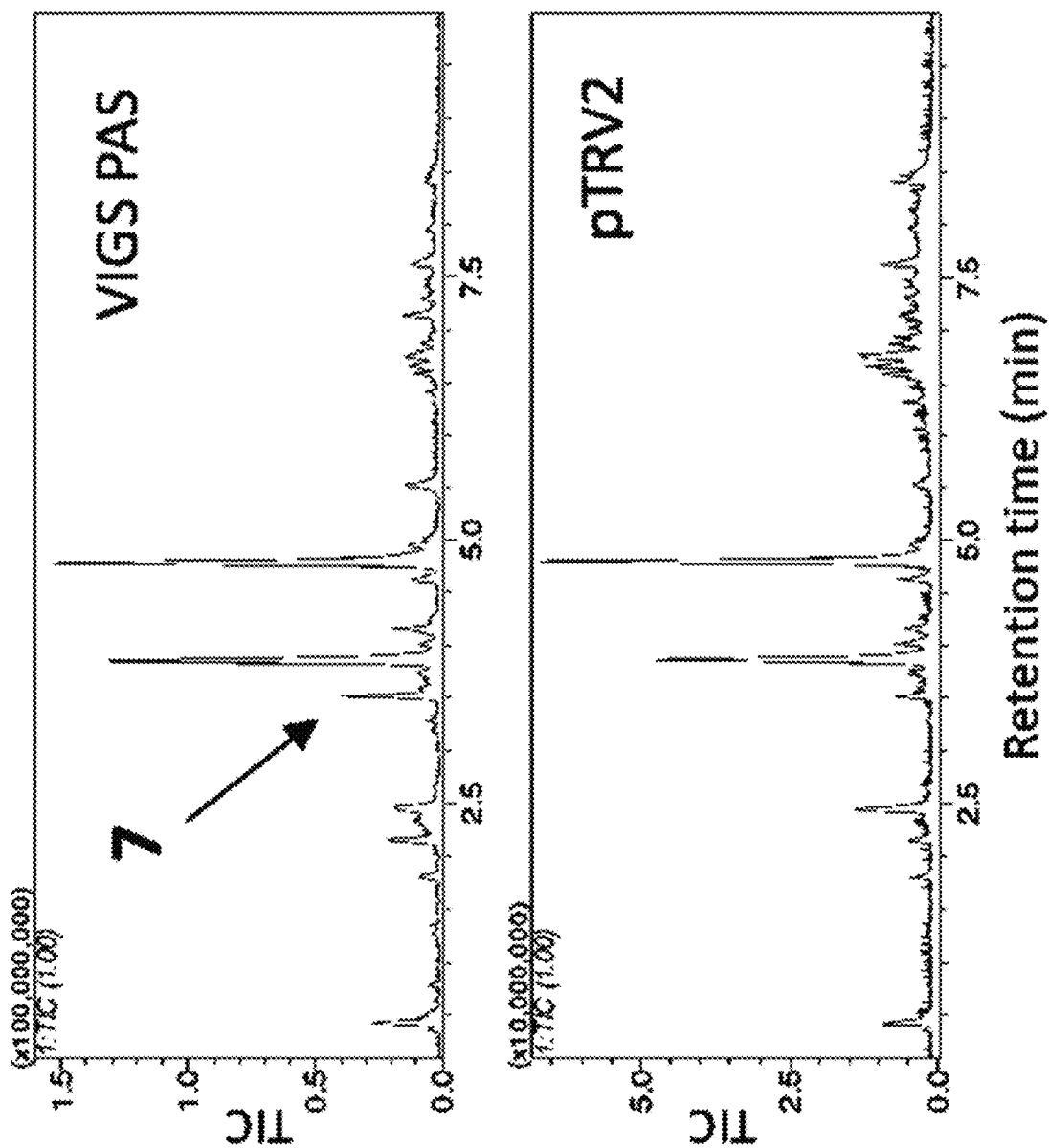

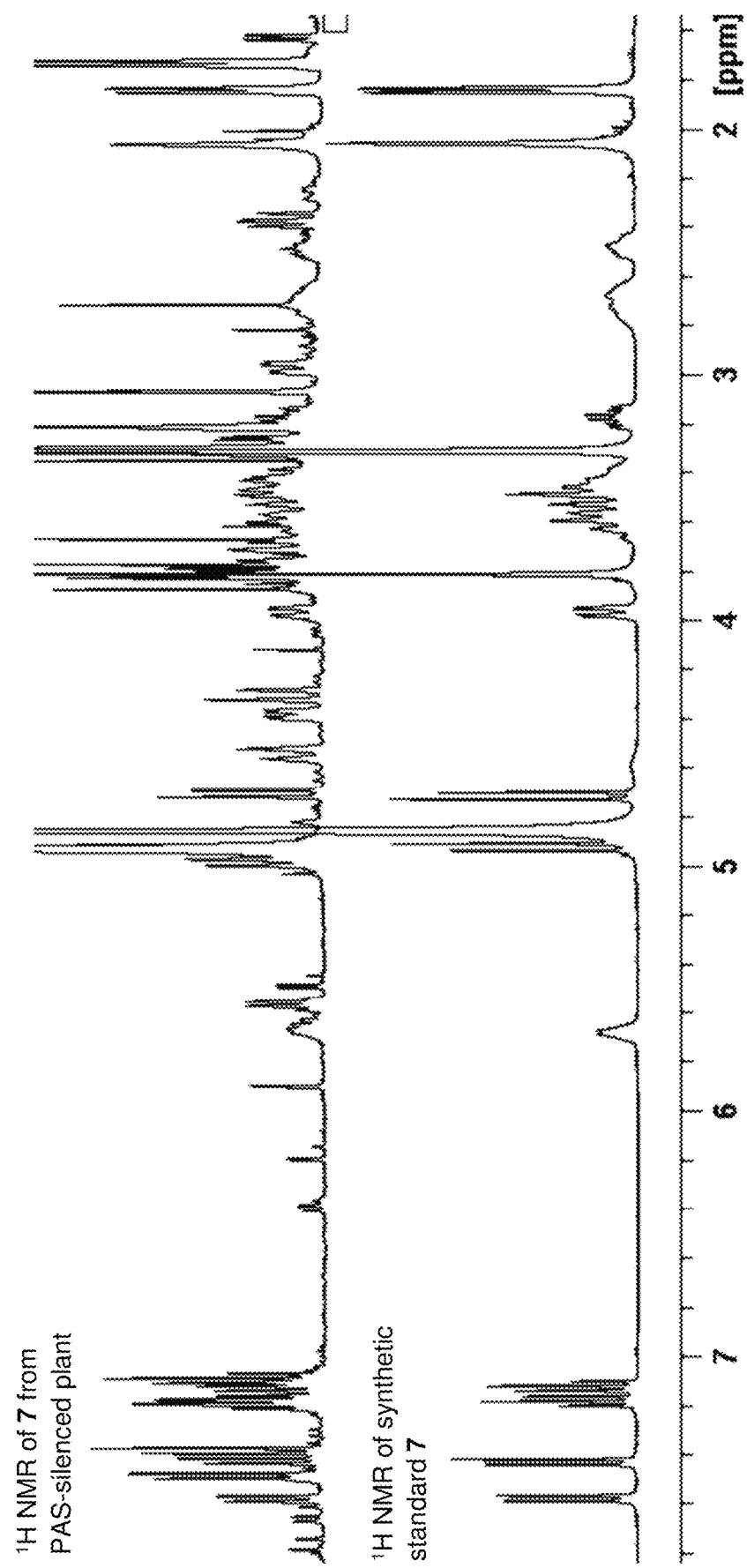

Fig. 12A
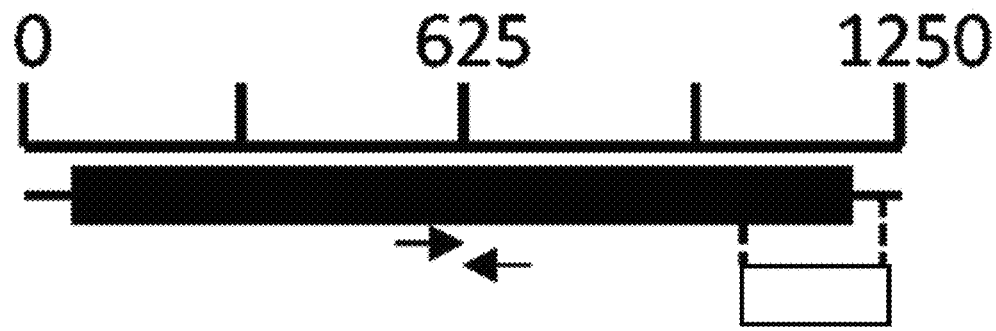
Fig. 12B
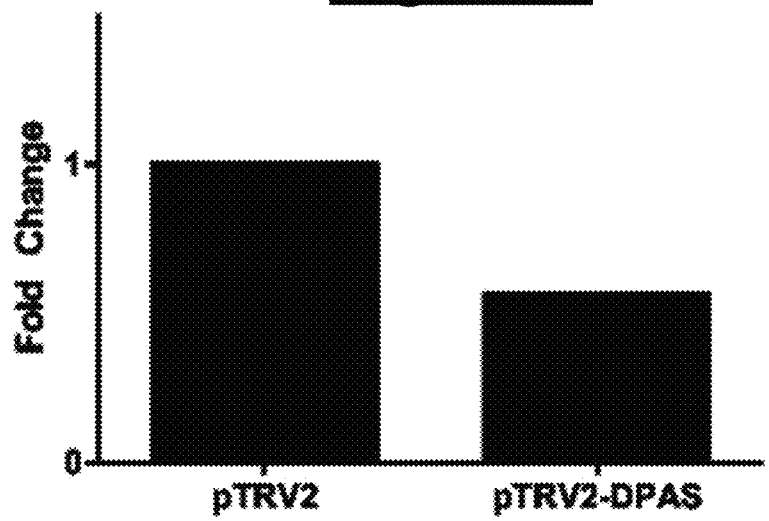
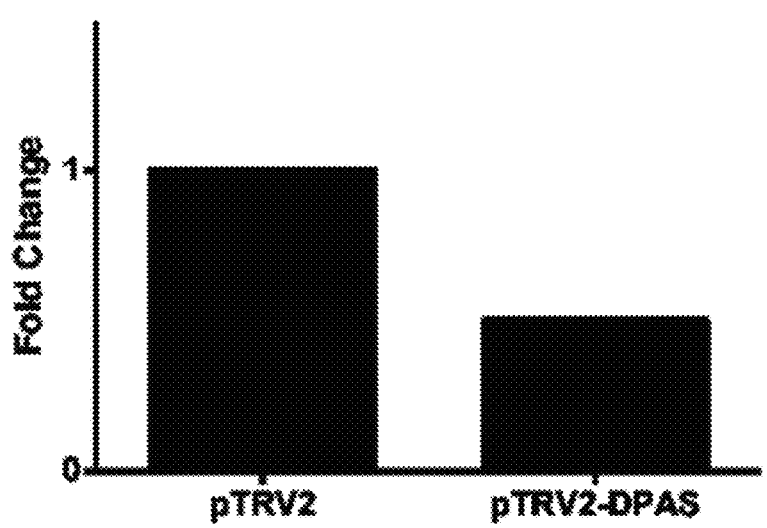

Fig. 12C
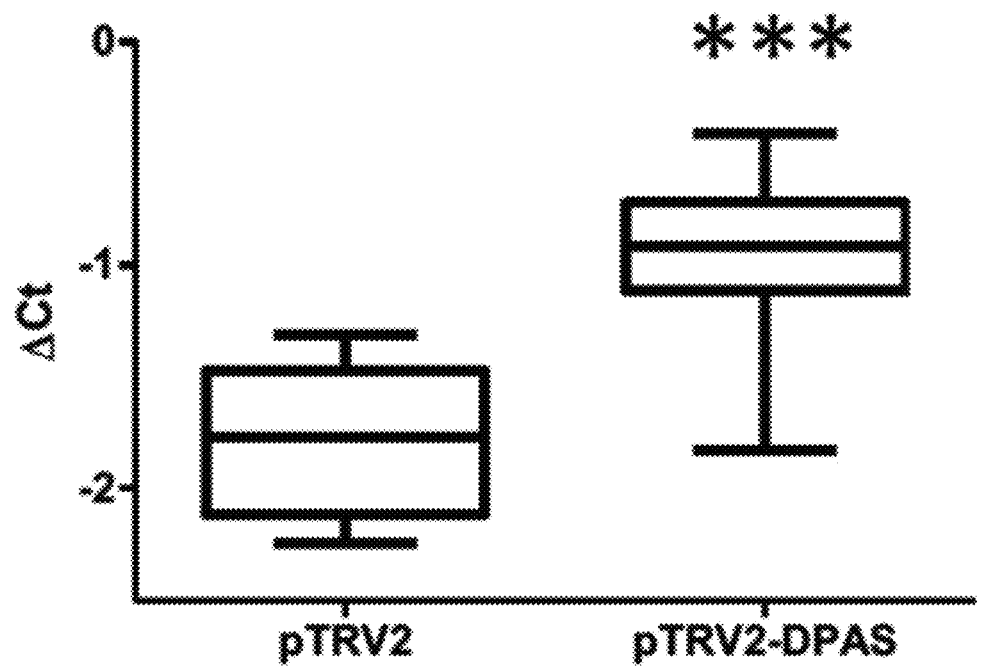
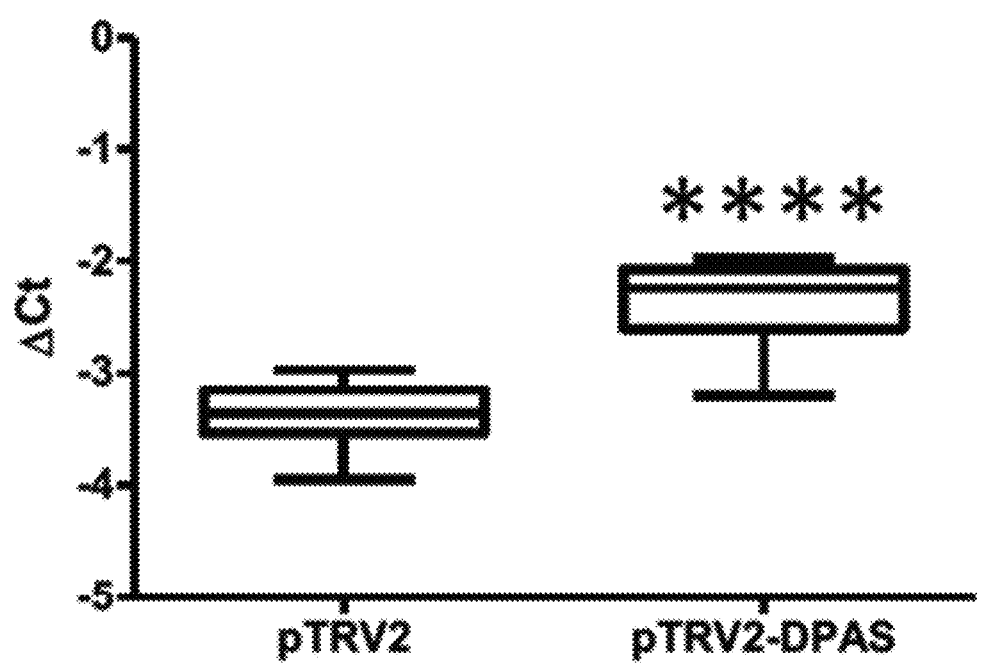

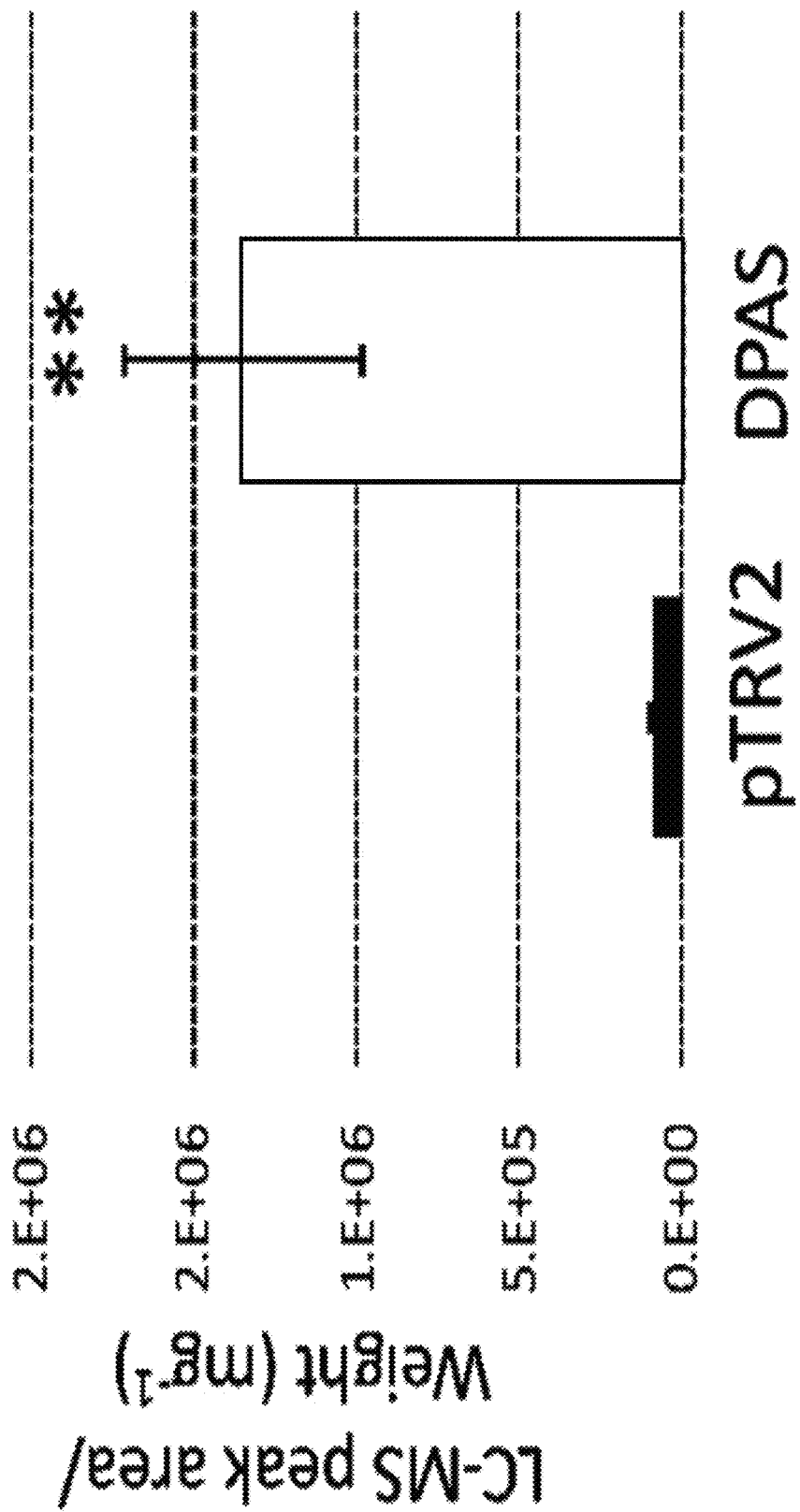

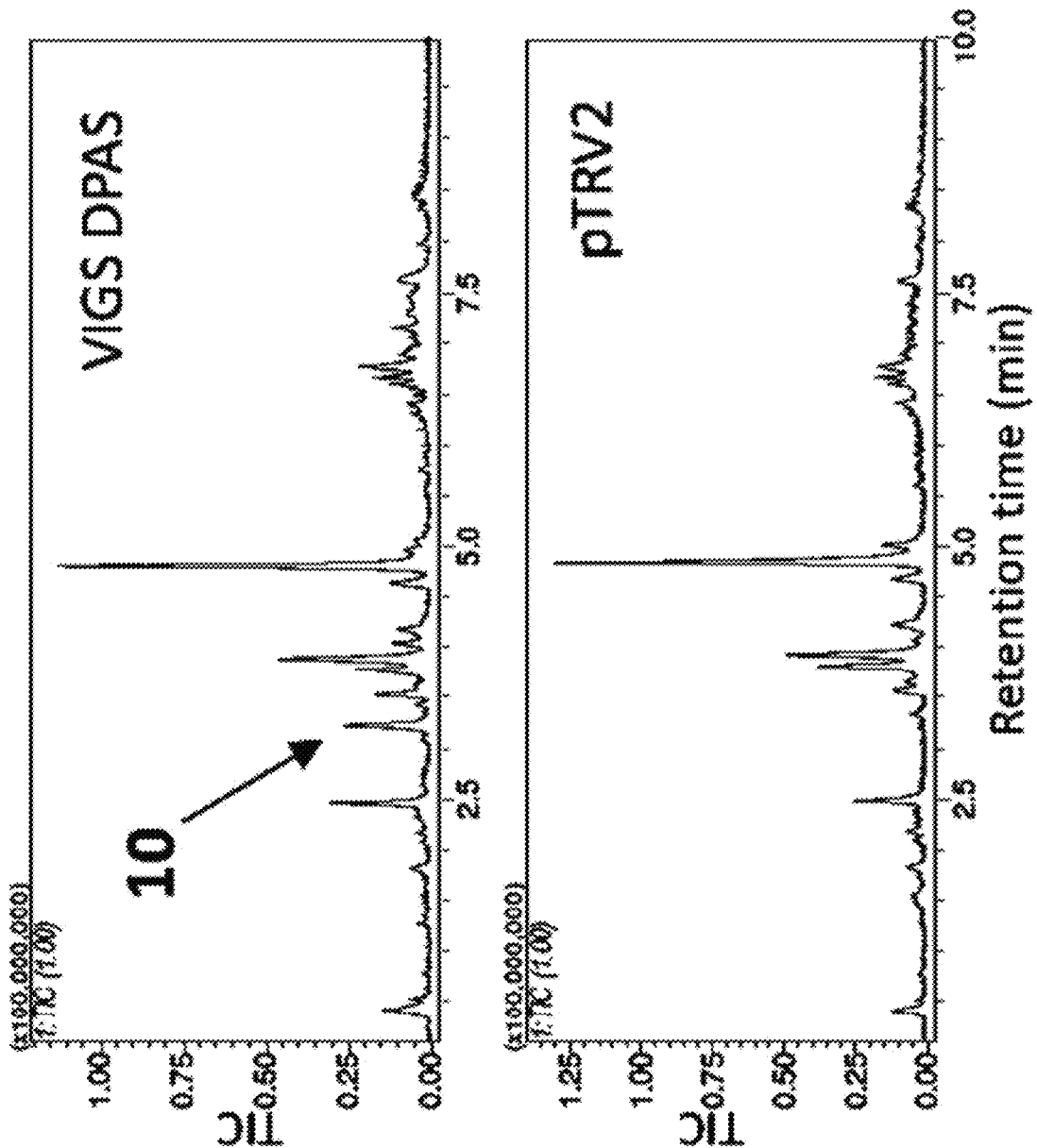

COSY

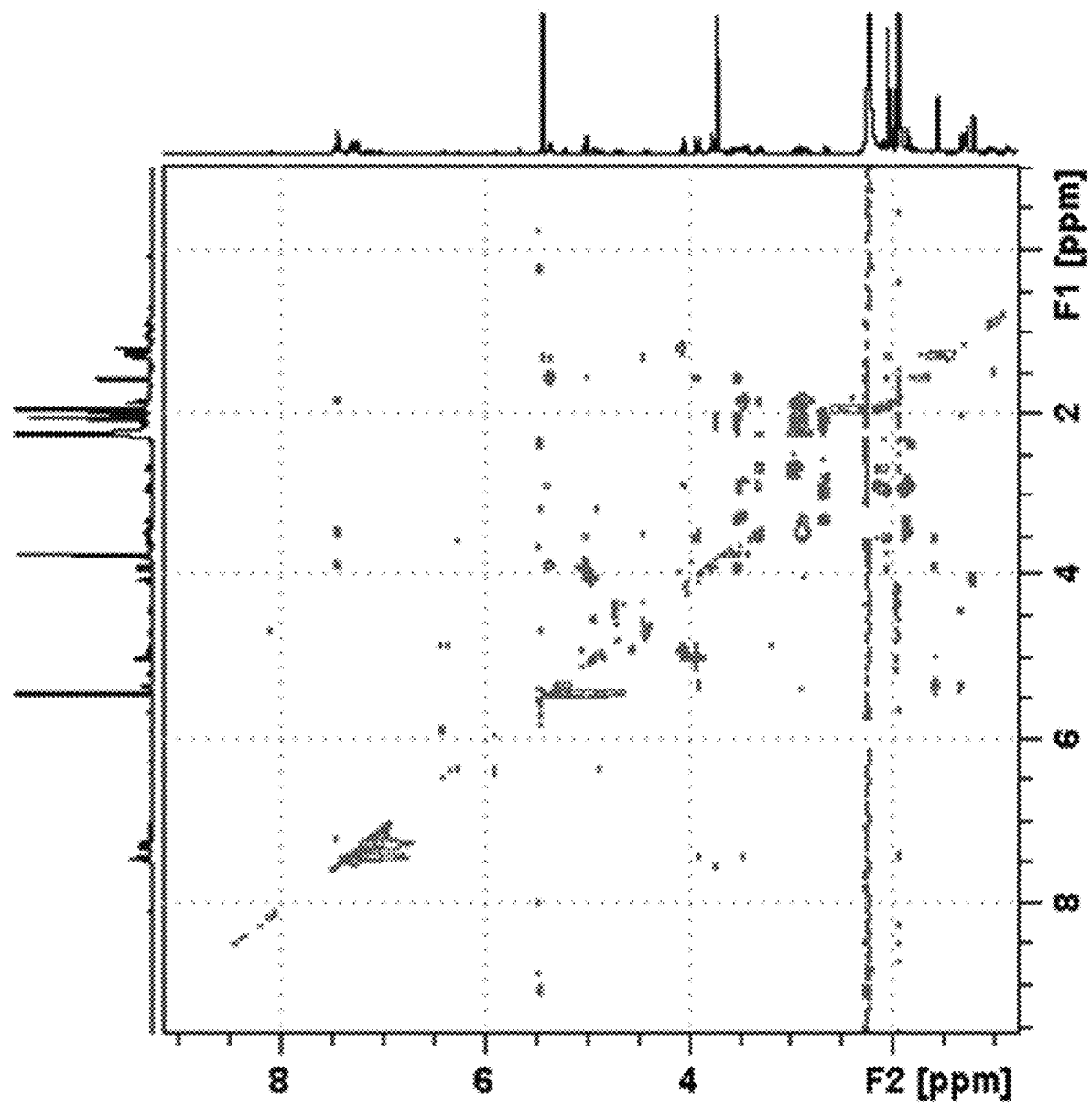

TOCSY

HMBC

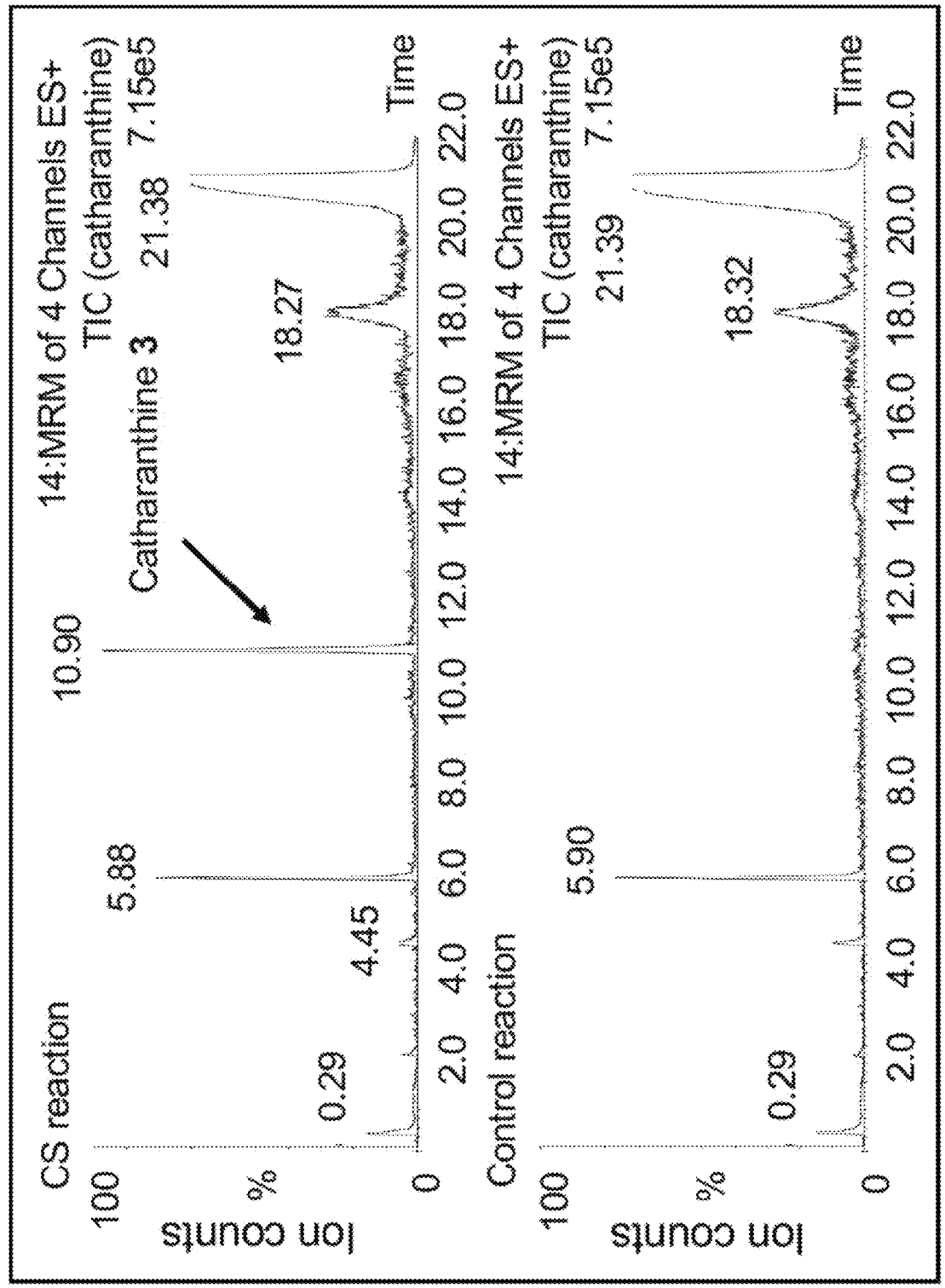

```
                              100         110         120         130         140
1. E.californica_BBE      NTIRCIRKGSWTIRLRSGGHSYEGLSYTSDTPFILIDLMNLNRVSIDL
2. P.somniferum_BBE       STVHCCTRESWTIRLRSGGHSYEGLSYTADTPFVIVDMMNLNRISIDV
3. C.sativa_CBDAsynthase  GTILCSKKVGLQIRTRSGGHDSEGMSYISQVPFVIVDLRNMRSIKIDV
4. C.sativa_THCAsynthase  ATILCSKKVGLQIRTRSGGHDAEGMSYISQVPFVVVDLRNMHSIKIDV
5. A.mexicana_STOX        TTVVCSKHGLDLKVRSGGHDVEGLSYVSDSPYVMIDLVDFRNITVNV
6. T.elegans_PAS-like     AAVCCKRAGLQIRSGGSDYEGLSYRSEVPYIILDLQNLRSITVDI
7. V.minor_PAS-like       AAVICTKRVGLQLIRSGGSDYEGLSYRSEVPFVLLDLQNLRSINVDI
8. C.roseus_PAS           SAVICTKQAGLQIRSGGADYEGLSYRSEVPFILLDLQNLRSISVDI
9. C.longifolius_PAS-like SAVICTKQAGLQIRSGGADYEGLSYRSEVPFILLDLQNLRSISVDI 150         160         170         180         190
1. E.californica_BBE      ESETAWVESGSTLGELYYAI-TESSSKLGFTAGWCPTVGTGGHISGGG
2. P.somniferum_BBE       LSETAWVESGATLGELYYAI-AQSTDTLGFTAGWCPTVGSGGHISGGG
3. C.sativa_CBDAsynthase  HSQTAWVEAGATLGEVYYWV-NEKNENLSLAAGYCPTVCAGGHFGGGG
4. C.sativa_THCAsynthase  HSQTAWVEAGATLGEVYYWI-NEKNENLSFPGGYCPTVGVGGHFGGGG
5. A.mexicana_STOX        KNATAWIQAGSSLGEVYYKVGNESKNTLGFPAGHCPTVGVGGHISGGG
6. T.elegans_PAS-like     EDNSAWVESGATIGELYYEI-ADQSPVHAFPAGVYPTVGVGGHLSGGG
7. V.minor_PAS-like       EDNSAWVESGATIGELYYEI-AEKSPVHGFPAGVYATVGVGGHLSGGG
8. C.roseus_PAS           EDNSAWVESGATIGEFYHEI-AQNSPVHAFPAGVSBSVGIGGHLSGGG
9. C.longifolius_PAS-like EDNSAWVESGATIGEFYHEI-AQNSPVHAFPAGVSPSVGIGGHLSGGG
```

Fig. 26C

```
                          200        210         220        230         240
1. E.californica_BBE      FGMMSRKYGLAADNVVDAILIDANGAILDRQAMGEDVFWAIRGGGGGV
2. P.somniferum_BBE       FGMMSRKYGLAADNVVDAILIDSNGAILDREKMGDDVFWAIRGGGGGV
3. C.sativa_CBDAsynthase  YGPLMRNYGLAADNIIDAHLVNVHGKVLDRKSMGEDLFWALRGGAES
4. C.sativa_THCAsynthase  YGALMRNYGLAADNIIDAHLVNVDGKVLDRKSMGEDLFWAIRGGGEN
5. A.mexicana_STOX        FGSLVRKYGLASDQVIDARIVTVNGEILNKETMGKDLYWAIRGGANN
6. T.elegans_PAS-like     FGTMLRKYGLAADNILDAHIVDAEGRLLNRESMGTDLFWAIRGGGAS
7. V.minor_PAS-like       FGTMRKHGLASDNIINAKIVDVRGRILDRKSMGEDLFWAIRGGGAS
8. C.roseus_PAS           FGTLLRKYGLAADNIIDAKIVDAARGRILDRESMGEDLFWAIRGGGAS
9. C.longifolius_PAS-like FGTLLRKYGLAADNIIDAKIVDARGRILDRESMGEDLFWAIRGGGAS 250        260         270        280
1. E.californica_BBE      WGAIYAWKIKLLPVPEKVTVFRVTKNVAIDEATSLLHKWQF-VAEELE
2. P.somniferum_BBE       WGAIYAWKIKLLPVPEKLTVFRVTKNVGIEDASSLLHKWQY-VADELD
3. C.sativa_CBDAsynthase  FGIIVAWKIRLVAVP-KSTMFSVKKIMEIHELVKLVNKWQN-IAYKYD
4. C.sativa_THCAsynthase  FGIIAAWKIKLVAVPSKSTIFSVKKNMEIHGLVKLFNKWQN-IAYKYD
5. A.mexicana_STOX        FGVLLSWKVKLVPVTPIVTVATIDRTLE-QGATNLVHKWQF-VADRLH
6. T.elegans_PAS-like     FGVIVAWKVKLVHVPPVVTVFDLAKTLE-EGAIDLIHKWQT-VGPNLN
7. V.minor_PAS-like       FGVIVAWKVKLVHVPPMVTVFDLSKTFE-EEALQLLNKWQY-IEHKLP
8. C.roseus_PAS           FGVIVSWKVKLVKVPPMVTVFILSKTYE-EGGLDLLHKWQY-IEHKLP
9. C.longifolius_PAS-like FGVIVSWKVKLVKVPPMVTVFILSKTYE-EGGLDLLHKWQY-IEHKLP
```

Fig. 26D

```
                          300              310              320              330
1.E.californica_BBE       EDFTLSVL----GGADEKQVWLT--MLGFHFGLKTVAKSTFDLLF
2.P.somniferum_BBE        EDFTVSVL----GGVNGNDAWLM--FLGLHLGRKDAAKTIIDEKF
3.C.sativa_CBDAsynthase   KDLLMTHFITRNITDNQGKNKTAIHTYFSSVFLGGVDSLVDLMNKSF
4.C.sativa_THCAsynthase   KDLVLMTHFITKNITDNHGKNKTTVHGYFSSIFHGGVDSLVDLMNKSF
5.A.mexicana_STOX         EDVYIGLTMVTAN--TSRAGEKTVVAQ-FSFLFLGNTDRLLQIMEESF
6.T.elegans_PAS-like      EDAFLAASIMA----DPSSESKTLVAG-FFSLFLGIADQLLKEMKESF
7.V.minor_PAS-like        EDLFLAVSIMA----PLPNGNKTLMAG-FTSLFLGNSDHLLKIIEENF
8.C.roseus_PAS            EDLFLAVSIMD----DSSSGNKTLMAG-FMSLFLGKTEDLLKVMAENF
9.C.longifolius_PAS-like  EDLFLAVSIMD----DSSSGNKTLMAG-FMSLFLGKTEDLLKVMAENF 340              350              360              370              380
1.E.californica_BBE       PELGLVEEDYLEMSWGESFAYLAGL----ETVSQLNNRFLKFDERA
2.P.somniferum_BBE        PELGLVDKEFQEMSWGESMAFLSGL----DTISELNNRFLKFDERA
3.C.sativa_CBDAsynthase   PELGIKKTDCRQLSWIDTIIFYSGVVNYDTDNFNKEILLDRSAGQNGA
4.C.sativa_THCAsynthase   PELGIKKTDCKEFSWIDTTIFYSGVVNFNTANFKKEILLDRSAGKKTA
5.A.mexicana_STOX         PELGLKRNDTTEMSWVESHVYF---YRRGQPIEFLWDRD-HLTKSF
6.T.elegans_PAS-like      PELGLRKEDCLEMSWIKAALHFSG---YEPGETVYALKNRKPPQPKQC
7.V.minor_PAS-like        PELGLTKEHCSEMSWIESVMHFSG---FPRGELRDSLKNRISPLPRTC
8.C.roseus_PAS            PDLGLTKEKEDCLEMNWIDAAMYFSG---HPIGESRSVLKNRESHLPKTC
9.C.longifolius_PAS-like  PQLGLKKEDCLEMNWIDAAMYFSG---HPIGESRSVLKNRESHLPKTC
```

Fig. 26E

```
                         390                 400                 410                 420                 430
1. E.californica_BBE         FKTKVDLTKEPLPSKAFYGLLERLSKEP--NGFIALNGFGGQMSKISS
2. P.somniferum_BBE          FKTKVDFTKVSVPLNVFRHALEMLSEQP--GGFIALNGFGGKMSEIST
3. C.sativa_CBDAsynthase     FKIKLDYVKKPIPESYFVQILEKLYEED-IGAGMYALYPYGGIMDEISE
4. C.sativa_THCAsynthase     FSIKLDYVKKPIPETAMVKILEKLYEEDVGAGMYVLYPYGGIMEEISE
5. A.mexicana_STOX           LKVKSDYVREPISKLGLEGIWKRYVGGD--SPAMLWTPFGGRMNQISE
6. T.elegans_PAS-like        ITVRSDFIQEPLSLPALDKLWKFLSEE--NTPIIVMLPHGGMMSKISE
7. V.minor_PAS-like          ISTTSDFIQEPLSLNGLEKLWNICTDEE--NTPIILLFPHGGIMNKISE
8. C.roseus_PAS              VSIKSDFIQEPQSMDALEKLWKFCREEE--NSPIILMLPLGGMMSKISE
9. C.longifolius_PAS-like    VSIKSDFIQEPQSMDAMEKLWKFCREEE--NSPIILMLPLGGMMSKISE 440                 450                 460                 470                 480
1. E.californica_BBE         DFTPFPHRSGTRLMVEYIVAWNQSEQKKTEFLDWLEKVYEFMKPFVS
2. P.somniferum_BBE          DFTPFPHRKGTKLMFEYIIAWNQDEESKIGEFSEWLAKFYDYLEPFVS
3. C.sativa_CBDAsynthase     SAIPFPHRAGILYELWYICSWEKQED--NEKHLNWIRNIYNFMTPYVS
4. C.sativa_THCAsynthase     SAIPFPHRAGIMYELWYTASWEKQED--NEKHINWVRSVYNFTTPYVS
5. A.mexicana_STOX           FESPYPHRAGNIYNIMYVGNWLNENE--SEKQLNWMRSFYSYMGRYVS
6. T.elegans_PAS-like        TEIPYPHRAGVIYSFLYELNWDCEDDSFSERYVSALTRLYDHMTPYVL
7. V.minor_PAS-like          SETPFPYRKDVIYS-IIYEVVWDCTNDESSKEYIDGLRRMKKLMTPYVM
8. C.roseus_PAS              SEIPFPYRKDVIYSMIYEIVWNCEDDESSEEYIDGLGRLEELMTPYV-
9. C.longifolius_PAS-like    SEIPFPYRKDVIYSMIYEILWNCEDDESSEEYIDGLGRLEELMTPYV-
```

Fig. 26F

```
                        490              500              510            520
1. E.californica_BBE    KNPRLGYVNHIDLDLGGIDWGNKTVVNN--AIEISRSWGESYFLSNYE
2. P.somniferum_BBE     KEPRVGYVNHIDLDLGGIDWRNKSSTTN--AVEIARNWGERYFSSNYE
3. C.sativa_CBDAsynthase KNPRLAYLNYRDLDLG----INDPKNPN--NYTQARIWGEKYFGKNFD
4. C.sativa_THCAsynthase QNPRLAYLNYRDLDLG----KTNHASPN--NYTQARIWGEKYFGKNFN
5. A.mexicana_STOX      KNPRSAYLNYKDLDLG----VNDNNVSEYIRYLKARSWGRKYFKNNFE
6. T.elegans_PAS-like   KHPRGGFLNMRCLEIG----KNDDYGT---TYSKAKEWGLKYFKNNFK
7. V.minor_PAS-like     KQPRGAFFNTRNLDIG----KNGGPOT---TYWEAKDWGLKYFKDNFR
8. C.roseus_PAS         KQPRGSWFSTRNLYTG----KNKGPGT---TYSKAKEWGFRYFNNNFK
9. C.longfolius_PAS-like KQPRGSWFSTRNLYTG----KNKGPGT---TYSKAKEWGFRYFNNNFK 530            540           550         560        571
1. E.californica_BBE    RLIRAKTLIDPNNVFNHPQSIPPMANFDYLEKTLGSDGGEVVI
2. P.somniferum_BBE     RLVKAKTLIDPNNVFNHPQSIPPMMKFEEIYMLK----EL
3. C.sativa_CBDAsynthase RLVKVKTLVDPNNFFRNEQSIPPLPRHRH
4. C.sativa_THCAsynthase RLVKVKTKVDPNNFFRNEQSIPPLPPHHH
5. A.mexicana_STOX      KLYKVKSMVDPDNFFKNKQSIPPIRSWGKELEAI------NIVI
6. T.elegans_PAS-like   RLAITKGAVDPDNFFYEQSIPPLASKDEL
7. V.minor_PAS-like     RLAIIKGEVDLENFFYYEQSIPPLISQDEL
8. C.roseus_PAS         KLALIKGOVDPENFFYYEQSIPPLHLOVEL
9. C.longfolius_PAS-like KLAVIKGQVDPENFFYYEQSIPPLHLQGEL
```

Fig. 27

SEQUENCE LISTING

```
<160> NUMBER OF SEQ ID NOS: 67

<210> SEQ ID NO 1
<211> LENGTH: 529
<212> TYPE: PRT
<213> ORGANISM: Catharanthus roseus

<400> SEQUENCE: 1

Met Ile Lys Lys Val Pro Ile Val Leu Ser Ile Phe Cys Phe Leu Leu
1               5                   10                  15

Leu Leu Ser Ser Ser His Gly Ser Ile Pro Glu Ala Phe Leu Asn Cys
                20                  25                  30

Ile Ser Asn Lys Phe Ser Leu Asp Val Ser Ile Leu Asn Ile Leu His
            35                  40                  45

Val Pro Ser Asn Ser Ser Tyr Asp Ser Val Leu Lys Ser Thr Ile Gln
        50                  55                  60

Asn Pro Arg Phe Leu Lys Ser Pro Lys Pro Leu Ala Ile Ile Thr Pro
65                  70                  75                  80

Val Leu His Ser His Val Gln Ser Ala Val Ile Cys Thr Lys Gln Ala
                85                  90                  95
```

```
Gly Leu Gln Ile Arg Ile Arg Ser Gly Gly Ala Asp Tyr Glu Gly Leu
                100                 105                 110

Ser Tyr Arg Ser Glu Val Pro Phe Ile Leu Leu Asp Leu Gln Asn Leu
            115                 120                 125

Arg Ser Ile Ser Val Asp Ile Glu Asp Asn Ser Ala Trp Val Glu Ser
        130                 135                 140

Gly Ala Thr Ile Gly Glu Phe Tyr His Glu Ile Ala Gln Asn Ser Pro
145                 150                 155                 160

Val His Ala Phe Pro Ala Gly Val Ser Ser Val Gly Ile Gly Gly
                165                 170                 175

His Leu Ser Ser Gly Gly Phe Gly Thr Leu Leu Arg Lys Tyr Gly Leu
            180                 185                 190

Ala Ala Asp Asn Ile Ile Asp Ala Lys Ile Val Asp Ala Arg Gly Arg
        195                 200                 205

Ile Leu Asp Arg Glu Ser Met Gly Glu Asp Leu Phe Trp Ala Ile Arg
210                 215                 220

Gly Gly Gly Gly Ala Ser Phe Gly Val Ile Val Ser Trp Lys Val Lys
225                 230                 235                 240

Leu Val Lys Val Pro Pro Met Val Thr Val Phe Ile Leu Ser Lys Thr
                245                 250                 255

Tyr Glu Glu Gly Gly Leu Asp Leu Leu His Lys Trp Gln Tyr Ile Glu
            260                 265                 270

His Lys Leu Pro Glu Asp Leu Phe Leu Ala Val Ser Ile Met Asp Asp
        275                 280                 285

Ser Ser Ser Gly Asn Lys Thr Leu Met Ala Gly Phe Met Ser Leu Phe
290                 295                 300

Leu Gly Lys Thr Glu Asp Leu Leu Lys Val Met Ala Glu Asn Phe Pro
305                 310                 315                 320

Gln Leu Gly Leu Lys Lys Glu Asp Cys Leu Glu Met Asn Trp Ile Asp
                325                 330                 335

Ala Ala Met Tyr Phe Ser Gly His Pro Ile Gly Glu Ser Arg Ser Val
            340                 345                 350

Leu Lys Asn Arg Glu Ser His Leu Pro Lys Thr Cys Val Ser Ile Lys
        355                 360                 365

Ser Asp Phe Ile Gln Glu Pro Gln Ser Met Asp Ala Leu Glu Lys Leu
370                 375                 380

Trp Lys Phe Cys Arg Glu Glu Asn Ser Pro Ile Ile Leu Met Leu
385                 390                 395                 400

Pro Leu Gly Gly Met Met Ser Lys Ile Ser Glu Ser Glu Ile Pro Phe
                405                 410                 415

Pro Tyr Arg Lys Asp Val Ile Tyr Ser Met Ile Tyr Glu Ile Val Trp
            420                 425                 430

Asn Cys Glu Asp Asp Glu Ser Ser Glu Glu Tyr Ile Asp Gly Leu Gly
        435                 440                 445

Arg Leu Glu Glu Leu Met Thr Pro Tyr Val Lys Gln Pro Arg Gly Ser
450                 455                 460

Trp Phe Ser Thr Arg Asn Leu Tyr Thr Gly Lys Asn Lys Gly Pro Gly
465                 470                 475                 480

Thr Thr Tyr Ser Lys Ala Lys Glu Trp Gly Phe Arg Tyr Phe Asn Asn
                485                 490                 495

Asn Phe Lys Lys Leu Ala Leu Ile Lys Gly Gln Val Asp Pro Glu Asn
            500                 505                 510

Phe Phe Tyr Tyr Glu Gln Ser Ile Pro Pro Leu His Leu Gln Val Glu
```

Leu

<210> SEQ ID NO 2
<211> LENGTH: 364
<212> TYPE: PRT
<213> ORGANISM: Catharanthus roseus

<400> SEQUENCE: 2

```
Met Ala Gly Lys Ser Ala Glu Glu His Pro Ile Lys Ala Tyr Gly
1               5                   10                  15

Trp Ala Val Lys Asp Arg Thr Thr Gly Ile Leu Ser Pro Phe Lys Phe
            20                  25                  30

Ser Arg Arg Ala Thr Gly Asp Asp Val Arg Ile Lys Ile Leu Tyr
        35                  40                  45

Cys Gly Ile Cys His Thr Asp Leu Ala Ser Ile Lys Asn Glu Tyr Glu
    50                  55                  60

Phe Leu Ser Tyr Pro Leu Val Pro Gly Met Glu Ile Val Gly Ile Ala
65                  70                  75                  80

Thr Glu Val Gly Lys Asp Val Thr Lys Val Lys Val Gly Glu Lys Val
                85                  90                  95

Ala Leu Ser Ala Tyr Leu Gly Cys Cys Gly Lys Cys Tyr Ser Cys Val
            100                 105                 110

Asn Glu Leu Glu Asn Tyr Cys Pro Glu Val Ile Ile Gly Tyr Gly Thr
        115                 120                 125

Pro Tyr His Asp Gly Thr Ile Cys Tyr Gly Gly Leu Ser Asn Glu Thr
    130                 135                 140

Val Ala Asn Gln Ser Phe Val Leu Arg Phe Pro Glu Arg Leu Ser Pro
145                 150                 155                 160

Ala Gly Gly Ala Pro Leu Leu Ser Ala Gly Ile Thr Ser Phe Ser Ala
                165                 170                 175

Met Arg Asn Ser Gly Ile Asp Lys Pro Gly Leu His Val Gly Val Val
            180                 185                 190

Gly Leu Gly Gly Leu Gly His Leu Ala Val Lys Phe Ala Lys Ala Phe
        195                 200                 205

Gly Leu Lys Val Thr Val Ile Ser Thr Thr Ser Lys Lys Asp Asp Ala
    210                 215                 220

Ile Asn Gly Leu Gly Ala Asp Gly Phe Leu Leu Ser Arg Asp Asp Glu
225                 230                 235                 240

Gln Met Lys Ala Ala Ile Gly Thr Leu Asp Ala Ile Ile Asp Thr Leu
                245                 250                 255

Ala Val Val His Pro Ile Ala Pro Leu Leu Asp Leu Leu Arg Ser Gln
            260                 265                 270

Gly Lys Phe Leu Leu Leu Gly Ala Pro Ser Gln Ser Leu Glu Leu Pro
        275                 280                 285

Pro Ile Pro Leu Leu Ser Gly Gly Lys Ser Ile Ile Gly Ser Ala Ala
    290                 295                 300

Gly Asn Val Lys Gln Thr Gln Glu Met Leu Asp Phe Ala Ala Glu His
305                 310                 315                 320

Asp Ile Thr Ala Asn Val Glu Ile Ile Pro Ile Glu Tyr Ile Asn Thr
                325                 330                 335

Ala Met Glu Arg Leu Asp Lys Gly Asp Val Arg Tyr Arg Phe Val Val
            340                 345                 350

Asp Ile Glu Asn Thr Leu Thr Pro Pro Ser Glu Leu
```

```
                   355                 360

<210> SEQ ID NO 3
<211> LENGTH: 329
<212> TYPE: PRT
<213> ORGANISM: Catharanthus roseus
<220> FEATURE:
<223> OTHER INFORMATION: CS

<400> SEQUENCE: 3

Met Ala Ser Gln Thr Pro Thr Ser Asp Glu Thr Ile Trp Asp Leu Ser
1               5                   10                  15

Pro Tyr Ile Lys Ile Phe Lys Asp Gly Arg Val Glu Arg Leu His Asn
            20                  25                  30

Ser Pro Tyr Val Pro Pro Ser Leu Asn Asp Pro Glu Thr Gly Val Ser
        35                  40                  45

Trp Lys Asp Val Pro Ile Ser Ser Gln Val Ser Ala Arg Val Tyr Ile
50                  55                  60

Pro Lys Ile Ser Asp His Glu Lys Leu Pro Ile Phe Val Tyr Val His
65                  70                  75                  80

Gly Ala Gly Phe Cys Leu Glu Ser Ala Phe Arg Ser Phe His Thr
                85                  90                  95

Phe Val Lys His Phe Val Ala Glu Thr Lys Val Ile Gly Val Ser Ile
            100                 105                 110

Glu Tyr Arg Leu Ala Pro Glu His Leu Leu Pro Ala Ala Tyr Glu Asp
        115                 120                 125

Cys Trp Glu Ala Leu Gln Trp Val Ala Ser His Val Gly Leu Asp Asn
130                 135                 140

Ser Gly Leu Lys Thr Ala Ile Asp Lys Asp Pro Trp Ile Ile Asn Tyr
145                 150                 155                 160

Gly Asp Phe Asp Arg Leu Tyr Leu Ala Gly Asp Ser Pro Gly Ala Asn
                165                 170                 175

Ile Val His Asn Thr Leu Ile Arg Ala Gly Lys Glu Lys Leu Lys Gly
            180                 185                 190

Gly Val Lys Ile Leu Gly Ala Ile Leu Tyr Tyr Pro Tyr Phe Ile Ile
        195                 200                 205

Pro Thr Ser Thr Lys Leu Ser Asp Asp Phe Glu Tyr Asn Tyr Thr Cys
210                 215                 220

Tyr Trp Lys Leu Ala Tyr Pro Asn Ala Pro Gly Gly Met Asn Asn Pro
225                 230                 235                 240

Met Ile Asn Pro Ile Ala Glu Asn Ala Pro Asp Leu Ala Gly Tyr Gly
                245                 250                 255

Cys Ser Arg Leu Leu Val Thr Leu Val Ser Met Ile Ser Thr Thr Pro
            260                 265                 270

Asp Glu Thr Lys Asp Ile Asn Ala Val Tyr Ile Glu Ala Leu Glu Lys
        275                 280                 285

Ser Gly Trp Lys Gly Glu Leu Glu Val Ala Asp Phe Asp Ala Asp Tyr
290                 295                 300

Phe Glu Leu Phe Thr Leu Glu Thr Glu Met Gly Lys Asn Met Phe Arg
305                 310                 315                 320

Arg Leu Ala Ser Phe Ile Lys His Glu
                325

<210> SEQ ID NO 4
<211> LENGTH: 320
<212> TYPE: PRT
```

<213> ORGANISM: Catharanthus roseus

<400> SEQUENCE: 4

```
Met Gly Ser Ser Asp Glu Thr Ile Phe Asp Leu Pro Pro Tyr Ile Lys
1               5                   10                  15
Val Phe Lys Asp Gly Arg Val Glu Arg Leu His Ser Ser Pro Tyr Val
            20                  25                  30
Pro Pro Ser Leu Asn Asp Pro Glu Thr Gly Gly Val Ser Trp Lys Asp
        35                  40                  45
Val Pro Ile Ser Ser Val Val Ser Ala Arg Ile Tyr Leu Pro Lys Ile
    50                  55                  60
Asn Asn His Asp Glu Lys Leu Pro Ile Ile Val Tyr Phe His Gly Ala
65                  70                  75                  80
Gly Phe Cys Leu Glu Ser Ala Phe Lys Ser Phe His Thr Tyr Val
                85                  90                  95
Lys His Phe Val Ala Glu Ala Lys Ala Ile Ala Val Ser Val Glu Phe
            100                 105                 110
Arg Leu Ala Pro Glu Asn His Leu Pro Ala Ala Tyr Glu Asp Cys Trp
        115                 120                 125
Glu Ala Leu Gln Trp Val Ala Ser His Val Gly Leu Asp Ile Ser Ser
    130                 135                 140
Leu Lys Thr Cys Ile Asp Lys Asp Pro Trp Ile Ile Asn Tyr Ala Asp
145                 150                 155                 160
Phe Asp Arg Leu Tyr Leu Trp Gly Asp Ser Thr Gly Ala Asn Ile Val
                165                 170                 175
His Asn Thr Leu Ile Arg Ser Gly Lys Glu Lys Leu Asn Gly Gly Lys
            180                 185                 190
Val Lys Ile Leu Gly Ala Ile Leu Tyr Tyr Pro Tyr Phe Leu Ile Arg
        195                 200                 205
Thr Ser Ser Lys Gln Ser Asp Tyr Met Glu Asn Glu Tyr Arg Ser Tyr
    210                 215                 220
Trp Lys Leu Ala Tyr Pro Asp Ala Pro Gly Gly Asn Asp Asn Pro Met
225                 230                 235                 240
Ile Asn Pro Thr Ala Glu Asn Ala Pro Asp Leu Ala Gly Tyr Gly Cys
                245                 250                 255
Ser Arg Leu Leu Ile Ser Met Val Ala Asp Glu Ala Arg Asp Ile Thr
            260                 265                 270
Leu Leu Tyr Ile Asp Ala Leu Glu Lys Ser Gly Trp Lys Gly Glu Leu
        275                 280                 285
Asp Val Ala Asp Phe Asp Lys Gln Tyr Phe Glu Leu Phe Glu Met Glu
    290                 295                 300
Thr Glu Val Ala Lys Asn Met Leu Arg Arg Leu Ala Ser Phe Ile Lys
305                 310                 315                 320
```

<210> SEQ ID NO 5
<211> LENGTH: 1590
<212> TYPE: DNA
<213> ORGANISM: Catharanthus roseus

<400> SEQUENCE: 5

```
atgataaaaa aagtcccaat agttctttca attttctgct tcttcttct actctcatca      60
tcccatggct caattcctga agctttctc aattgtattt ccaataaatt ttcattagat     120
gtatccattt taaacattct tcatgttccc agcaattctt cctatgattc tgttctcaaa     180
tctactatcc aaaatccaag attcctcaaa tcacccaagc ccttagctat aatcacccca     240
```

```
gtacttcact cccatgtcca atctgctgtt atctgtacca aacaagccgg tttacaaatt    300
agaatccgaa gcggaggagc tgattacgag ggcttatcct atcgttctga ggttcccttt    360
attctgctag atctccagaa tcttcgatca atttccgttg atattgaaga caacagcgct    420
tgggtcgaat caggagcaac aattggtgaa ttctatcatg agatagctca gaacagccct    480
gttcatgcgt ttccagctgg ggtctcttcc tctgttggaa ttggcggcca tttgagtagc    540
ggcggttttg gtacattgct tcggaaatat ggattagcag ccgataatat aatcgatgca    600
aaaattgttg atgccagagg cagaattctt gatagggaat caatgggaga agatctattt    660
tgggctatta gaggaggagg aggagctagt tttggtgtta tagtttcttg gaaggttaaa    720
cttgtaaaag tccctccgat ggtaactgtt ttcatcttgt ccaagactta tgaagaagga    780
ggtttagatc ttctacacaa atggcaatat atagaacaca aactccctga agatttattc    840
cttgctgtaa gcatcatgga tgattcatct agtggaaata aaacacttat ggcaggtttt    900
atgtctctgt ttcttggaaa aacagaggac cttctgaaag taatggcgga aaatttccca    960
caacttggat tgaaaaagga agattgctta gaaatgaatt ggattgatgc agcaatgtat   1020
ttttcaggac acccaattgg agaatcccga tctgtgctta aaaccgaga atctcatctt   1080 ccaaagacat gcgtttcgat caaatcagac tttattcaag aaccacaatc catggatgca   1140
ttggaaaagt tatggaagtt ttgtagggaa gaagaaaata gtcccataat actgatgctt   1200
ccactggggg gaatgatgag taaaatatca gaatcagaaa tcccatttcc ttacagaaaa   1260
gatgtgattt acagtatgat atacgaaata gtttggaatt gtgaagacga tgaatcatcg   1320
gaagaatata tcgatggatt gggaaggctt gaggaattaa tgactccata tgtgaaacaa   1380
ccaagaggtt cttggttcag caccagaaac ctttataccg gtaaaaataa aggtccagga   1440
acaacttatt ccaaagctaa agaatgggga tttcggtatt ttaataataa tttcaaaaag   1500 ttggcccctta tcaaaggaca agttgatcca gaaaacttct tctactatga acaaagcatt   1560 cccctctcc atttacaagt cgaactttga                                      1590
```

```
<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
ggttgcgaut ccaattcatt tctaagcaat cttccttttt ca                         42

<210> SEQ ID NO 7
<211> LENGTH: 1098
<212> TYPE: DNA
<213> ORGANISM: Catharanthus roseus

<400> SEQUENCE: 7
atggccggaa aatcagcaga agaagaacat cccattaagg cttacggatg ggctgttaaa     60
gatagaacaa ctgggattct ttctcccttc aaattttcca aagggcaac aggtgatgat    120 gatgtccgaa ttaagatact ctactgtgga atttgtcaca ctgatcttgc ctcaatcaag    180
aacgaatacg agtttctttc ttatcctctt gtgcccggga tggagatcgt tggaatagca    240
acggaggttg gaaagatgt cacaaaagtg aaagttggcg aaaaagtagc attatcagcc    300
tatttaggat gttgtggcaa atgctatagt tgtgtaaatg aactcgagaa ttattgtccg    360
```

```
gaagtaatca taggttatgg cacccccatac catgacggaa caatttgcta tgggggcctt      420
tcaaacgaaa ctgtcgcaaa tcaaagtttt gttcttcgtt ttcctgaaag actttctcca      480
gctggcggag ctccttttgct tagcgccgga attacttcgt ttagtgcaat gagaaatagc     540
ggcatcgaca aacctggatt acacgtggga gtcgtcggtc tcggcggatt aggtcatctt     600
gctgtaaaat ttgctaaggc ttttggtctt aaagtaactg ttattagcac cactcccagc     660
aagaaggatg atgctataaa tggtcttggt gctgatggat tcttactcag ccgcgatgat     720
gaacaaatga aggctgctat tggaaccttg gatgcaatta ttgatacact ggcggttgtt    780
catcccatag caccattgct tgatctcctg agaagtcaag ggaaattttt gttacttggg     840
gcgccatctc aatcacttga gttgccacct attcctttat tatcaggtgg gaaatctatc    900 attgaagtg cggccggaaa tgtgaagcaa actcaagaaa tgcttgattt tgcagcggag      960
catgatataa ctgcaaatgt tgagattatt ccaatagagt acataaatac tgcaatggaa    1020
cgtttagaca agggcgatgt tagataccga tttgtagttg acatcgaaaa taccttgact    1080
cctccgtcag agttataa                                                  1098

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
cgaggatcct aatattcatc tttgttttac gttcttactt tc                         42

<210> SEQ ID NO 9
<211> LENGTH: 990
<212> TYPE: DNA
<213> ORGANISM: Catharanthus roseus

<400> SEQUENCE: 9
atggcttccc aaactccaac ctcagatgag actatttggg atctttctcc atatattaaa      60
attttcaaag atggaagagt agaaagactc cataatagtc cttatgttcc cccatcactt     120
aatgatccag aaactggcgt ttcttggaaa gatgtcccga tttcatcaca agtttccgct     180
agggtataca ttccaaaaat cagcgaccat gaaaaactcc ctattttgt gtatgtgcat     240 ggggctggct tttgtctaga atctgccttc agatcatttt tccacacttt tgtcaaacac     300
ttcgtagccg aaaccaaagt tattgggggtt tcgattgaat atagacttgc cccagagcac    360
cttttacccg cagcttatga agattgttgg gaagcccttc aatgggttgc ttctcatgtg    420
ggtctcgaca attccggcct aaagacagct attgataaag atccatggat aataaactat     480
ggtgatttcg atagactgta tttggcgggt gacagtcctg gtgctaatat tgttcacaac     540
acacttatca gagctggaaa agagaaactg aagggcggag tgaaaatttt ggggcaatt     600 ctttactacc catatttcat tatcccaacc agcacgaaac ttagtgatga tttttgagtat    660 aactacacat gttactggaa attggcttat ccaaatgctc ctggcgggat gaataaccca    720
atgataaacc ccatagctga aaatgctcca gacttggctg gatacggttg ctcgaggttg    780
ttggttaccc tggtttccat gatttcaacg actccagatg agactaaaga cataaatgcg    840
gtttatattg aggcattaga aaagagtgga tggaaagggg aattggaagt ggctgatttt     900
gacgcagatt attttgaact cttcaccttg gaaacggaga tgggcaagaa tatgttcaga    960
cgtttagcat ctttcatcaa acatgagtaa                                     990
```

<210> SEQ ID NO 10
<211> LENGTH: 963
<212> TYPE: DNA
<213> ORGANISM: Catharanthus roseus
<220> FEATURE:
<221> NAME/KEY: misc_feature
<222> LOCATION: 920
<223> OTHER INFORMATION: /note="A, C, T or G"

<400> SEQUENCE: 10

```
atgggttcct cagatgagac tattttttgat cttcctccat acatcaaagt cttcaaagat      60
ggaagagtag aaagactcca ttcttcccca tatgttcccc catctcttaa tgatccagaa     120
accggtggag tctcttggaa agacgtccca atttcttcag tagtttcagc tagaatttac     180
cttcctaaaa tcaacaacca tgatgaaaaa ctccccatta tagtctattt ccatggagct     240
ggttttttgtc ttgaatcggc cttcaaatca ttttttccaca cttatgtgaa acactttgta     300
gcagaagcca aagctattgc ggtttctgtt gagttcaggc tcgcccctga aaaccattta     360
cccgcagctt atgaagattg ctgggaagcc cttcaatggg ttgcttctca tgtgggtctc     420
gacatttcca gcttgaagac atgtattgat aaagatccat ggataatcaa ctatgccgat     480
ttcgatagac tctatttgtg gggtgatagc accggtgcca atattgttca acacacactt     540
atcagatctg gtaaagagaa attgaacggc ggcaaagtga agattttggg ggcaattctt     600
tactacccat atttcttaat caggacgagt tcaaaacaga gtgattatat ggagaatgag     660
tatagatctt actggaaatt ggcttaccca gatgctcctg gtggaaatga taacccaatg     720
ataaacccta cagctgagaa tgctcctgat ctggctggat atggttgctc gaggttgctg     780
atttccatgg ttgccgatga agctagagat ataactcttc tttatattga tgcattggaa     840
aagagtggat ggaaaggtga attagatgtg gctgattttg ataaacagta ttttgaactg     900
tttgaaatgg aaacagaggn tgccaagaac atgctcagac gtttagcttc tttcatcaag     960
taa                                                                  963
```

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11

```
cgactcgagc gcattattca aatttttttac ttatcttctc                           40
```

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12

```
cgaggatcca aaaaggcaaa atttccttgc                                       30
```

<210> SEQ ID NO 13
<211> LENGTH: 53
<212> TYPE: DNA
<213> ORGANISM: Artificial Sequence
<220> FEATURE:
<223> OTHER INFORMATION: Primer -continued

<400> SEQUENCE: 13
cgactcgagt aagcatttaa cattattatt attatcatat tttatcaaaa tca    53

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
cgaggatccg agttgccacc tattccttta ttatcag    37

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
cgactcgagc agagtacaca cttatgactt ttatgtgc    38

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
ggcgcgautc tcttcctctg ttggaattgg c    31

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
aagttctgtt tcagggcccg gcttcccaaa ctccaacctc agatga    46

<210> SEQ ID NO 18
<211> LENGTH: 45
<212> TYPE: DNA
<213> ORGANISM: Artificial Sequence
<220> FEATURE:
<223> OTHER INFORMATION: Primer

<400> SEQUENCE: 18
atggtctaga aagctttact catgtttgat gaaagatgct aaacg    45

<210> SEQ ID NO 19
<211> LENGTH: 46
<212> TYPE: DNA
<213> ORGANISM: Artificial Sequence
<220> FEATURE:
<223> OTHER INFORMATION: Primer

<400> SEQUENCE: 19
aagttctgtt tcagggcccg gcttcccaaa ctccaacctc agatga    46

<210> SEQ ID NO 20
<211> LENGTH: 46

```
<212> TYPE: DNA
<213> ORGANISM: Artificial Sequence
<220> FEATURE:
<223> OTHER INFORMATION: Primer

<400> SEQUENCE: 20
atggtctaga aagctttatt tgatgaaaga cgttaagcgt ctaatc            46

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
aagttctgtt tcagggcccg ggttcctcag atgagactat ttttg             45

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
atggtctaga aagctttact tgatgaaaga agctaaacgt ctg               43

<210> SEQ ID NO 23
<211> LENGTH: 49
<212> TYPE: DNA
<213> ORGANISM: Artificial Sequence
<220> FEATURE:
<223> OTHER INFORMATION: Primer

<400> SEQUENCE: 23
ggggacaagt ttgtacaaaa aagcaggctt aatgataaaa aaagtccca         49

<210> SEQ ID NO 24
<211> LENGTH: 49
<212> TYPE: DNA
<213> ORGANISM: Artificial Sequence
<220> FEATURE:
<223> OTHER INFORMATION: Primer

<400> SEQUENCE: 24
ggggaccact ttgtacaaga aagctgggta aagttcgact tgtaaatgg         49

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
ctgagaacta gtctcatgtt tgatgaaaga tgctaaacg                    39

<210> SEQ ID NO 26
<211> LENGTH: 48
<212> TYPE: DNA
<213> ORGANISM: Artificial Sequence
<220> FEATURE:
<223> OTHER INFORMATION: Primer

<400> SEQUENCE: 26
```

```
tctctcgaga aaaggtcaat tcctgaagct tttctcaatt gtatttcc        48
```

<210> SEQ ID NO 27
<211> LENGTH: 41
<212> TYPE: DNA
<213> ORGANISM: Artificial Sequence
<220> FEATURE:
<223> OTHER INFORMATION: Primer

<400> SEQUENCE: 27

```
ttaaatggcc ggccgaagtt cgacttgtaa atggagaggg g               41
```

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28

```
taatacgact cactataggg                                       20
```

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29

```
tagccagaag tcagatgct                                        19
```

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30

```
tcgcgttaac gctagcatgg atctc                                 25
```

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31

```
gtaacatcag agattttgag acac                                  24
```

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32

```
ggagaaagat tgttaagctt ctgt                                  24
```

<210> SEQ ID NO 33
<211> LENGTH: 24
<212> TYPE: DNA
<213> ORGANISM: Artificial Sequence

```
<220> FEATURE:
<223> OTHER INFORMATION: Primer

<400> SEQUENCE: 33
aacatagaaa tgcacaccga ataa                                      24

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gactggttcc aattgacaag c                                         21

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
gcgtgaatgt aagcgtgac                                            19

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
acaataccat cgccatcac                                            19

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
aagaggactg ctggaagg                                             18

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tccttacgcc gcattatcag                                           20

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
agatgagaca gtaacgcctt g                                         21
```

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
cttcactccc atgtccaatc t                                              21

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
cgataggata agccctcgta atc                                            23

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
gaaatagcgg catcgacaaa c                                              21

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
gctgggagtg gtgctaataa                                                20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ctcctggcgg gatgaataac                                                20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ggaaaccagg gtaaccaaca                                                20

<210> SEQ ID NO 46
<211> LENGTH: 20
<212> TYPE: DNA
<213> ORGANISM: Artificial Sequence
<220> FEATURE:
<223> OTHER INFORMATION: Primer

```
<400> SEQUENCE: 46
agatgctcct ggtggaaatg                                              20

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
caaccatgga aatcagcaac c                                            21

<210> SEQ ID NO 48
<211> LENGTH: 43
<212> TYPE: DNA
<213> ORGANISM: Artificial Sequence
<220> FEATURE:
<223> OTHER INFORMATION: Primer

<400> SEQUENCE: 48
ctgagaacta gtatgataaa aaaagtccca atagttcttt caa                    43

<210> SEQ ID NO 49
<211> LENGTH: 43
<212> TYPE: DNA
<213> ORGANISM: Artificial Sequence
<220> FEATURE:
<223> OTHER INFORMATION: Primer

<400> SEQUENCE: 49
ctgagaacta gtatctaatg aaaatttatt ggaaatacaa ttg                    43

<210> SEQ ID NO 50
<211> LENGTH: 41
<212> TYPE: DNA
<213> ORGANISM: Artificial Sequence
<220> FEATURE:
<223> OTHER INFORMATION: Primer

<400> SEQUENCE: 50
ctgagaacta gttttgagaa cagaatcata ggaagaattg c                      41

<210> SEQ ID NO 51
<211> LENGTH: 34
<212> TYPE: DNA
<213> ORGANISM: Artificial Sequence
<220> FEATURE:
<223> OTHER INFORMATION: Primer

<400> SEQUENCE: 51
ctgagaacta gtatggccgg aaaatcagca gaag                              34

<210> SEQ ID NO 52
<211> LENGTH: 43
<212> TYPE: DNA
<213> ORGANISM: Artificial Sequence
<220> FEATURE:
<223> OTHER INFORMATION: Primer

<400> SEQUENCE: 52
ctgagaacta gtttataact ctgacggagg agtcaaggta ttt                    43

<210> SEQ ID NO 53
```

```
<211> LENGTH: 39
<212> TYPE: DNA
<213> ORGANISM: Artificial Sequence
<220> FEATURE:
<223> OTHER INFORMATION: Primer

<400> SEQUENCE: 53
ctgagaacta gtatgggttc ctcagatgag actattttt                               39

<210> SEQ ID NO 54
<211> LENGTH: 39
<212> TYPE: DNA
<213> ORGANISM: Artificial Sequence
<220> FEATURE:
<223> OTHER INFORMATION: Primer

<400> SEQUENCE: 54
ctgagaacta gtttacttga tgaaagaagc taaacgtct                               39

<210> SEQ ID NO 55
<211> LENGTH: 39
<212> TYPE: DNA
<213> ORGANISM: Artificial Sequence
<220> FEATURE:
<223> OTHER INFORMATION: Primer

<400> SEQUENCE: 55
ctgagaacta gtcttgatga agaagctaa acgtctgag                                39

<210> SEQ ID NO 56
<211> LENGTH: 42
<212> TYPE: DNA
<213> ORGANISM: Artificial Sequence
<220> FEATURE:
<223> OTHER INFORMATION: Primer

<400> SEQUENCE: 56
ctgagaacta gtatgaattc tcaactaat ccaacttcag at                            42

<210> SEQ ID NO 57
<211> LENGTH: 42
<212> TYPE: DNA
<213> ORGANISM: Artificial Sequence
<220> FEATURE:
<223> OTHER INFORMATION: Primer

<400> SEQUENCE: 57
ctgagaacta gtttactcat gtttgatgaa agatgctaaa cg                           42

<210> SEQ ID NO 58
<211> LENGTH: 538
<212> TYPE: PRT
<213> ORGANISM: Eschscholzia californica

<400> SEQUENCE: 58

Met Glu Asn Lys Thr Pro Ile Phe Phe Ser Leu Ser Ile Phe Leu Ser
1               5                   10                  15

Leu Leu Asn Cys Ala Leu Gly Gly Asn Asp Leu Leu Ser Cys Leu Thr
                20                  25                  30

Phe Asn Gly Val Arg Asn His Thr Val Phe Ser Ala Asp Ser Asp Ser
            35                  40                  45

Asp Phe Asn Arg Phe Leu His Leu Ser Ile Gln Asn Pro Leu Phe Gln
        50                  55                  60

Asn Ser Leu Ile Ser Lys Pro Ser Ala Ile Ile Leu Pro Gly Ser Lys
```

```
            65                  70                  75                  80
Glu Glu Leu Ser Asn Thr Ile Arg Cys Ile Arg Lys Gly Ser Trp Thr
                85                  90                  95
Ile Arg Leu Arg Ser Gly Gly His Ser Tyr Glu Gly Leu Ser Tyr Thr
               100                 105                 110
Ser Asp Thr Pro Phe Ile Leu Ile Asp Leu Met Asn Leu Asn Arg Val
               115                 120                 125
Ser Ile Asp Leu Glu Ser Glu Thr Ala Trp Val Glu Ser Gly Ser Thr
       130                 135                 140
Leu Gly Glu Leu Tyr Tyr Ala Ile Thr Glu Ser Ser Lys Leu Gly
145                 150                 155                 160
Phe Thr Ala Gly Trp Cys Pro Thr Val Gly Thr Gly His Ile Ser
               165                 170                 175
Gly Gly Gly Phe Gly Met Met Ser Arg Lys Tyr Gly Leu Ala Ala Asp
               180                 185                 190
Asn Val Val Asp Ala Ile Leu Ile Asp Ala Asn Gly Ala Ile Leu Asp
               195                 200                 205
Arg Gln Ala Met Gly Glu Asp Val Phe Trp Ala Ile Arg Gly Gly Gly
       210                 215                 220
Gly Gly Val Trp Gly Ala Ile Tyr Ala Trp Lys Ile Lys Leu Leu Pro
225                 230                 235                 240
Val Pro Glu Lys Val Thr Val Phe Arg Val Thr Lys Asn Val Ala Ile
               245                 250                 255
Asp Glu Ala Thr Ser Leu Leu His Lys Trp Gln Phe Val Ala Glu Glu
               260                 265                 270
Leu Glu Glu Asp Phe Thr Leu Ser Val Leu Gly Gly Ala Asp Glu Lys
       275                 280                 285
Gln Val Trp Leu Thr Met Leu Gly Phe His Phe Gly Leu Lys Thr Val
       290                 295                 300
Ala Lys Ser Thr Phe Asp Leu Leu Phe Pro Glu Leu Gly Leu Val Glu
305                 310                 315                 320
Glu Asp Tyr Leu Glu Met Ser Trp Gly Glu Ser Phe Ala Tyr Leu Ala
               325                 330                 335
Gly Leu Glu Thr Val Ser Gln Leu Asn Asn Arg Phe Leu Lys Phe Asp
               340                 345                 350
Glu Arg Ala Phe Lys Thr Lys Val Asp Leu Thr Lys Glu Pro Leu Pro
       355                 360                 365
Ser Lys Ala Phe Tyr Gly Leu Leu Glu Arg Leu Ser Lys Glu Pro Asn
       370                 375                 380
Gly Phe Ile Ala Leu Asn Gly Phe Gly Gly Gln Met Ser Lys Ile Ser
385                 390                 395                 400
Ser Asp Phe Thr Pro Phe Pro His Arg Ser Gly Thr Arg Leu Met Val
               405                 410                 415
Glu Tyr Ile Val Ala Trp Asn Gln Ser Glu Gln Lys Lys Lys Thr Glu
               420                 425                 430
Phe Leu Asp Trp Leu Glu Lys Val Tyr Glu Phe Met Lys Pro Phe Val
               435                 440                 445
Ser Lys Asn Pro Arg Leu Gly Tyr Val Asn His Ile Asp Leu Asp Leu
       450                 455                 460
Gly Gly Ile Asp Trp Gly Asn Lys Thr Val Val Asn Asn Ala Ile Glu
465                 470                 475                 480
Ile Ser Arg Ser Trp Gly Glu Ser Tyr Phe Leu Ser Asn Tyr Glu Arg
               485                 490                 495
```

```
Leu Ile Arg Ala Lys Thr Leu Ile Asp Pro Asn Asn Val Phe Asn His
                500                 505                 510

Pro Gln Ser Ile Pro Pro Met Ala Asn Phe Asp Tyr Leu Glu Lys Thr
            515                 520                 525

Leu Gly Ser Asp Gly Gly Glu Val Val Ile
        530                 535

<210> SEQ ID NO 59
<211> LENGTH: 535
<212> TYPE: PRT
<213> ORGANISM: Papaver somniferum

<400> SEQUENCE: 59

Met Met Cys Arg Ser Leu Thr Leu Arg Phe Phe Leu Phe Ile Val Leu
1               5                   10                  15

Leu Gln Thr Cys Val Arg Gly Gly Asp Val Asn Asp Asn Leu Leu Ser
            20                  25                  30

Ser Cys Leu Asn Ser His Gly Val His Asn Phe Thr Thr Leu Ser Thr
        35                  40                  45

Asp Thr Asn Ser Asp Tyr Phe Lys Leu Leu His Ala Ser Met Gln Asn
    50                  55                  60

Pro Leu Phe Ala Lys Pro Thr Val Ser Lys Pro Ser Phe Ile Val Met
65                  70                  75                  80

Pro Gly Ser Lys Glu Glu Leu Ser Ser Thr Val His Cys Cys Thr Arg
                85                  90                  95

Glu Ser Trp Thr Ile Arg Leu Arg Ser Gly Gly His Ser Tyr Glu Gly
            100                 105                 110

Leu Ser Tyr Thr Ala Asp Thr Pro Phe Val Ile Val Asp Met Met Asn
        115                 120                 125

Leu Asn Arg Ile Ser Ile Asp Val Leu Ser Glu Thr Ala Trp Val Glu
    130                 135                 140

Ser Gly Ala Thr Leu Gly Glu Leu Tyr Tyr Ala Ile Ala Gln Ser Thr
145                 150                 155                 160

Asp Thr Leu Gly Phe Thr Ala Gly Trp Cys Pro Thr Val Gly Ser Gly
                165                 170                 175

Gly His Ile Ser Gly Gly Gly Phe Gly Met Met Ser Arg Lys Tyr Gly
            180                 185                 190

Leu Ala Ala Asp Asn Val Val Asp Ala Ile Leu Ile Asp Ser Asn Gly
        195                 200                 205

Ala Ile Leu Asp Arg Glu Lys Met Gly Asp Asp Val Phe Trp Ala Ile
    210                 215                 220

Arg Gly Gly Gly Gly Val Trp Gly Ala Ile Tyr Ala Trp Lys Ile
225                 230                 235                 240

Lys Leu Leu Pro Val Pro Glu Lys Leu Thr Val Phe Arg Val Thr Lys
                245                 250                 255

Asn Val Gly Ile Glu Asp Ala Ser Ser Leu His Lys Trp Gln Tyr
            260                 265                 270

Val Ala Asp Glu Leu Asp Glu Asp Phe Thr Val Ser Val Leu Gly Gly
        275                 280                 285

Val Asn Gly Asn Asp Ala Trp Leu Met Phe Leu Gly Leu His Leu Gly
    290                 295                 300

Arg Lys Asp Ala Ala Lys Thr Ile Ile Asp Glu Lys Phe Pro Glu Leu
305                 310                 315                 320

Gly Leu Val Asp Lys Glu Phe Gln Glu Met Ser Trp Gly Glu Ser Met
```

```
                        325                 330                 335
Ala Phe Leu Ser Gly Leu Asp Thr Ile Ser Glu Leu Asn Asn Arg Phe
                340                 345                 350

Leu Lys Phe Asp Glu Arg Ala Phe Lys Thr Lys Val Asp Phe Thr Lys
            355                 360                 365

Val Ser Val Pro Leu Asn Val Phe Arg His Ala Leu Glu Met Leu Ser
        370                 375                 380

Glu Gln Pro Gly Gly Phe Ile Ala Leu Asn Gly Phe Gly Gly Lys Met
385                 390                 395                 400

Ser Glu Ile Ser Thr Asp Phe Thr Pro Phe Pro His Arg Lys Gly Thr
                405                 410                 415

Lys Leu Met Phe Glu Tyr Ile Ile Ala Trp Asn Gln Asp Glu Glu Ser
            420                 425                 430

Lys Ile Gly Glu Phe Ser Glu Trp Leu Ala Lys Phe Tyr Asp Tyr Leu
        435                 440                 445

Glu Pro Phe Val Ser Lys Glu Pro Arg Val Gly Tyr Val Asn His Ile
    450                 455                 460

Asp Leu Asp Ile Gly Gly Ile Asp Trp Arg Asn Lys Ser Ser Thr Thr
465                 470                 475                 480

Asn Ala Val Glu Ile Ala Arg Asn Trp Gly Glu Arg Tyr Phe Ser Ser
                485                 490                 495

Asn Tyr Glu Arg Leu Val Lys Ala Lys Thr Leu Ile Asp Pro Asn Asn
            500                 505                 510

Val Phe Asn His Pro Gln Ser Ile Pro Pro Met Met Lys Phe Glu Glu
        515                 520                 525

Ile Tyr Met Leu Lys Glu Leu
        530                 535

<210> SEQ ID NO 60
<211> LENGTH: 544
<212> TYPE: PRT
<213> ORGANISM: Cannabis sativa

<400> SEQUENCE: 60

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160
```

```
Trp Val Asn Glu Lys Asn Glu Asn Leu Ser Leu Ala Ala Gly Tyr Cys
                165                 170                 175
Pro Thr Val Cys Ala Gly Gly His Phe Gly Gly Gly Tyr Gly Pro
            180                 185                 190
Leu Met Arg Asn Tyr Gly Leu Ala Ala Asp Asn Ile Ile Asp Ala His
        195                 200                 205
Leu Val Asn Val His Gly Lys Val Leu Asp Arg Lys Ser Met Gly Glu
    210                 215                 220
Asp Leu Phe Trp Ala Leu Arg Gly Gly Gly Ala Glu Ser Phe Gly Ile
225                 230                 235                 240
Ile Val Ala Trp Lys Ile Arg Leu Val Ala Val Pro Lys Ser Thr Met
                245                 250                 255
Phe Ser Val Lys Lys Ile Met Glu Ile His Glu Leu Val Lys Leu Val
            260                 265                 270
Asn Lys Trp Gln Asn Ile Ala Tyr Lys Tyr Asp Lys Asp Leu Leu Leu
        275                 280                 285
Met Thr His Phe Ile Thr Arg Asn Ile Thr Asp Asn Gln Gly Lys Asn
    290                 295                 300
Lys Thr Ala Ile His Thr Tyr Phe Ser Ser Val Phe Leu Gly Gly Val
305                 310                 315                 320
Asp Ser Leu Val Asp Leu Met Asn Lys Ser Phe Pro Glu Leu Gly Ile
                325                 330                 335
Lys Lys Thr Asp Cys Arg Gln Leu Ser Trp Ile Asp Thr Ile Ile Phe
            340                 345                 350
Tyr Ser Gly Val Val Asn Tyr Asp Thr Asp Asn Phe Asn Lys Glu Ile
        355                 360                 365
Leu Leu Asp Arg Ser Ala Gly Gln Asn Gly Ala Phe Lys Ile Lys Leu
    370                 375                 380
Asp Tyr Val Lys Lys Pro Ile Pro Glu Ser Val Phe Val Gln Ile Leu
385                 390                 395                 400
Glu Lys Leu Tyr Glu Glu Asp Ile Gly Ala Gly Met Tyr Ala Leu Tyr
                405                 410                 415
Pro Tyr Gly Gly Ile Met Asp Glu Ile Ser Glu Ser Ala Ile Pro Phe
            420                 425                 430
Pro His Arg Ala Gly Ile Leu Tyr Glu Leu Trp Tyr Ile Cys Ser Trp
        435                 440                 445
Glu Lys Gln Glu Asp Asn Glu Lys His Leu Asn Trp Ile Arg Asn Ile
    450                 455                 460
Tyr Asn Phe Met Thr Pro Tyr Val Ser Lys Asn Pro Arg Leu Ala Tyr
465                 470                 475                 480
Leu Asn Tyr Arg Asp Leu Asp Ile Gly Ile Asn Asp Pro Lys Asn Pro
                485                 490                 495
Asn Asn Tyr Thr Gln Ala Arg Ile Trp Gly Glu Lys Tyr Phe Gly Lys
            500                 505                 510
Asn Phe Asp Arg Leu Val Lys Val Lys Thr Leu Val Asp Pro Asn Asn
        515                 520                 525
Phe Phe Arg Asn Glu Gln Ser Ile Pro Pro Leu Pro Arg His Arg His
    530                 535                 540

<210> SEQ ID NO 61
<211> LENGTH: 545
<212> TYPE: PRT
<213> ORGANISM: Cannabis sativa

<400> SEQUENCE: 61
```

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
        20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
                100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
        130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Tyr Gly Ala
                180                 185                 190

Leu Met Arg Asn Tyr Gly Leu Ala Ala Asp Asn Ile Ile Asp Ala His
            195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Ala Val Pro Ser Lys Ser Thr
            245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
            275                 280                 285

Leu Met Thr His Phe Ile Thr Lys Asn Ile Thr Asp Asn His Gly Lys
            290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
            325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
            355                 360                 365

Ile Leu Leu Asp Arg Ser Ala Gly Lys Lys Thr Ala Phe Ser Ile Lys
            370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415
```

```
Tyr Pro Tyr Gly Gly Ile Met Glu Glu Ile Ser Glu Ser Ala Ile Pro
                420                 425                 430

Phe Pro His Arg Ala Gly Ile Met Tyr Glu Leu Trp Tyr Thr Ala Ser
        435                 440                 445

Trp Glu Lys Gln Glu Asp Asn Glu Lys His Ile Asn Trp Val Arg Ser
450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asn
        515                 520                 525

Asn Phe Phe Arg Asn Glu Gln Ser Ile Pro Pro Leu Pro Pro His His
        530                 535                 540

His
545

<210> SEQ ID NO 62
<211> LENGTH: 543
<212> TYPE: PRT
<213> ORGANISM: Argemone mexicana

<400> SEQUENCE: 62

Met Ile Pro Asn Ser Ser Ser Ser Ile Leu Ser Leu Leu Val Leu
1               5                   10                  15

Leu Leu Phe Ser Thr Ser Ser Trp Ala Thr Asn Ser Ile His Glu
                20                  25                  30

Asp Phe Leu Asn Cys Leu Ser Ile Tyr Lys Ser Ser Phe Pro Ile Pro
            35                  40                  45

Ile Tyr Thr Ser Lys Asn Ser Ser Phe Asn Thr Leu Phe Arg Ser Ser
50                  55                  60

Ala Arg Asn Leu Arg Phe Leu Ser Pro Asn Ser Thr Gln Lys Pro Glu
65                  70                  75                  80

Phe Ile Ile Thr Pro Thr Leu Glu Ser His Val Gln Thr Thr Val Val
                85                  90                  95

Cys Ser Lys Lys His Gly Leu Asp Leu Lys Val Arg Ser Gly Gly His
            100                 105                 110

Asp Val Glu Gly Leu Ser Tyr Val Ser Asp Ser Pro Tyr Val Met Ile
        115                 120                 125

Asp Leu Val Asp Phe Arg Asn Ile Thr Val Asn Val Lys Asn Ala Thr
130                 135                 140

Ala Trp Ile Gln Ala Gly Ser Ser Leu Gly Glu Val Tyr Tyr Lys Val
145                 150                 155                 160

Gly Asn Glu Ser Lys Asn Thr Leu Gly Phe Pro Ala Gly Phe Cys Pro
                165                 170                 175

Thr Val Gly Val Gly Gly His Ile Ser Gly Gly Phe Gly Ser Leu
            180                 185                 190

Val Arg Lys Tyr Gly Leu Ala Ser Asp Gln Val Ile Asp Ala Arg Ile
        195                 200                 205

Val Thr Val Asn Gly Glu Ile Leu Asn Lys Glu Thr Met Gly Lys Asp
210                 215                 220

Leu Tyr Trp Ala Ile Arg Gly Gly Gly Ala Asn Asn Phe Gly Val Leu
225                 230                 235                 240
```

Leu Ser Trp Lys Val Lys Leu Val Pro Val Thr Pro Ile Val Thr Val
                245                 250                 255

Ala Thr Ile Asp Arg Thr Leu Glu Gln Gly Ala Thr Asn Leu Val His
            260                 265                 270

Lys Trp Gln Phe Val Ala Asp Arg Leu His Glu Asp Val Tyr Ile Gly
        275                 280                 285

Leu Thr Met Val Thr Ala Asn Thr Ser Arg Ala Gly Glu Lys Thr Val
    290                 295                 300

Val Ala Gln Phe Ser Phe Leu Phe Gly Asn Thr Asp Arg Leu Leu
305                 310                 315                 320

Gln Ile Met Glu Glu Ser Phe Pro Glu Leu Gly Leu Lys Arg Asn Asp
                325                 330                 335

Thr Thr Glu Met Ser Trp Val Glu Ser His Val Tyr Phe Tyr Arg Arg
            340                 345                 350

Gly Gln Pro Ile Glu Phe Leu Trp Asp Arg Asp His Leu Thr Lys Ser
        355                 360                 365

Phe Leu Lys Val Lys Ser Asp Tyr Val Arg Glu Pro Ile Ser Lys Leu
    370                 375                 380

Gly Leu Glu Gly Ile Trp Lys Arg Tyr Val Gly Gly Asp Ser Pro Ala
385                 390                 395                 400

Met Leu Trp Thr Pro Phe Gly Gly Arg Met Asn Gln Ile Ser Glu Phe
                405                 410                 415

Glu Ser Pro Tyr Pro His Arg Ala Gly Asn Ile Tyr Asn Ile Met Tyr
            420                 425                 430

Val Gly Asn Trp Leu Asn Glu Asn Ser Glu Lys Gln Leu Asn Trp
        435                 440                 445

Met Arg Ser Phe Tyr Ser Tyr Met Gly Arg Tyr Val Ser Lys Asn Pro
    450                 455                 460

Arg Ser Ala Tyr Leu Asn Tyr Lys Asp Leu Asp Leu Gly Val Asn Asp
465                 470                 475                 480

Asn Asn Val Ser Glu Tyr Ile Arg Tyr Leu Lys Ala Arg Ser Trp Gly
                485                 490                 495

Arg Lys Tyr Phe Lys Asn Phe Glu Lys Leu Val Lys Val Lys Ser
            500                 505                 510

Met Val Asp Pro Asp Asn Phe Phe Lys Asn Lys Gln Ser Ile Pro Pro
    515                 520                 525

Ile Arg Ser Trp Gly Lys Glu Leu Glu Ala Ile Asn Ile Val Ile
530                 535                 540

<210> SEQ ID NO 63
<211> LENGTH: 531
<212> TYPE: PRT
<213> ORGANISM: Theopropus elegans

<400> SEQUENCE: 63

Met Tyr Thr Thr Glu Val His Lys Val Phe Ile Ser Tyr Cys Phe Leu
1               5                   10                  15

Leu Leu Leu Ser Gln Cys His Cys Leu Ile Pro Glu Ser Phe Ile Ser
            20                  25                  30

Cys Leu Ser Lys Lys Phe Pro Ser Asp Glu Pro Ile Phe Ser Val Leu
        35                  40                  45

His Asp Pro Arg Asn Ala Ser Tyr Gln Ala Val Leu Glu Ser Asn Leu
    50                  55                  60

Gln Asn Leu Arg Phe Leu Lys Ser Ala Lys Pro Leu Ala Ile Ile Thr

```
              65                  70                  75                  80
Pro Leu His Tyr Thr His Val Gln Ala Ala Val Val Cys Cys Lys Arg
                    85                  90                  95

Ala Gly Leu Gln Ile Arg Ile Arg Ser Gly Gly Ser Asp Tyr Glu Gly
                100                 105                 110

Leu Ser Tyr Arg Ser Glu Val Pro Tyr Ile Ile Leu Asp Leu Gln Asn
                115                 120                 125

Leu Arg Ser Ile Thr Val Asp Ile Glu Asp Asn Ser Ala Trp Val Glu
            130                 135                 140

Ser Gly Ala Thr Ile Gly Glu Leu Tyr Tyr Glu Ile Ala Asp Gln Ser
145                 150                 155                 160

Pro Val His Ala Phe Pro Ala Gly Val Tyr Ser Thr Val Gly Val Gly
                    165                 170                 175

Gly His Leu Ser Gly Gly Gly Phe Gly Thr Met Leu Arg Lys Tyr Gly
                180                 185                 190

Leu Ala Ala Asp Asn Ile Leu Asp Ala His Ile Val Asp Ala Glu Gly
                195                 200                 205

Arg Leu Leu Asn Arg Glu Ser Met Gly Thr Asp Leu Phe Trp Ala Ile
            210                 215                 220

Arg Gly Gly Gly Gly Ala Ser Phe Gly Val Ile Val Ala Trp Lys Val
225                 230                 235                 240

Lys Leu Val His Val Pro Pro Val Val Thr Val Phe Asp Leu Ala Lys
                    245                 250                 255

Thr Leu Glu Glu Gly Ala Ile Asp Leu Ile His Lys Trp Gln Thr Val
                260                 265                 270

Gly Pro Asn Leu Asn Glu Asp Ala Phe Leu Ala Ala Ser Ile Met Ala
            275                 280                 285

Asp Pro Ser Ser Glu Ser Lys Thr Leu Val Ala Gly Phe Phe Ser Leu
290                 295                 300

Phe Leu Gly Ile Ala Asp Gln Leu Leu Lys Glu Met Lys Glu Ser Phe
305                 310                 315                 320

Pro Glu Leu Gly Leu Arg Lys Glu Asp Cys Leu Glu Met Ser Trp Ile
                    325                 330                 335

Lys Ala Ala Leu His Phe Ser Gly Tyr Glu Pro Gly Glu Thr Val Tyr
                340                 345                 350

Ala Leu Lys Asn Arg Lys Pro Pro Gln Pro Lys Gln Cys Ile Thr Val
            355                 360                 365

Arg Ser Asp Phe Ile Gln Glu Pro Leu Ser Leu Pro Ala Leu Asp Lys
370                 375                 380

Leu Trp Lys Phe Leu Ser Glu Glu Asn Thr Pro Ile Ile Val Met
385                 390                 395                 400

Leu Pro His Gly Gly Met Met Ser Lys Ile Ser Glu Thr Glu Ile Pro
                    405                 410                 415

Tyr Pro Tyr Arg Glu Gly Val Ile Tyr Ser Phe Leu Tyr Glu Leu Asn
                420                 425                 430

Trp Asp Cys Glu Asp Asp Ser Phe Ser Glu Arg Tyr Val Ser Ala Leu
            435                 440                 445

Thr Arg Leu Tyr Asp His Met Thr Pro Tyr Val Leu Lys His Pro Arg
450                 455                 460

Gly Gly Phe Leu Asn Met Arg Cys Leu Glu Ile Gly Lys Asn Asp Asp
465                 470                 475                 480

Tyr Gly Thr Thr Tyr Ser Lys Ala Lys Glu Trp Gly Leu Lys Tyr Phe
                    485                 490                 495
```

```
Lys Asn Asn Phe Lys Arg Leu Ala Ile Thr Lys Gly Ala Val Asp Pro
            500                 505                 510

Asp Asn Phe Phe Tyr Phe Glu Gln Ser Ile Pro Pro Leu Ala Ser Lys
            515                 520                 525

Asp Glu Leu
    530

<210> SEQ ID NO 64
<211> LENGTH: 530
<212> TYPE: PRT
<213> ORGANISM: Vinca minor

<400> SEQUENCE: 64

Met Phe Thr Leu Ile Ser Lys Val His Pro Leu Phe Phe Leu Ile
1               5                   10                  15

Leu Leu Ser Leu Ser Ser Ser Lys Ala Ser Ile Pro Glu Pro Phe
                20                  25                  30

Phe Asn Cys Ile Ser Asn Lys Phe Pro Ser Asp Ile Leu His Glu Pro
            35                  40                  45

Thr Asn Ser Ser Tyr Asp Ser Val Leu Lys Ser Thr Ile His Asn Leu
 50                  55                  60

Arg Phe Leu Asn Ser Pro Lys Pro Leu Ala Ile Ile Thr Pro Phe Leu
 65                  70                  75                  80

Tyr Ser His Val Gln Ala Ala Val Ile Cys Thr Lys Arg Val Gly Leu
                85                  90                  95

Gln Leu Arg Ile Arg Ser Gly Gly Ser Asp Tyr Glu Gly Leu Ser Tyr
            100                 105                 110

Arg Ser Glu Val Pro Phe Val Leu Leu Asp Leu Gln Asn Leu Arg Ser
            115                 120                 125

Ile Asn Val Asp Ile Glu Asp Asn Ser Ala Trp Val Glu Ser Gly Ala
            130                 135                 140

Thr Ile Gly Glu Leu Tyr Tyr Glu Ile Ala Glu Lys Ser Pro Val His
145                 150                 155                 160

Gly Phe Pro Ala Gly Val Tyr Ala Thr Val Gly Val Gly Gly His Phe
                165                 170                 175

Ser Gly Gly Gly Phe Gly Thr Met Met Arg Lys His Gly Leu Ala Ser
            180                 185                 190

Asp Asn Ile Ile Asn Ala Lys Ile Val Asp Val Arg Gly Arg Ile Leu
            195                 200                 205

Asp Arg Lys Ser Met Gly Glu Asp Leu Phe Trp Ala Ile Arg Gly Gly
210                 215                 220

Gly Gly Ala Ser Phe Gly Val Ile Val Ala Trp Lys Val Lys Leu Val
225                 230                 235                 240

His Val Pro Pro Met Val Thr Val Phe Asp Leu Ser Lys Thr Phe Glu
                245                 250                 255

Glu Glu Ala Leu Gln Leu Leu Asn Lys Trp Gln Tyr Ile Ile Glu His
            260                 265                 270

Lys Leu Pro Glu Asp Leu Phe Leu Ala Val Ser Ile Met Ala Ile Pro
            275                 280                 285

Leu Pro Asn Gly Asn Lys Thr Leu Met Ala Gly Phe Thr Ser Leu Phe
            290                 295                 300

Leu Gly Asn Ser Asp His Leu Leu Lys Ile Ile Glu Glu Asn Phe Pro
305                 310                 315                 320

Asp Leu Gly Leu Thr Lys Glu His Cys Ser Glu Met Ser Trp Ile Glu
```

```
            325                 330                 335
Ser Val Met His Phe Ser Gly Phe Pro Arg Gly Glu Leu Arg Asp Ser
        340                 345                 350

Leu Lys Asn Arg Ile Ser Pro Leu Pro Arg Thr Cys Ile Ser Thr Thr
        355                 360                 365

Ser Asp Phe Ile Gln Glu Pro Leu Ser Leu Asn Gly Leu Glu Lys Leu
        370                 375                 380

Trp Asn Ile Cys Thr Asp Glu Asn Thr Pro Ile Ile Leu Leu Phe
385                 390                 395                 400

Pro His Gly Gly Ile Met Asn Lys Ile Ser Glu Ser Glu Thr Pro Phe
                405                 410                 415

Pro Tyr Arg Lys Gly Val Ile Tyr Ser Ile Ile Tyr Glu Val Val Trp
                420                 425                 430

Asp Cys Thr Asn Asp Glu Ser Ser Lys Glu Tyr Ile Asp Gly Leu Arg
                435                 440                 445

Arg Met Lys Lys Leu Met Thr Pro Tyr Val Met Lys Gln Pro Arg Gly
                450                 455                 460

Ala Phe Phe Asn Thr Arg Asn Leu Asp Ile Gly Lys Asn Gly Gly Pro
465                 470                 475                 480

Asp Thr Thr Tyr Trp Glu Ala Lys Asp Trp Gly Leu Lys Tyr Phe Lys
                485                 490                 495

Asp Asn Phe Arg Arg Leu Ala Ile Ile Lys Gly Glu Val Asp Leu Glu
                500                 505                 510

Asn Phe Phe Tyr Tyr Glu Gln Ser Ile Pro Pro Leu Ile Ser Gln Asp
                515                 520                 525

Glu Leu
    530

<210> SEQ ID NO 65
<211> LENGTH: 529
<212> TYPE: PRT
<213> ORGANISM: Catharanthus longifolius

<400> SEQUENCE: 65

Met Leu Lys Lys Val Pro Ile Val Leu Ser Ile Phe Cys Phe Leu Leu
1               5                   10                  15

Leu Leu Ser Ser Ser His Gly Ser Ile Pro Glu Ala Phe Leu Asn Cys
                20                  25                  30

Ile Ser Asn Lys Phe Ser Leu Asp Val Ser Ile Leu Asn Ile Leu His
            35                  40                  45

Val Pro Ser Asn Ser Ser Tyr Asp Ser Val Leu Lys Ser Thr Ile Gln
        50                  55                  60

Asn Pro Arg Phe Leu Lys Ser Pro Lys Pro Leu Ala Ile Ile Thr Pro
65                  70                  75                  80

Val Leu His Ser His Val Gln Ser Ala Val Ile Cys Thr Lys Gln Ala
                85                  90                  95

Gly Leu Gln Ile Arg Ile Arg Ser Gly Gly Ala Asp Tyr Glu Gly Leu
                100                 105                 110

Ser Tyr Arg Ser Glu Val Pro Phe Ile Leu Leu Asp Leu Gln Asn Leu
                115                 120                 125

Arg Ser Ile Ser Val Asp Ile Glu Asp Asn Ser Ala Trp Val Glu Ser
            130                 135                 140

Gly Ala Thr Ile Gly Glu Phe Tyr His Glu Ile Ala Gln Asn Ser Pro
145                 150                 155                 160
```

```
Val His Ala Phe Pro Ala Gly Val Ser Ser Val Gly Ile Gly Gly
            165                 170                 175

His Leu Ser Ser Gly Gly Phe Gly Thr Leu Leu Arg Lys Tyr Gly Leu
            180                 185                 190

Ala Ala Asp Asn Ile Ile Asp Ala Lys Ile Val Asp Ala Arg Gly Arg
            195                 200                 205

Ile Leu Asp Arg Glu Ser Met Gly Glu Asp Leu Phe Trp Ala Ile Arg
        210                 215                 220

Gly Gly Gly Gly Ala Ser Phe Gly Val Ile Val Ser Trp Lys Val Lys
225                 230                 235                 240

Leu Val Lys Val Pro Pro Met Val Thr Val Phe Ile Leu Ser Lys Thr
                245                 250                 255

Tyr Glu Glu Gly Gly Leu Asp Leu Leu His Lys Trp Gln Tyr Ile Glu
            260                 265                 270

His Lys Leu Pro Glu Asp Leu Phe Leu Ala Val Ser Ile Met Asp Asp
            275                 280                 285

Ser Ser Ser Gly Asn Lys Thr Leu Met Ala Gly Phe Met Ser Leu Phe
        290                 295                 300

Leu Gly Lys Thr Glu Asp Leu Leu Lys Val Met Ala Glu Asn Phe Pro
305                 310                 315                 320

Gln Leu Gly Leu Lys Lys Glu Asp Cys Leu Glu Met Asn Trp Ile Asp
                325                 330                 335

Ala Ala Met Tyr Phe Ser Gly His Pro Ile Gly Glu Ser Arg Ser Val
            340                 345                 350

Leu Lys Asn Arg Glu Ser His Leu Pro Lys Thr Cys Val Ser Ile Lys
        355                 360                 365

Ser Asp Phe Ile Gln Glu Pro Gln Ser Met Asp Ala Met Glu Lys Leu
370                 375                 380

Trp Lys Phe Cys Arg Glu Glu Glu Asn Ser Pro Ile Ile Leu Met Leu
385                 390                 395                 400

Pro Leu Gly Gly Met Met Ser Lys Ile Ser Ser Glu Ile Pro Phe
                405                 410                 415

Pro Tyr Arg Lys Asp Val Ile Tyr Ser Met Ile Tyr Glu Ile Leu Trp
            420                 425                 430

Asn Cys Glu Asp Asp Glu Ser Ser Glu Glu Tyr Ile Asp Gly Leu Gly
        435                 440                 445

Arg Leu Glu Glu Leu Met Thr Pro Tyr Val Lys Gln Pro Arg Gly Ser
450                 455                 460

Trp Phe Ser Thr Arg Asn Leu Tyr Thr Gly Lys Asn Lys Gly Pro Gly
465                 470                 475                 480

Thr Thr Tyr Ser Lys Ala Lys Glu Trp Gly Phe Arg Tyr Phe Asn Asn
                485                 490                 495

Asn Phe Lys Lys Leu Ala Val Ile Lys Gly Gln Val Asp Pro Glu Asn
            500                 505                 510

Phe Phe Tyr Tyr Glu Gln Ser Ile Pro Pro Leu His Leu Gln Gly Glu
        515                 520                 525

Leu

<210> SEQ ID NO 66
<211> LENGTH: 366
<212> TYPE: PRT
<213> ORGANISM: Catharanthus roseus

<400> SEQUENCE: 66
```

```
Met Ala Arg Lys Ser Pro Glu Asp Glu His Pro Val Lys Ala Tyr Gly
1               5                   10                  15

Trp Ala Val Lys Asp Gly Thr Thr Gly Ile Leu Ser Pro Phe Lys Phe
            20                  25                  30

Ser Ile Arg Ala Thr Gly Asp Asn Asp Val Arg Ile Lys Ile Leu Tyr
        35                  40                  45

Cys Gly Val Cys Arg Thr Asp Leu Ala Ala Thr Lys Asn Ala Phe Gly
50                  55                  60

Phe Leu Ser Tyr Pro Leu Val Pro Gly Ser Arg Glu Ile Val Gly Ile
65                  70                  75                  80

Val Ser Glu Ile Gly Lys Asn Val Lys Lys Val Lys Val Gly Glu Lys
                85                  90                  95

Val Gly Val Ala Pro His Val Gly Ser Cys Gly Lys Cys Lys Ser Cys
            100                 105                 110

Val Asn Glu Val Glu Asn Phe Cys Pro Lys Leu Ile Ile Pro Tyr Gly
        115                 120                 125

Thr Pro Tyr His Asp Gly Thr Ile Cys Tyr Gly Phe Ser Asn Glu
    130                 135                 140

Thr Val Arg Asp Glu Arg Phe Val Phe Arg Phe Pro Glu Asn Leu Ser
145                 150                 155                 160

Leu Pro Gly Gly Ala Pro Leu Val Ser Ala Gly Val Thr Thr Tyr Gly
                165                 170                 175

Ala Leu Arg Asn Asn Gly Leu Asp Lys Pro Gly Leu His Val Gly Val
            180                 185                 190

Val Gly Leu Gly Gly Leu Gly His Leu Ala Val Lys Phe Ala Lys Ala
        195                 200                 205

Leu Gly Val Lys Val Thr Val Ile Ser Thr Asn Pro Ser Lys Glu His
    210                 215                 220

Asp Ala Ile Asn Gly Phe Gly Ala Asp Ala Phe Ile Leu Thr His His
225                 230                 235                 240

Glu Glu Gln Met Lys Ala Ala Met Gly Thr Leu Asp Gly Ile Leu Tyr
                245                 250                 255

Thr Val Pro Val Val His Ala Ile Ala Pro Leu Leu Ser Leu Leu Gly
            260                 265                 270

Ser Gln Gly Lys Phe Val Leu Ile Gly Ala Pro Ser Gln Leu Leu Glu
    275                 280                 285

Val Pro Pro Ile Gln Leu Leu Phe Gly Gly Lys Ser Ile Ile Gly Ser
290                 295                 300

Ala Ala Gly Asn Val Lys Gln Ile Gln Glu Met Leu Glu Phe Ala Ala
305                 310                 315                 320

Lys His Asp Ile Ile Ala Asn Val Glu Ile Ile Gln Met Asp Tyr Ile
            325                 330                 335

Asn Thr Ala Met Glu Arg Leu Asp Lys Gly Asp Val Arg Tyr Arg Phe
        340                 345                 350

Val Ile Asp Ile Glu Asn Ser Leu Thr Leu Pro Ser Glu Val
    355                 360                 365
```

<210> SEQ ID NO 67
<211> LENGTH: 1098
<212> TYPE: DNA
<213> ORGANISM: Catharanthus roseus

<400> SEQUENCE: 67
atggccagaa aatcaccaga agatgaacat cccgtgaagg cttacggatg ggccgtcaaa        60

```
gatggaacaa ctggaattct ttctcccttc aaattttcca taagggcaac aggtgataat    120
gatgttcgaa tcaagatcct ctattgtgga gtttgtcgta ccgatcttgc ggcaaccaag    180
aacgcattcg ggtttctttc ttatcctctt gtgcctggta gagagatcgt gggaatagtg    240
agcgagatag ggaaaaatgt gaaaaaagtt aaagttggag aaaaagttgg agtagcccccg   300 catgtgggta gctgtggcaa atgcaagagt tgtgtgaatg aggtggagaa tttctgtccg    360
aaactgatca tcccttatgg cacccccatac cacgatggta ctatttgcta cggtggtttc    420
tccaacgaga ctgtcagaga tgaacgcttt gtttttcgtt ttcctgaaaa tctttcgctg    480
cctggcggag ctcccttggt tagtgctggg gttaccacgt acggtgcatt gagaaataat    540
ggcctcgaca agcccggatt acacgtggga gtcgtcggtc taggtggact aggtcatctg    600
gctgttaaat ttgctaaggc tttaggcgtc aaagtaactg ttattagtac caatcctagc    660
aaggagcatg atgctataaa tggtttcggt gctgatgcct tcatcctcac ccaccatgag    720
gaacaaatga aggctgccat gggaacttta gatggaattc tttatacagt gcctgttgtt    780
catgccattg caccattact tagtctactg ggaagtcaag ggaaatttgt gttgattggg    840
gcaccatctc aattacttga ggtgccacct attcaattat tatttggtgg aaaatctatt    900
attggaagtg cggctggaaa tgtgaagcaa atccaagaaa tgcttgaatt tgcagcaaaa    960
catgatataa ttgcgaatgt tgagattatc caaatggatt atataaatac tgcaatggaa   1020
cgtctagaca aaggtgatgt tagatatcga tttgtaattg atatcgaaaa ctctctcact   1080
cttccatcag aggtgtga                                                 1098
```

METHOD AND MEANS FOR MANUFACTURING TERPENE INDOLE ALKALOIDS

FIELD OF THE INVENTION

The invention relates to methods and products for producing terpene indole alkaloid derivatives.

INCORPORATION BY REFERENCE OF SEQUENCE LISTING

The Sequence Listing in the ASCII text file, named as 38825.SubSequenceListing of 68 KB, created on Aug. 9, 2021 and submitted to the United States Patent and Trademark Office via EFS-Web, is incorporated herein by reference.

BACKGROUND OF THE INVENTION

Vinblastine, a potent anticancer drug, is produced by Madagascar periwinkle (*Catharanthus roseus*) in small quantities. Heterologous reconstitution of vinblastine biosynthesis could greatly improve access to this drug. The complex chemistry underlying the extensive transformations observed in vinblastine synthesis makes identification of the biosynthetic genes challenging.

With reference to Scheme 1 (below), the biosynthesis of vincristine 5 and vinblastine 6, plant-derived anticancer drugs, has been studied for decades, but the genes that comprise this metabolic pathway have remained elusive. Specifically, it is unknown how the biosynthetic intermediate stemmadenine 1 is transformed into tabersonine 2 and catharanthine 3, the two scaffolds that are ultimately dimerized to yield vinblastine and vincristine (Scheme 1A). These chemical transformations are poorly understood, making it exceptionally challenging to identify the corresponding biosynthetic enzymes.

WO 2017/152273 and the related paper Qu et al. (2018, "Solution of the multistep pathway for assembly of corynanthean, strychnos, iboga, and aspidosperma monoterpenoid indole alkaloids from 19E-geissoschizine", PNAS pH: 201719979) describe the enzymes which we refer to herein as Tabersonine Synthase ("TS") and Catharanthine Synthase ("CS") involved in the terpenoid indole alkaloid biochemical pathway. However, the substrates of the CS and TS enzymes were not identified in those reports and the catalytic functions of CS and TS remain cryptic.

Scheme 1. Vincristine and vinblastine biosynthesis.

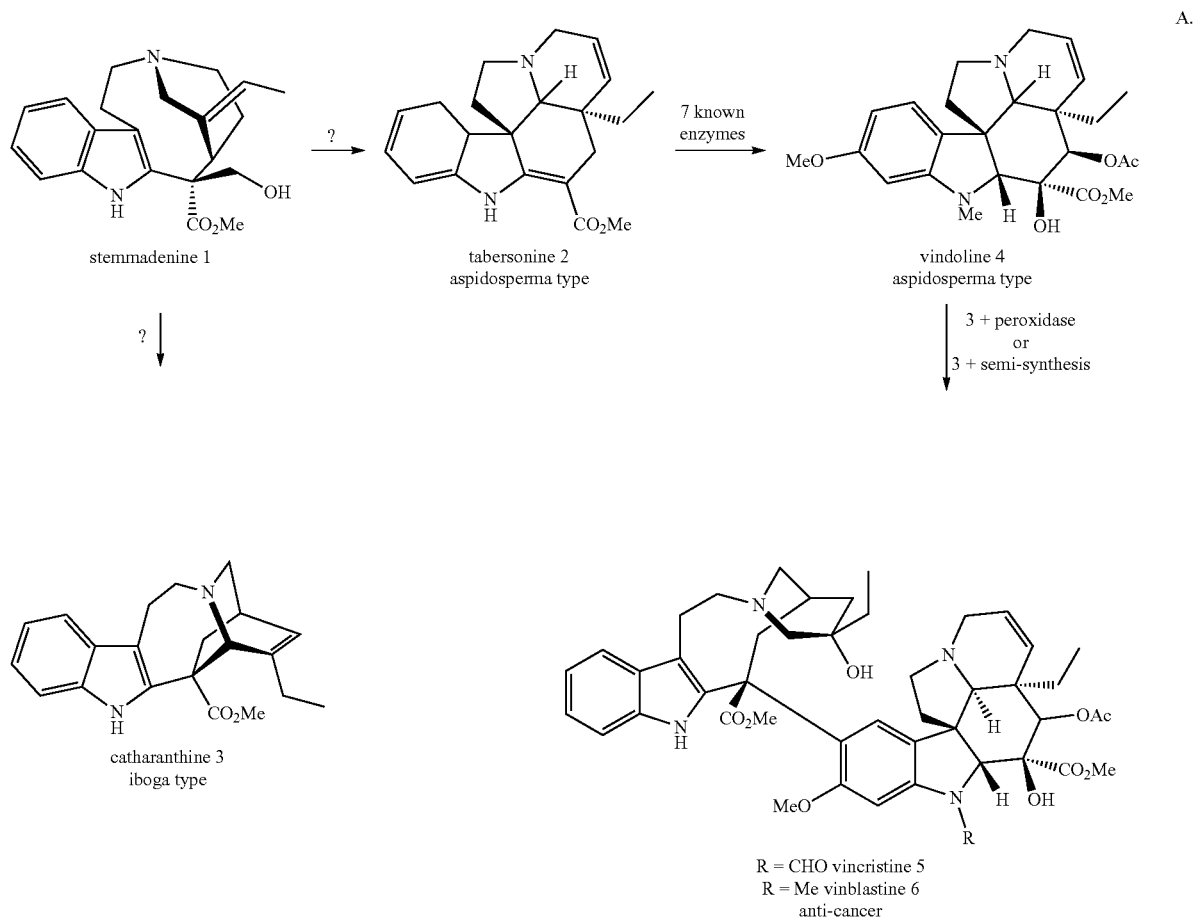

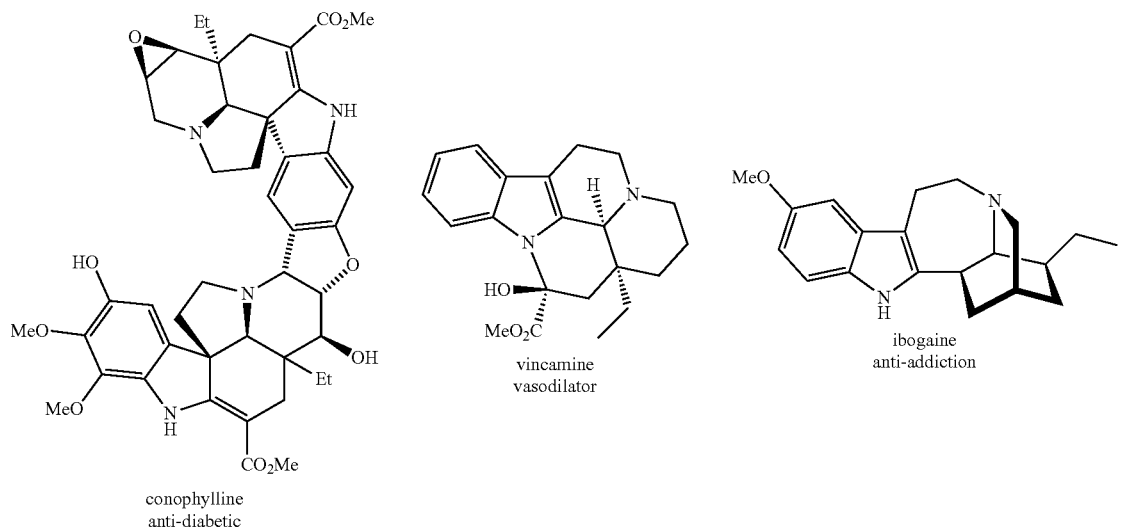

conophylline
anti-diabetic vincamine
vasodilator ibogaine
anti-addiction

A. Vincristine 5 and vinblastine 6 are formed by dimerization from the monomers catharanthine 3 and vindoline 4. Catharanthine 3 and vindoline 4 can be dimerized by a peroxidase or using chemical methods. The biosynthetic genes that convret tabersonine 2 to vindoline 4 have been identified, but the biosynthesis of tabersonine 2 and catharanthine 3 from stemmadenine 1 is ascertained in this study. B. Representative additional bioactive Aspidosperma and iboga alkaloids.

Qureshi & Scott (1968; Chemical Communications 16: 948-950) suggests a pathway for alkaloid biosynthesis in *V. rosea* seeds. Stavrinides et al. (2016; Nature Communications 7: 12116) describes 3 heteroyohimbine synthases isolated from *C. roseus*.

SUMMARY OF THE INVENTION

In a first aspect the invention relates to a method for producing a terpene indole alkaloid derivative, comprising the steps of:
(1) providing a terpene indole alkaloid;
(2) providing:
  (a) a first enzyme (also referred to herein as "Precondylocarpine Acetate Synthase", or its acronym "PAS") having a first amino acid sequence comprising SEQ ID NO: 1 or a functional variant or homologue thereof; and/or
  (b) a second enzyme (also referred to herein as "Dehydroprecondylocarpine Acetate Synthase", or its acronym "DPAS") having a second amino acid sequence comprising SEQ ID NO: 2 or SEQ ID NO: 66, or a functional variant or homologue thereof;
(3) optionally also providing:
  (c) a third enzyme (also referred to herein as "CS") having an amino acid sequence comprising SEQ ID NO: 3 or a functional variant or homologue thereof; and/or
  (d) a fourth enzyme (also referred to herein as "TS") comprising an amino acid sequence comprising SEQ ID NO: 4 or a functional variant or homologue thereof; and
(4) contacting the terpene indole alkaloid with the first and/or second enzyme, and optionally also the third and/or fourth enzyme, under catalytic conditions to produce a terpene indole alkaloid derivative.

Qureshi & Scott (1968; supra) suggests a pathway for alkaloid biosynthesis in *V. rosea* seeds and Stavrinides et al. (2016; supra) describes 3 heteroyohimbine synthases isolated from *C. roseus*. However, the prior art does not describe the actual enzymes involved in the processes of producing a terpene indole alkaloid derivative. The invention is based on the identification of missing steps in vinblastine biosynthesis, namely the identification of an oxidase and reductase that isomerize stemmadenine acetate into dihydroprecondylocarpine acetate, which is then deacetoxylated and cyclized to either catharanthine or tabersonine via two distinct hydrolases. These enzymes provide insight into how plants create extensive chemical diversity and enable development of heterologous platforms for generation of many stemmadenine-derived bioactive compounds.

The inventors have identified two redox enzymes that convert stemmadenine acetate 7 into an unstable molecule, which although not isolatable, is most likely dihydroprecondylocarpine acetate 11 (see Scheme 2). Dihydroprecondylocarpine acetate 11 acts as the substrate for two distinct hydrolases reported here that deacetoxylate this substrate and then catalyze one of two possible formal Diets-Alder cyclizations to either tabersonine 2 or catharanthine 3. Notably, the catharanthine 3 scaffold can form spontaneously from substrate 11 under certain conditions, while formation of tabersonine 2 appears to be strictly dependent on enzymatic catalysis. Particularly, the biochemistry required for tabersonine 2 and catharanthine 3 formation from the known alkaloid intermediate stemmadenine 1 is disclosed.

The biochemistry required for tabersonine 2 and catharanthine 3 formation from the known alkaloid intermediate stemmadenine 1 is disclosed. The identification of these enzymes provides insight into the mechanisms that plants use to create extensive chemical diversity. Moreover, in addition to serving as the precursors for vincristine 5 and vinblastine 6, tabersonine 2 and catharanthine 3 are also precursors for dozens of other biologically active alkaloids (Scheme 1 B). Therefore, the discovery of these enzymes and their function enables heterologous production of vincristine 5, vinblastine 6, and many other rare, high value alkaloids (Scheme 1 B).

Scheme 2.
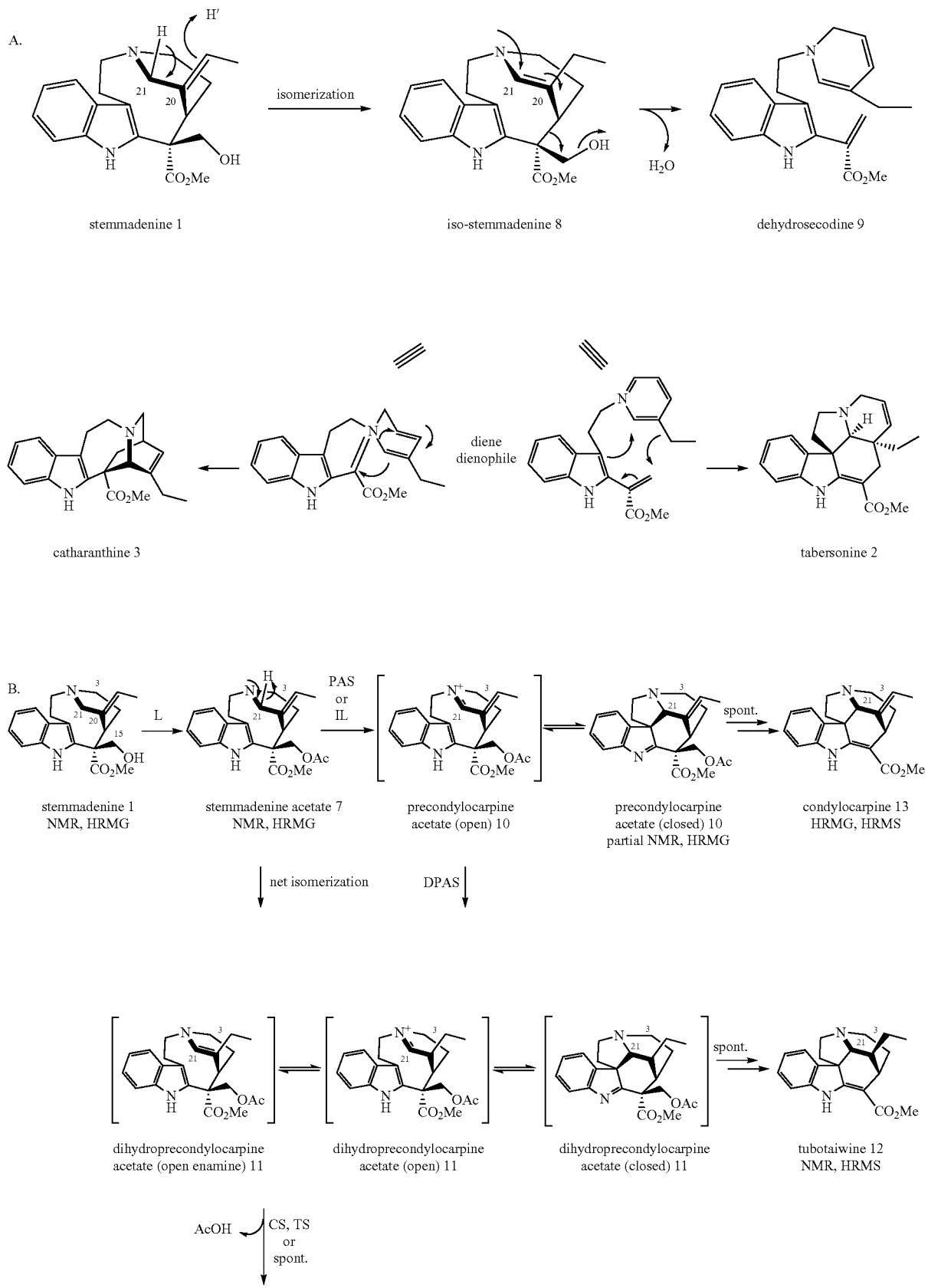

-continued

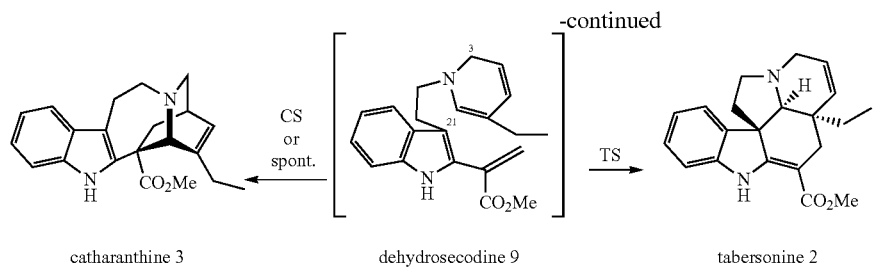

catharanthine 3          dehydrosecodine 9          tabersonine 2

Biosynthesis of catharanthine and tabersonine scaffolds. A. Initial hypothesis. Stemmadenine 1 undegoes a push-pull isomerization to generate a double bond at C20-21 (iso-stemmadenine 8). Collapse of the enamine and dehydration yields dehydrosecodine 9, which can then cyclize, possibly via a Diels-Alder reaction, to form either catharanthine 3 or tabersonine 2. B. Revised hypothesis. Stemmadenine acetate 7 (generated from stemmadenine 1 using conditions i. (Ac$_2$O (excess) pyridine (excess) r.t., 4 h, >99%) undergoes an oxidation to form precondylocarpine acetate 10. This is catalyzed enzymatically by the reticuline oxidase homologue PAS, or alternatively can be generated synthetically using conditions as reported by Scott and co-workers (Scott & Wei, 1972, J. Am. Chem. Soc. 94: 8264-8265) ii. (Pt (from 7.5 eq. PtO$_2$), EtOAc, O$_2$ atm., r.t., 10 h, yields varied). Next, precondylocarpine acetate 10 is reduced by the alcohol dehydrogenase DPAS. This reduced intermediate could not be isolated due to its lability, but it is assumed to be dihydroprecondylocarpine acetate 11 based on the degradation product tubotaiwine 12. Dihydroprecondylocarpine acetate 11, in the open form, can form dehydrosecodine 9 either through the action of CS, TS or spontaneously. CS controls the cyclization to form catharanthine 3, while TS controls the cyclization to form tabersonine 2. Catharathine 3 can also form spontaneously.

Co-expression analysis for biosynthetic gene candidates. A. Expression profile of some of the genes involved in *C. roseus* MIA pathway and those investigated in this study. Data were extracted from the http://medicinalplantgenomics.msu.edu/index.shtml database. B. Snapshot of the RNA seq dataset showing the presence of several genes annotated as acetyl-transferases. C. Co-expression profile of TS and PAS. The FPKM values for PAS were multiplied by a factor 10 in order to be comparable to those of TS. TDC=Tryptophan decarboxylase; 8HGO=Geraniol 8-hydroxylase; CrISY=Iridoid synthase; SLS=Secologanin synthase; STR=Strictosidine synthase; SGD=Strictosidine-O-beta-D-glucosidase; PAS=Precondylocarpine acetate synthase; DPAS=Dehydroprecondylocarpine acetate synthase; TS=Tabersonine synthase. TS was initially annotated in the transcriptome dataset as 2-hydroxyisoflavanone dehydratase.

Figure 2D:
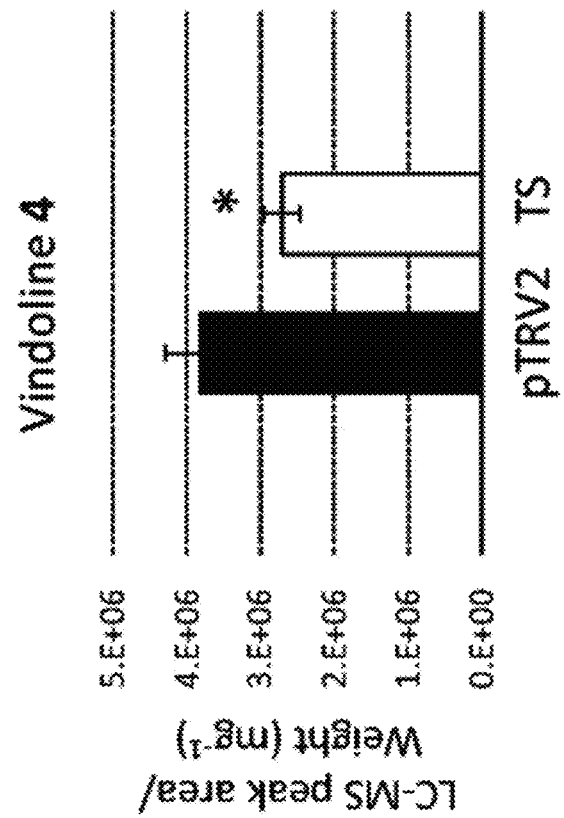
Figure 2E:
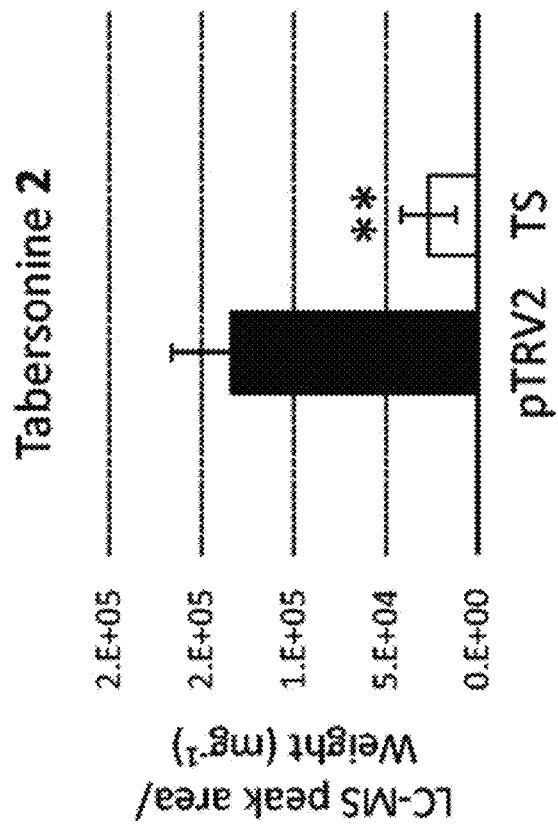

FIG. 2. Virus-induced gene silencing of TS in *C. roseus* using a unique region of the gene.

Virus-induced gene silencing of TS in *C. roseus* using a unique region of the gene. A. Fragment (grey box) of TS cDNA used to assemble the pTRV2 construct. The black box represents the coding region, whereas the black lines are the flanking untranslated reaions. Arrows show the annealing sites of the primers used for qRT-PCR analysis (Table 1). B. Fold transcript change in TS silenced (pTRV2-TS) plants compared to TS control (pTRV2) plants. Values were calculated using $2^{-\Delta\Delta Ct}$. Upper panel calculated using the EXP reference gene. Lower panel calculated using the N2227 reference gene. C. Box plots of ΔCt values of 8 biological replicates for control (pTRV2) and CrTS silenced (pTRV2-TS) plants with median, min and max values indicated. Asterisks represent significant differences determined using an unpaired, two-tailed t test (****=p<0.0001). Upper panel calculated using the EXP reference gene. Lower panel calculated using the N2227 reference gene. D. UPLC-MS analysis of TS silenced leaves showed a significant decrease of tabersonine and vindoline E. Data shown corresponds to average measurements of 12 plants. Error bars indicate standard error of the mean. Statistical significance calculated with Student's t test (pTRV2 in comparison to pTRV2-TS) is indicated as followed: *=p<0.05 and **=p<0.005.

FIG. 3. Virus-induced gene silencing of CS in *C. roseus* using a unique region of the gene.

Virus-induced gene silencing of CS in *C. roseus* using a unique region of the gene. A. Fragment (grey box) of CS cDNA used to assemble the pTRV2 construct. The black box represents the coding region, whereas the black lines are the flanking untranslated reaions. Arrows show the annealing sites of the primers used for qRT-PCR analysis (see Table 1). B. Fold transcript change in CS silenced (pTRV2-CS) plants compared to CS control (pTRV2) plants. Values were calculated using $2^{-\Delta\Delta Ct}$. Upper panel calculated using the EXP reference aene Lower panel calculated using the N2227 reference gene. C. Box plots of ΔCt values of 8 biological replicates for control (pTRV2) and CS silenced (pTRV2-CS) plants with median, min and max values indicated. Asterisks represent significant differences determined using an unpaired, two-tailed t-test (*=p<0.05). Upper panel calculated using the EXP reference gene. Lower panel calculated using the N2227 reference gene. D. UPLC-MS analysis of CS silenced leaves showed a significant decrease of catharanthine and increase of vindoline (E). Data shown corresponds to average measurements of 12 plants. Error bars indicate standard error of the mean. Statistical significance calculated with Student's t test (pTRV2 in comparison to pTRV2-CS) is indicated as followed: *=p<0.05.

FIG. 4. SDS-PAGE and proteomics analysis of the proteins used in in vitro activity assays.

SDS-PAGE and proteomics were used to analyze the proteins purified for in vitro activity assays. A. SDS-PAGE of DPAS, CS and TS expressed in *E. coli* and purified by His-trap and gel-filtration. Lane 1: protein molecular markers; lane 2: DPAS; lane 3: CS; lane 4: TS. B. Snapshot of the proteomics results (complete analysis can be found in dataset jic002601) of NiNTA-purified PAS, DPAS and CS or PAS, DPAS and TS (pathway reconstitution in *N. benthamiana*) expressed in *N. benthamiana* leaves. C. SDS-PAGE of PAS expressed in *P. pastoris*. Lanes indicated with 5 were loaded with PAS enriched medium; lane 6: protein molecular markers. The box indicates the section of the gel that was excised and used for proteomics analysis. D. Snapshot of the proteomics results (complete analysis can be found in dataset jic002561) showing that PAS was indeed present in the sample and it was amongst the most abundant proteins.

FIG. 5. NMR spectra for stemmadenine 1.

NMR spectra for stemmadenine 1 (MeOD, 300 K, 400 MHz) A. Skeletal formula of sternmadenine. B. Proton: 64 scans; C. COSY: 32 scans, D. NOESY: 32 scans; E. Carbon; F. HSQC: 32 scans; G. HMBC: 32 scans.

FIG. 6. NMR spectra for stemmadenine acetate 7.

NMR spectra for stemmadenine acetate 7 (MeOD, 300 K, 400 MHz). A. Skeletal formula of stemmadenine acetate B. Proton: 16 scans; C. COSY: 4 scans; D. TOCSY: 4 scans; E. NOESY: 4 scans; F. Carbon: 4096 scans; G. HSQC: 4 scans; H. HMBC: 8 scans.

Figure 7A:
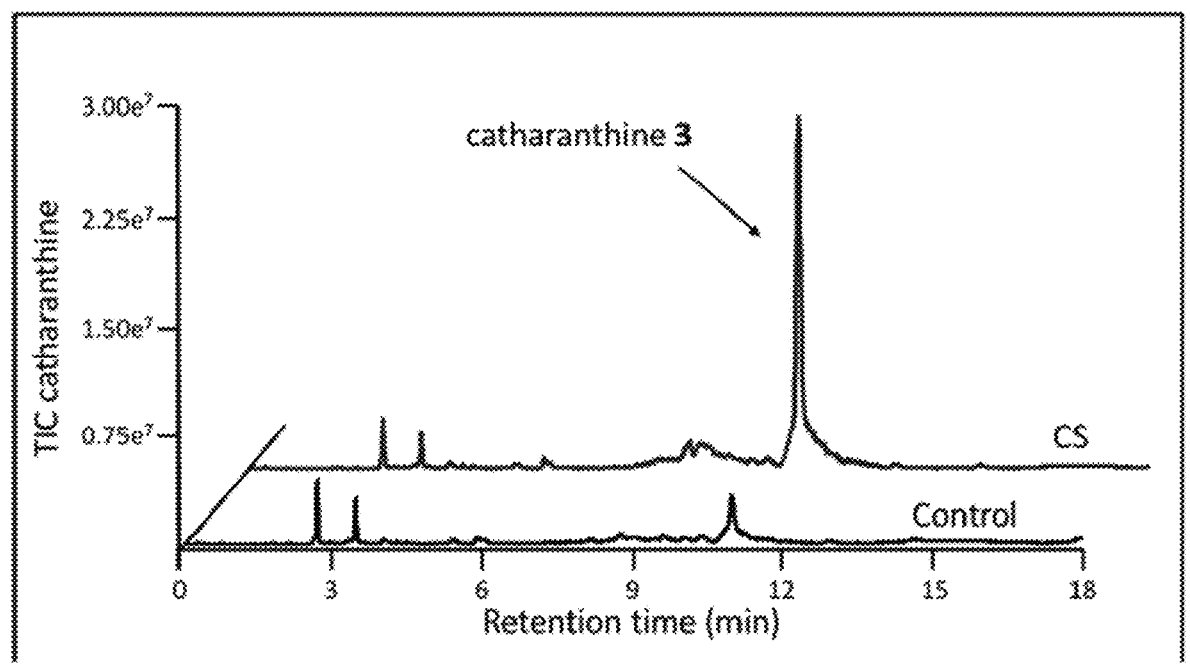
Figure 7B:
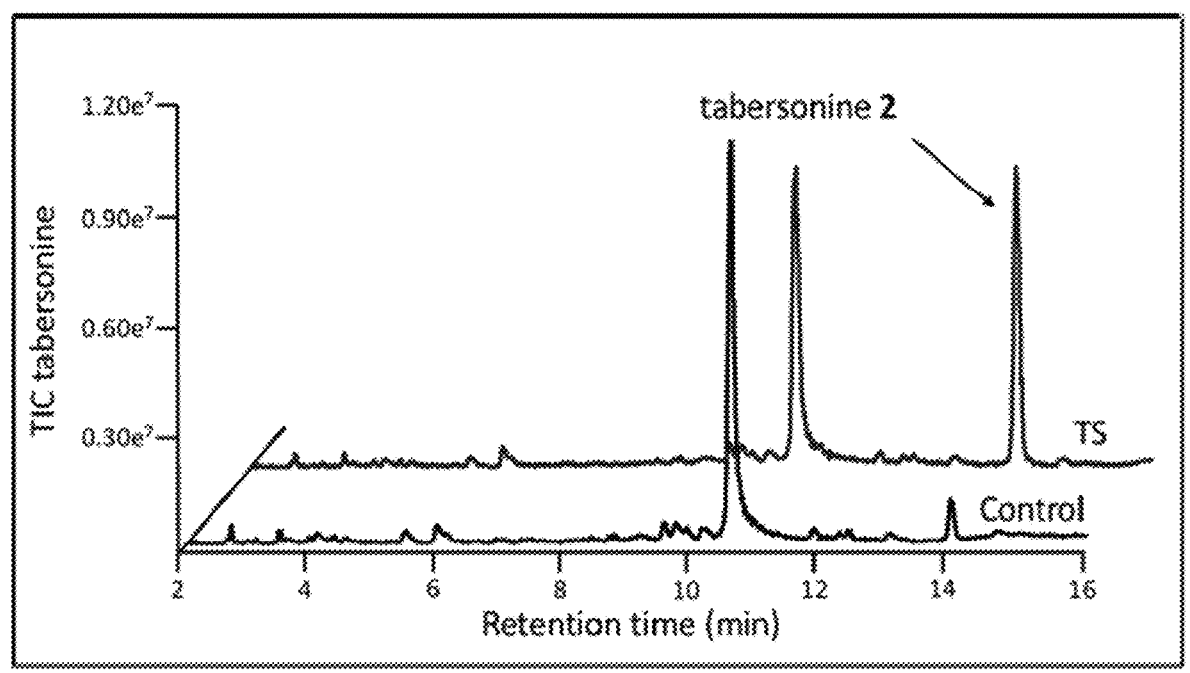
Figure 8A:
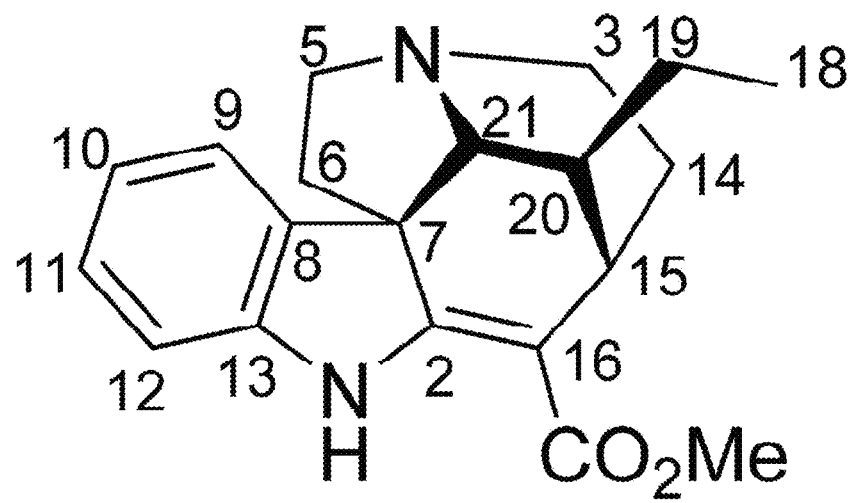
Figure 8B:
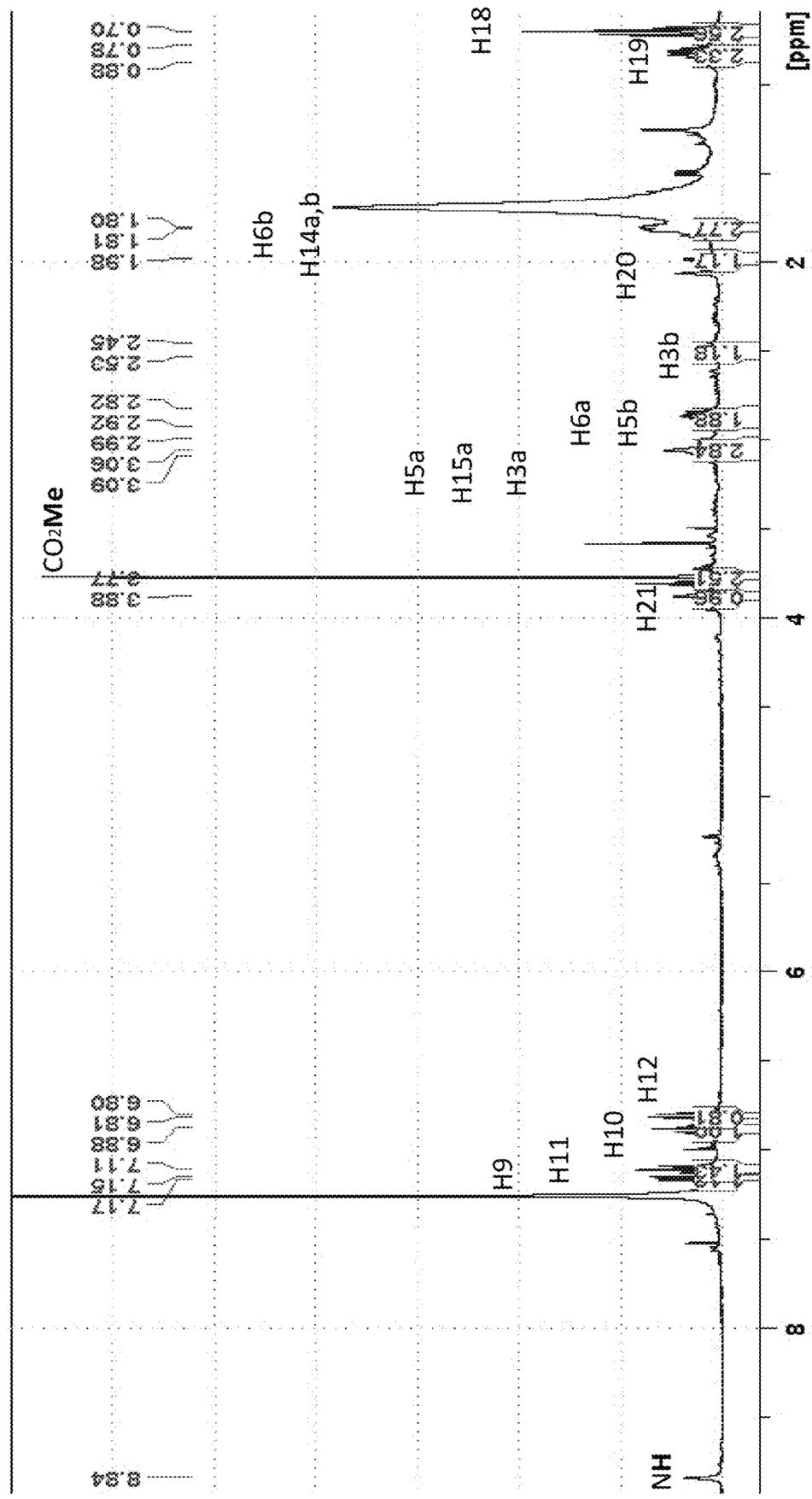
Figure 8D:
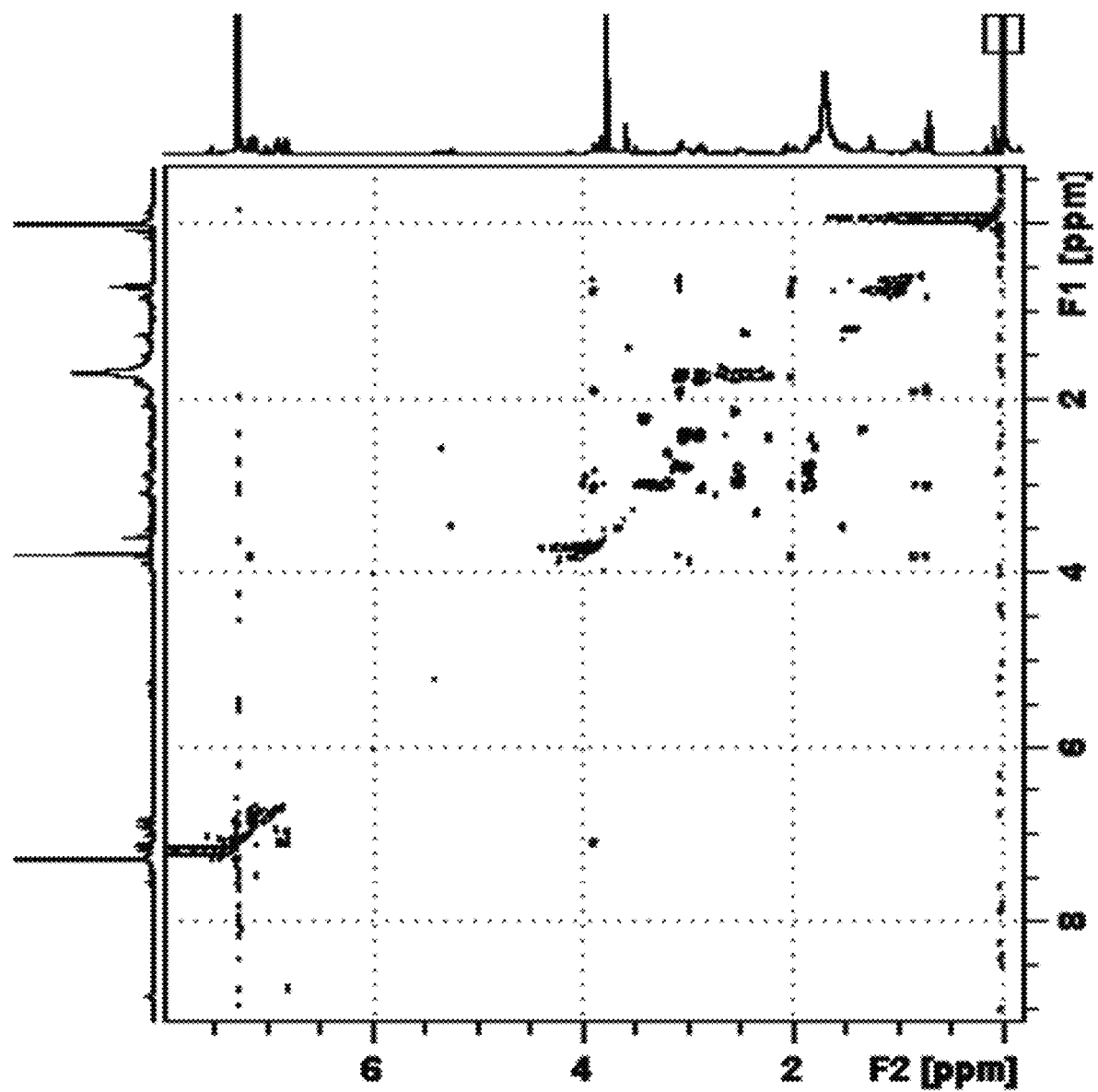
Figure 8E:
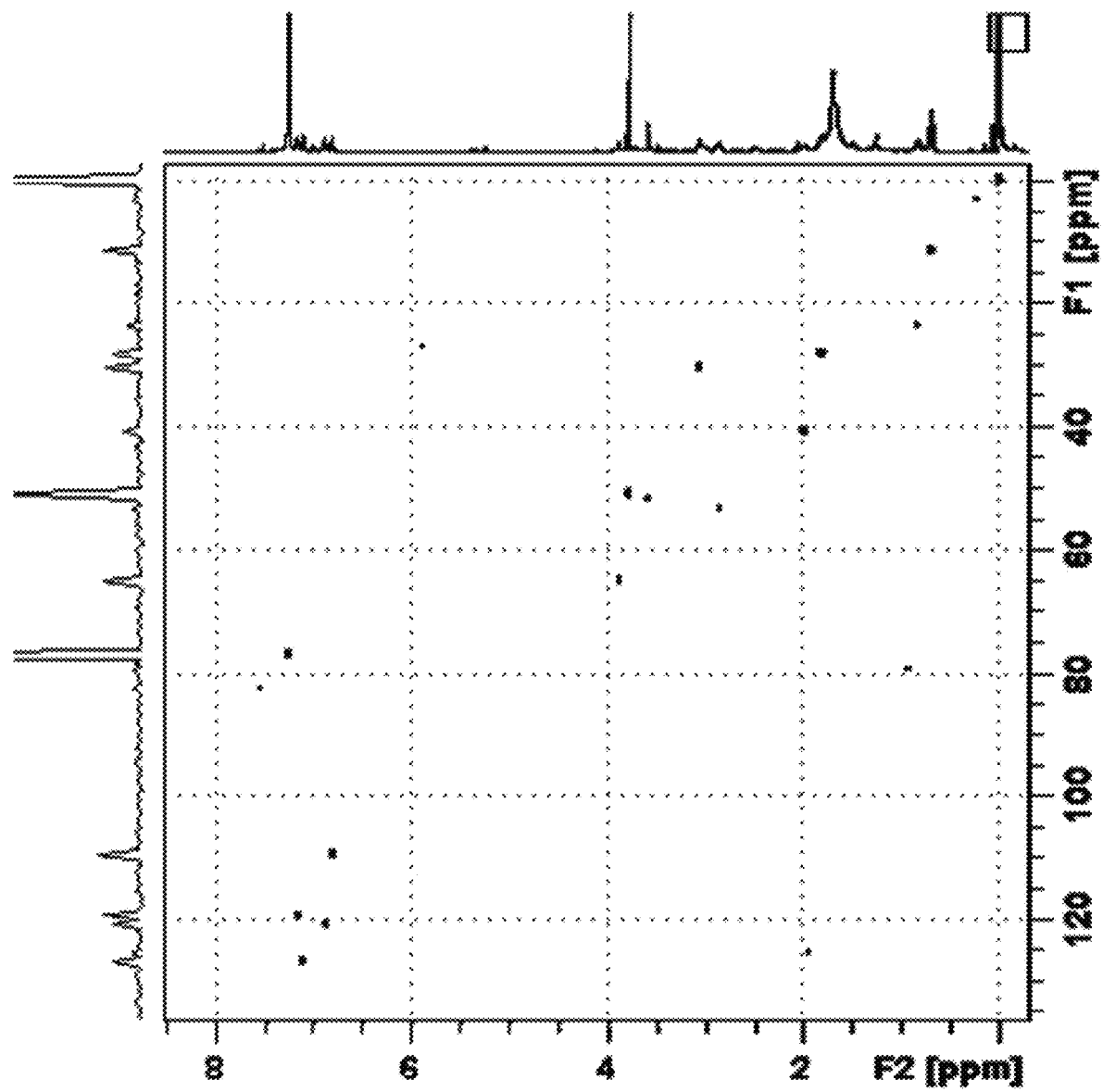
Figure 8F:
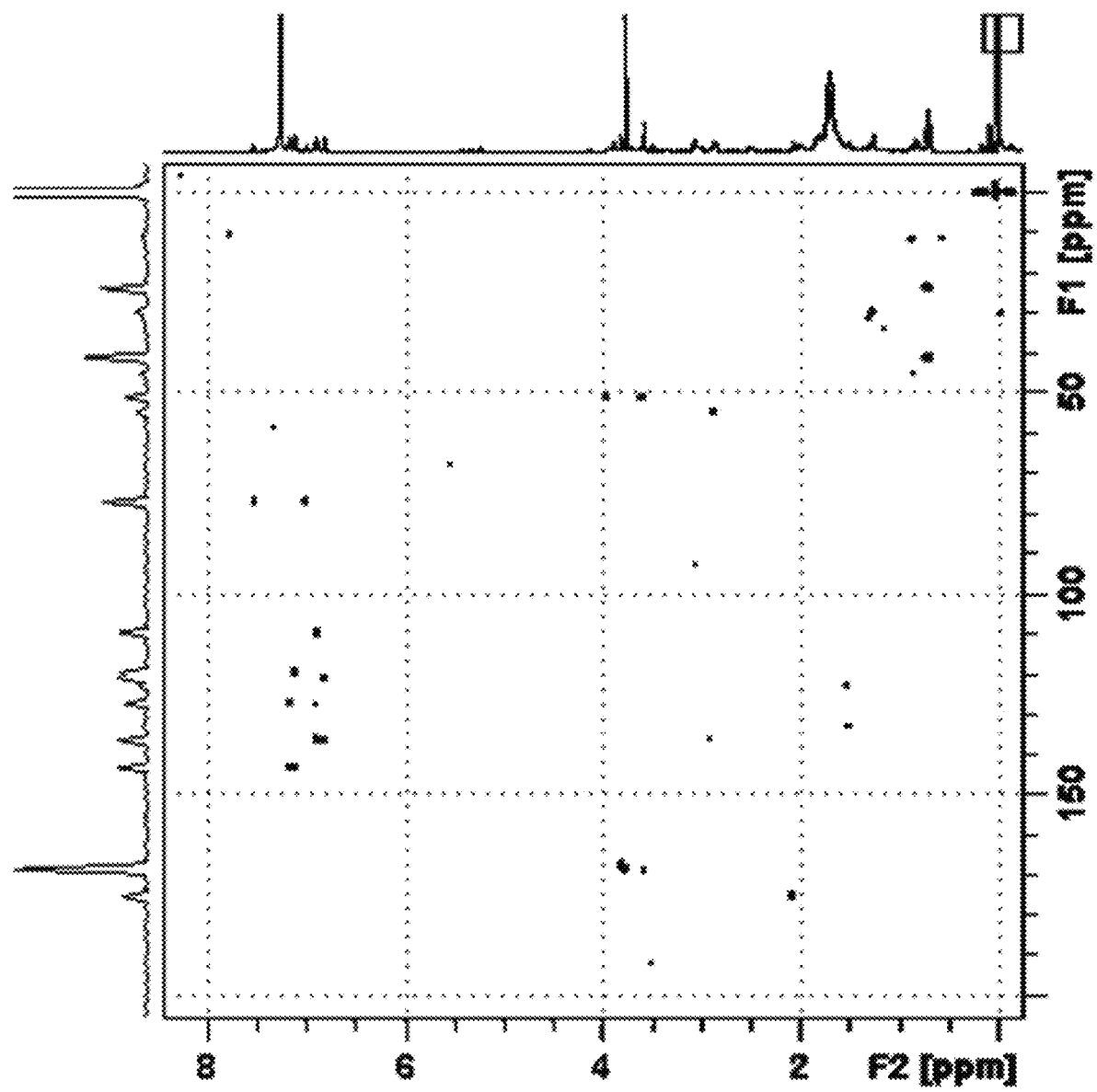

FIG. 7. Activity guided fractionation of CS/TS substrate from *Tabernaemontana divaricata* leaves.

Activity guided fractionation of CS/TS substrate from *Tabernaemontana divaricata* leaves. Fractions collected during preparative HPLC were assayed for the presence of the substrate using CS and TS. A. A fraction reacted with CS showed formation of catharanthine 3 after UPLC/QqQ-MS analysis. Catharanthine 3 was not formed in the control samples (no enzyme). B. The same fraction reacted with TS showed formation of tabersonine 2 after UPLC/QqQ-MS analysis. Tabersonine 2 was not formed in the control samples (no enzyme). Very small peaks of endogenous catharanthine and tabersonine co-purifying with the CS/TS substrate were present in the control samples.

FIG. 8. NMR data of decomposed substrate isolated from plants, tubotaiwine 12.

NMR data of decomposed CS/TS substrate isolated from plants, tubotaiwine 12 ($CDCl_3$, 300 K, 400 MHz); see also Table 7. A. Skeletal formula of tubotaiwine. B. Proton: 512 scans; C. COSY: 16 scans; D. NOESY: 24 scans; E. HSQC: 32 scans; F. HMBC: 500 scans.

Figure 9D:
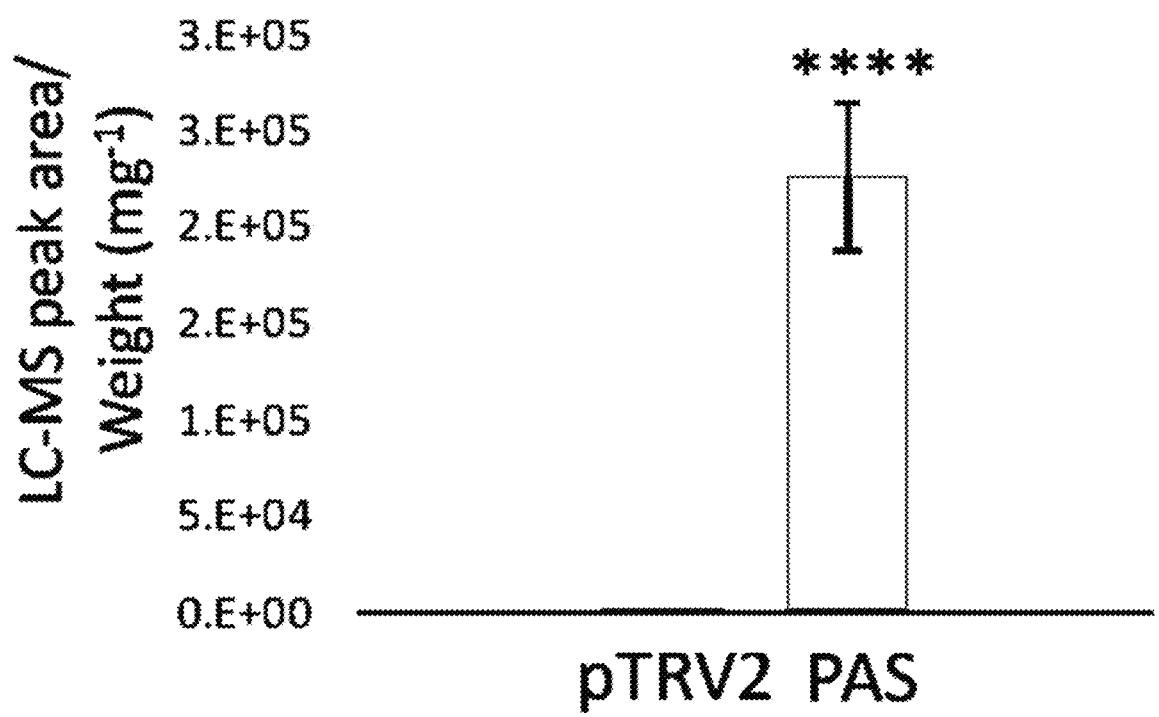

FIG. 9. Virus-induced gene silencing of PAS in *C. roseus* using a unique region of the gene.

Virus-induced gene silencing of PAS in *C. roseus* using a unique region of the gene. A. Fragment (grey box) of PAS cDNA used to assemble the pTRV2 construct. The black box represents the coding region, whereas the black lines are the flanking untranslated regions. Arrows show the annealing sites of the primers used for qRT-PCR analysis (Table 1). B. Fold transcript change in PAS silenced (pTRV2-PAS) plants compared to PAS control (pTRV2) plants. Values were calculated using $2^{-\Delta\Delta Ct}$. Upper panel calculated using the EXP reference gene. Lower panel calculated using the N2227 reference gene. C. Box plots of $\Delta Ct$ values of 8 biological replicates for control (pTRV2) and PAS silenced (pTRV2-PAS) plants with median, min and max values indicated. Asterisks represent significant differences determined using an unpaired, two-tailed t-test (=$p<0.01$). Upper panel calculated using the EXP reference gene. Lower panel calculated using the N2227 reference gene. D. UPLC-MS analysis of PAS silenced leaves showed accumulation of stemmadenine acetate 7 (for identification see FIGS. 10 and 11). Data shown corresponds to average measurements of 12 plants. Error bars indicate standard error of the mean. Statistical significance calculated with Student's t test (pTRV2 in comparison to pTRV2-PAS) is indicated as **=$p<0.0001$. E. UPLC/MS analysis of VIGS extracts showed the appearance of a new peak assigned as stemmadenine acetate 7 (see FIGS. 10 and 11) in the pTRV2-PAS silenced plants that was not present in the pTRV2 empty vector controls.

Figure 10:
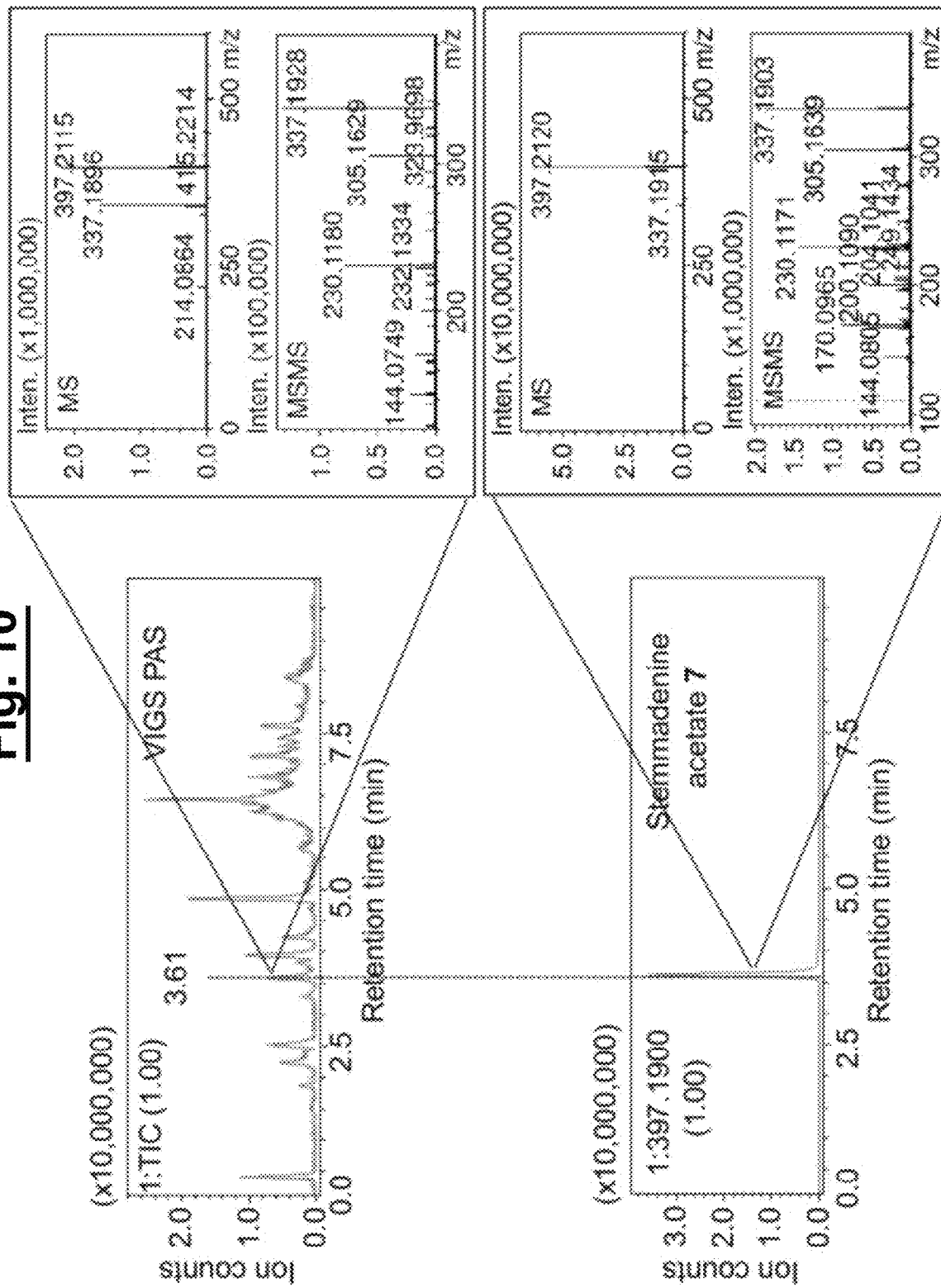

FIG. 10. UPLC/MS analysis of VIGS PAS extracts.

UPLC/MS analysis of VIGS plant extracts. The analysis showed that the new peak at m/z 397.19 and RT 3.61 in the pTRV2-PAS silenced plants (top) co-eluted with a semi-synthetic standard of stemmadenine acetate 7 (bottom). The insets show a comparison between the MS and MS/MS spectra of the two chemical species.

FIG. 11. $^1$H NMR comparison between synthetic stemmadenine acetate 7 and that obtained from extraction of PAS-silenced plants.

$^1$H NMR comparison between synthetic stemmadenine acetate 7 and that obtained by partial purification from PAS-silenced plants.

FIG. 12. Virus-induced gene silencing of DPAS in *C. roseus* using a unique region of the gene.

Virus-induced gene silencing of DPAS in *C. roseus* using a unique region of the gene. A. Fragment (grey box) of DPAS cDNA used to assemble the pTRV2 construct. The black box represents the coding region, whereas the black lines are the flanking untranslated regions. Arrows show the annealing sites of the primers used for qRT-PCR analysis (Table 1). B. Fold transcript change DPAS silenced (pTRV2-DPAS) plants compared to DPAS control (pTRV2) plants. Values were calculated using $2^{-\Delta\Delta Ct}$. Upper panel calculated using the EXP reference gene. Lower panel calculated using the N2227 reference gene. C. Box plots of $\Delta Ct$ values of 8 biological replicates for control (pTRV2) and DPAS silenced (pTRV2-DPAS) plants with median, min and max values indicated. Asterisks represent significant differences determined using an unpaired, two-tailed t-test (*=$p<0.001$, =$p<0.0001$). Upper panel calculated using the EXP reference gene. Lower panel calculated using the N2227 reference gene. D. UPLC-MS analysis of DPAS silenced leaves showed accumulation of precondylocarpine acetate 10 (identification see FIGS. 13 and 14). Data shown corresponds to average measurements of 12 plants. Error bars indicate standard error of the mean. Statistical significance calculated with Student's t test (pTRV2 in comparison to pTRV2-DPAS) is indicated as =$p<0.01$. E. UPLC/MS analysis of VIGS extracts showed a marked increase in a peak with m/z 395.19 in pTRV2-DPAS silenced plants that was not very abundant in the pTRV2 empty vector controls (see FIGS. 13 and 14).

Figure 13:
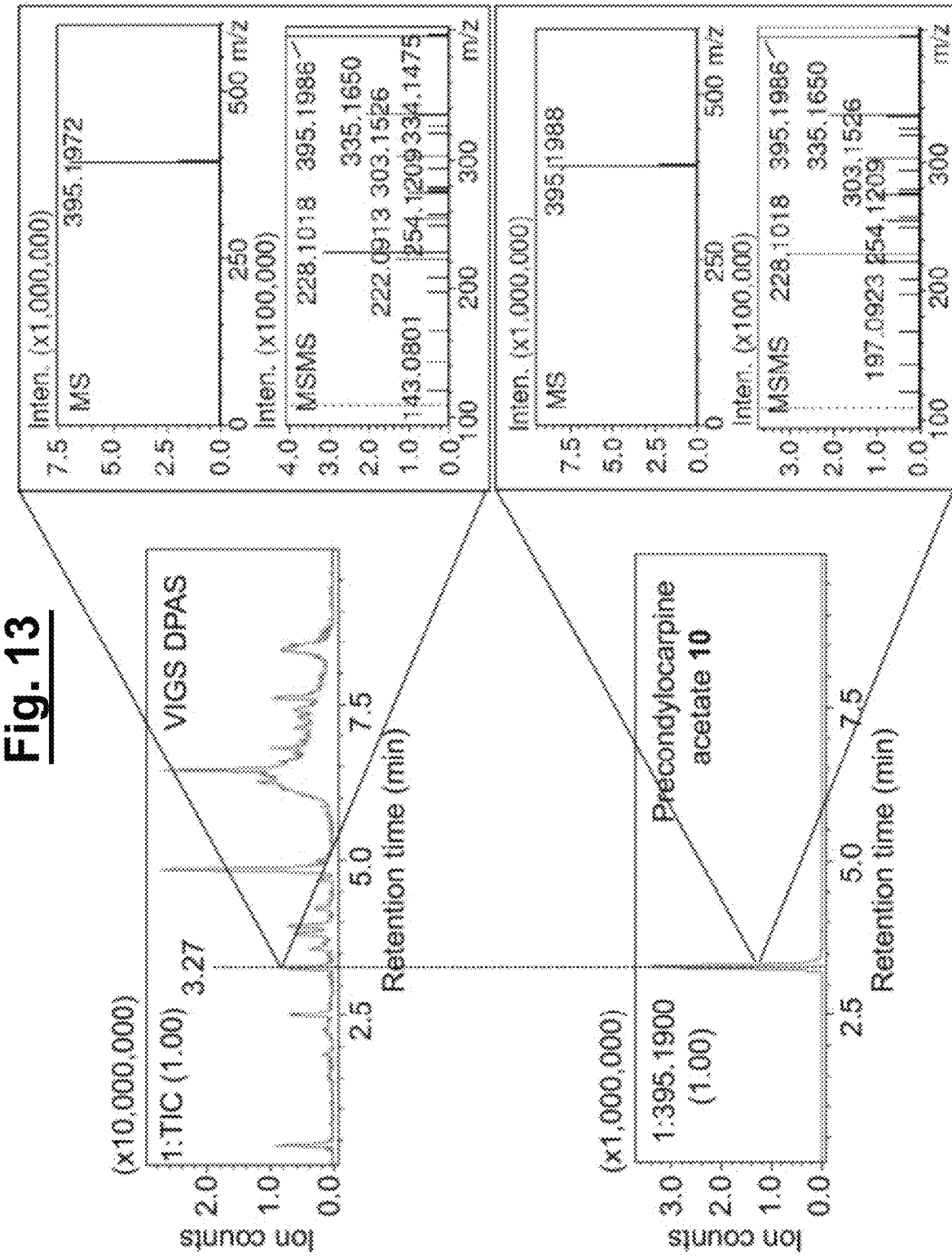
Figure 14A:
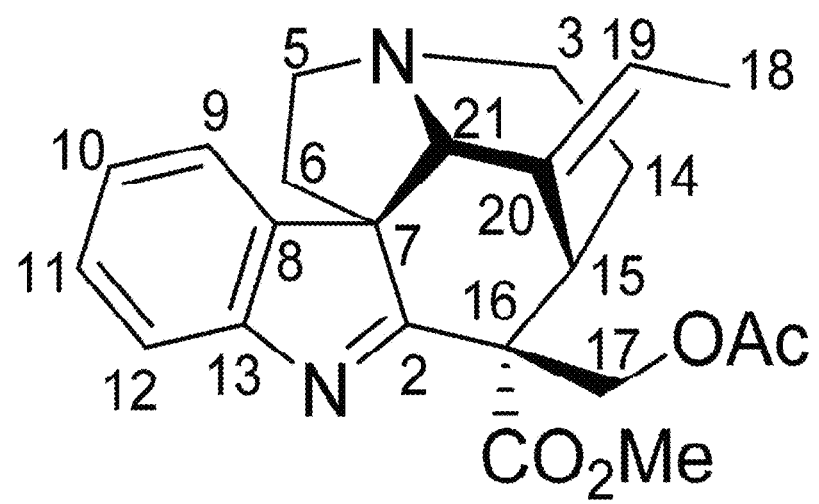
Figure 14B:
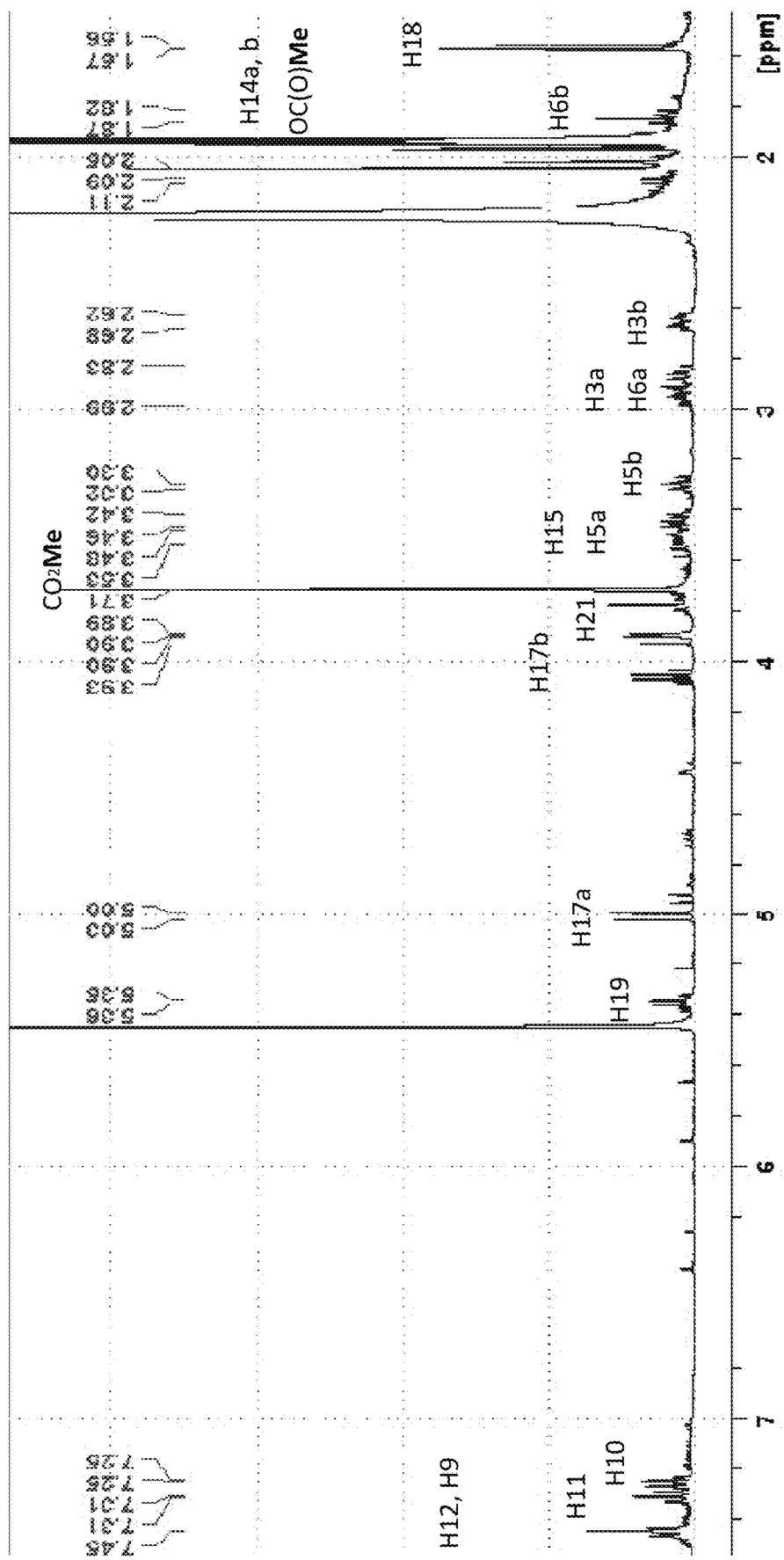
Figure 14C:
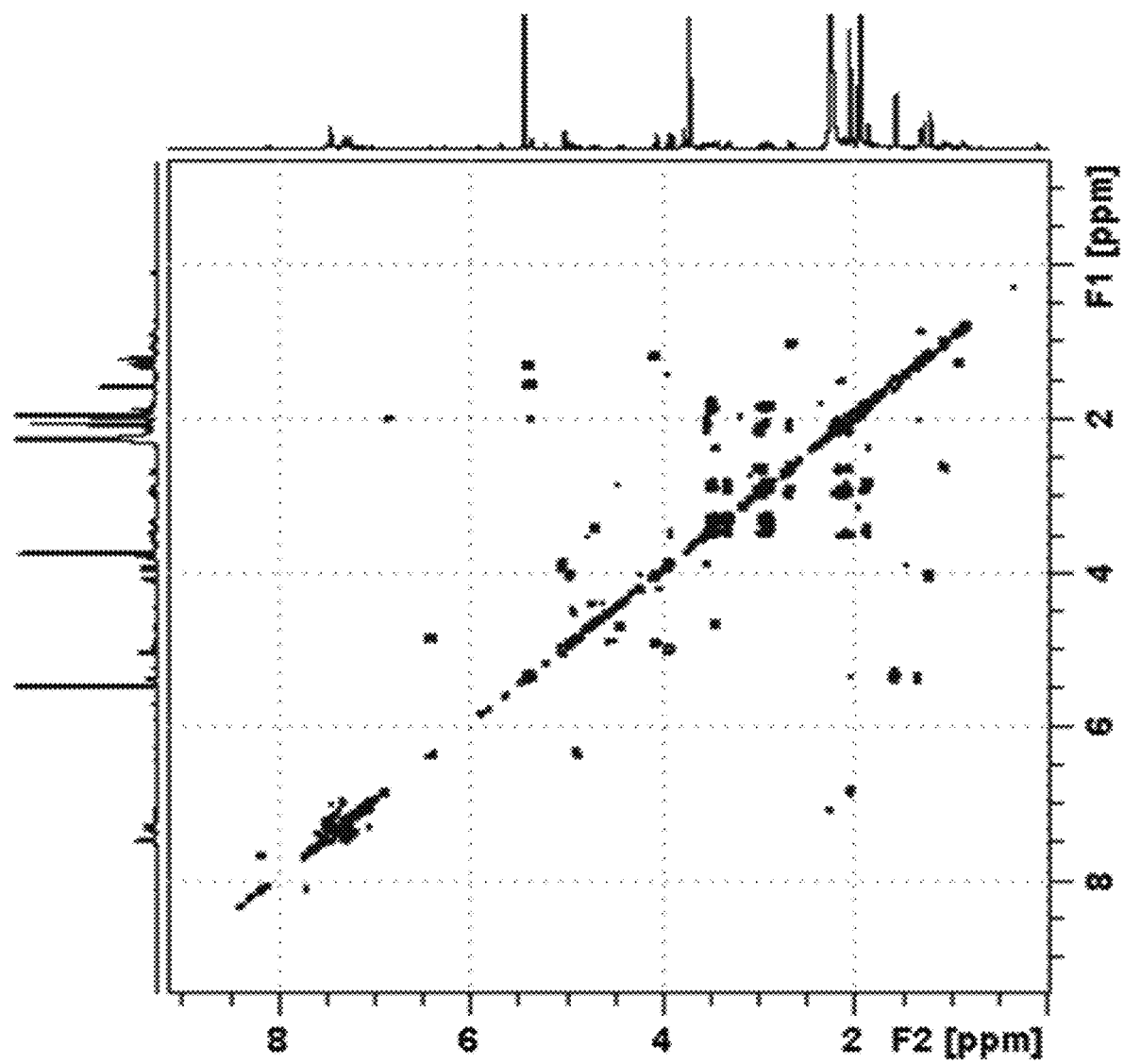
Figure 14E:
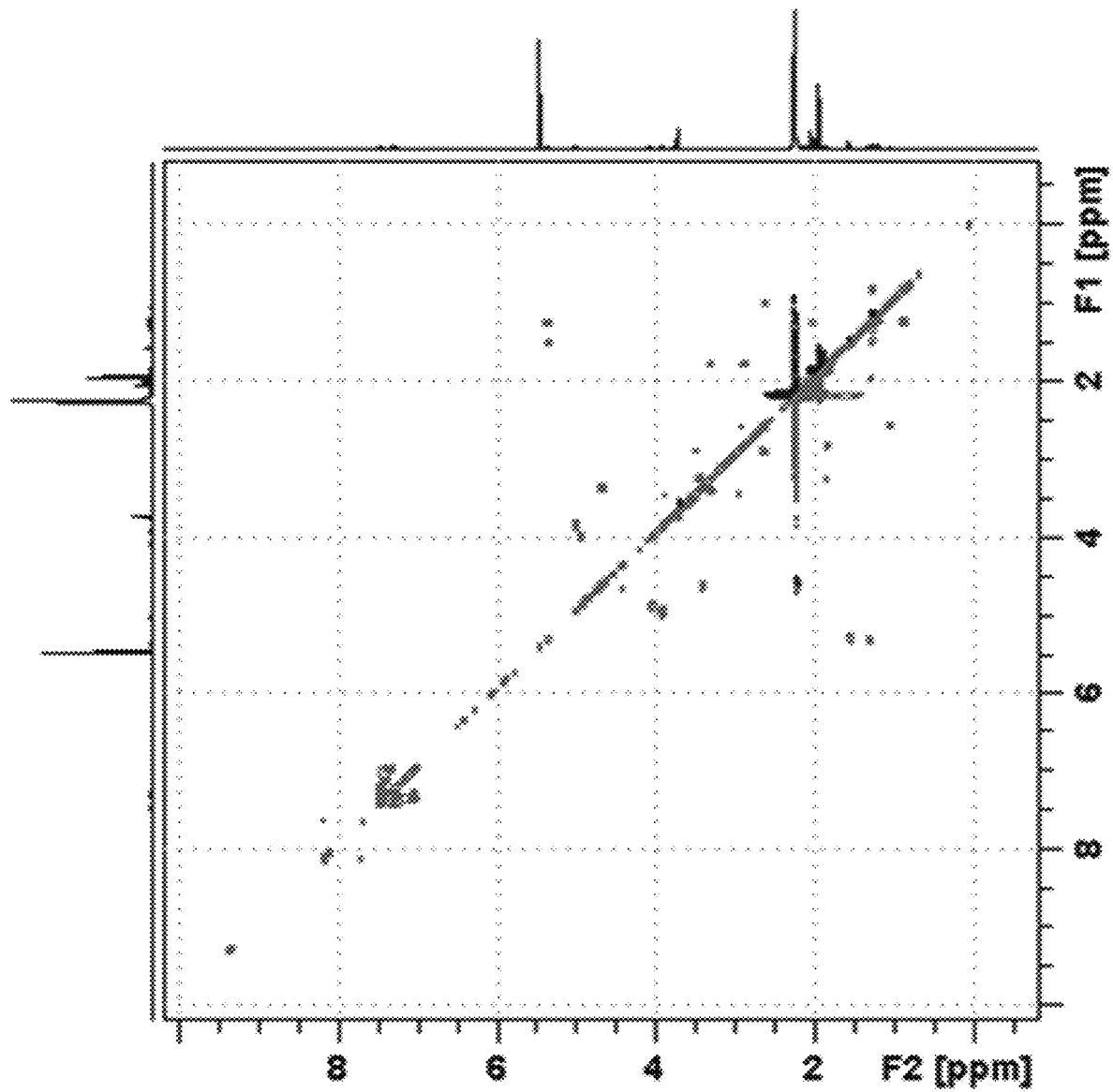
Figure 14F:
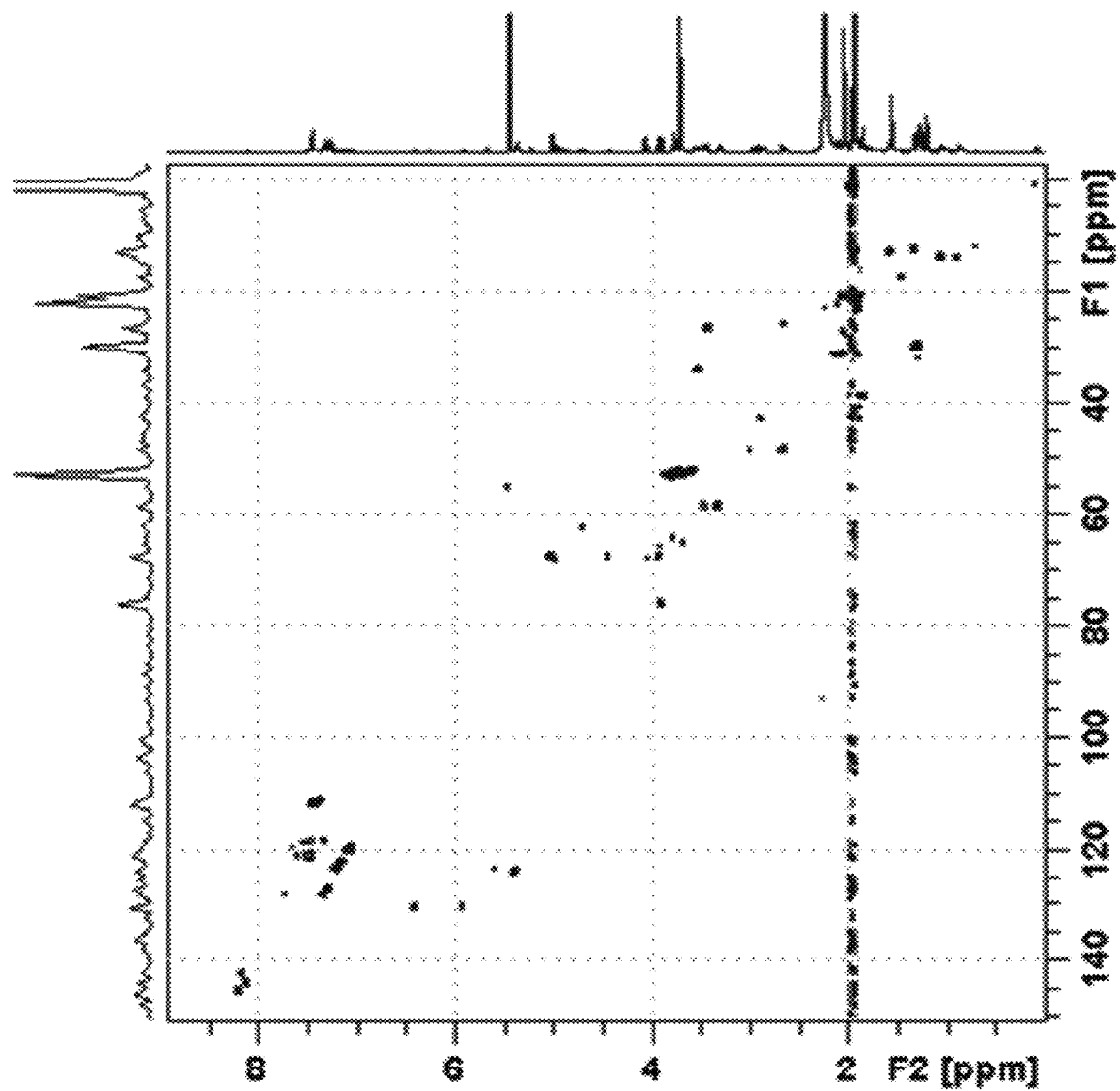
Figure 14G:
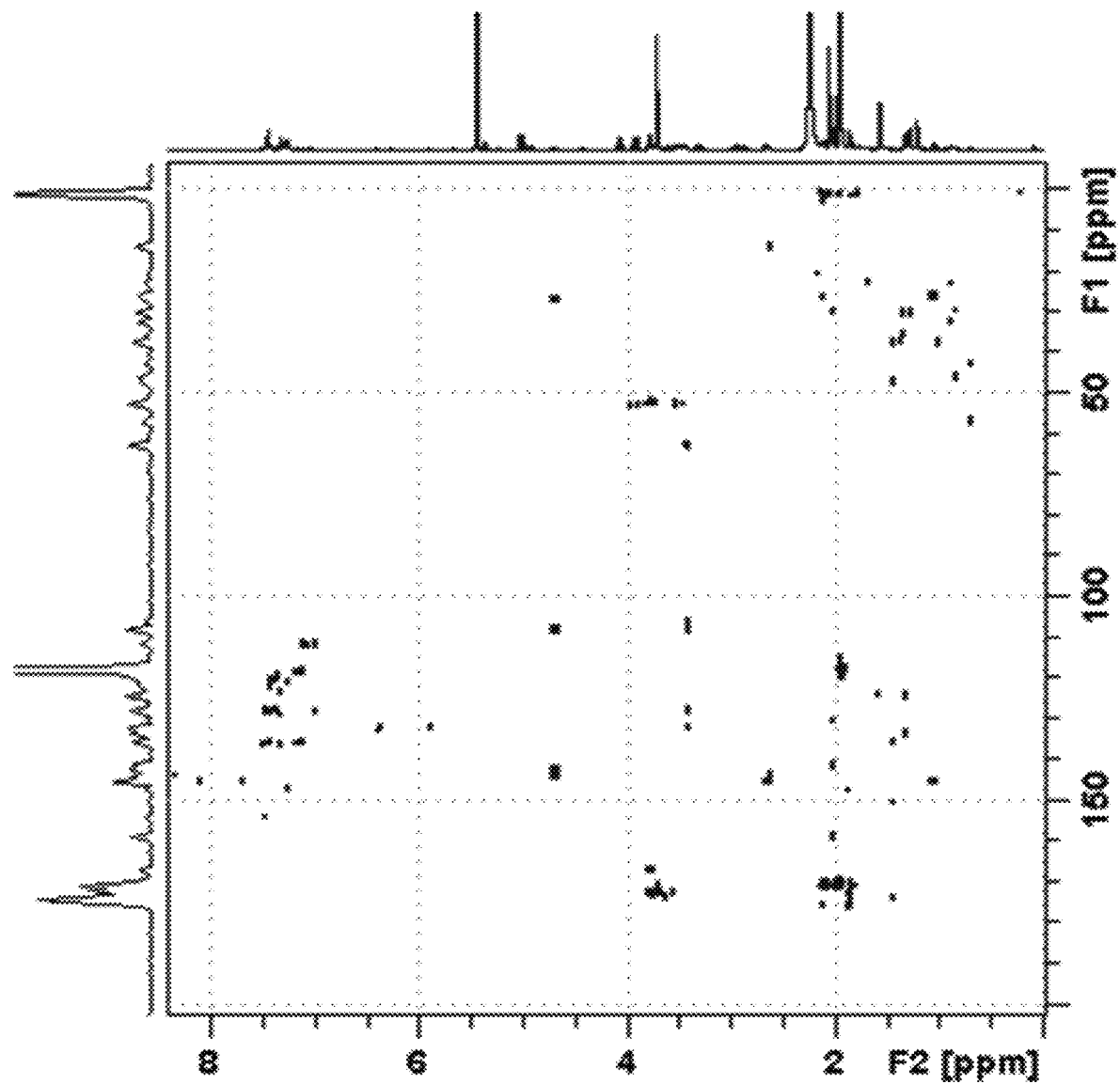

FIG. 13. UPLC/MS analysis of VIGS DPAS extracts.

UPLC/MS analysis of VIGS DPAS extracts. The analysis showed that the new peak at m/z 395.19 and RT 3.27 in the pTRV2-DPAS silenced plants (top) co-eluted with a semi-synthetic standard of precondylocarpine acetate 10 (bottom). The insets show a comparison between the MS and MS/MS spectra of the two chemical species.

FIG. 14. NMR data of synthetic precondylocarpine acetate 10.

NMR data of synthetic precondylocarpine acetate 10 ($CD_3CN$, 300 K, 400 MHz); see also Table 6. A. Skeletal formula of precondylocarpine acetate. B. Proton: 256 scans; C. COSY: 32 scans; D. NOESY: 16 scans; E. TOCSY: 24 scans; F. HSQC: 72 scans, G. HMBC: 425 scans (during HMBC acquisition degradation occurred, so not all cross peaks in HMBC match 1H NMR sprectrum).

Figure 15:
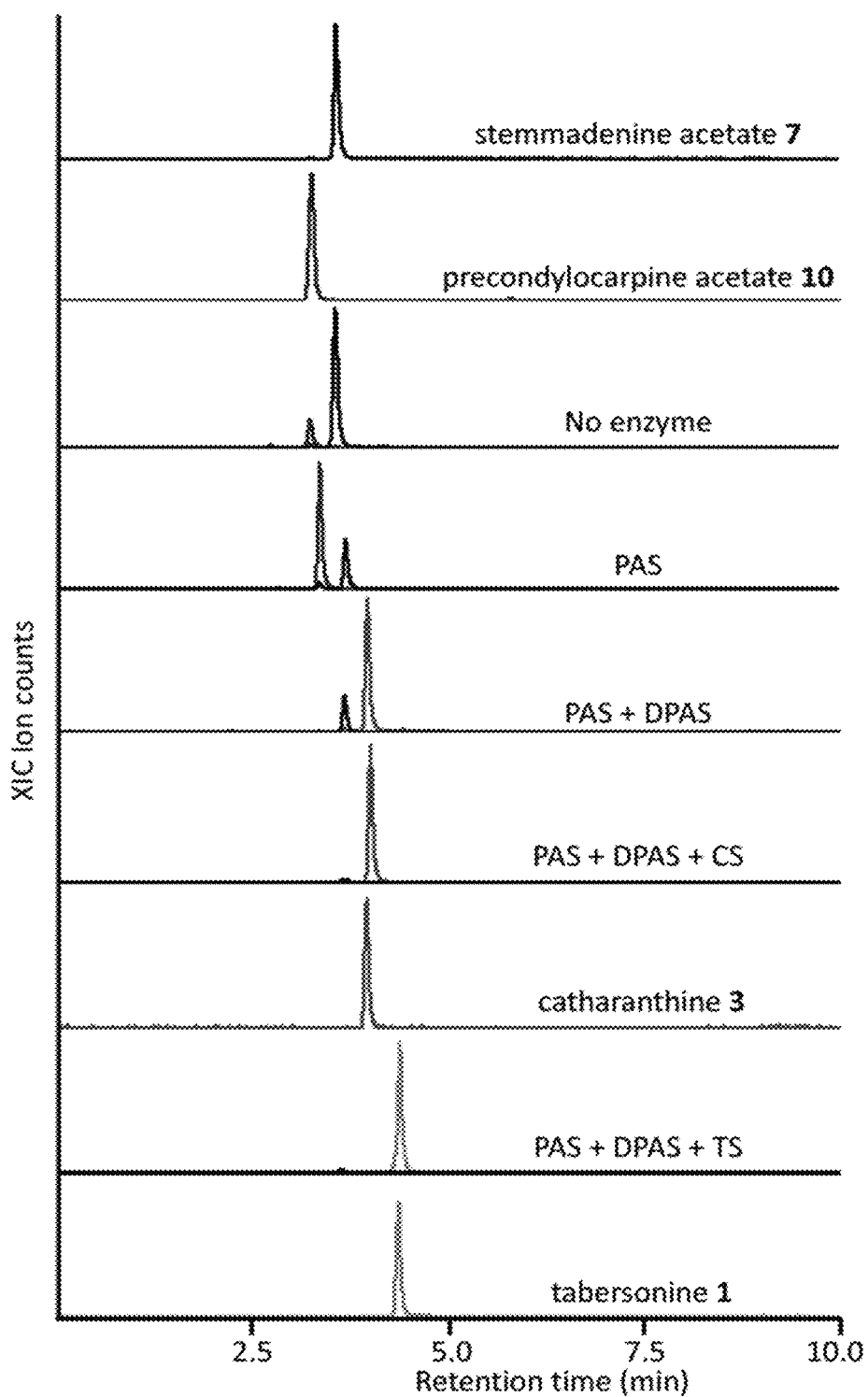

FIG. 15. Pathway reconstitution in vitro using PAS expressed in *N. benthamiana* leaves.

Pathway reconstitution in vitro using PAS expressed in *N. benthamiana* leaves. The figure shows the extracted ion chromatograms for ions m/z 397.19 (sternmadenine acetate, the starting material), m/z 395.19 (precondylocarpine acetate) and m/z 337.19 (catharanthine at RT 4.0 and tabersonine at RT 4.4). Heterologously expressed and purified proteins were used to reconstitute the biosynthetic pathway from stemmadenine acetate 7 to catharanthine 3 and tabersonine 2. Extracted ion chromatograms for each compound are shown. When no enzymes were present, very small amounts of precondylocarpine acetate 10 were observed in the reaction, likely due to spontaneous oxidation. After addition of PAS, most of the substrate was converted to precondylocarpine acetate 10. Addition of DPAS resulted in complete consumption of precondylocarpine acetate 10 and catharanthine 3 started to appear in the samples. However, when CS was present, all the initial substrate (stemmadenine acetate 7) was converted to catharanthine 3. When PAS, DPAS and TS were combined together in the reaction, all initial substrate was converted to tabersonine 2. Formation of catharanthine 3 and tabersonine 2 was validated by co-elution with commercial standards. Formation of precondylocarpine acetate 10 was validated by co-elution with the semi-synthetic compound.

Figure 16A:
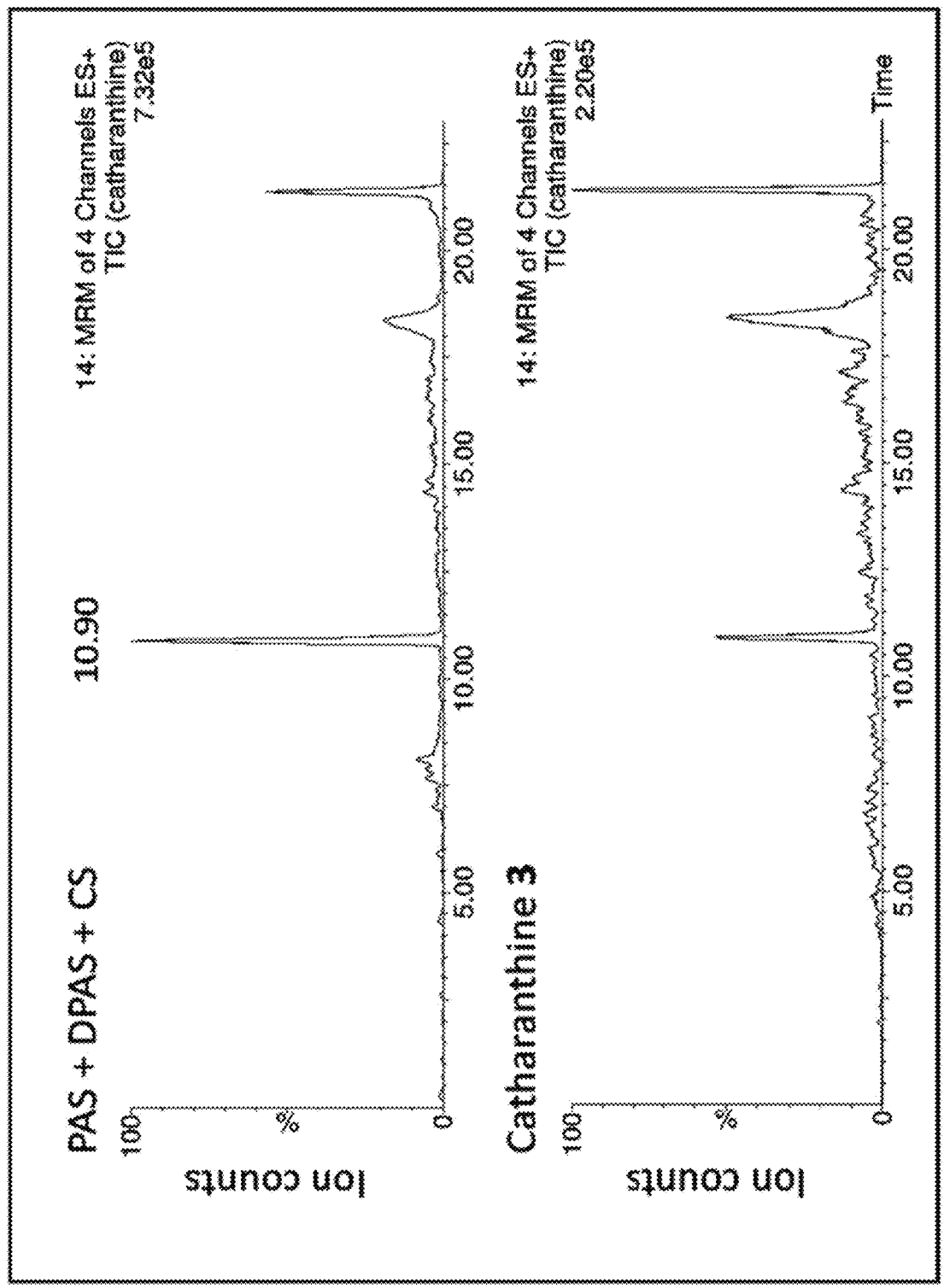
Figure 16B:
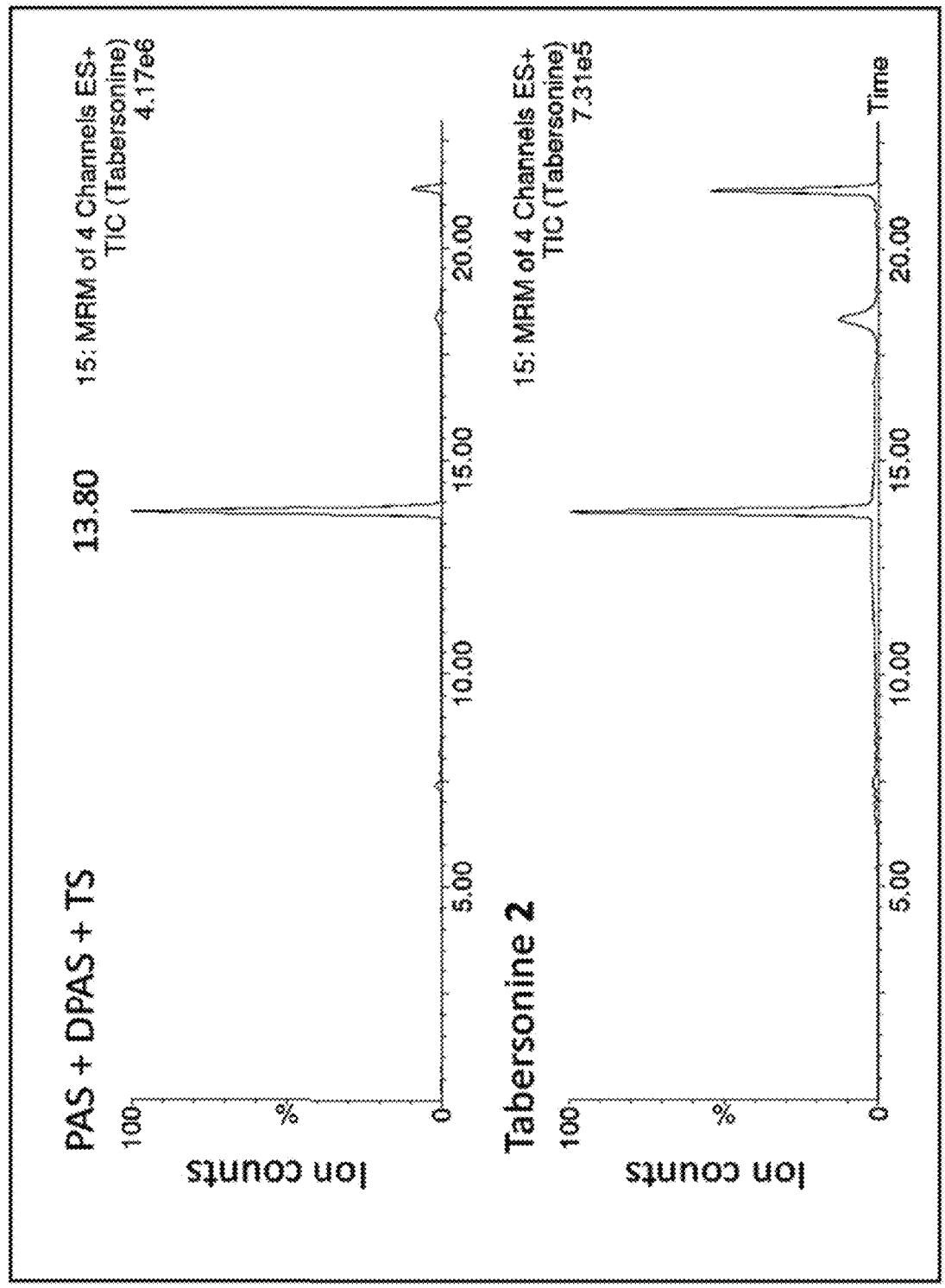

FIG. 16. Pathway reconstitution in vitro using PAS expressed in *P. pastoris*.

Pathway reconstitution in vitro using PAS expressed in *P. pastoris*. A. Total ion chromatograms for MRMs of catharanthine 3 (RT=10.90) for the reaction of PAS, DPAS and CS with stemmadenine acetate 7, compared to a commercial standard of catharanthine 3. B. Total ion chromatograms for MRMs of tabersonine 2 (RT=13.80) for the reaction of PAS, DPAS and TS with stemmadenine acetate 7, compared to a commercial standard of tabersonine 2.

Figure 17:
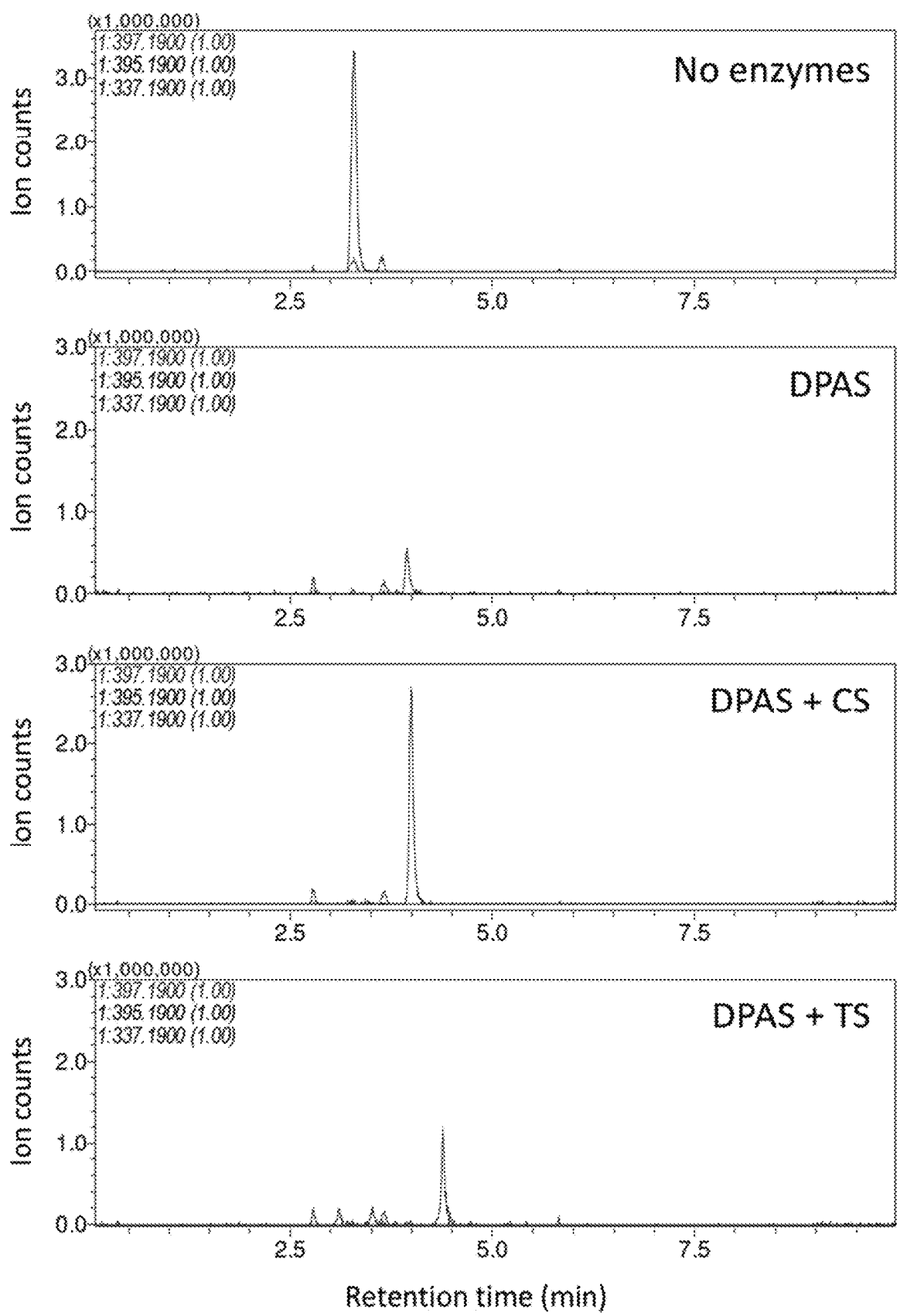

FIG. 17. In vitro pathway reconstitution from synthetic precondylocarpine acetate 10.

In vitro pathway reconstitution from synthetic precondylocarpine acetate 10. The figure shows the extracted ion chromatograms for ions m/z 397.19 (stemmadenine acetate), m/z 395.19 (precondylocarpine acetate 10) and m/z 337.19 (catharanthine 3 at RT 4.0 and tabersonine 2 at RT 4.4). Addition of DPAS to the reaction mixture resulted in complete consumption of precondylocarpine acetate and appearance of a small amount of catharanthine 3 but no reduced product (dihydroprecondylocarpine acetate 11) at m/z 397.19 was observed. When DPAS and CS were present, all substrate was converted into catharanthine 3. When DPAS and TS were incubated with precondylocarpine acetate 10, tabersonine 2 was formed.

Figure 18B:
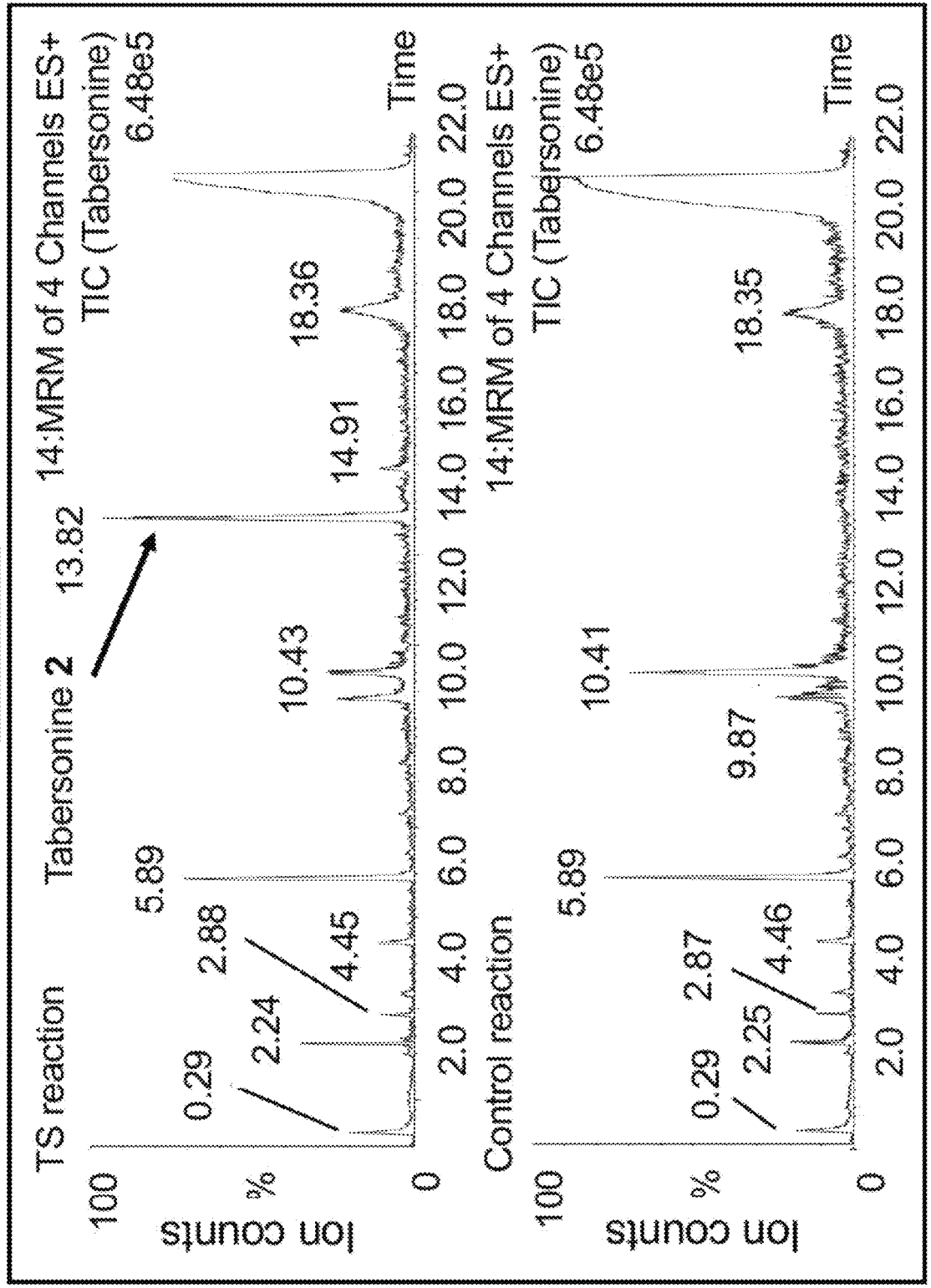

FIG. 18. In vitro reaction of crude dihydroprecondylocarpine acetate with CS and TS.

In vitro reaction of crude dihydroprecondylocarpine acetate 11 with CS and TS. A. Total ion chromatograms for MRMs of catharanthine 3 (RT=10.90) for the reaction of CS with dihydroprecondylocarpine acetate 11, compared to a control reaction without CS. B. Total ion chromatograms for MRMs of tabersonine 2 (RT=13.82) for the reaction of TS with dihydroprecondylocarpine acetate 11, compared to a control reaction without TS.

Figure 19:
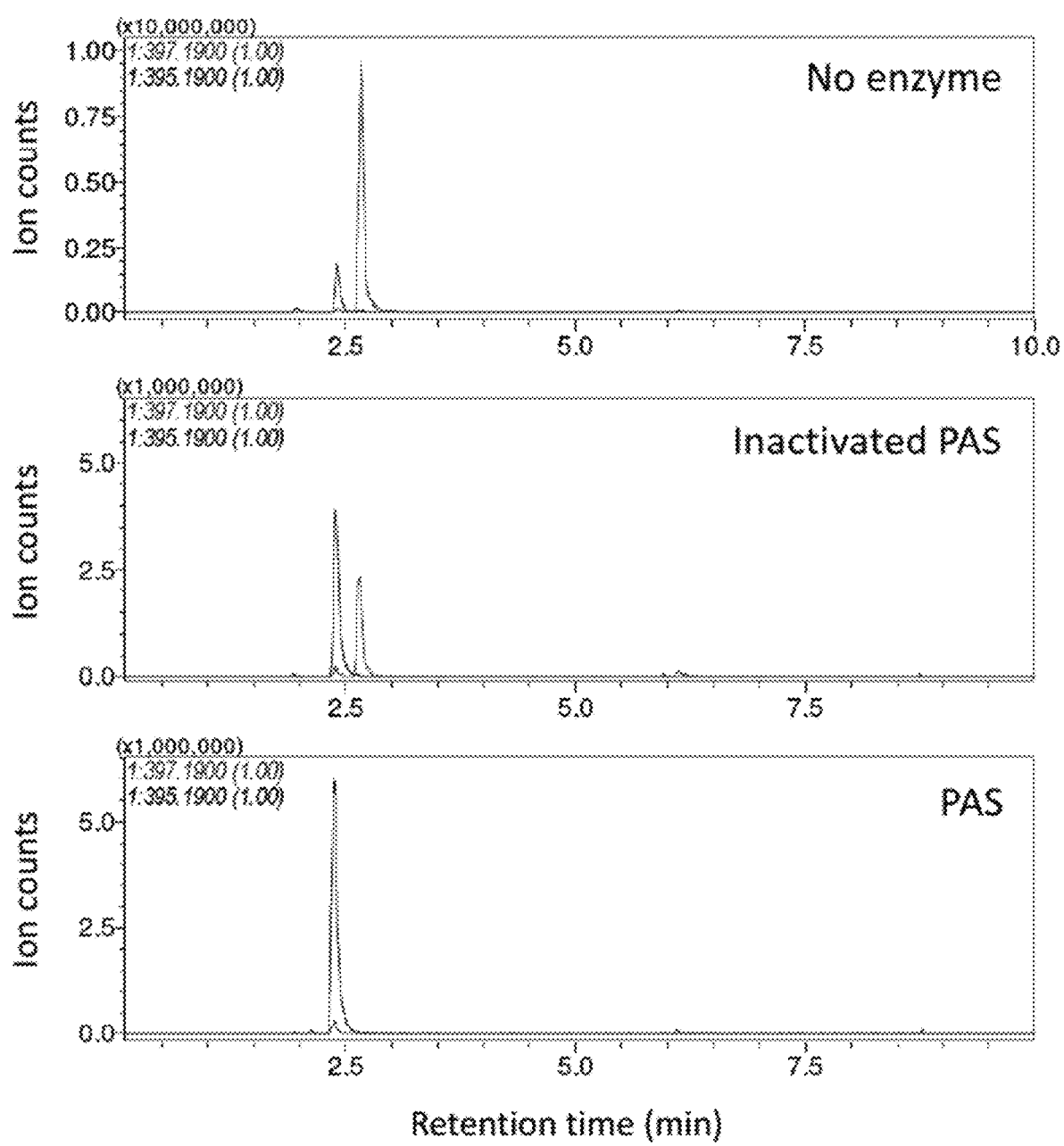

FIG. 19. In vitro activity of PAS purified from *P. pastoris* culture medium.

In vitro activity of PAS purified from *P. pastoris* culture medium. The figure shows the extracted ion chromatograms for ions m/z 397.19 (stemmadenine acetate 7) and m/z 395.19 (precondylocarpine acetate 10). Addition of PAS to the reaction mixture resulted in complete conversion of stemmadenine acetate 7 to precondylocarpine acetate 10. However, heat inactivated enzyme (20 min in boiling water) was still able to consume some of the substrate, suggesting that this enzyme is quite resilient to heat inactivation.

Figure 20:
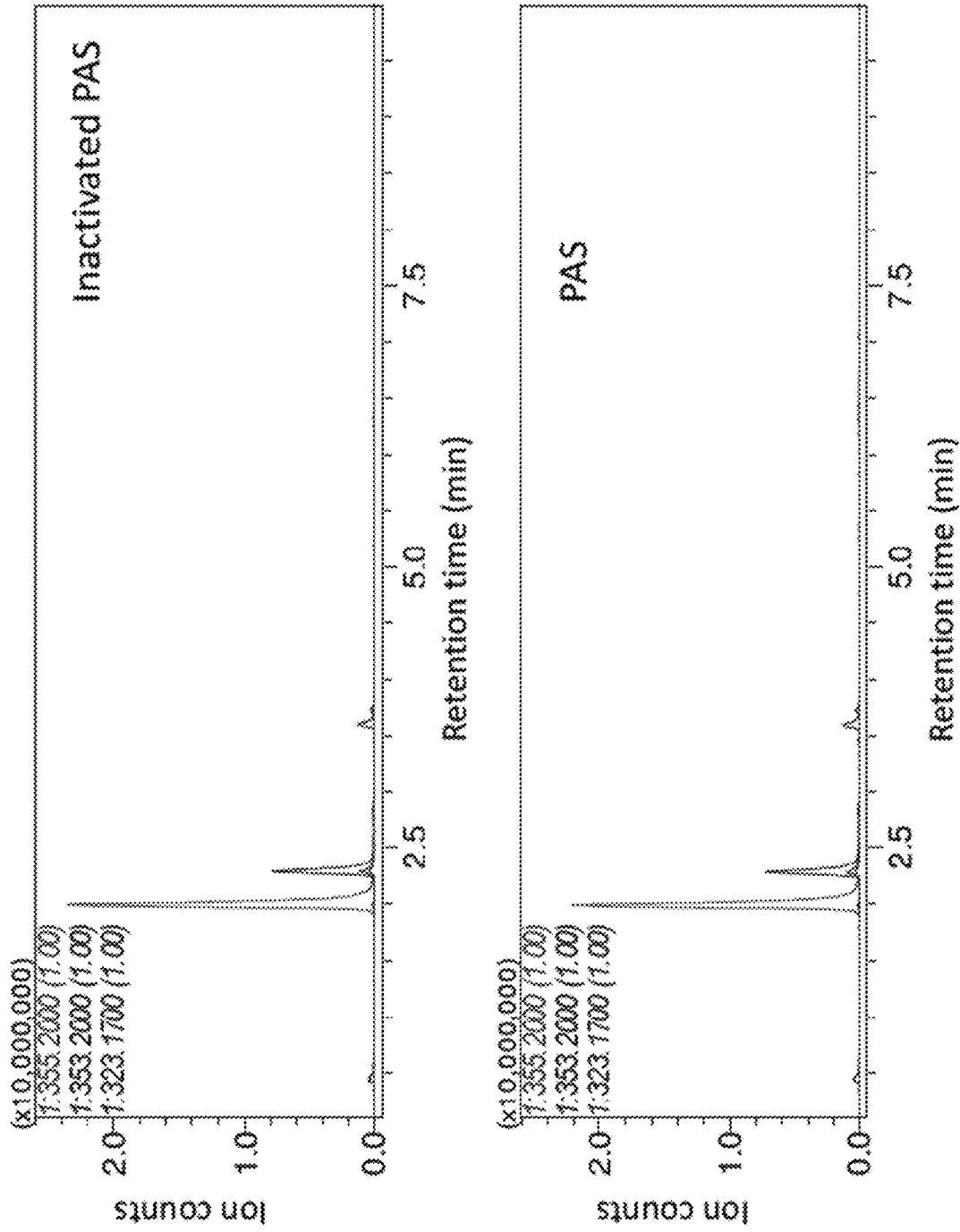

FIG. 20. Assay of PAS with stemmadenine 1.

Assay of PAS with stemmadenine 1. UPLC/MS analysis of reactions in which stemmadenine 1 was used as substrate for PAS showed neither consumption of substrate or formation of new products. Extracted ion chromatograms for m/z 355.2 (stemmadenine) and m/z 353.2 (mass of the expected oxidation product) are shown. The peak at m/z 353.2 present in both samples was not a product of PAS activity. Extracted ion chromatogram for m/z 323.17 showed that no condylocarpine 13 was formed during the reaction.

Figure 21A:
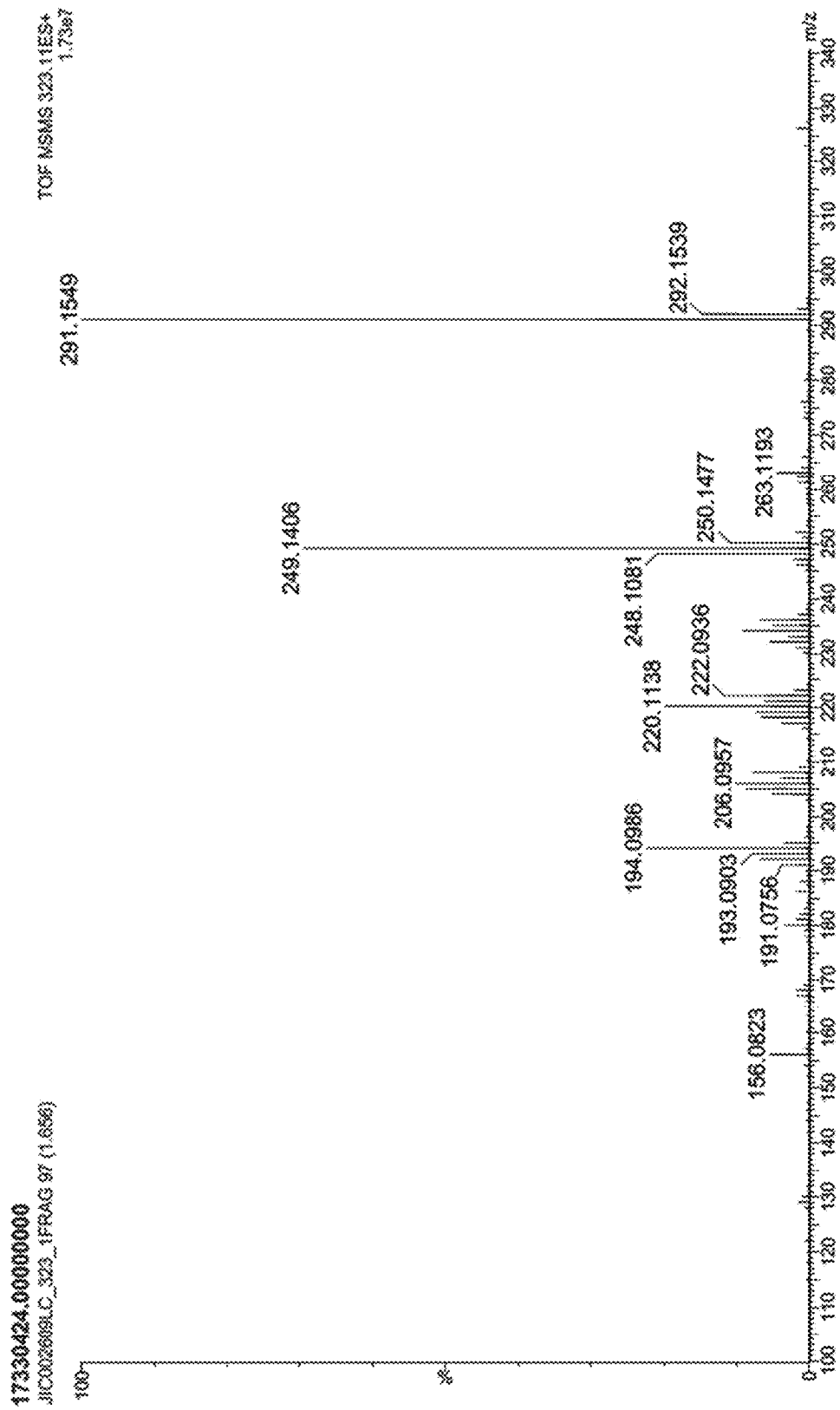
Figure 21B:
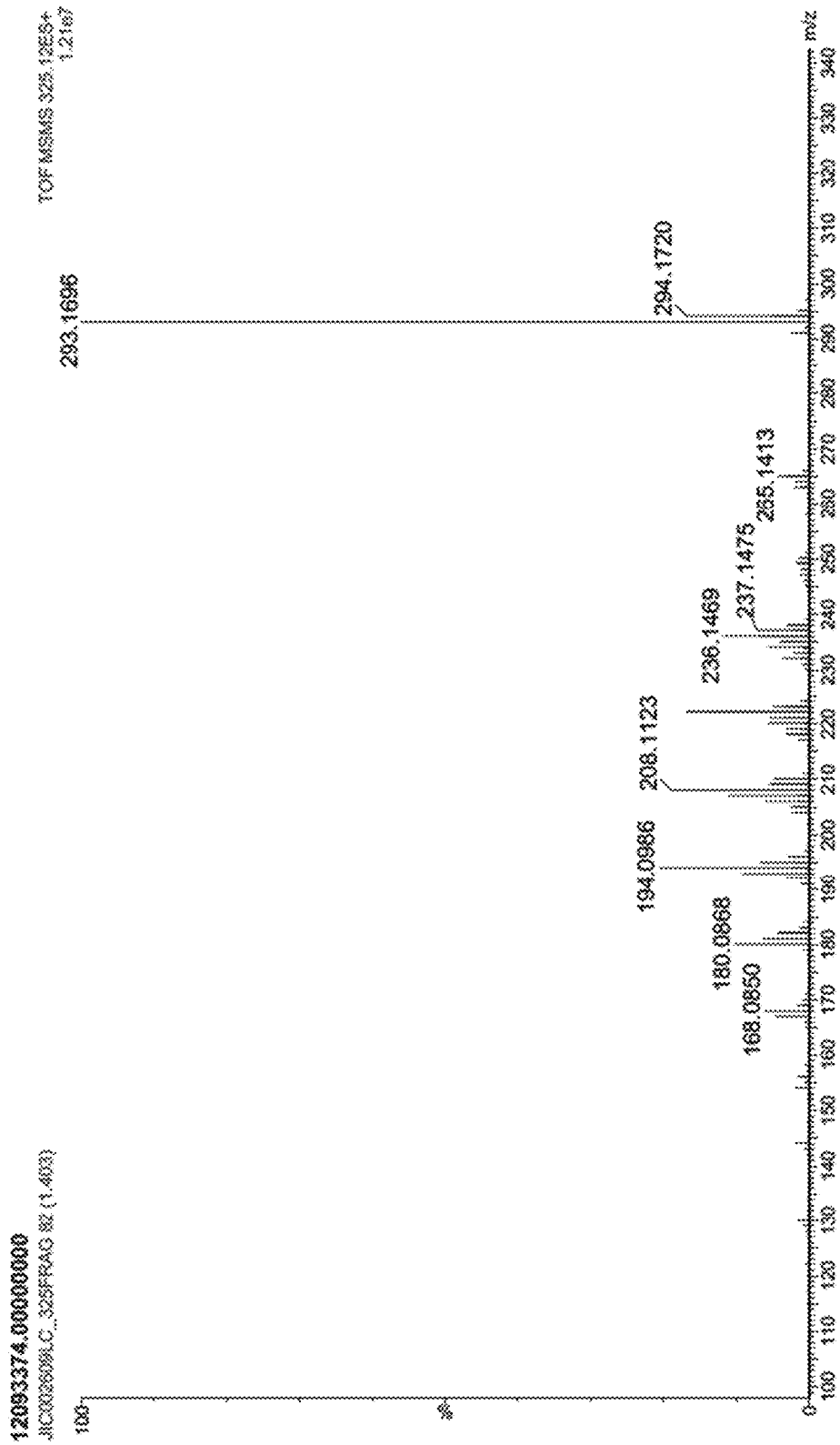

FIG. 21. MSMS spectra of condylocarpine 13 and tubotaiwine 12.

MSMS spectra of condylocarpine 13 and tubotaiwine 12. A. MSMS spectrum of condylocarpine 13 (precursor ion m/z 323.17) at high energy. B. MSMS spectrum of tubotaiwine 12 (precursor ion m/z 325.19) at high energy.

Figure 22:
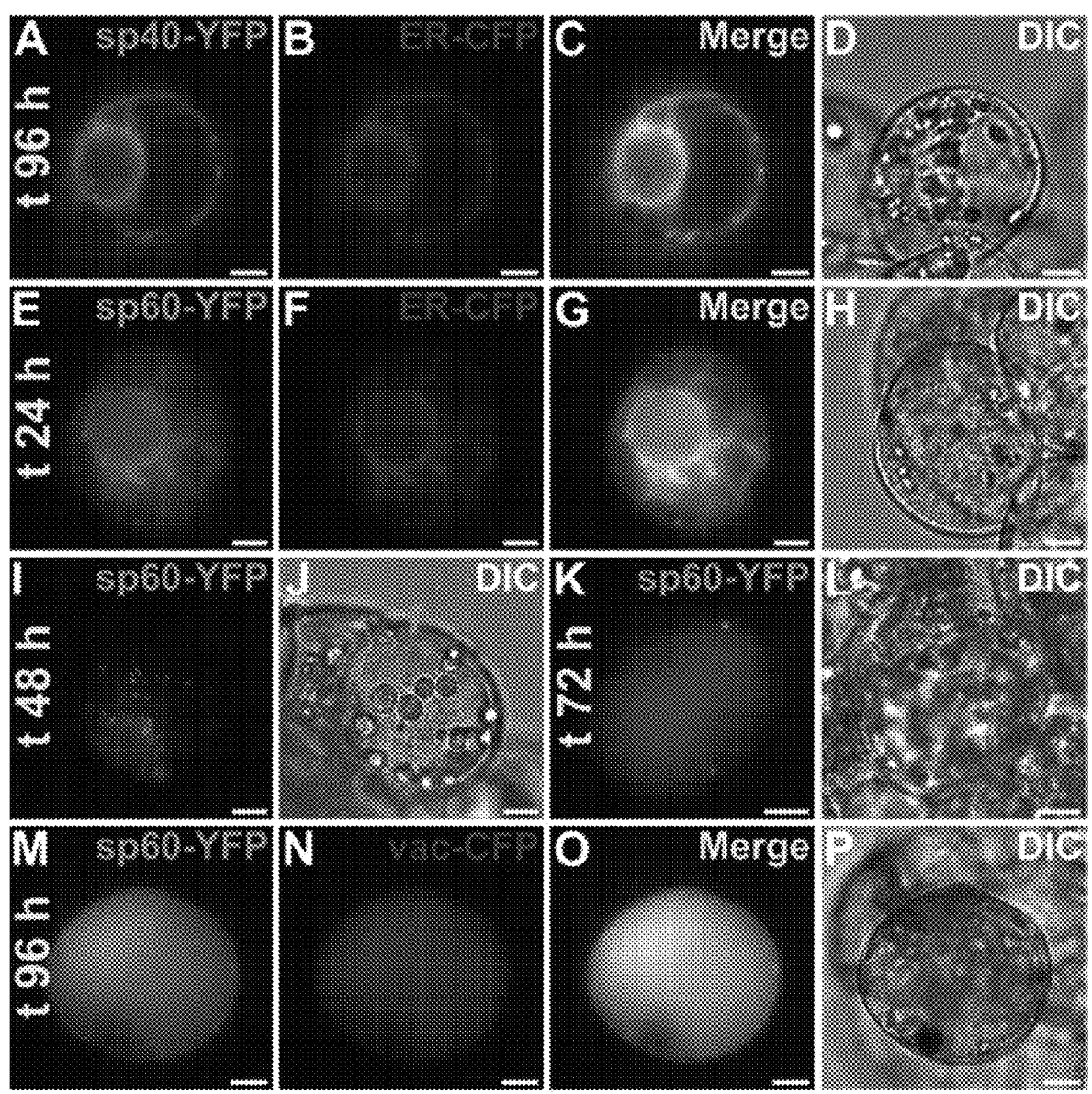

FIG. 22. Localization of PAS.

PAS is targeted to endoplasmic reticulum and progressively secreted to vacuole by ER-derived vesicles. *C. roseus* cells were transiently co-transformed with plasmids expressing the 40-first (sp40; A) or 60-first (sp60; E, I, K, M) PAS residues fused to YFP and the endoplasmic (ER)-CFP marker (B, F) or vacuole (vac-) CFP marker (N). Localization was investiaated during 96 h and representative photos were taken at 24, 48, 72 and 96 h post-transformation to highlight permanent ER localization of sp40-YFP during 96 h (A) and the progressive translocation of sp60-YFP from ER at 24 h(E), vesicles at 48 h (I), to vacuole at 72 h and 96 h (K, M), Co-localization of the fluorescence signals appears when merging the two individual false colour images (C, G, O). Cell morphology is observed with differential interference contrast (DIC) (D, H, J, L, P). Scale bars, 10 µm.

Figure 23:
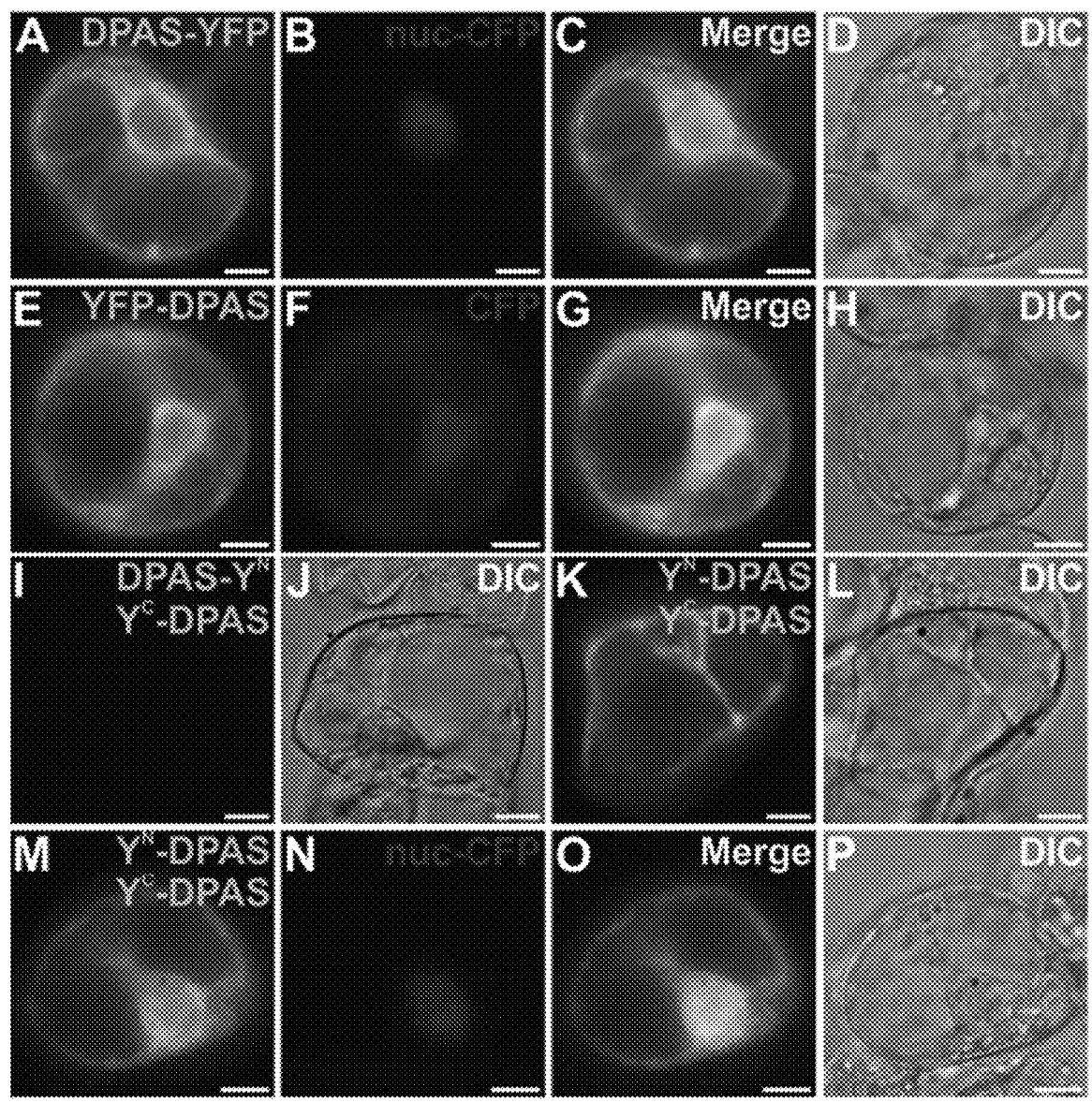

FIG. 23. Localization of DPAS.

DPAS displays a cytosolic localization and homodimerizes. *C. roseus* cells were transiently co-transformed with plasmids expressing DPAS-YFP (A) or YFP-DPAS (E) and the plasmid encoding the nuclear (nuc)-CFP marker (B) or the nucleocytosolic marker CFP (F). DPAS dimerization was analyzed by bimolecular fluorescence complementation (BiFC) assays through transient co-expression of DPAS-YFPN and YFPC-DPAS (I) or YFPN-DPAS and YFPC-DPAS (K, M) with the nuc-CFP marker (N). Co-localization of the fluorescence signals appears when merging the two individual false colour images (C, G, O). Cell morphology is observed with differential interference contrast (DIC) (D, F, J, L, P). Scale bars, 10 µm.

Figure 24:
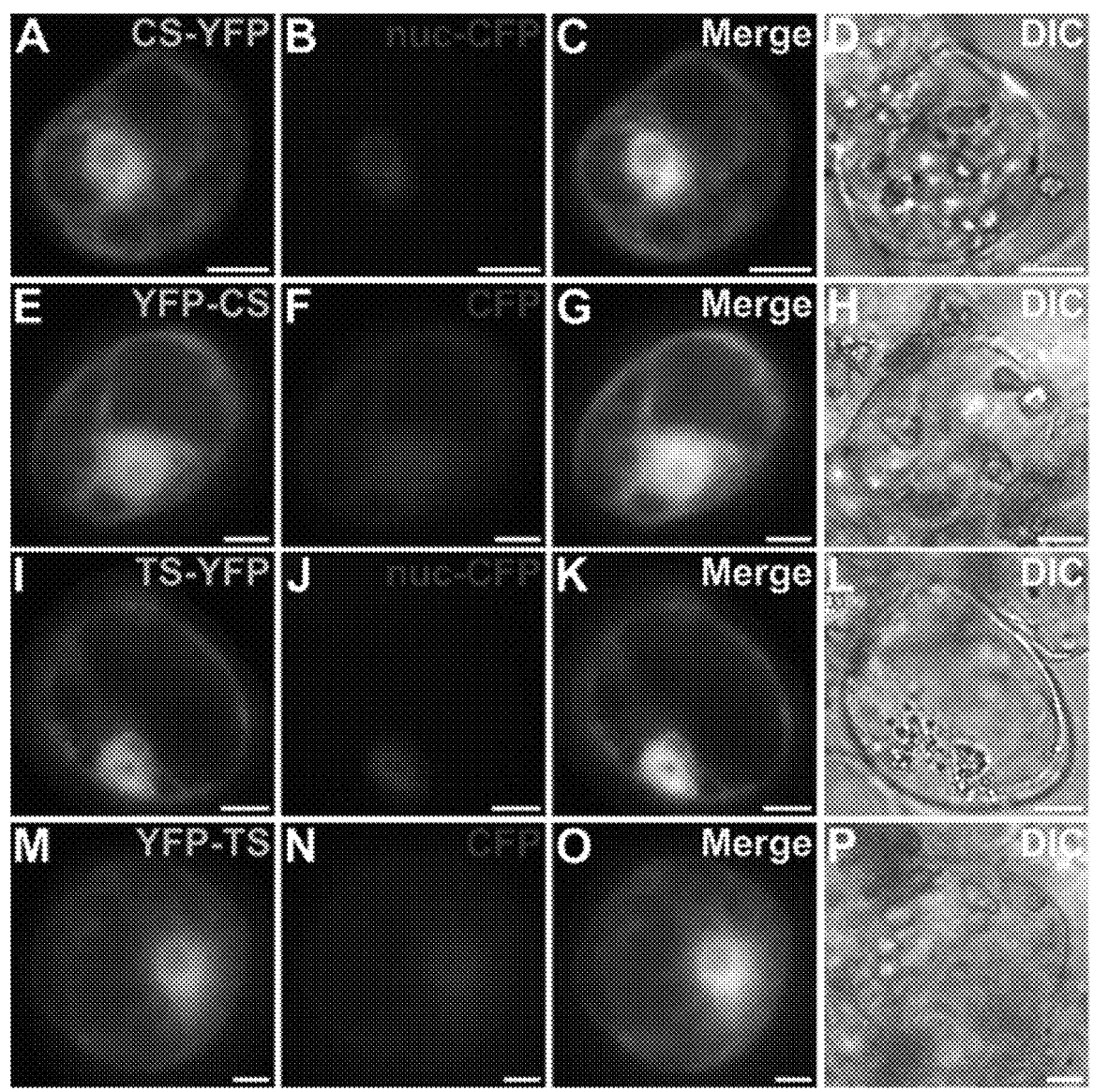

FIG. 24. Localization of CS and TS.

CS and TS both display nucleocytosolic localization. *C. roseus* cells were transiently co-transformed with plasmids expressing either CS-YFP (A), YFP-CS (E), TS-YFP (I) or YFP-TS (M) and the nuclear (nuc)-CFP marker (B, J) or the cytosolic CFP marker (F, N). Co-localization of the fluorescence signals appears when merging the two individual false colour images (C, G, K, O). Cell morphology is observed with differential interference contrast (DIC) (D, H, L, P). Scale bars, 10 µm.

Figure 25:
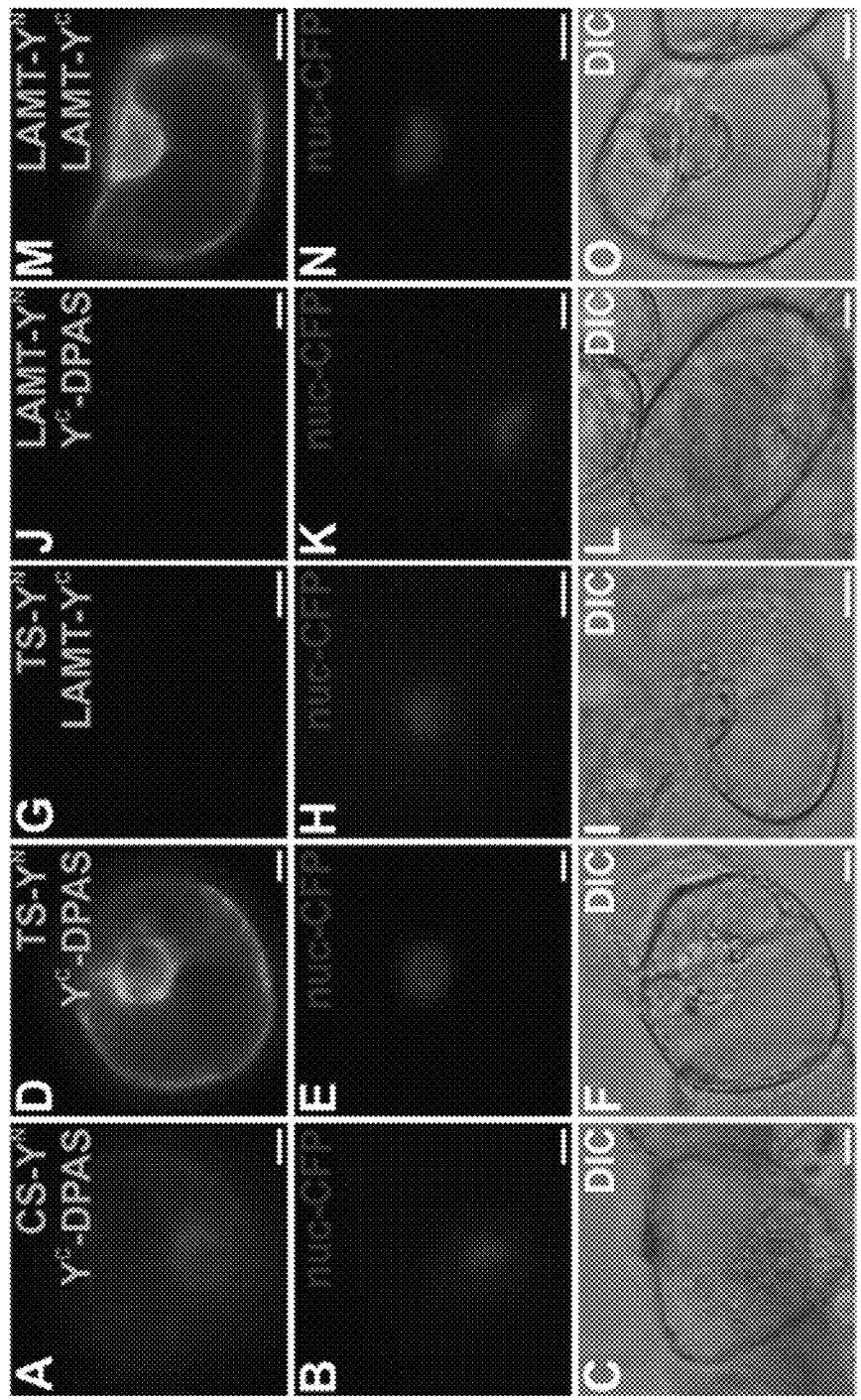

FIG. 25. Interaction of DPAS with TS and CS.

Interaction of DPAS with TS and CS. DPAS/CS and DPAS/TS interactions were analyzed by BiFC in *C. roseus* cells transiently transformed by distinct combinations of plasmids encoding fusions with the two split YFP fragments, YFPN (YN) and YFPC (YC) as indicated on each pictures of the first row (A, D, G, J, M). Identification of transiently transformed cells was achieved by co-transformation with the nucleus (nuc)-CFP marker (B, E, H, K, N). Efficient (TS-YN/YC-DPAS) and weak (CS-YN/YC-DPAS) reconstitutions of BiFC complexes revealed by fluorescence intensity reflect corresponding interaction levels. Interactions of DPAS and TS with loganic acid methyltransferase (LAMT)-YN and LAMT-YC were also studied to evaluate the specificity of DPAS/TS interactions. Cell morphology is observed with differential interference contrast (DIC) (C, F, I, L, O). Scale bars, 10 µm.

Figure 26A:
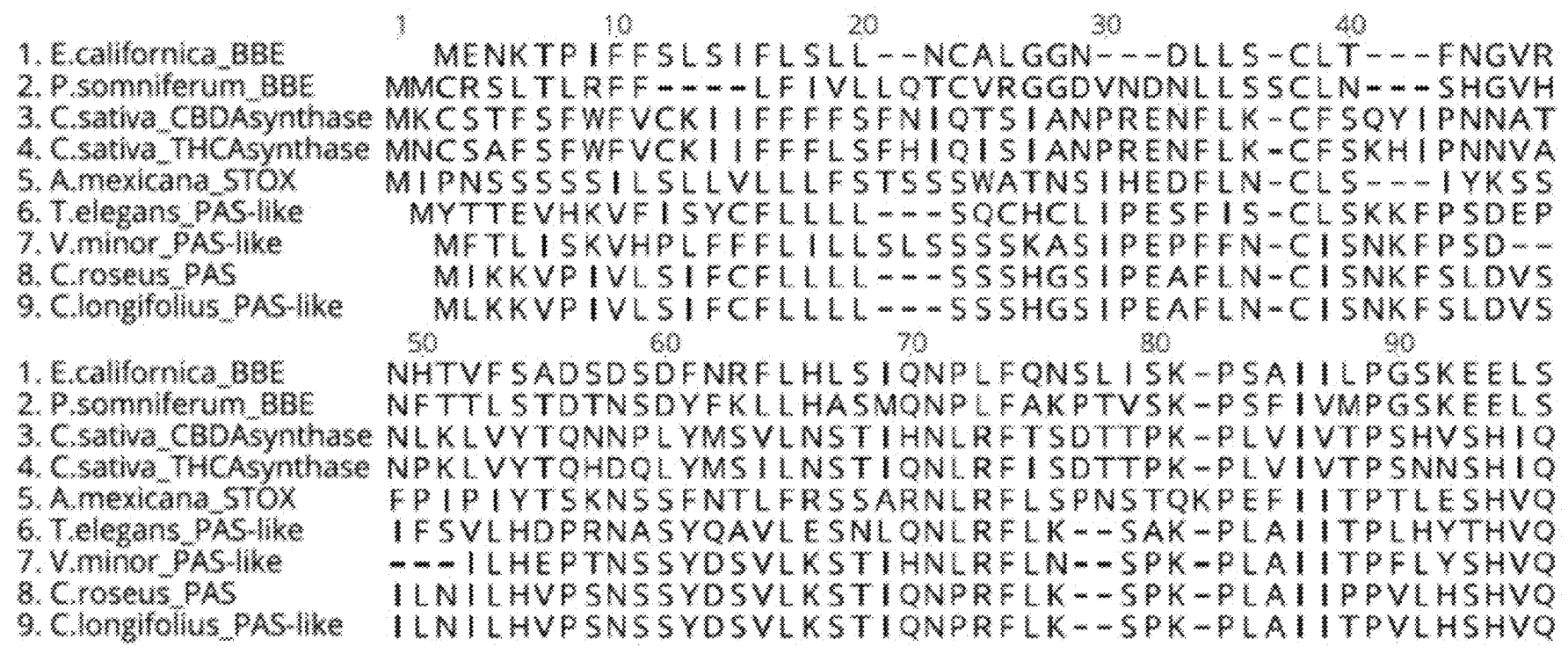

FIG. 26. Amino acid sequence alignment of PAS with other functionally characterized enzymes Amino acid sequence alignment (over parts A-F) of PAS with other functionally characterised berberine bridge enzymes and PAS-like proteins identified from other aspidosperma and iboga alkaloids producing plants. Boxes highlight the residues (His and Cys) involved in bicovalent attachment of the FAD in berberine bridge enzymes involved in benzylisoquinoline alkaloids that are mutated in PAS and other PAS-like enzymes identified in aspidosperma and iboga alkaloids producing plants. Alignment was performed using MUSCLE algorithm characterized berberine bridge enzymes and PAS-like proteins identified from other aspidosperma and iboga alkaloids producing plants. 1. SEQ ID NO: 58; 2. SEQ ID NO: 59; 3. SEQ ID NO: 60; 4. SEQ ID NO: 61; 5. SEQ ID NO: 62; 6. SEQ ID NO: 63; 7. SEQ ID NO: 64; 8. SEQ ID NO: 1; 9. SEQ ID NO: 65.

Figure 27:
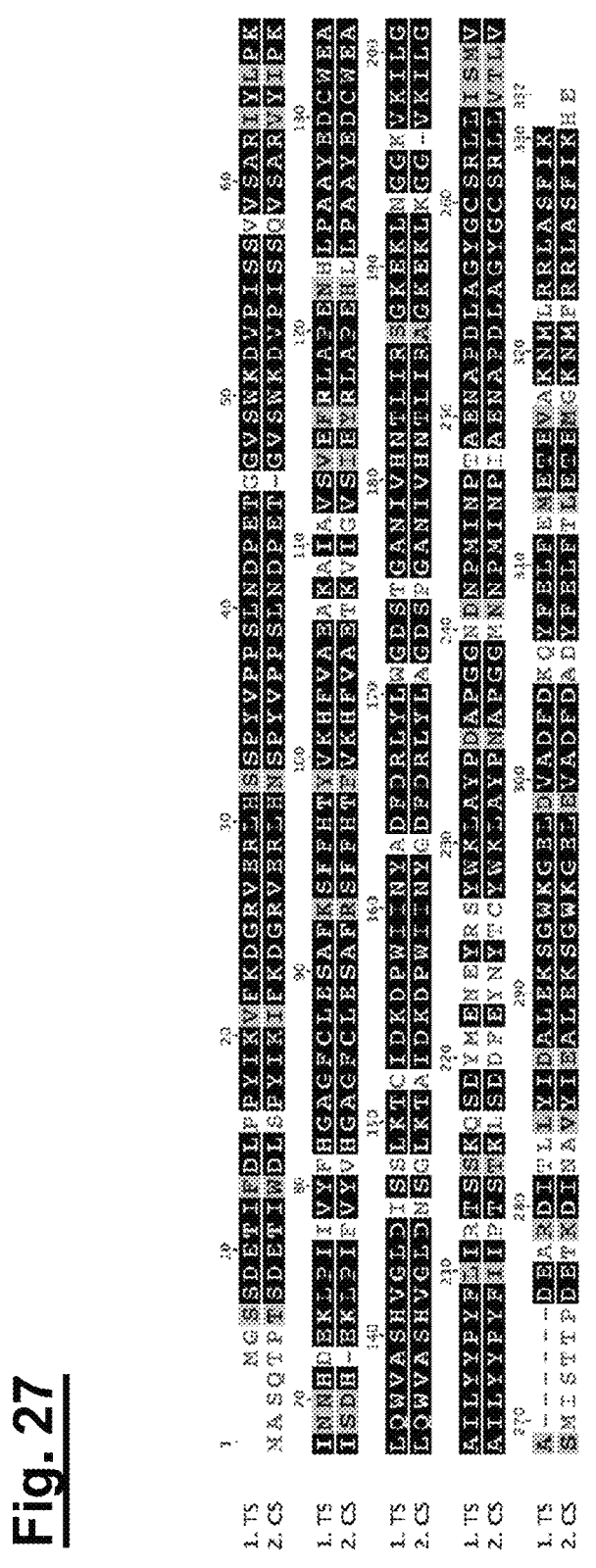

FIG. 27. Amino acid sequence alignment of CS and TS.

Amino acid sequence alignment of CS (SEQ ID NO: 3) and TS (SEQ ID NO: 4), Alignment was performed using MUSCLE algorithm.

FIG. 28. Biosynthesis of tabersonine 2 and catharanthine 3 from stemmadenine acetate 7 starting substrate.

A. Reconstitution in *N. benthamiana* from stemmadenine acetate 7. Extracted ion chromatograms for ions rniz 397.19 (stemmadenine acetate 7), m/z 395.19 (precondylocarpine acetate 10) and m/z 337.19 (catharanthine at RT 4.0 and tabersonine at RT 4.4 min) are shown. Plants infiltrated with the empty vector (EV) and PAS were able to convert 7 into 10 but no 2 or 3 were detected. Co-expression of PAS, DPAS and CS resulted in formation of 3. When PAS, DPAS and TS were combined together in the reaction, all initial substrate was converted to 2. Formation of 3 and 2 was validated by co-elution with commercial standards. Formation of 10 was validated by co-elution with the semi-synthetic compound. B. Interaction of CS and TS with DPAS by biomolecular fluorescence complementation (BiFC) in *C. roseus* cells. Efficiency of BiFC complex reformation reflected by YFP fluorescence intensity highlighted that CS and DPAS performed weak interactions (i-iii) while TS and DPAS strongly interacted (iv-vi). No interactions with loganic acid methyltransferase (LAMT) were observed (vii-ix). C. Phylogenetic relationship of PAS with other functionally characterized berberine bridge enzymes, PAS and PAS-like homologues identified in other Aspidosperma and iboga alkaloids producing plants form a separate cluster.

DETAILED DESCRIPTION OF THE INVENTION

In a first aspect the invention relates to a method for producing a terpene indole alkaloid derivative, comprising the steps of:
(1) providing a terpene indole alkaloid;
(2) providing:
  (a) a first enzyme having a first amino acid sequence comprising SEQ ID NO: 1 or a functional variant or homologue thereof; and/or
  (b) a second enzyme having a second amino acid sequence comprising SEQ ID NO: 2 or SEQ ID NO: 66, or a functional variant or homologue thereof;
(3) optionally also providing:
  (c) a third enzyme having an amino acid sequence comprising SEQ ID NO: 3 or a functional variant or homologue thereof; and/or
  (d) a fourth enzyme comprising an amino acid sequence comprising SEQ ID NO: 4 or a functional variant or homologue thereof; and
(4) contacting the terpene indole alkaloid with the first and/or second enzyme, and optionally also the third and/or fourth enzyme, under catalytic conditions to produce a terpene indole alkaloid derivative.

See Tables 1 and 2, FIG. 26 and the co-filed SEQUENCE LISTING for full sequence information.

The term "terpene indole alkaloid" encompasses a terpene indole alkaloid which have halogens (for example, fluorine) or other substituents on the indole ring.

The terpene indole alkaloid may be stemmadenine acetate.

The stemmadenine acetate may be contacted with the first enzyme and the terpene indole alkaloid derivative may be precondylocarpine acetate (which may be open or closed tautomer form). The stemmadenine acetate may be contacted with the first and second enzymes to produce dihydroprecondylocarpine acetate and/or catharanthine. Alternatively, the stemmadenine acetate may be contacted with the first, second and third enzymes and the terpene indole alkaloid derivative produced may be catharanthine. Alternatively, the stemmadenine acetate may be contacted with the first, second and fourth enzymes and the terpene indole alkaloid derivative produced may be tabersonine.

The terpene indole alkaloid may be precondylocarpine acetate. The precondylocarpine acetate may be contacted with the second enzyme and the terpene indole alkaloid derivative(s) produced may be dihydroprecondylocarpine acetate and/or catharanthine. Alternatively, the precondylocarpine acetate may be contacted with the second and third enzymes and the terpene indole alkaloid derivative produced may be catharanthine. Alternatively, the precondylocarpine acetate may be contacted with the first, second and fourth enzymes and the terpene indole alkaloid derivative produced may be tabersonine.

The terpenoid indole alkaloid may be dihydroprecondylocarpine acetate. The dihydroprecondylocarpine acetate may be contacted with the third enzyme and the terpene indole alkaloid derivative may be catharanthine. Alternatively, the dihydroprecondylocarpine acetate may be contacted with the fourth enzyme and the terpene indole alkaloid derivative may be tabersonine. Alternatively, the dihydroprecondylocarpine acetate may be contacted with the third and fourth enzymes and the terpene indole alkaloid derivatives may be tabersonine and catharanthine.

The first enzyme may be encoded by a first nucleotide comprising SEQ ID NO: 5, or a functional variant or homologue thereof. The first nucleotide may comprise the nucleotide sequence SEQ ID NO: 6.

The second enzyme may be encoded by a second nucleotide comprising SEQ ID NO: 7 or SEQ ID NO: 67, or a functional variant or homologue thereof.

The third enzyme may be encoded by a third nucleotide comprising SEQ ID NO: 9, or a functional variant or homologue thereof.

The fourth enzyme may be encoded by a fourth nucleotide comprising SEQ ID NO: 10, or a functional variant or homologue thereof.

The nucleotide(s) used in the method of the invention may be plant sequences. The plant sequences may be from an ibogaine-producing plant (for example, Tabernanthe iboga, also known as "iboga") and/or aspidosperma-producing plant, for example *Catharanthus roseus*.

The method of the invention may be performed in vivo, for example in planta. The terpene indole alkaloid may be provided by injection into the plant. The plant may be *Nicotiana benthamiana*.

The enzyme or enzymes used in the method of the invention may be provided by expression in vivo, for example heterologous expression.

The method of the invention may be performed in vitro, for example in an isolated plant cell. The plant cell may be a *Nicotiana benthamiana* cell. The method may alternatively be performed in yeast, for example *Pichia pastoris* or *Saccharomyces cerevisiae*. The method of the invention may alternatively be performed in bacteria, for example *E. coli*.

The enzyme or enzymes may be provided by expression, for example heterologous expression, in the yeast, bacteria or plant cell.

In another aspect, the invention relates to a method for producing a biologically active composition, comprising the steps of:
(1) providing a terpene indole alkaloid;
(2) providing:
  (a) a first enzyme having a first amino acid sequence comprising SEQ ID NO: 1 or a functional variant or homologue thereof; and/or
  (b) a second enzyme having a second amino acid sequence comprising SEQ ID NO: 2, or SEQ ID NO: 66 or a functional variant or homologue thereof;
(3) optionally also providing:
  (c) a third enzyme having an amino acid sequence comprising SEQ ID NO: 3 or a functional variant or homologue thereof; and/or
  (d) a fourth enzyme comprising an amino acid sequence comprising SEQ ID NO: 4 or a functional variant or homologue thereof;
(4) contacting the terpene indole alkaloid with the first and/or second enzyme, and optionally also the third and/or fourth enzyme, under catalytic conditions to produce a terpene indole alkaloid derivative; and
(5) converting the terpene indole alkaloid derivative into a biologically active composition.

In step (5), the converting may be enzymatic or synthetic.

The composition produced by the method of the invention may have anti-cancer activity, and may be, for example, vinblastine.

The methods of the invention may exclude naturally occurring processes, i.e. processes in which one or more of the recited enzymes of the invention are not provided.

The terpene indole alkaloid derivative may be tabersonine, wherein converting the tabersonine into vinblastine comprises the steps of:
(1) converting the tabersonine to vindoline; and
(2) synthetically and/or enzymatically coupling the vindoline with catharanthine to produce vinblastine.

The composition may have anti-diabetic activity, and may be, for example, conophylline.

The composition may be a vasodilator, and may be, for example, vincamine.

The composition may have anti-addiction activity, and may be, for example, ibogaine.

In another aspect, the invention relates to a kit comprising:
(1) a first enzyme having a first amino acid sequence comprising SEQ ID NO: 1 or a functional variant or homologue thereof; and optionally also comprising:
(2) a second enzyme having a second amino acid sequence comprising SEQ ID NO: 2, or SEQ ID NO: 66 or a functional variant or homologue thereof;
(3) a third enzyme having an amino acid sequence comprising SEQ ID NO: 3 or a functional variant or homologue thereof; and/or
(4) a fourth enzyme comprising an amino acid sequence comprising SEQ ID NO: 4, or a functional variant or homologue thereof.

In another aspect, the invention relates to an isolated enzyme having an amino acid sequence comprising SEQ ID NO: 1, or a functional variant or homologue thereof.

In another aspect, the invention relates to an isolated nucleic acid having a nucleotide sequence comprising SEQ ID NO: 5, or a functional variant or homologue thereof.

In another aspect, the invention relates to an expression vector encoding an enzyme having an amino acid sequence comprising SEQ ID NO: 1, or a functional variant or homologue thereof, and optionally also encoding: a second enzyme having an amino acid sequence comprising SEQ ID NO: 2 or SEQ ID NO: 66, or a functional variant or homologue thereof; and/or a third enzyme having an amino acid sequence comprising SEQ ID NO: 3 or a functional variant or homologue thereof; and/or a fourth enzyme comprising an amino acid sequence comprising SEQ ID NO: 4 or a functional variant or homologue thereof.

The expression vector may include an artificial regulatory sequence.

In another aspect, the invention relates to a host cell comprising a nucleic acid having a nucleotide sequence comprising SEQ ID NO: 5, or a functional variant or homologue thereof, and/or an expression vector according to the invention.

In another aspect, the invention relates to a host cell which has been genetically modified to express the enzyme of the invention and optionally also to express: a second enzyme having an amino acid sequence comprising SEQ ID NO: 2 or SEQ ID NO: 66, or a functional variant or homologue thereof; and/or a third enzyme having an amino acid sequence comprising SEQ ID NO: 3 or a functional variant or homologue thereof; and/or a fourth enzyme comprising an amino acid sequence comprising SEQ ID NO: 4 or a functional variant or homologue thereof.

The host cell may be a yeast cell such as a *Pichia pastoris* cell, or a plant cell, for example a *Nicotiana benthamiana* cell.

In another aspect, the invention relates to a genetically modified plant comprising the nucleic acid of the invention and/or the expression vector of the invention.

In another aspect, the invention relates to a plant which has been gene edited to express the enzyme of the invention, and optionally also gene edited to express: a second enzyme having an amino acid sequence comprising SEQ ID NO: 2 or SEQ ID NO: 66, or a variant, homologue, or functional variant thereof; and/or a third enzyme having an amino acid sequence comprising SEQ ID NO: 3 or a functional variant or homologue thereof; and/or a fourth enzyme comprising an amino acid sequence comprising SEQ ID NO: 4 or a functional variant or homologue thereof. The plant may be *Nicotiana benthamiana*.

The present invention also encompasses identification or selection of organisms such as plants with modified activity of one or more of the enzymes described herein. Markers for such identification or selection may be developed using methods known in the art from the nucleic acid sequences described herein.

As used herein, a "functional variant or homologue" is defined as a polypeptide or nucleotide with at least 50% sequence identity, for example at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity with the reference sequence.

Sequence identity between nucleotide or amino acid sequences can be determined by comparing an alignment of the sequences. When an equivalent position in the compared sequences is occupied by the same base or amino acid, then the molecules are identical at that position, Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector, Examples include MatGat (Campanella et al., 2003, BMC Bioinformatics 4: 29; program available from http://bitincka.com/ledion/matgat), Gap (Needleman & Wunsch, 1970, J. Mol. Biol. 48: 443-453), FASTA (Altschul et al., 1990, J. Mol. Biol. 215: 403-410; program available from http://www.ebi.ac.uk/fasta), Clustal W 2.0 and X 2.0 (Larkin et al., 2007, Bioinformatics 23: 2947-2948; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley; programs available from http://www.ebi.ac.uk/tools/emboss/align). All programs may be run using default parameters.

For example, sequence comparisons may be undertaken using the "Needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62, Default parameters for nucleotide sequence comparisons ("DNA Molecule" option) may be Gap Extend penalty: 0.5, Gap Open penalty: 10.0, Matrix: DNAfull.

In one aspect of the invention, the sequence comparison may be performed over the full length of the reference sequence.

Particular non-limiting embodiments of the present invention will now be described in detail.

EXAMPLES

Example 1

Introduction

The biochemistry required for tabersonine 2 and catharanthine 3 formation from the known alkaloid intermediate stemmadenine 1 is described below.

Results

It has been hypothesized that catharanthine 3 (iboga-type alkaloid) and tabersonine 2 (aspidosperma-type) scaffolds are generated by dehydration of the known biosynthetic intermediate stemmadenine 1 to dehydrosecodine 9, which can then cyclize to either catharanthine 3 or tabersonine 2 via a net [44-2] cycloaddition reaction (Scheme 2A). Since the dehydration product dehydrosecodine 9 is highly unstable, we though that it would be too reactive to diffuse from an enzyme active site without decomposing. Therefore, we concluded that the dehydration and cyclization reactions would be catalyzed by a single enzyme.

Figure 1B:
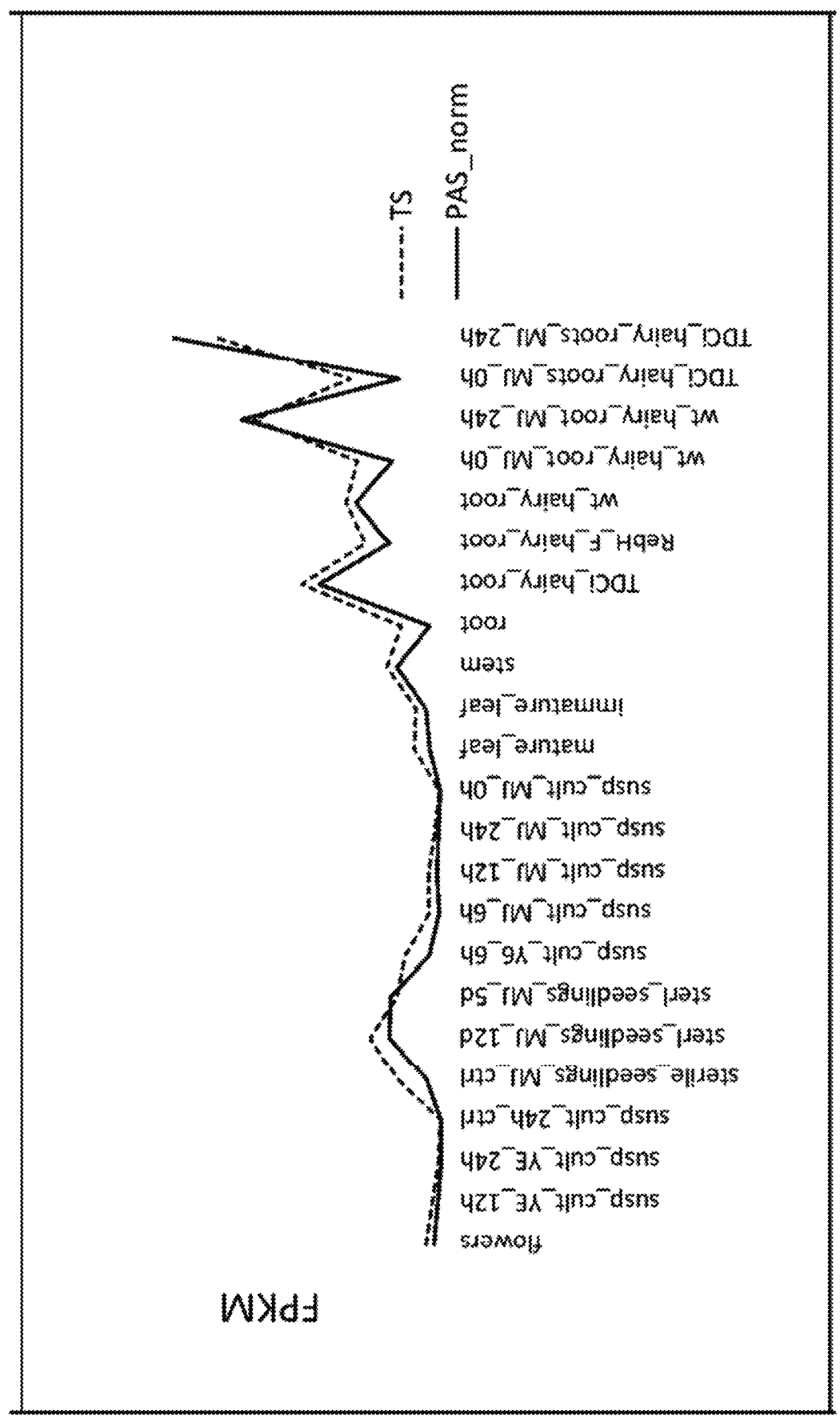
FIG. 1. Co-expression analysis for biosynthetic gene candidates.

Since the biosynthetic genes for vincristine 5 and vinblastine 6 are not clustered in the plant aenome, RNA-seq data was searched for gene candidates in RNA-sea data from the vincristineivinblastine producing plant *Catharanthus roseus*. These data revealed that a gene annotated as 2-hydroxyisoflavanone dehydratase shared a similar co-expression profile with previously identified vinblastine pathway genes (FIG. 1). In addition, further analysis revealed the existence of a close homologue (80% amino acid identity) that has low expression levels in all the tissues included in the RNA-seq experiment. These dehydratase genes were selected as candidates to be tested using virus-induced gene silencing (VIGS) in *C. roseus*. Silencing of the highly expressed gene, herein named Tabersonine Synthase (TS), caused a substantial decrease in the accumulation of tabersonine 2 (p=0.0048) and vindoline 4 (p=0.02) (Scheme 1, FIG. 2), the major tabersonine-derived alkaloid in *C. roseus* leaves, while silencing of the gene expressed at lower levels, herein named Catharanthine Synthase (CS), resulted in a statistically significant decrease in catharanthine (p=0.01) and in an increase of vindoline (p=0.01) (FIG. 3).

These silencing experiments therefore strongly support the involvement of CS and TS in catharanthine 3 and tabersonine 2 biosynthesis in *C. roseus*. However, when CS and TS were heterologously expressed in *E. coli* (FIG. 4A) and tested for reactivity with stemmadenine 1, no reaction occurred. Previous work showed that certain monoterpene indole alkaloids with similar scaffolds have a propensity to spontaneously deformylate. It was speculated, particularly given the abundance of acetyl-transferases in the RNA-seq dataset (FIG. 1 B), that an acetylated version of stemmadenine 1, in which deformylation would be hindered, is the actual substrate for CS and/or TS (Scheme 2B). This compound could be readily synthesized from stemmadenine 1 (FIGS. 5 and 6, Tables 4 and 5), but stemmadenine acetate 7 was also not turned over by CS or TS. Frequently, when a gene is silenced in planta, the substrate of the corresponding enzyme will accumulate. However, no new compound that accumulated in the tissue of the silenced plants was detected, so in this case, gene silencing provided no clues to the identity of the CS/TS substrate(s).

An attempt was made to isolate the active substrate for the TS and CS enzymes from various aspidosperma- and ibogaalkaloid producing plants using enzyme-assay guided fractionation. *Tabernaemontana* plants were used, as they are known to accumulate more stemmadenine 1 intermediate relative to the downstream alkaloids, in the hope that these plants would accumulate more of the TS/CS substrate for purification. These experiments demonstrated that TS and CS were always active with the same fractions (FIG. 7), consistent with the hypotheses that both enzymes utilize the same substrate. However, attempts to structurally characterize the substrate were complicated by the rapid decomposition of the molecule, and the deformylated product tubotaiwine 12 was the major compound detected by NMR (Scheme 2B, Fig. 8, Table 7). Given the propensity for deformylation in these structural systems, it was rationalized that tubotaiwine 12 could be the result of the actual substrate, which would correspond to iso-stemmadenine 8 (dihydroprecondylocarpine) or its protected form (dihydroprecondylocarpine acetate 11) (Scheme 2B). Both dihydroprecondylocarpine 8 and dihydroprecondylocarpine acetate 11 are susceptible to fragmentation, and would not be expected to accumulate in TS/CS-silenced tissues, consistent with our VIGS experiments. However, with a lead for the identity of the TS/CS substrate in hand, it was surmised that a coupled oxidation-reduction cascade could perform a net isomerization to generate dihydroprecondylocarpine 8 (or dihydroprecondylocarpine acetate 11) from stemmadenine 1 (or stemmadenine acetate 7). The RNA-seq dataset was examined for two redox enzymes that could convert stemmadenine acetate 7 to dihydroprecondylocarpine acetate 11.

It was noted that a gene annotated as reticuline oxidase had low absolute expression levels, but a similar tissue expression pattern to the TS gene (FIG. 1C), identified by using a self-organizing map algorithm. The chemistry of previously reported reticuline oxidase enzymes, such as berberine bridge enzyme and dihydrobenzophenanthridine oxidase, suggests that these enzymes are capable of C—N bond oxidation, which is what would be required in this reaction sequence (Scheme 2B). When this oxidase gene was silenced in *C. roseus*, a compound with a mass and $^1$H NMR spectrum corresponding to semi-synthetically prepared stemmadenine acetate 7 (the proposed oxidase substrate) accumulated, suggesting that this gene encoded the correct oxidase, and was thus named precondylocarpine acetate synthase (PAS) (FIGS. 9-11). Similarly, silencing of a medium chain alcohol dehydrogenase, as part of an ongoing screen of alcohol dehydrogenase function in *C. roseus* metabolism, resulted in accumulation of a compound with a mass, retention time and fragmentation pattern consistent with a partially characterized synthetic standard of precondylocarpine acetate 10 (the proposed reductase substrate) (FIGS. 12-14; Table 6). This standard could be synthesized from stemmadenine acetate 7 using Pt and $O_2$, yields were low and variable, and the product decomposed during characterization. However, the limited 2D NMR data set was consistent with an assignment of precondylocarpine acetate 10. Thus, this alcohol dehydrogenase was renamed dihydroprecondylocarpine acetate synthase (DPAS). Collectively, these silencing data strongly suggest that PAS and DPAS act in concert with CS or TS to generate catharanthine 3 and tabersonine 2.

Figure 4A:
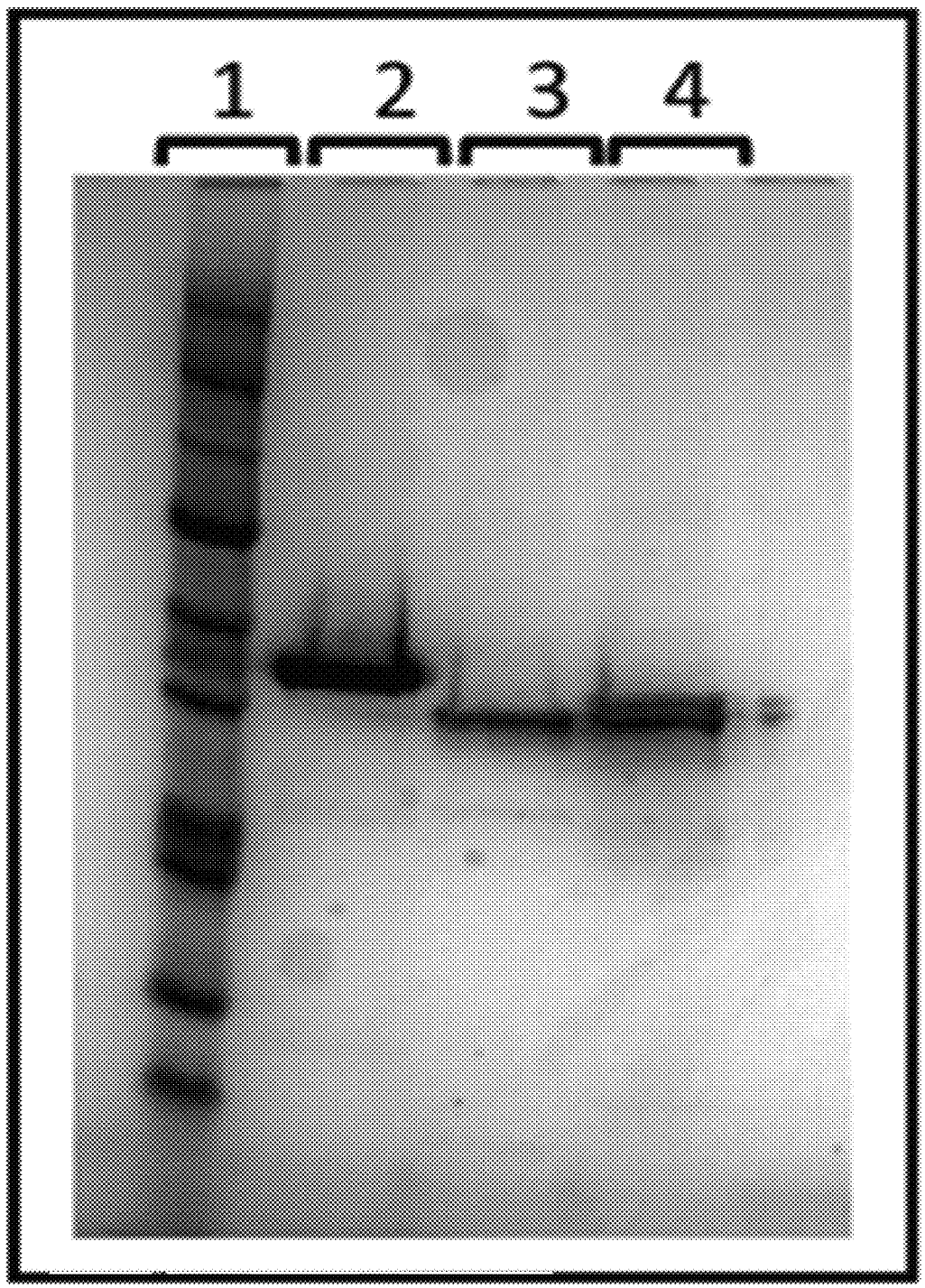
Figure 4B:
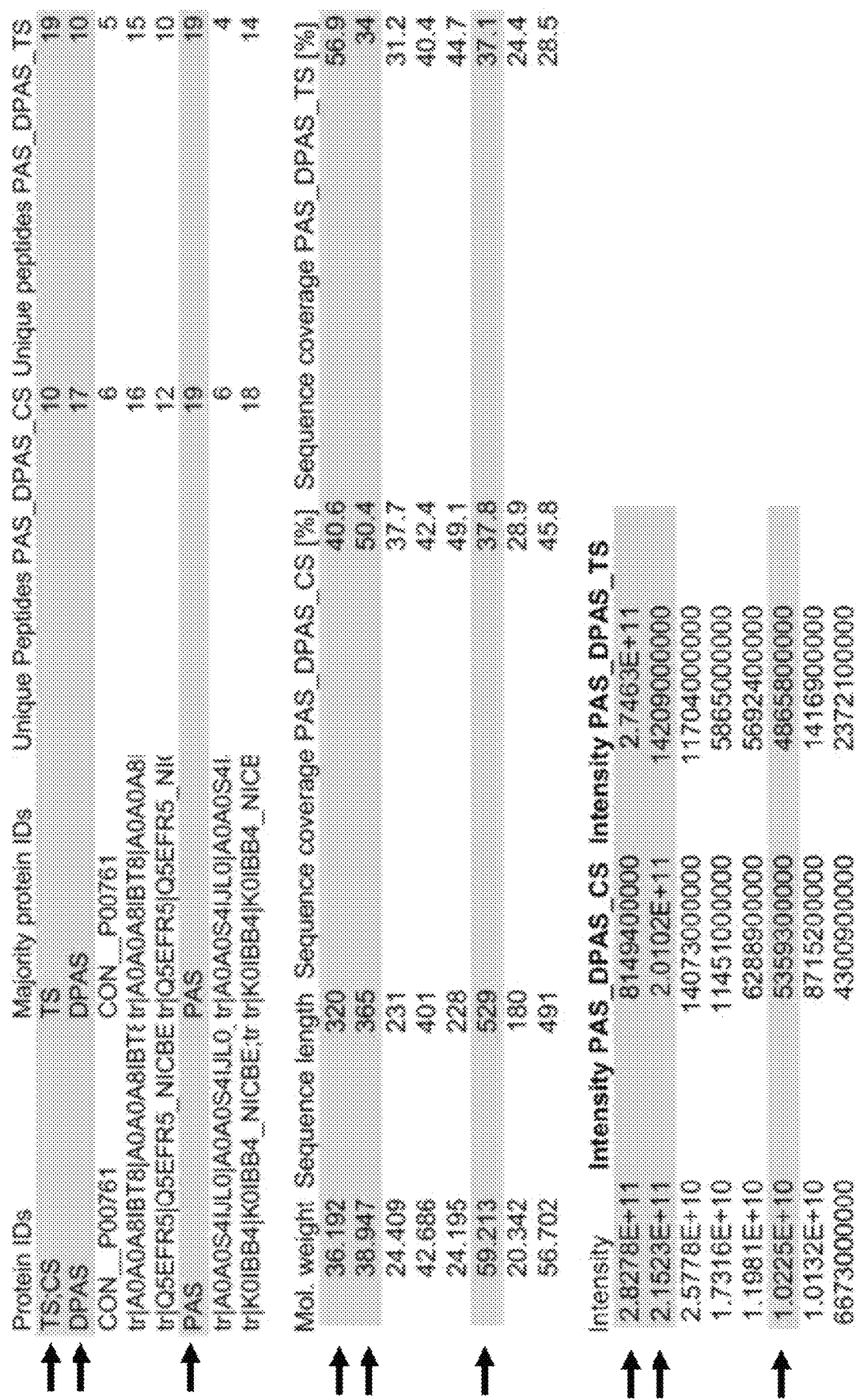
Figure 28A:
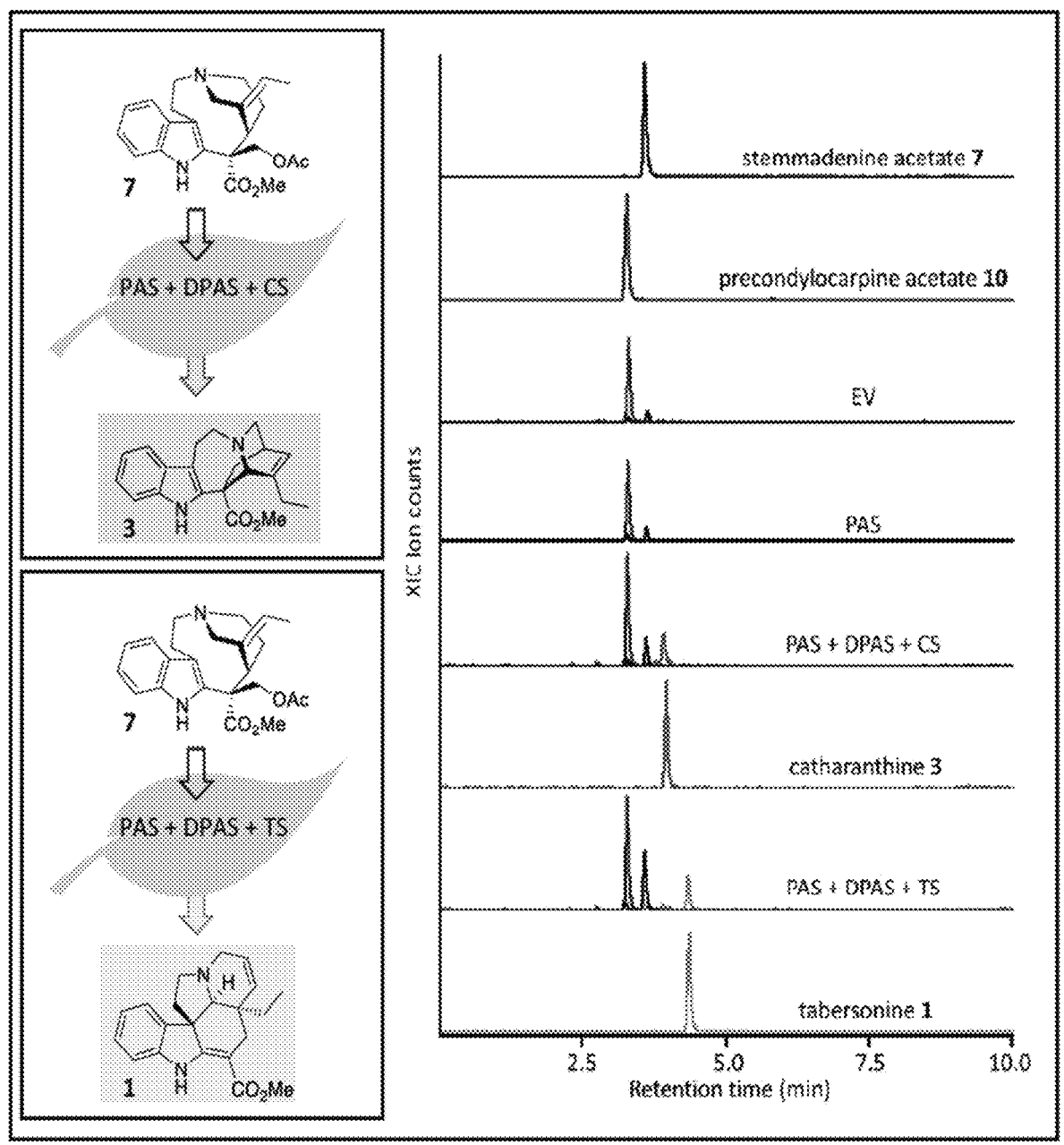

To validate whether these enzymes produce catharanthine 3 and tabersonine 2, PAS, DPAS and CS or TS were transiently co-expressed in the presence of stemmadenine acetate 7 in *Nicotiana benthamiana*, a convenient plant expression host. These experiments illustrated the sequential activity of the newly discovered enzymes, whereby the formation of catharanthine 3 with plant tissue expressing PAS/DPAS/CS was observed, as well as tabersonine 2 with experiments containing PAS/DPAS/TS, when the leaf was also co-infiltrated with stemmadenine acetate 7 (FIG. 28A). The presence of all proteins was validated by proteomics analysis (FIG. 4B). Formation of precondylocarpine acetate 10 was observed when stemmadenine acetate 7 was infiltrated into *N. benthamiana* in the absence of any heterologous enzymes (FIG. 28A), suggesting that an endogenous redox enzyme(s) of *N. benthamiana* can oxidize stemmadenine acetate 7.

In addition to serving as the precursors for vincristine 5 and vinblastine 6, tabersonine 2 and catharanthine 3 are precursors for dozens of other biologically active alkaloids (Scheme 1B).

Figure 4C:
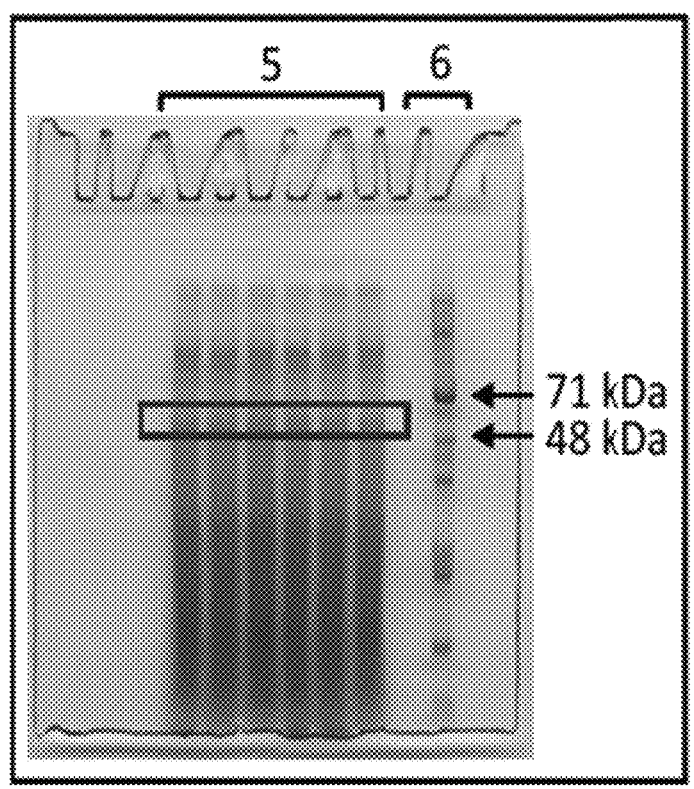
Figure 4D:
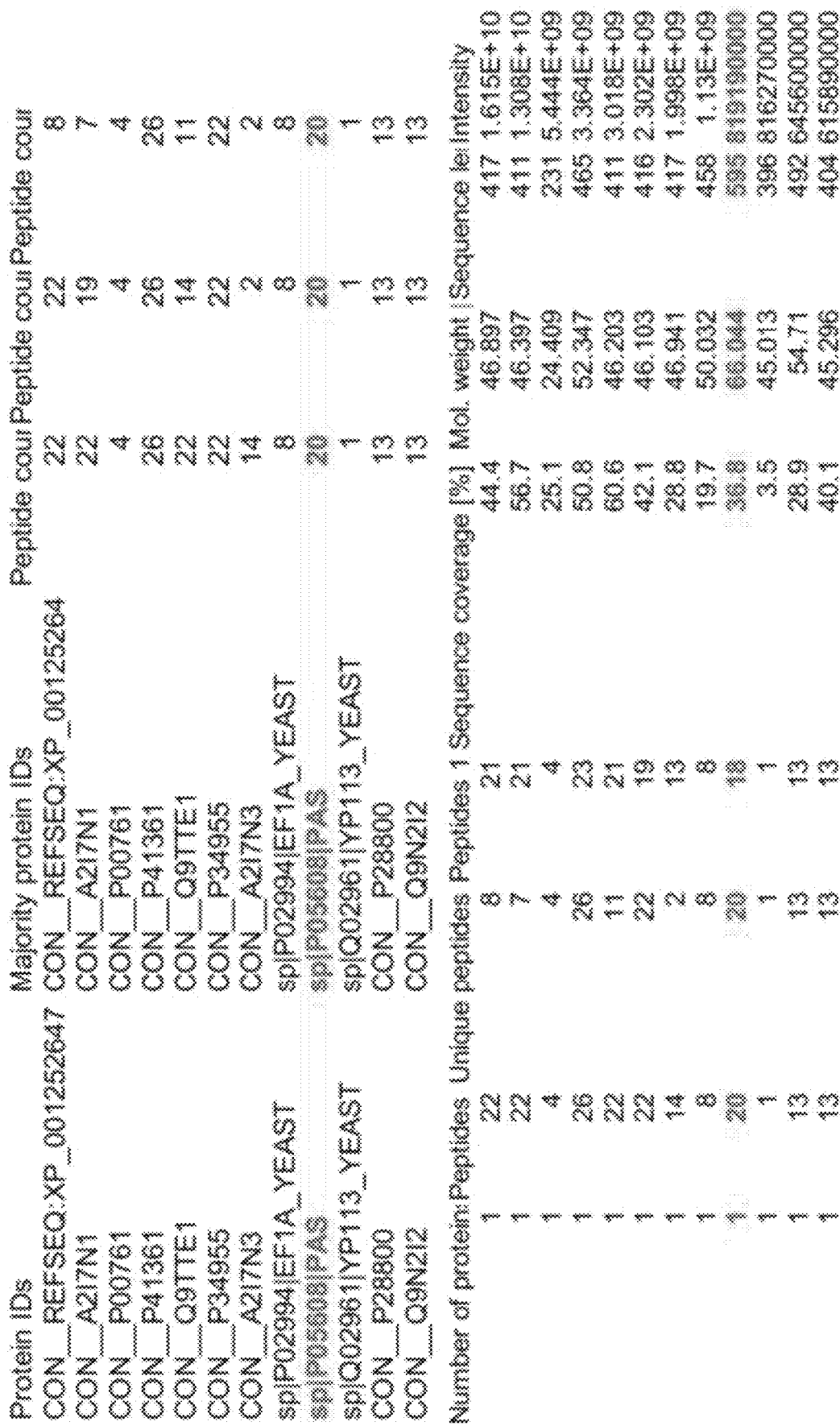
Figure 5A:
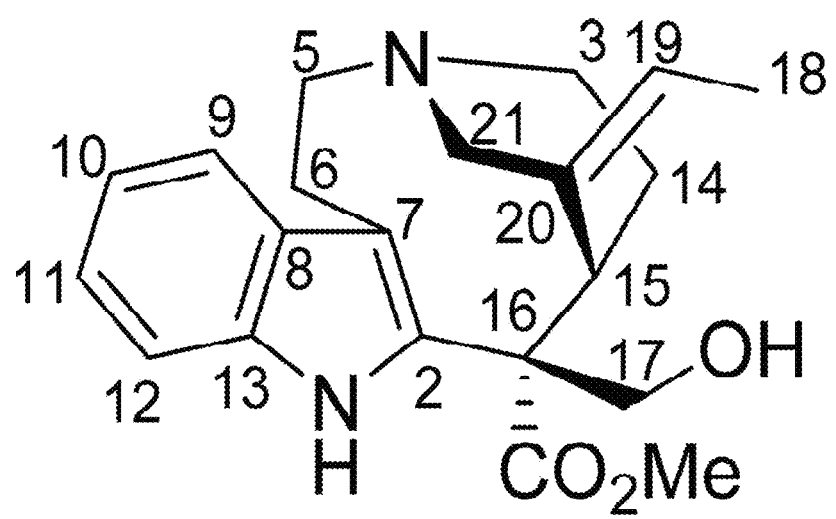
Figure 5B:
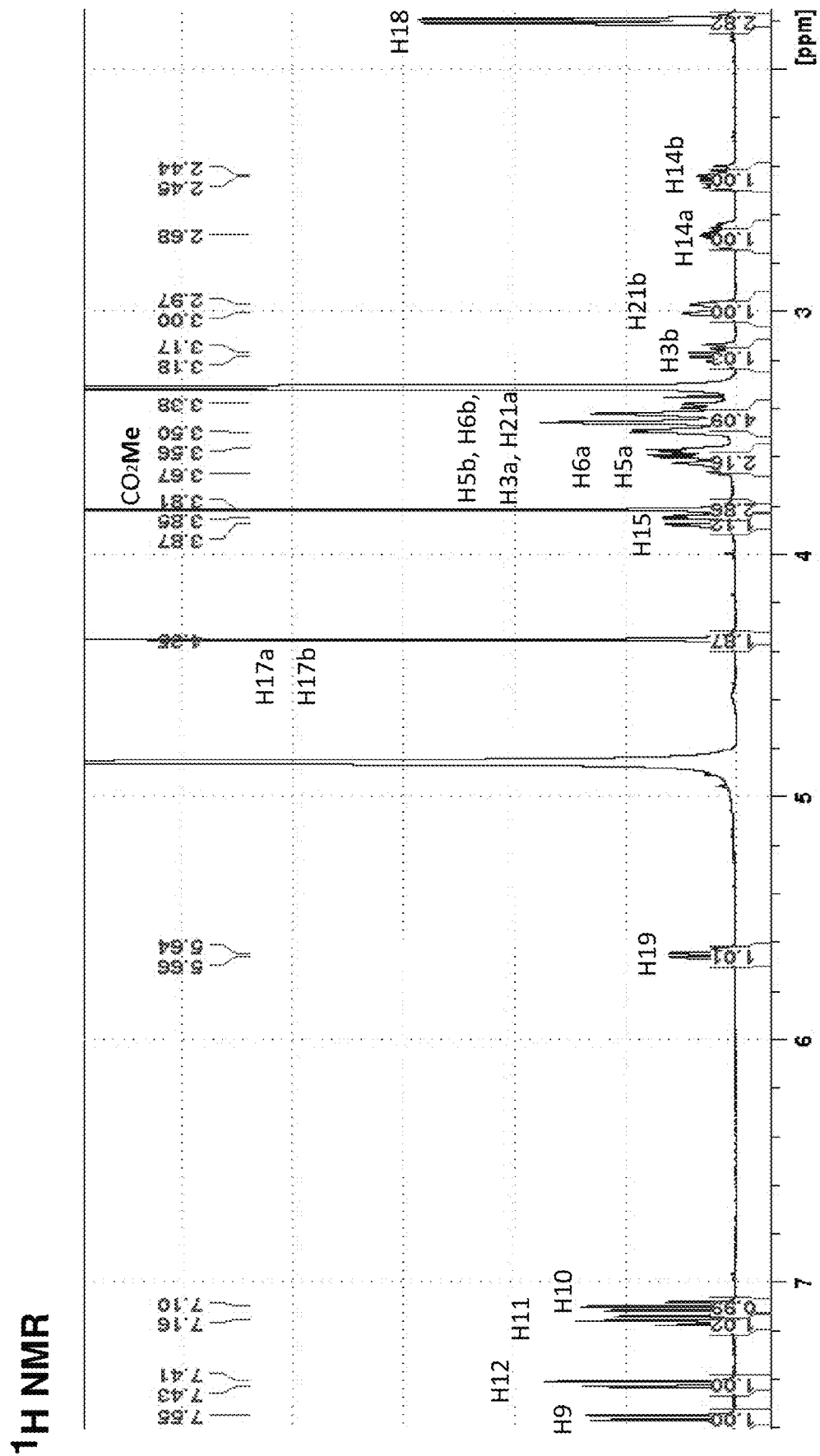
Figure 5C:
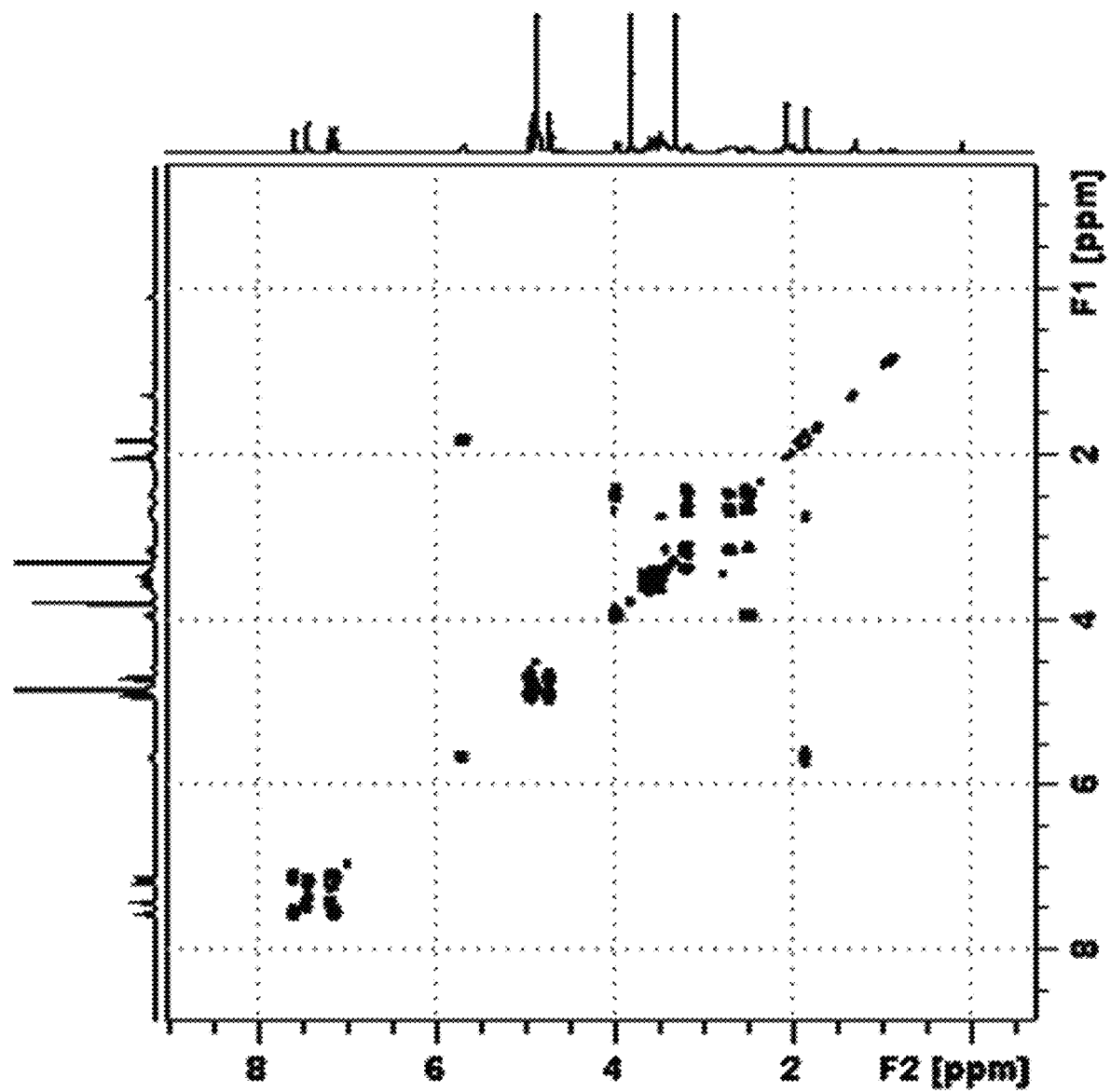
Figure 5D:
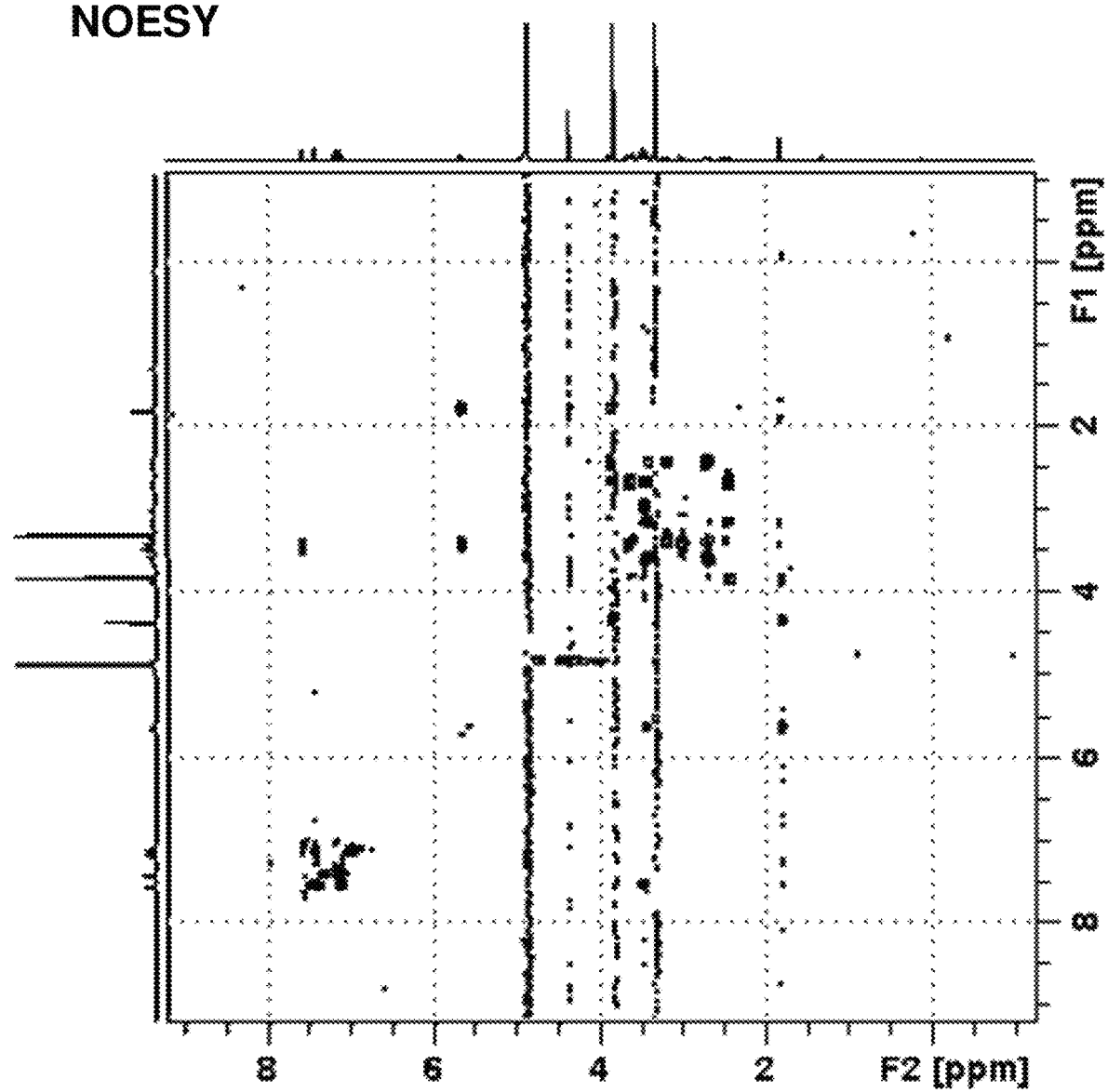
Figure 5E:
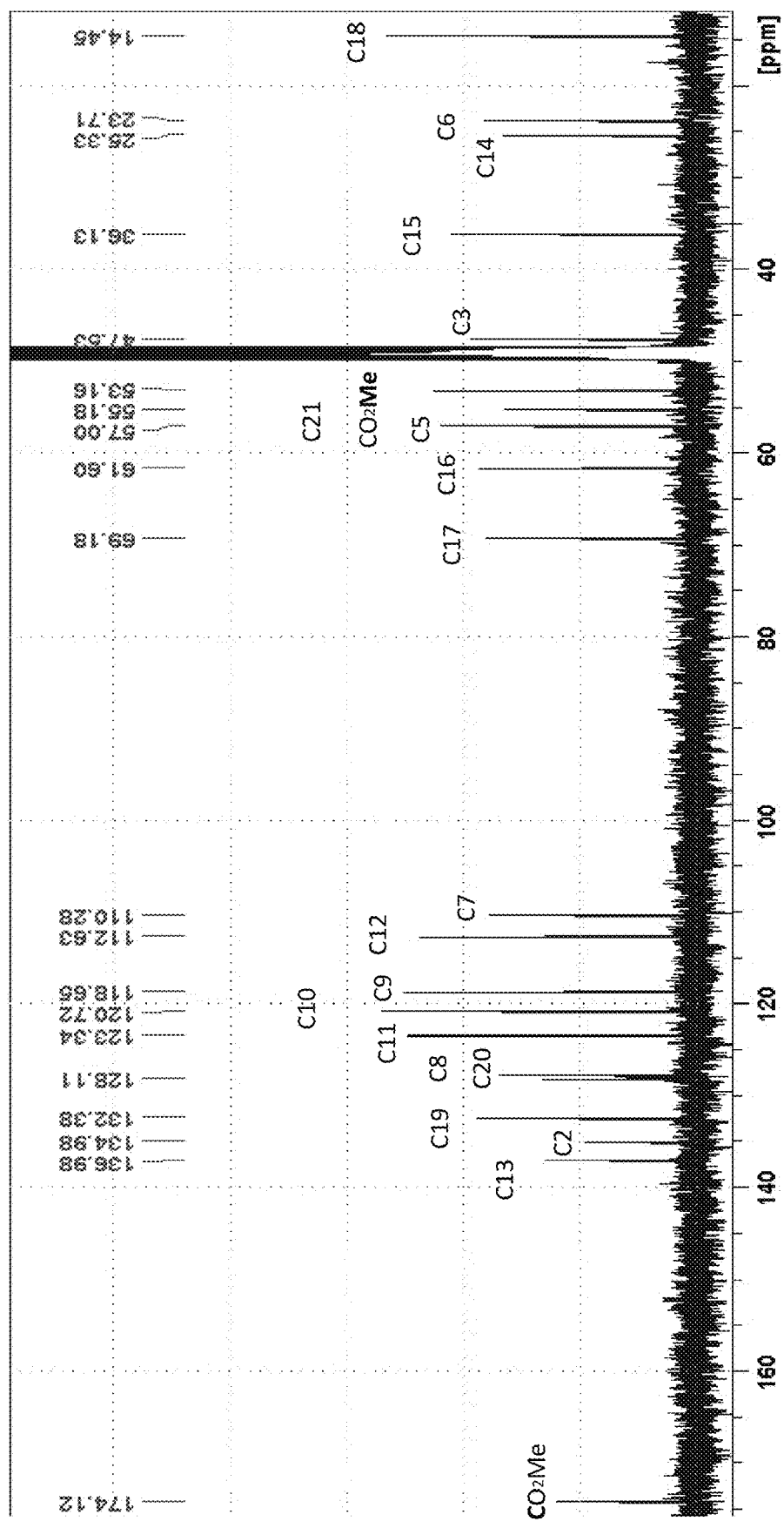
Figure 5F:
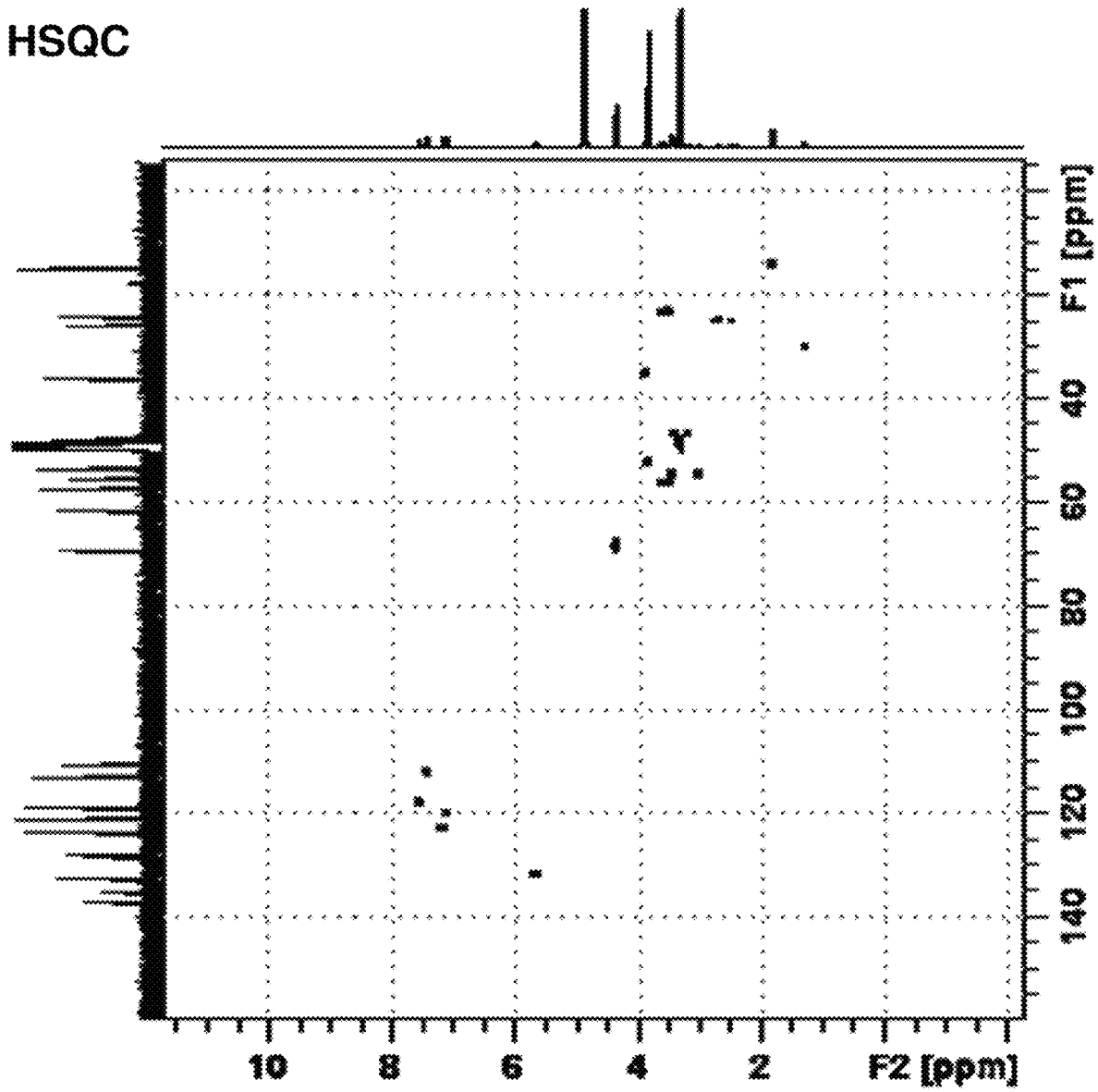
Figure 5G:
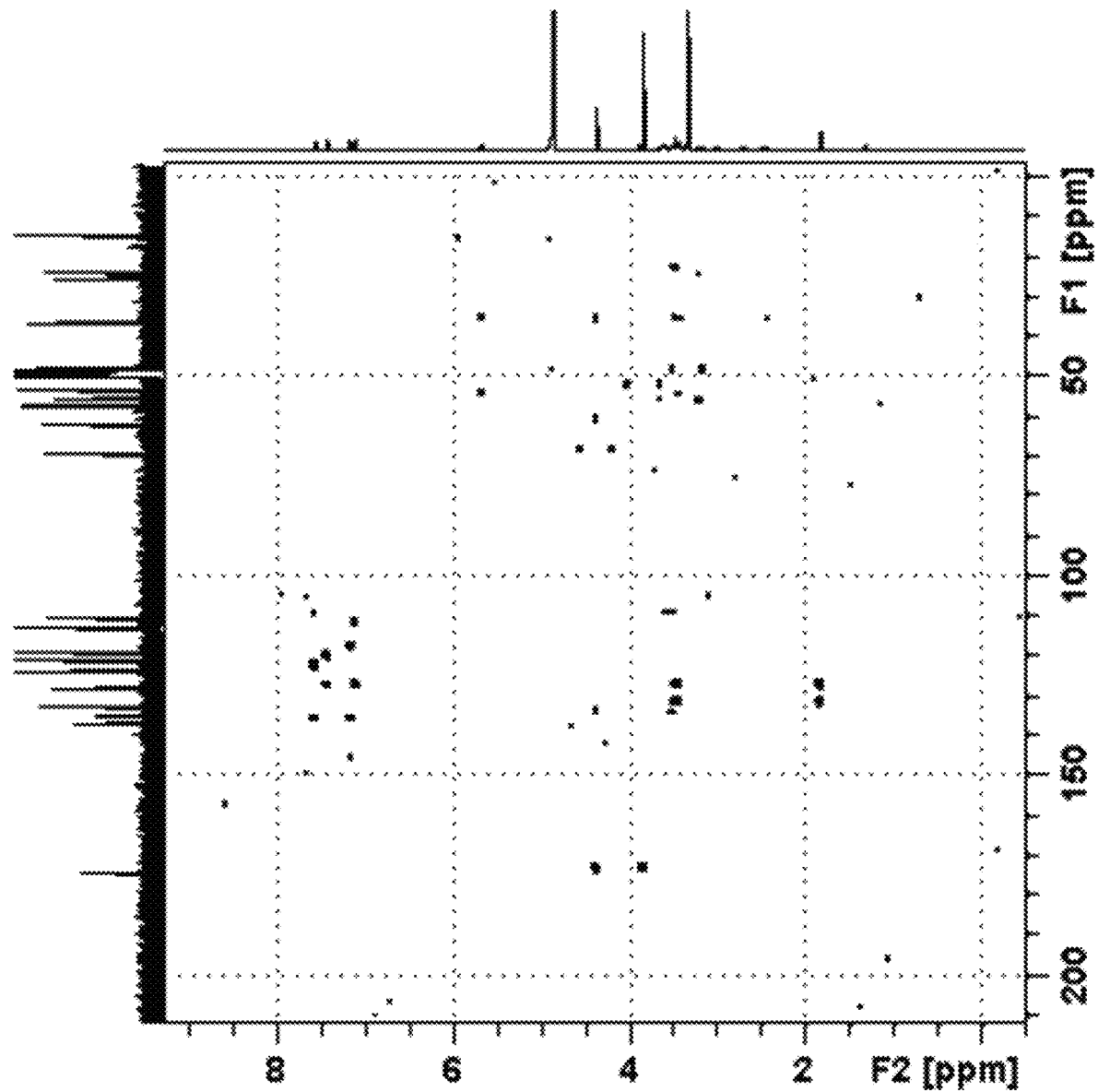
Figure 6A:
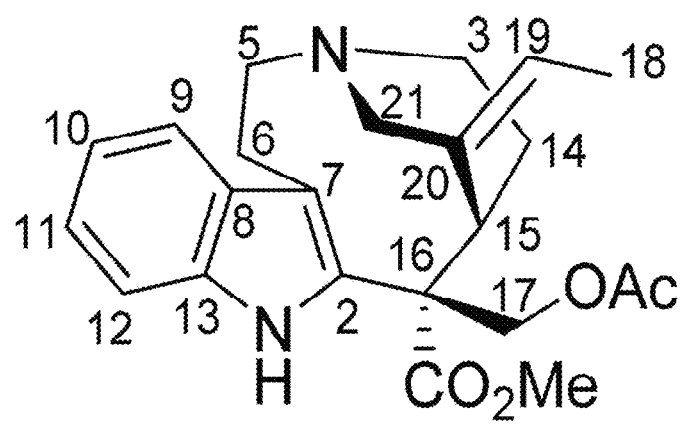
Figure 6B:
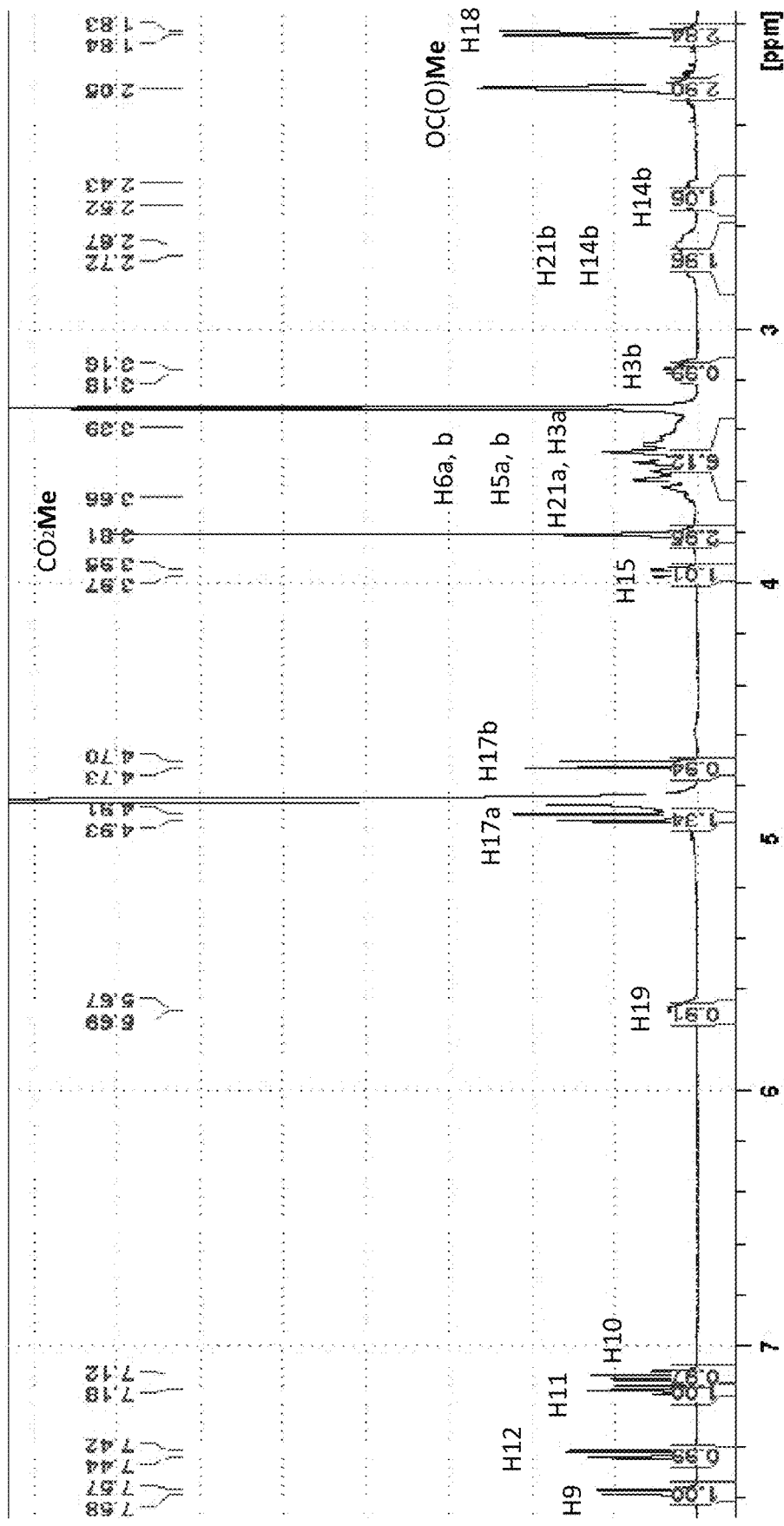
Figure 6C:
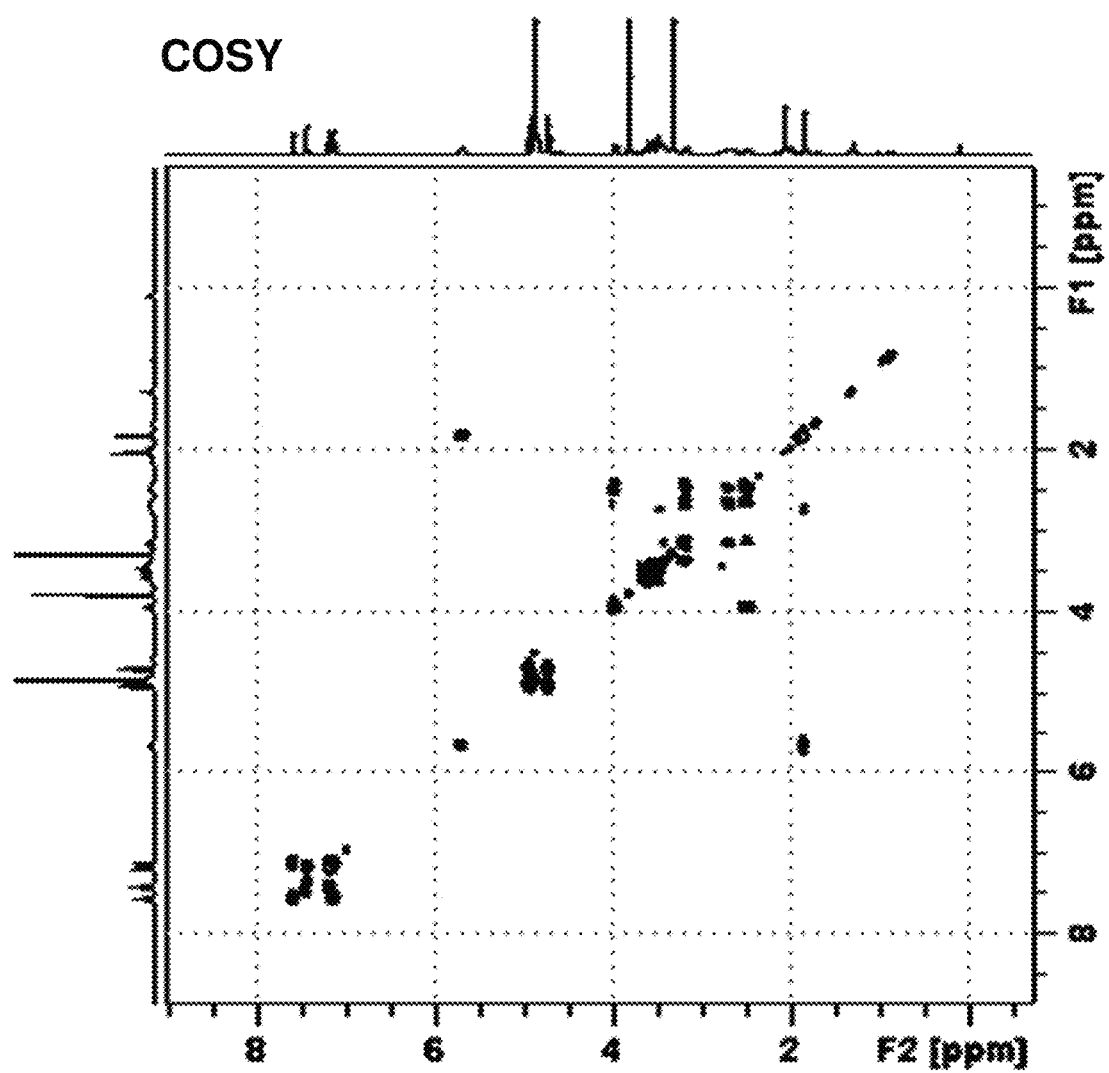
Figure 6D:
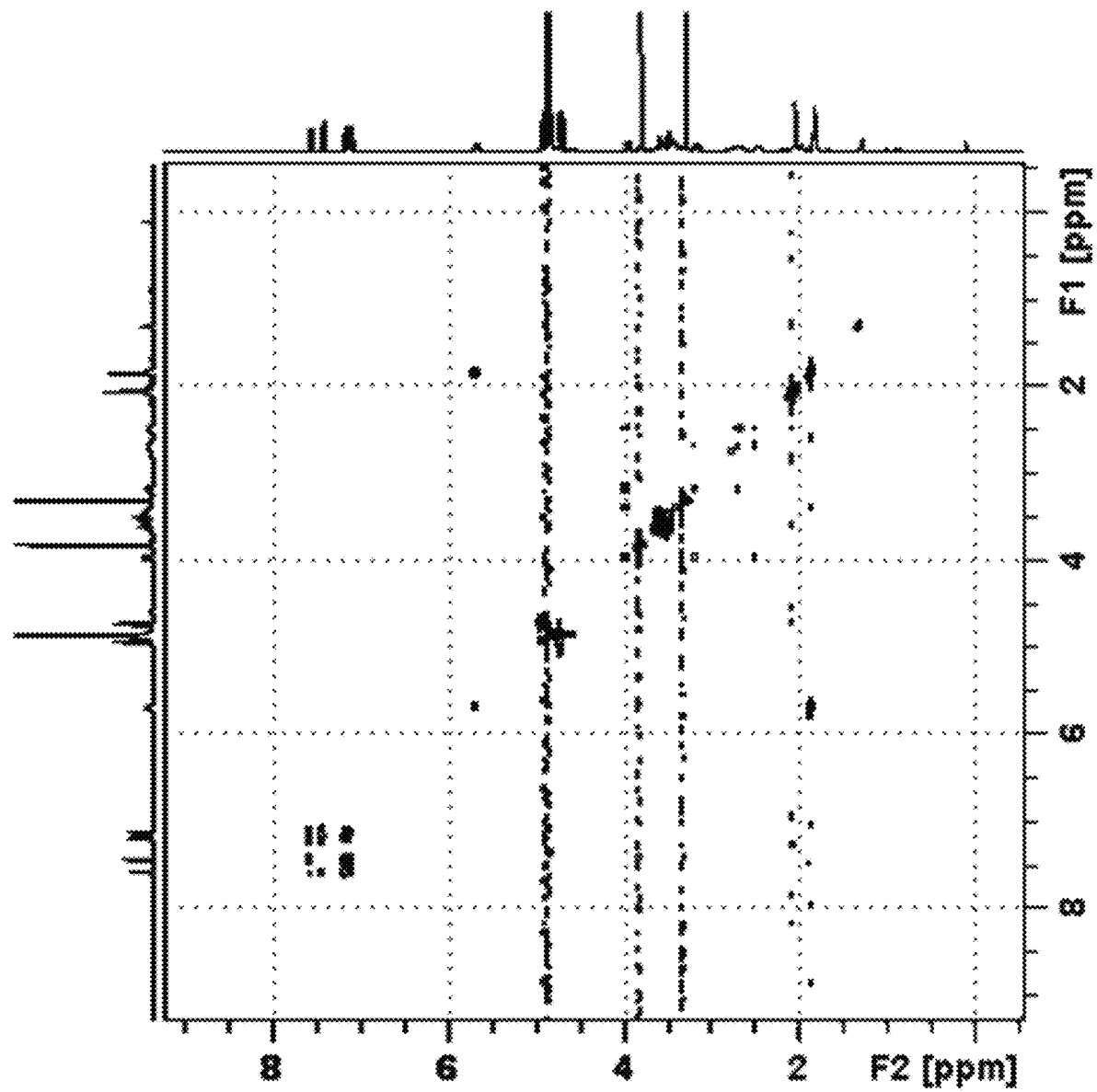
Figure 6E:
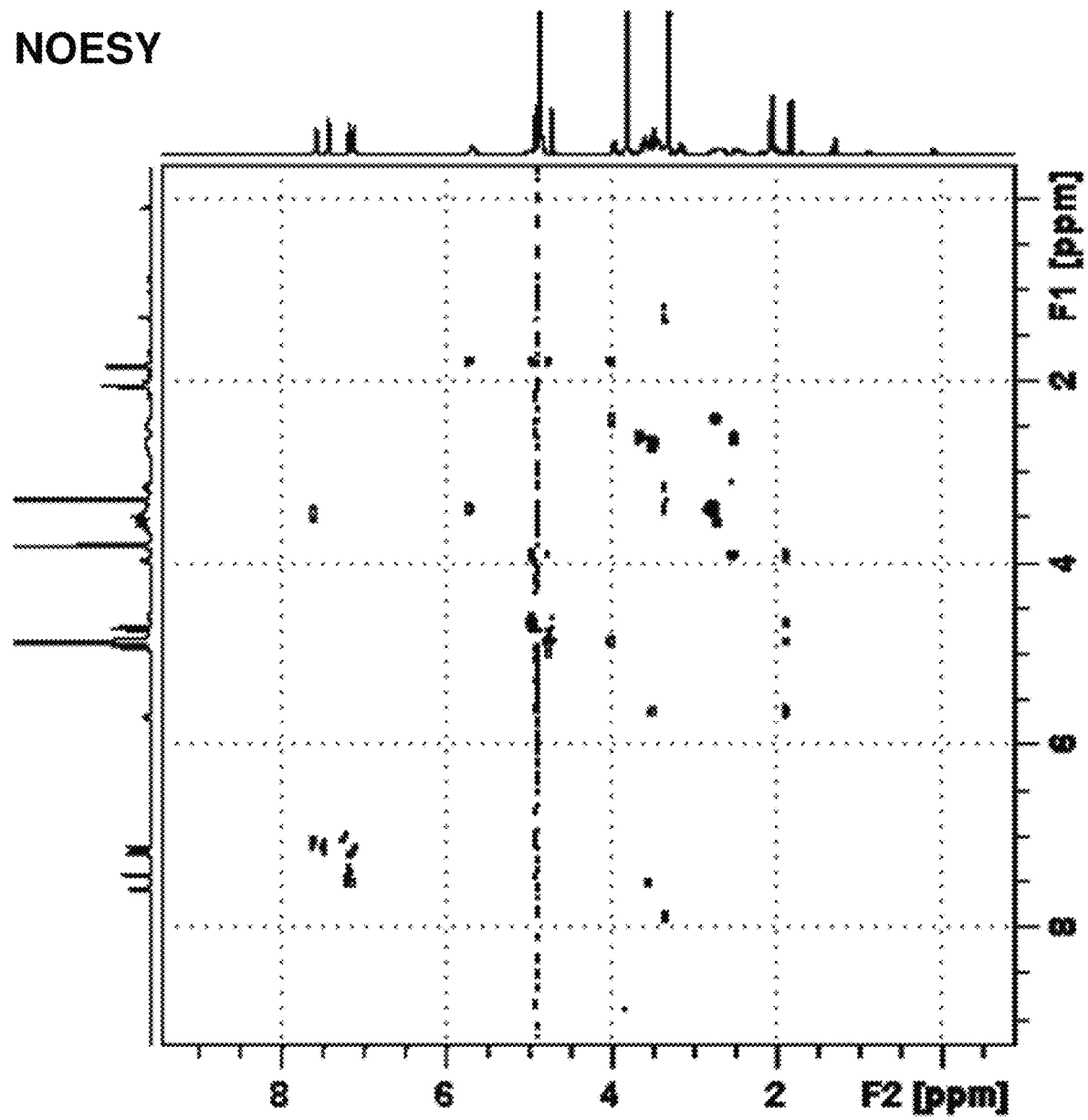
Figure 6F:
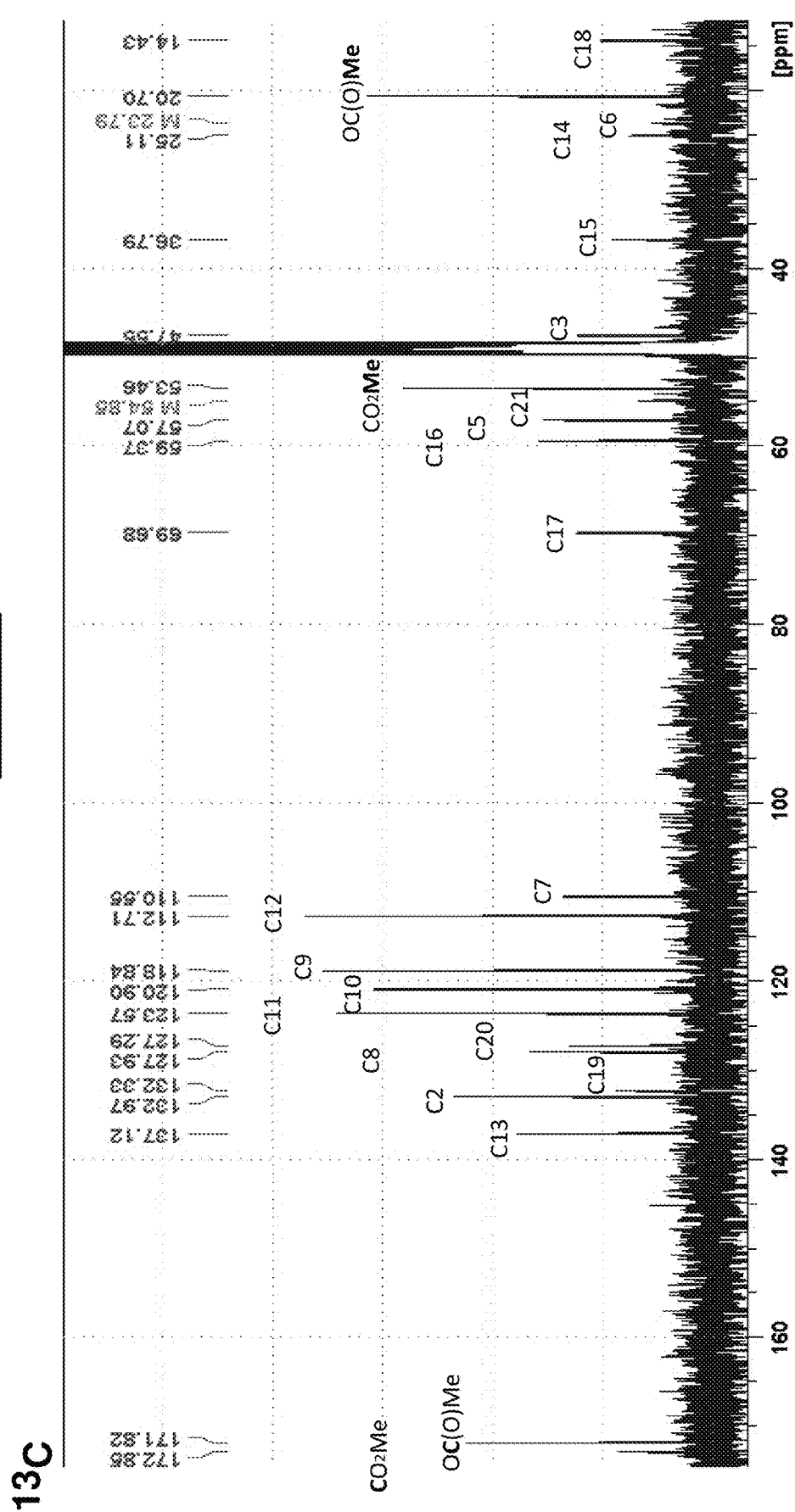
Figure 6G:
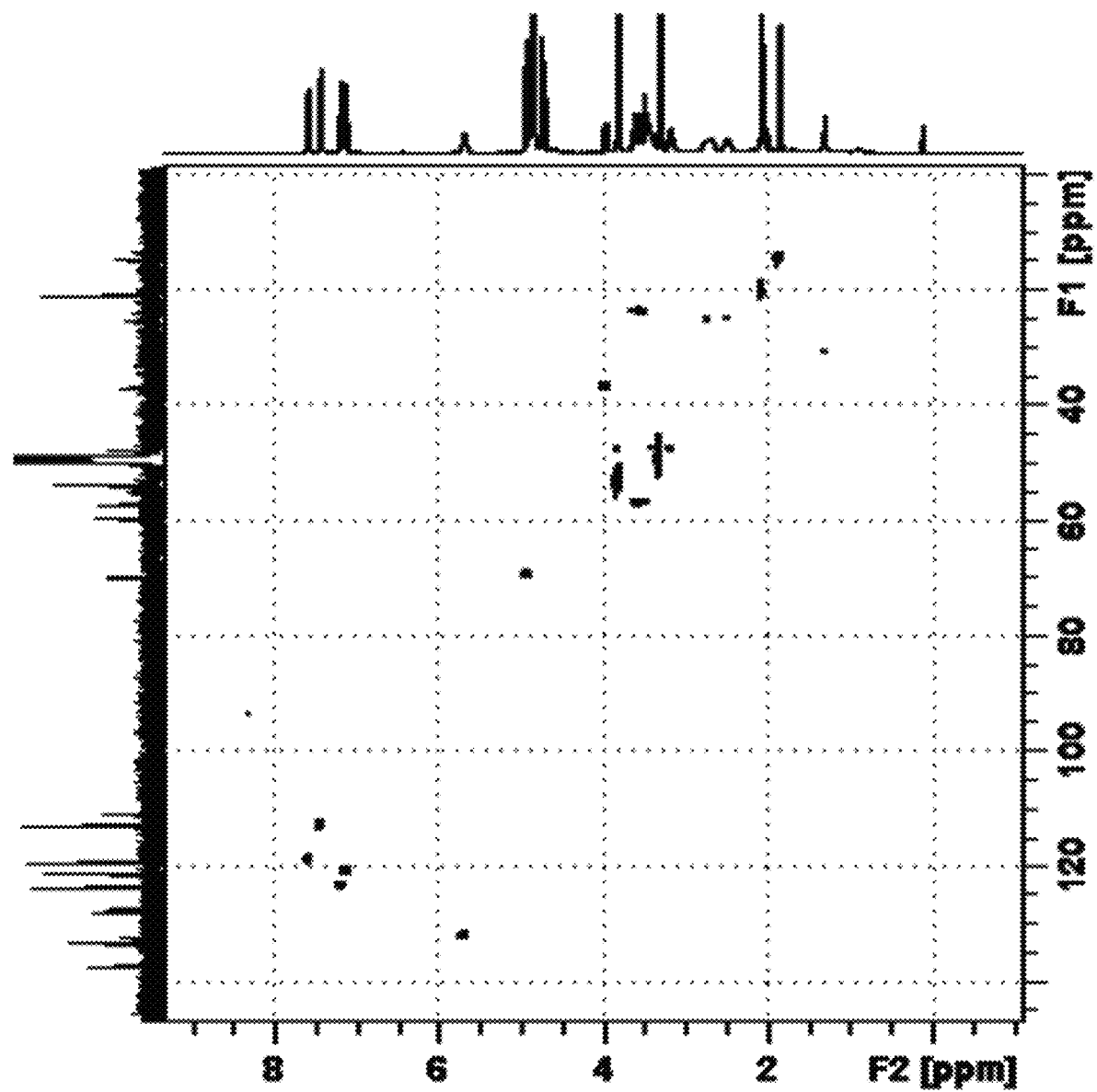
Figure 6H:
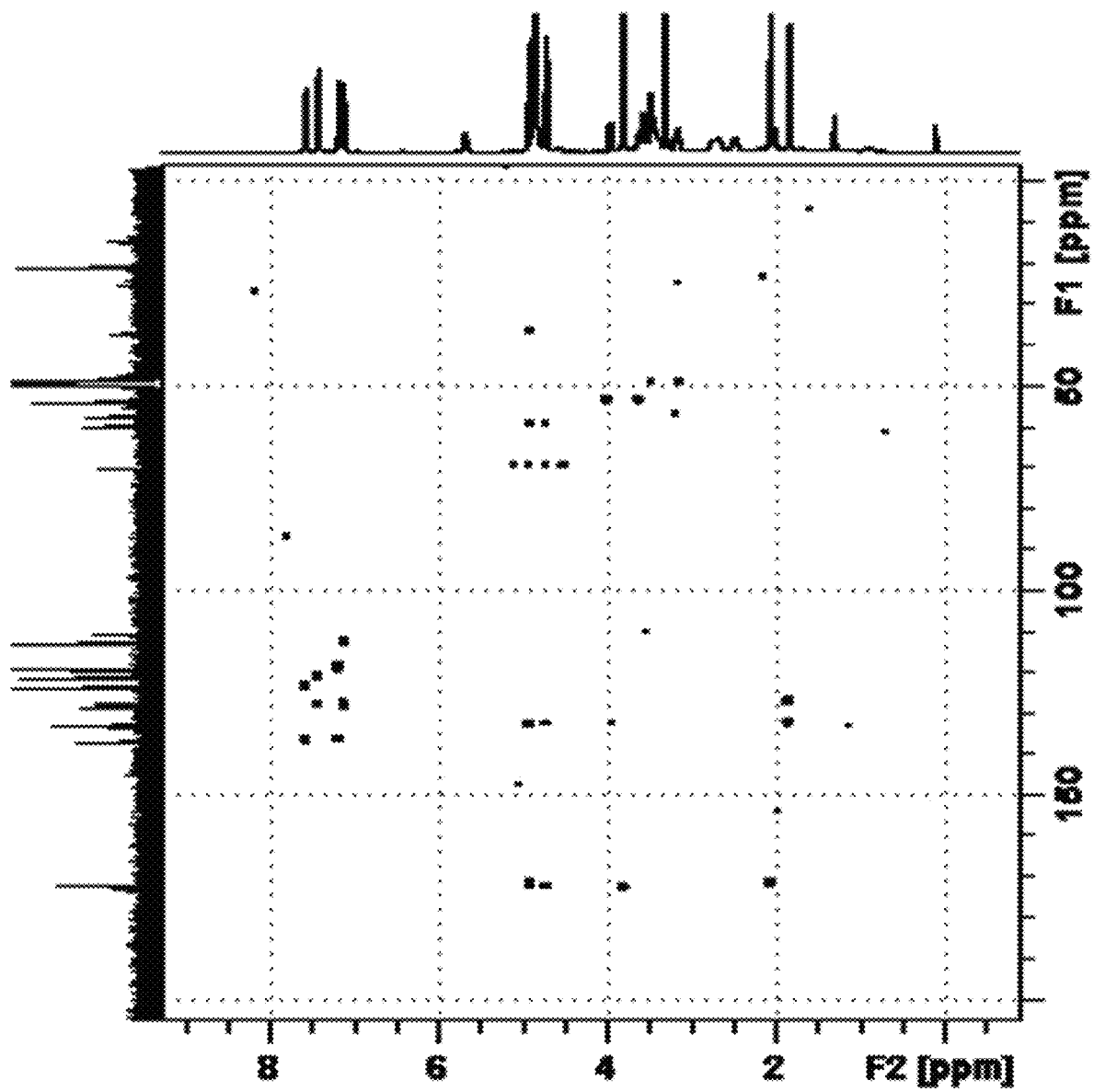

Purified, heterologous protein was required to validate the biochemical steps of this reaction sequence in vitro. While CS, TS and DPAS all expressed in soluble form in *E. coli* (FIG. 4A), the flavin-dependent enzyme PAS failed to express in standard expression hosts such as *E. coli* or *S. cerevisiae*. To overcome this obstacle, the native full-length PAS was expressed in *N. benthamiana* plants using a transient expression system (FIG. 4B) and a chimeric version of the protein, in which the N-terminal signal peptide was replaced with a yeast secretory signal sequence, in *Pichia pastoris* (FIGS. 4C and D). In both cases, the presence of PAS was validated by proteomic data. When the PAS proteins, along with stemmadenine acetate 7, were combined with heterologous DPAS and CS, catharanthine 3 was formed, and when combined with DPAS and TS, tabersonine 2 was observed (FIGS. 15 and 16). Moreover, reaction of PAS with stemmadenine acetate 7 produced a compound that had an identical mass and retention time to our semi-synthetic standard of precondylocarpine acetate 10 (FIGS. 15 and 16). Semi-synthetic precondylocarpine acetate 10 could be reacted with DPAS and TS/CS to yield tabersonine 2 and catharanthine 3, respectively (FIG. 17). In addition, a crude preparation of dihydroprecondylocarpine acetate 11 was converted to catharanthine 3 and tabersonine 2 by the action of CS and TS, respectively (FIG. 18). The enzymatic assays with PAS protein derived from *P. pastoris* ensure that formation of the expected products is not the result of a protein contaminant found in the plant-expressed PAS proteins. Although the yeast-produced PAS was less active than the plant-produced enzyme, formation of a compound corresponding to precondylocarpine acetate 10 was observed when PAS (*P. pastoris*) was reacted with stemmadenine acetate 7 (FIG. 19), along with formation of catharanthine 3 or tabersonine 2 when DPAS and CS or TS were also included (FIG. 16).

Reaction of PAS (purified from *N. benthamiana*) and DPAS with stemmadenine acetate 7 yielded catharanthine 3, suggesting that cyclization to catharanthine 3 can occur spontaneously under these reaction conditions (FIG. 15). Tabersonine 2 was never observed in the absence of TS, suggesting that, at least under the aqueous (pH 8.5) conditions used in the enzyme assays, dehydrosecodine 9 does not spontaneously form the aspidosperma-type scaffold. As observed during attempts to purify the CS/TS substrate from *Tabernaernontana* plants, dihydroprecondylocarpine acetate 11 can also deformylate to form tubotaiwine 12. It is likely that the solvent and reaction conditions play a significant role in how the highly reactive dihydroprecondylocarpine acetate 11 decomposes.

Notably, PAS failed to react with stemmadenine 1, indicating that the acetyl group is an important recognition group for this enzyme (FIG. 20). It was noted that upon oxidation of stemmadenine 1, a compound with a mass consistent with that of the shunt product condylocarpine 13 resulted; this was additionally supported by comparison of the MS/MS spectrum to the closely related compound tubotaiwine 12 (FIG. 21). It is hypothesized that the acetylation of stemmadenine 1 is necessary to slow spontaneous deformylation after oxidation, while also serving as a good leaving group to allow formation of dehydrosecodine 9. Acetylation has also served a role as a protecting group in the biosynthesis of noscapine in opium poppy.

Figure 28B:
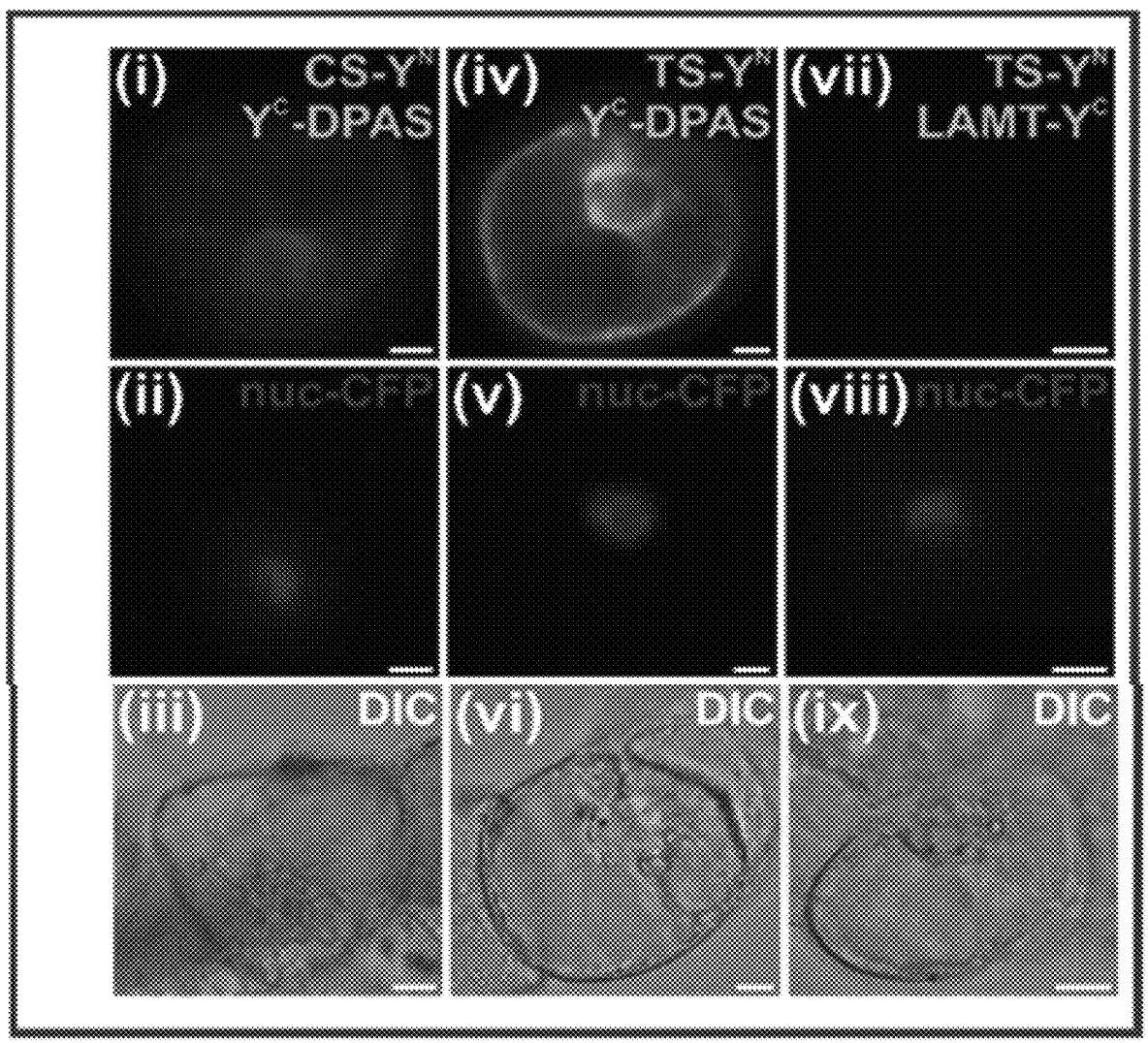

The reactivity of the intermediates involved in the transformation of stemmadenine acetate 7 to catharanthine 3 or tabersonine 2 suggests that PAS, DPAS and CS/TS should be co-localized, since the unstable post precondylocarpine acetate 10 intermediates may not survive transport between cell types or compartments. Using YFP-tagged proteins in *C. roseus* cell suspension culture, the inventors showed that PAS is targeted to the vacuole through small vesicles budding from the endoplasmic reticulum (ER), as was previously observed for the PAS homologue, berberine bridge enzyme (FIG. 22). This expected localization indicates that stemmadenine acetate 7 oxidation occurs in the ER-lumen, ER-derived vacuole-targeted vesicles and/or vacuole. In contrast, co-localization of DPAS, CS and TS were confirmed in the cytosol (FIGS. 23 and 24). Furthermore, bimolecular fluorescence complementation showed strong interactions between DPAS and TS, along with much weaker interactions between DPAS and CS (FIG. 28B, FIG. 25). Strong DPAS/TS interactions may not only prevent undesired reactions on the reactive dihydroprecondyocarpine acetate 11 intermediate but may also play a role in controlling the flux of 11 into tabersonine 2.

Figure 28C:
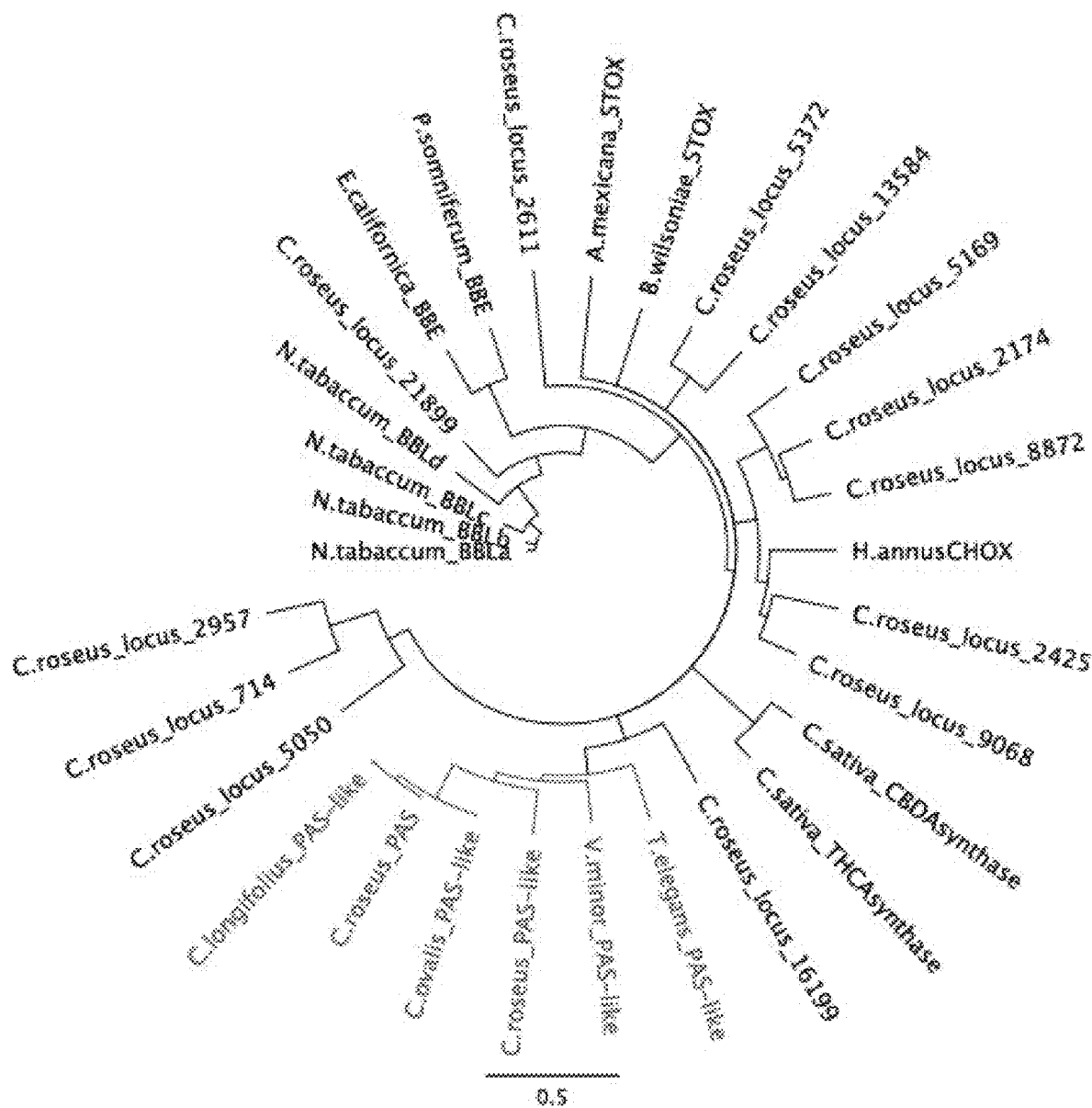

Homologues of PAS are utilized widely throughout benzylisoquinoline and pyridine alkaloid biosynthesis, but there are key sequence mutations in PAS that appear to be unique to the enzymes found in aspidosperma and iboga alkaloid producing plant clades (FIG. 28C). For instance, PAS lacks the His and Cys residues involved in covalent binding of the FAD cofactor (FIG. 26). It is anticipated that these aspidosperma-associated PAS homologues will be a rich source of biosynthetic enzymes for the wide range of aspidosperma alkaloids found in nature. DPAS is a member of the medium chain alcohol dehydrogenase family, an enzyme class that has been previously shown to play numerous roles in monoterpene indole alkaloid biosynthesis. CS and TS represent the first hydrolase-type enzymes implicated in monoterpene indole alkaloid biosynthesis. It was hypothesized that CS and TS retain the hydrolysis function of the putative ancestor hydrolase enzyme to allow formation of dehydrosecodine 9 from dihydroprecondylocarpine acetate 11. However, the non-enzymatic formation of catharanthine 3 suggests that formation of dehydrosecodine 9 via deacetoxylation can also occur spontaneously. In principle, the formation of tabersonine 2 and catharanthine 3 is formed via two different modes of cyclization, and it has been noted that dehydrosecodine 9 can undergo two distinct Diels-Alder reactions to form either catharanthine 3 or tabersonine 2 (Scheme 2A). The handful of putative Diels-Alderases have been isolated from microbes; CS and TS would constitute the first examples of Diels-Alderases from plants. Through detailed analysis of the structure and active site composition of TS and CS (amino acid identity of CS and TS is 80%, FIG. 27), it will be revealed whether this cyclization is actually concerted. Active site features that control the cyclization modes can be determined. We propose that TS/CS could be engineered to produce other naturally occurring dehydrosecodine-derived alkaloid scaffolds such as ent-catharanthine (Beatty & Stephenson, 2014, J. Am. Chem. Soc. 136: 10270-10273), iso-catharanthine (Yun et al., 2016, Chem. Sci. 7: 5530-5536), allo-catharanthine (Szántay et al., 1990, Tetrahedron 46: 1711-1732) or pseudotabersonine.

Discussion

Herein is disclosed four enzymes that convert stemmadenine acetate 7 to tabersonine 2 and catharanthine 3. This completes the biosynthetic pathway for vindoline 4 and catharanthine 3, compounds that can be used to semi-synthetically prepare vinblastine. Heteroiogous production of catharanthine 3 and vindoline 4, which is of high interest to synthetic biologists, is now possible. These discoveries are the first step to enhanced production of catharanthine 3 and vindoline 4, as well as the many other aspidosperma and iboga alkaloids that also use these enzymes in their biosynthesis.

Materials and Methods 1.1. Chemicals and Molecular Biology Kits

All solvents used for extractions, chemical synthesis and preparative HPLC were of HPLC grade, whilst solvents for UPLC/MS analysis were of MS grade. Ali were purchased from Fisher Scientific, Catharanthine 3 was purchased from Sigma Aldrich, whilst tabersonine 2 was obtained from Ava Chem Scientific. Stemmadenine was. Kanamycin sulfate, carbenicillin and gentamycin were from Formedium, whilst rifampicin was from Sigma Aldrich. All gene and fragment amplifications were performed using Platinum Superfi polymerase (Thermo Fisher) whilst colony PCRs were performed using Phire II master mix (Thermo Fisher). PCR product purifications were performed using the Macherey-Nagel PCR clean-up kit. Plasmids purifications were performed using Promeaa Wizard minipreps. cDNA was prepared using Superscript IV VILO master mix and Turbo DNAse (Thermo Fisher). qPCR was performed using Sensi-FAST Sybr No-ROX kit (Bioline). All restriction enzymes and ligase were from NEB.

1.2. RNA-Seq Data and Analysis for Biosynthetic Gene Candidates

Analysis of the *C. roseus* gene expression profile data was performed on the transcriptorne dataset available from the Medicinal Plant Genomics Resource website (http://medicinalplantgenomics.msu.edu/final version release info.shtml), Co-expression analysis by hierarchical clustering was performed on the FPKM matrix using the algorithms embedded in the Multi Experiment Viewer (MeV v.4.8), whilst self-organizing maps analysis was performed. A cluster of ca. 3600 co-regulated contigs was identified. This cluster contained all the known genes involved in the *C. roseus* MIA biosynthetic pathway. After further analysis based on functional annotation and gene onthology, a list of ca. 300 genes of interest was compiled, from which the inventors selected candidates for VIGS analysis based on putative function, 1.3. Virus Induced Gene Silencing, Metabolite Analysis and qPCR Fragments for CS and TS silencing were selected on the 3'-UTR regions, due to the high sequence similarity between the two genes, whilst fragments for PAS and DPAS silencing were designed using sequence from the ORF regions. Primers are shown in Table 1. A BLAST search against the transcriptome for each of the regions suggested that the VIGS fragments selected did not contain regions of homology that have significant overlap to other genes in the plant that could cause potential cross-silencing. The silencing fragments for CS, TS and DPAS were amplified from cDNA using the primers listed in Table 1, treated with restriction enzymes BamHl and Xhol and ligated into pTRV2 vector using T4 ligase. The fragment for PAS silencing was amplified from cDNA using the set of primers in Table 1 and cloned into the USER compatible VIGS plasmid pTRV2u as previously described (Geu-Flores et al., 2012, Nature 492: 138-142).

VIGS experiments were performed using the *C. roseus* Little Bright Eye variety grown in a growth chamber at 25° C. with a 12 h dark/12 h light regime. Briefly, each construct was infiltrated into 10 to 12 *C. roseus* seedlings (8 weeks old). Additionally, eight seedlings were infiltrated with pTRV2 lacking an insert (empty vector negative control) and four plants were infiltrated with a vector containing a fragment of the protoporphyrin IX magnesium chelatase gene (ChlH), which provided a visual marker (bleaching) to act as a positive control. After 21 days, seedlings infiltrated with the pTRV-ChlH vector displayed substantial yellowing of leaves; the last leaf pair to emerge above the inoculation site was harvested, frozen in liquid nitrogen and homogenized using a cryo bead mill. A portion of each sample (10-20 mg) was used for metabolite analysis, whilst the remaining of the samples were used for RNA extraction.

Samples for metabolite analysis were extracted with 1 mL of MeOH containing 1 µg/mL ajmaline as internal standard, filtered and diluted 1:4 with MeOH before LC/MS analysis using the method described in the UPLC/MS section.

Relative transcript abundance was determined by qRT-PCR on a BioRad CFX96 Q-PCR instrument using cDNA synthesized from isolated total RNA and the primers listed in Table 1. Eight biological replicates and three technical replicates were analyzed for each gene using two reference genes: Expressed protein, EXP, and N2227-like family protein, N2227. Efficiencies for all primer sets were approximately equal and always >90%. The entire VIGS experiment was performed in triplicate with essentially identical results.

1.4. Expression and Purification of Proteins

CS, TS and DPAS Expression in *E. coli*

The full-length sequences of CS, TS and DPAS were amplified from *C. roseus* cDNA using the primers listed in Table 1. The PCR products were purified from agarose gel, ligated into the Bam1-11 and Kpnl restriction sites of the pOPINF vector using the In-Fusion kit (Clontech Takara) and transformed into chemically competent *E. coli* Stellar cells. Recombinant colonies were selected on LB agar plates supplemented with carbenicillin (100 µg/mL). Positive clones were identified by colony PCR using T7_Fwd and pOPIN_Rev primers (see Table 1). Plasmids were isolated from positive colonies grown overnight. Identities of the inserted sequences were confirmed by Sanger sequencing.

Chemically competent SoluBL21 *E. coli* cells (Amsbio) were transformed by heat shock at 42° C. Transformed cells were selected on LB agar plates supplemented with carbenicillin (100 µg/mL). Single colonies were used to inoculate starter cultures in 50 mL of 2 x YT medium supplemented with carbenicillin (100 µg/mL) that were grown overnight at 37° C. Starter culture (10 mL) was used to inoculate 1 L of 2 x YT medium containing the antibiotic. The cultures were incubated at 37° C. until OD600 reached 0.6 and then transferred to 16° C. for 30 min before induction of protein expression by addition of IPTG (0.2 mM). Protein expression was carried out for 16 h. Cells were harvested by centrifugation and re-suspended in 50 mL of Buffer A (50 mM Tris-HCl pH 8, 50 mM glycine, 500 mM NaCl, 5% glycerol, 20 mM imidazole) with EDTA-free protease inhibitors (Roche Diagnostics Ltd.). Cells were lysed by sonication for 4 minutes on ice. Cell debris was pelleted by centrifugation at 35,000 g for 20 min.

His$_6$-tagged enzymes were purified on an AKTA Pure system (GE Healthcare) using a HisTrap HP 5 mL column (GE Healthcare) equilibrated with Buffer A. Samples were loaded at a flow rate of 2 mlJminute and step-eluted using Buffer B (50 mM Tris-HCl pH 8, 50 mM glycine, 500 mM NaCl, 5% glycerol, 500 mM imidazole). Eluted proteins were subjected to further purification on a Superdex Hiload 16/60 S200 gel filtration column (GE Healthcare) at a flow rate of 1 mL/minute using Buffer C (20 mM HEPES pH 7.5, 150 mM NaCl) and collected in 1.5 mL fractions.

Transient Expression of Proteins in *N. benthamiana*

CS, TS and DPAS full-length sequences were cloned into a modified TRBO vector (Lindbo, 2007, Plant Physiol. 145: 1232-1240) in which the cloning cassette of the pOPINF vector was inserted in the Notl restriction site. This allowed the vector to be compatible with the PCR products generated for cloning into pOPINF vector and to obtain N-terminal Hiss-tagged recombinant proteins. Cloning was performed using the In-Fusion kit, PAS full-length, instead, was cloned into pDONR207 (Thermo Fisher) using primers with attB1 and attB2 overhangs (see Table 1) via BP Clonase reaction, then recombined into pEAQ-HT-DEST3 vector for transient expression with a C-terminal His$_6$-tag using LR Clonase reaction.

The constructs were used for *E. coli* Stellar cells transformation by heat shock and recombinant colonies were selected on LB+Kanamycin (100 µg/mL). Positive colonies were also screened by colony PCR using the primers listed in Table 1 and sequenced. The constructs were then used to transform electrocompetent *A. tumefaciens* strain GV3101 by electroporation. Recombinant colonies were selected on LB agar containing rifampicin (100 pa/1114 gentamycin (50 µg/mL) and kanamycin (100 µg/mL). Single colonies were grown in 10 mL of LB with antibiotics for 48 h at 28° C., then the cells were collected by centrifugation and re-suspended in 10 mL infiltration buffer (10 mM NaCl, 1.75 mM CaCl$_2$ and 100 µM acetosyringone). After incubation at room temperature for 2 h, the cell cultures were diluted to OD600 0.1 and used to infiltrate *N. benthamiana* leaves. When multiple constructs were infiltrated simultaneously, the corresponding *A. tumefaciens* cell cultures were mixed so that the final OD600 of each would be 0.1. Infiltration was performed using a syringe without needle on leaves of 3-4 weeks old plants. Leaves were harvested 5 days post-infiltration.

Protein purification for proteomics analysis was performed by extraction of 2 g of pulverized frozen tissue in 10 mL of cold Tris-HCl buffer (50 mM, pH 8.0) containing EDTA-free protease inhibitors. After incubation on ice for 1 h and vortexing, the samples were centrifuged for 20 min at 35,000 g. The supernatants were collected and incubated with 300 µL of Ni-NTA slurry for 1 h. The slurry was then collected by centrifugation at 1,000 g for 1 min and washed 3 times with 10 mL of Tris-HCl buffer. Proteins were eluted by washing the slurry with 600 µL of Tris-HCl buffer containing 500 mM imidazole.

To purify PAS for in vitro enzyme activity assays, 300 g of fresh *N. benthamiana* leaves that had been infiltrated with the PAS expression construct were homogenized in 600 mL of Tris-HCl buffer (50 mM, pH 8.0) containing EDTA-free protease inhibitors and 1% insoluble polyvinylpolypyrrolidone (PVPP) using a blender. The homogenate was filtered through two layers of miracloth and then centrifuged at 3,500 g for 10 min to remove the insoluble PVPP and tissue debris. The supernatant was further clarified by centrifugation at 35,000 g for 20 min. PAS was then bound to a 5 mL Ni-NTA column and eluted with 20 mL of Tris-HCl buffer containing 500 mM imidazole. The eluted protein was dialyzed in ConA binding buffer (20 mtvl Tris-HCl buffer pH 7.4, 500 mM NaCl, 1 mtvl MnCl$_2$ and 1 mM CaCl$_2$) and manually applied to a ConA HiTrap 1 mL column (GE Healthcare) at a low flow rate using a syringe. After loading of the protein, the column was washed with 10 mL of binding buffer and then eluted with 10 mL of ConA elution buffer (20 mM Tris-HCl buffer pH 7.4, 500 mM NaCl and 300 mM methyl-D-glucoside). The protein was then dialyzed into Tris-HCl buffer (50 mM, pH 8.0), concentrated and stored at −20° C.

Expression of PAS in *Pichia pastoris*

A truncated version of PAS, lacking the initial 23 amino acids, was generated by PCR (Table 1) and cloned into the pPINK-HC vector (Thermo Fisher) according to the manufacturer's instructions. In this way, the native plant N-terminal signal peptide was replaced with the yeast α-mating sequence for extracellular secretion. The pPINK-HC::PAS construct was transformed into *P. pastoris* by electroporation in accordance with the PichiaPinkrm Expression System protocol.

A single colony of a *P. pastoris* transformant was inoculated in 10 mL BMGY medium in a 250-mL Erlenmeyer flask and grown for 24 hours at 250 rpm and 30° C. The inoculation was then transferred to 100 mL BMGY medium in a 500-mL baffled flask and cultured in the same conditions. After another 24 hours, this culture was transferred to 2 L BMGY medium, split equally into three 2-L baffled flasks, and grown at 220 rpm, 30° C. for approximately two days until $OD_{600}$ reached 2 to 3. The cells were then collected by centrifugation at 5,000 g for 5 minutes, re-suspended in 700 mL BMMY medium (containing 0.5% methanol) for protein expression, split equally into two 2-L non-baffled flasks. The culture was allowed to grow at 28° C. and 250 rpm. After 120 hours, the culture was centrifuged at 10,000 g for 10 minutes.

The medium containing secreted proteins (supernatant) was concentrated using 30,000 MWCO concentrators (Merck Millipore) to approximately 20 mL, dialyzed into 50 mM HEPES buffer pH 7.0 using PD-10 desalting columns (GE Healthcare), and further concentrated to 3 mL. The sample was subjected to IEX chromatography on a HiTrap Q HP 1 mL column (GE Healthcare) to enrich the PAS protein. After loading of the sample, the column was washed with 10 mL of 50 mM HEPES buffer pH 7.0 before elution of the protein with 50 mM HEPES buffer pH 7.0 containing 500 mM NaCl. The sample was dialyzed in 50 mM Tris-HCl pH 8.5 and concentrated to a final volume of 1 mL. BMGY and BMMY media were prepared in accordance with the PichiaPink™ Expression System protocol.

Concentrated *P. pastoris* culture medium containing secreted proteins was analyzed on SDS-PAGE with Coomassie staining. A band corresponding to the size of PAS (ca. 57 kDa) was visible. To confirm the identity of the protein, the band was excised, de-stained and subjected to trypsin digestion and LC/MS/MS analysis on a nanoLC-orbitrap (Thermo Fisher Scientific).

1.5. Pathway Reconstitution in *N. benthamiana*

Leaves of 3-4 weeks old *N. benthamiana* plants were infiltrated with *A. tumefaciens* GV3101 cultures harbouring the transient protein expression constructs, as described above. After 4 days, each leaf was infiltrated with 1 mL of 50 µM stemmadenine acetate dissolved in infiltration buffer. After 24 h, the infiltrated leaves were harvested and flash-frozen in liquid nitrogen. After grinding in liquid nitrogen, 200-300 mg of pulverised tissue were extracted with 1 volume (w/v) of MeOH containing ajmaline as internal standard. After incubation at room temperature for 1 h and vortexing, the samples were centrifuged at 17,000 g for 10 min, filtered and analyzed by UPLC/MS using the same method described in the UPLC/MS section.

1.6. In Vitro Enzyme Assays

In vitro assays of PAS alone were performed in 50 mM Tris-HCl buffer pH 9.0, whilst those in which PAS was coupled with the other enzymes were performed in 50 mM Tris-HCl pH 8.5. In all cases 20 µM FAD was added as co-factor. Each assay contained 50 µM stemmadenine acetate (substrate) delivered in methanol (not exceeding 5% of the reaction volume). Due to the very low amounts of PAS purified, the amount of protein in the assays was not accurately determined. However, the amount of enzyme added to each reaction was consistent throughout each set of experiments.

Reactions involving DPAS, CS and TS were performed in 50 mrVI HEPES buffer pH 7.5. DPAS requires NADPH for activity, therefore 100 µM NADPH was added to each assay. Precondylocarpine acetate (DPAS substrate) (50 µM) delivered in MeOH (not exceeding 5% of the reaction volume) was added to each reaction. 10-20 µg of enzymes were used in the assays. All reactions were performed at 37° C. for 1 h. For controls, protein sample was replaced with boiled protein sample or sample from culture of non-transformed yeast. After incubation, the reactions were quenched by addition of 1 volume of methanol, filtered through 0.22-µm nylon Spin-X centrifuge filters (Corning) and analyzed by LC/MS as described in the UPLC/MS and UPLC/QqQ-MS sections.

1.7. Purification of CS/TS Substrate from Plant Material

Alkaloids from fully expanded leaves of *Tabernaemontana divaricata* "Fiore pleno" (50 g) were extracted with acetonitrile (300 mL x 3). The extract was concentrated in vacuo and reconstituted in acetonitrile:water (70:30). The hydrophobic components were removed by passing through a $C_{18}$ SPE cartridge (10 g). The flow-through was collected, dried and dissolved in 20 mL of 50 mM phosphate buffer pH 7.0. 5 mL of solution was sequentially applied to 500 mg WCX OASIS cartridges (Waters) equilibrated with phosphate buffer. Each cartridge was washed with buffer (6 mL), acetonitrile (6 mL), acetonitrile:water (50:50) solutions before elution with 100 mM $CaCl_2$ in acetonitrile:water (6 mL, 50:50). Fractions were lyophilized and reconstituted in acetonitrile:water (2 mL, 50:50) before subjection to reverse-phase preparative HPLC.

Preparative HPLC was performed on a Thermo Dionex Ultimate 3000 chromatography apparatus using a Phenomenex Luna C18 (5 µm, 30×250 mm) column. The solvents used were 0.01% acetic acid, solvent A, and acetonitrile, solvent B. A linear gradient from 5% B to 50% B over 25 min was used to separate the alkaloids. Chromatography was performed at a flow rate of 30 mUrnin and monitored with a UV detector at 254 nm. Fractions (30 mL) were collected and assayed for CS and TS activity as follows. A 200 µL aliquot of each fraction was dried in vacuo and re-dissolved in 50 µL of 50 mM HEPES buffer pH 7.5. CS or TS enzyme (1 µg) was added to each sample and the reactions were incubated at 37° C. for 1 h. Control reactions without enzyme were also prepared. After incubation, the reactions were quenched by addition of 50 µL of MeOH, filtered and analyzed by UPLC/QqQ-MS as described above.

1.8. Purification of Stemmadenine Acetate from *C. roseus* Leaves.

Leaves of plants in which PAS was silenced by VIGS were harvested 21 days post infection and frozen in liquid nitrogen. 20-50 g of frozen leaves were ground and extracted 3 times with acetonitrile (300 mL×3). The extract was concentrated in vacuo and reconstituted in 100 mL acetonitrile:water (70:30). The hydrophobic components were removed by passing the sample through a $C_{18}$ SPE cartridge (10 g). The flow-through was collected, dried and dissolved in 10 mL of acetonitrile:water (50:50).

Stemmadenine acetate 7 was purified by semi preparative HPLC on a Thermo Dionex Ultimate 3000 chromatography apparatus using a Waters Xbridge BEH C18 (5 µm, 10µ250 mm) column. Mobile phase A was water containing 0.1% formic acid; mobile phase B was acetonitrile. The flow rate was 5 mL/min, and the gradient profile was 0 min, 10% B;

from 0 to 30 min, linear gradient to 35% B; from 30 to 35 min, isocratic 35% B; from 35.1 to 37 min, wash at 95% B then back to the initial conditions of 10% B for 3 min. The injection volume was 500 µL. Elutions of the compounds was monitored at 268 nm. 5 mL fractions were collected throughout the purification and tested for the presence of the compounds by direct injection on an Advion express-ion Compact Mass Spectrometer in ESI⁺ mode. Fractions containing the compound of interest were lyophilized, 1.9. Liquid-Chromatography Mass Spectrometry Analysis

UPLC/MS

This method was applied to the analysis of VIGS leaf extract, in vitro enzyme assays and synthetic products, unless otherwise indicated in the description of the experiments. UPLC/MS analysis was performed on a Shimadzu LCMS-IT-TOF Mass Spectrometer coupled to a Nexera 2 chromatographic system. Chromatographic separation was carried out on a Phenomenex Kinetex column 2.6 µm XB-018 (100×2.10 mm), and the binary solvent system consisted of solvent A, $H_2O$+0.1% formic acid, and solvent B, acetonitrile. Flow rate was 600 µL/min. A linear gradient from 10% to 30% solvent B in 5 min, allowed the separation of the alkaloids of interest. The column was then washed at 100% B for 1.5 min and re-equilibrated to 10% B. Injection volume was 1 µL.

Mass spectrometry was performed in positive ion mode with scanning over the m/z range from 150-1,200. The source settings were the following: heat block temperature 300° C., nebulizing gas flow 1.4 L/min, CDL temperature 250° C., detector voltage 1.6 kV. Data analysis was performed using the Shimadzu Profiling Solution software.

UPLC/QqQ-MS

This method was used to analyse samples from the in vitro pathway reconstitution using PAS expressed in *P. pastoris* and CS/TS reactions of alkaloid fractions purified from *Tabemaemontana divaricata* "Fiore Pleno" leaves. UPLC/QqQ-MS analysis was carried out on a UPLC (Waters) equipped with an Acquity BEH C18 1.7 µm (2.1×50 mm) column connected to Xevo TOS (Waters). Chromatographic separation was performed using 0.1% NH4OH as mobile phase A and acetonitrile as mobile phase B. A linear gradient from 0 to 65% B in 17.5 min was applied for separation of the compounds followed by an increase to 100% B at 18 min, a 2-min wash step and a re-equilibration at 0% B for 3 min before the next injection. The column was kept at 60° C. throughout the analysis and the flow rate was 0.6 mL/min.

MS detection was performed in positive ESI. Capillary voltage was 3.0 kV; the source was kept at 150° C.; desolvation temperature was 500° C.; cone gas flow, 50 Uh; and desolvation gas flow, 800 L/h. Unit resolution was applied to each quadrupole. The MRM transitions used to monitor the elution of the alkaloids of interest are reported in Table 3.

HR-MS

For high resolution MS analysis, compounds were infused at 5-10 µL/min using a Harvard Apparatus syringe pump onto a Synapt G2 HDMS mass spectrometer (Waters) calibrated using a sodium formate solution. Samples were analyzed for 1 minute with a scan time 1 sec in the mass range of 50-1200 m/z. Capillary voltage was 3.5 V, cone voltage 40 V, source temperature 120° C., desolvation temperature 350° C., desolvation gas flow 800 L/h. Leu-enkephaline peptide (1 ng/µL) was used to generate a dual lock-mass calibration with $[M+H]^+$=556.2766 and m/z=278.1135 measured every 10 sec. Spectra were generated in MassLynx 4.1 by combining a number of scans, and peaks were centred using automatic peak detection with lock mass correction.

1.10. Proteomic Analysis

PAS, DPAS, CS and TS transiently expressed in *N. benthamiana* leaves and pre-purified on NiNTA resin were precipitated with chloroform/methanol and dissolved in 0.2 M TEAB/1% sodium deoxycholate (SDC), whilst PAS expressed in *P. pastoris* was extracted from SDS-PAGE. Protein concentration was determined using the Direct Detect™ Assay (Merck). 10 µg of protein was treated with DTT and iodoacetamide to reduce and alkylate cysteine residues and digested with 1 µg of trypsin (Promega) at 50° C. for 8 h. Approx. 0.5 µg of the digested protein was used for data dependent LC-MS/MS analysis on an Orbitrap-Fusion™ mass spectrometer (Thermo Fisher, Hemel Hempstead, UK) equipped with an UltiMate™ 3000 RSLCnano System (Thermo Fisher) using a nanoEase M/Z HSS 018 T3 1.8 µm, 150 µm×100 mm, (Waters). The samples were loaded and trapped using a pre-column which was then switched in-line to the analytical column for separation. Peptides were eluted with a gradient of acetonitrile in water/0.1% formic acid (main step from 11-30.5% at a rate of 0.19% $min^{-1}$). The column was connected to a 10 µm SilicaTip™ nanospray emitter (New Objective, Woburn, Mass., USA) for infusion into the mass spectrometer. Data dependent analysis was performed using an HCD fragmentation method with the following parameters: positive ion mode, orbitrap MS resolution=60 k, mass range (quadrupole)=300-1800 m/z, MS2 in ion trap, threshold $2e^4$, isolation window 1.6 Da, charge states 2-5, MS2 top20, AGO target $1.9e^4$, max inject time 35 ms, dynamic exclusion 1 count, 15 s exclusion, exclusion mass window±5 ppm. MS scans were saved in profile mode while MS2 scans were saved in centroid mode.

Raw files were processed with MaxQuant (version 1.6.1.0) (http://maxquant.org). The searches were performed using the Andromeda search engine in MaxQuant on a custom database of the *N. benthamiana* sequences available from Uniprot to which the protein sequences of interest were added using trypsin/P with 2 missed cleavages, carbamidomethylation (C) as fixed and oxidation (M), acetylation (protein N-terminus), and deamidation (N,Q) as variable modifications. Mass tolerances were 4.5 ppm for precursor ions and 0.5 Da for fragment ions.

1.11. Synthesis Procedures

General and NMR Analysis

Progress of the reactions was monitored by direct injection on an Advion express-ion Compact Mass Spectrometer in ESI⁺ mode. The mobile phase was 0.1% formic acid in water:methanoi (10:90). LC/MS analysis was performed using the method described in the UPLC/MS section, unless otherwise stated. High-resolution mass spectrometry was performed as described in the HR-MS section. NMR spectra (1 D and 2D NMR) were acquired using a Bruker Avance III 400 NMR spectrometer equipped with a BBFO plus 5 mm probe, unless stated otherwise. The residual $^1H$ and $^{13}C$ NMR signals of $CD_3OD$ (δ 3.31 and 49.0, respectively), $CD_3CN$ (δ 1.94 and 1.32, respectively) and $CDCl_3$ (δ 7.26 and 77.16, respectively) were used for calibration. The number of scans depended on sample concentration and are indicated in Figures and Tables accordingly.

Synthesis of Stemmadenine Acetate (7)

To a 1.5-mL HPLC vial containing stemmadenine 1 (10.2 mg, 0.0289 mmol), pyridine (400 µL) was added. The mixture was sonicated and stirred at r.t until complete dissolution was achieved. Acetic anhydride (50 µL, 0.529 mmol) was subsequently added to the reaction vessel and the reaction was allowed to stir at r.t for 4 h. Reaction progress was monitored by MS direct-injection of 1 μL of the reaction mixture in 100 μL of methanol. The reaction was quenched with methanol (1 mL) once peak for SM at m/z 355 was no longer observed. The reaction was then concentrated in vacuo at 30° C. Toluene (350 μL) and methanol (150 μL) was added to reaction vial, sonicated to homogeneity and concentrated in vacuo at 30° C. (repeated x4) to afford 33 (ca. 11.4 mg, 0.0287 mmol, 99%) as a dark brown solid.

Synthesis of Precondylocarpine Acetate (10)

Synthesis of precondylocarpine acetate was performed as reported by Scott and co-workers (1972; see above) with some modifications. Briefly, Adam's catalyst (≥75 m$^2$/g, 25.2 mg, 0.112 mmol, 7.5 equivalents) was reduced with H$_2$ in ethyl acetate (1 mL) for 2 h. The apparatus was flushed with nitrogen for 5 min. The freshly prepared platinum in ethyl acetate was transferred to a 25-mL pear-shaped flask containing stemmadenine acetate 7 (6 mg, 0.0152 mmol) dissolved in ethyl acetate (1 mL) via glass pipette. An oxygen atmosphere was introduced by a balloon to the reaction vessel via Agani 1.5-inch needle. The reaction mixture was allowed to stir vigorously at r.t. Reaction progress was monitored by dissolving 1 μL of the reaction mixture in 100 μl of methanol, filtered through a Fisherbrand™ porosity 0.2 μm PTFE syringe filter before injection on the Advion MS. Fresh batch of Pt catalyst was prepared and added as above when product:SM ratio appeared to stagnate. The reaction was stopped when amount of SM was <5% product (estimated via Advion MS) to prevent formation of by-product(s). After flushing the reaction vessel with N$_2$, gravity filtration with ethyl acetate (10 mL) gave a pale-yellow solution. The filtrate was concentrated in vacuo at 25° C. to afford a dark yellow solid (crude yield: 2.6 mg, ~60% pure based on $^1$H NMR; see also Table 6).

Synthesis of Dihydroprecondylocarpine Acetate (11)

Synthesis of dihydroprecondylocarpine acetate was performed. Briefly, Adam's catalyst (≥75 m$^2$/g, 0.8 mg, 3.524 μmol) was reduced with H$_2$ in ethanol (400 μL) for 2 h. The apparatus was flushed with nitrogen for 5 min. The freshly prepared platinum in ethanol was transferred to a 1.5-mL HPLC vial containing crude precondylocarpine acetate 10 (ca. 200 μg, 0.508 μmol) dissolved in ethanol (100 μL) via glass pipette. A hydrogen atmosphere was introduced by a balloon to the reaction vessel. The reaction mixture was allowed to stir vigorously at r.t. overnight. The reaction vessel was flushed with N$_2$, followed by filtration of the reaction mixture using Fisherbrand™ porosity 0.2 μm PTFE syringe filter, and washing of the filter with EtOH (200 μL×2), and concentrating the filtrate in vacuo yielded a compound (yield undetermined due to small scale) which showed activity in enzymatic assays with CS, and TS, forming catharanthine 3, and tabersonine 2, respectively. Due to the small scale and instability, the compound could not be further characterized though.

Synthesis of Condylocarpine (13)

Synthesis of condylocarpine was performed analogously to that for precondylocaprine acetate 10. Adam's catalyst (≥75 m2/g., 2.30 mg, 10.1 μmol, 7.5 equivalents) was reduced with H$_2$ in ethyl acetate (1 mL) until solution turned black. The apparatus was flushed with nitrogen for 5 min. The freshly prepared platinum in ethyl acetate was transferred to a 1.5-mL HPLC vial containing stemmadenine 1 (0.48 mg, 1.36 μmol). An oxygen atmosphere was introduced by a balloon to the reaction vessel via Agani 1.5-inch needle. Reaction progress was monitored by dissolving 1 μL of the reaction mixture in 100 μl of methanol, filtered through a Fisherbrand™ porosity 0.2 μm PTFE syringe filter before injection on the Advion MS in ESI+ mode. After 2 h, conversion reached ca. 26%, which did not improve by 4 h. The reaction was stopped to prevent formation of by-product(s). After flushing the reaction vessel with N2, the reaction mixture was filtered as above and the catalyst was washed with ethyl acetate (6 mL), and concentrating in vacuo yielded a yellow residue. The product was the isolated by preparative HPLC on a Waters Xbridge BEH C18 (5 μm, 10×250 mm) column. Mobile phase A was water containing 0.1% formic acid; mobile phase B was acetonitrile. The flow rate was 5 mUmin, and the gradient profile was 0 min, 10% B; from 0 to 30 min, linear gradient to 40% B; from 30 to 35 min, linear gradient to 95% B; from 35 to 39 min, wash at 95% B then back to the initial conditions of 10% B in 1 min for 5 min. The injection volume was 500 μL. Elution of the compounds was monitored at 290 nm. 2.5 mL fractions were collected throughout the purification and tested for the presence of the compounds by direct injection on the Advion MS in ESI+ mode.

1.12. Localization and Interaction studies

Subcellular localizations of DPAS, CS and TS were studied by creating fluorescent fusion proteins using the pSCA-cassette YFPi plasmid. Full-length open reading frames encoding each enzyme were amplified using specific primer couples (Table 1), which were designed to introduce the Spel restriction site at both cDNA extremities. PCR products were sequenced and cloned at the 5'-end of the yellow fluorescent protein (YFP) coding sequence, to generate the DPAS-, TS-, CS-YFP fusion proteins or at the 3'-end to express the YFP-DPAS, YFP-TS and YFP-CS fusions. The coding sequences of the first forty or sixty amino acids of PAS encompassing the ER-to-vacuole targeting sequence were amplified by mixing PAS-YFP for with PAS40-YFPrev or PAS60-YFPrev (Table 1) before cloning into the Spel restriction site of pSCA-cassette YFPi to express sp40-YFP and sp60-YFP.

Interactions of DPAS with CS and TS were characterized by bimolecular fluorescence complementation (BiFC) assays using the previously amplified CS and TS PCR products cloned via Spel into the pSCA-SPYNE173 to express CS-YFPN and TS-YFPN; and using DPAS amplicon cloned into pSCA-SPYCE (MR) to express YFPC-DPAS. Plasmids encoding LAMT-YFPN and LAMT-YFPC were used as controls.

Transient transformation of C. roseus cells by particle bombardment and fluorescence imaging were performed. Briefly, C. roseus plated cells were bombarded with DNA-coated gold particles (1 μm) and 1,100 psi rupture disc at a stopping-screen-to-target distance of 6 cm, using the Bio-Rad PDS1000/He system. Cells were cultivated for 16 h to 38 h (DPAS, CS and TS) or up to 96 h for PAS before being harvested and observed. The subcellular localization was determined using an Olympus BX-51 epifluorescence microscope equipped with an Olympus DP-71 digital camera and a combination of YFP and CFP filters. The pattern of localization presented in this work is representative of circa 100 observed cells. Localizations of the different fusion proteins were confirmed by co-transformation experiments using a nuclear-CFP marker, an ER-CFP marker, vacuole-CFP marker or a nucleocytosolic-CFP marker. Such plasmid transformations were performed using 400 ng of each plasmid or 100 ng for BiFC assays. In these assays, transformed cells were identified via co-transformation with the nucleus CFP marker.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

TABLES

TABLE 1

Primer sequences used in this study. Cloning/restriction sites are underlined.

| | |
|---|---|
| For VIGS plasmid construction | |
| CS_Fwa | CGA<u>GGATCC</u>TAATATTCATCTTTGTTTTACGTTCTTACTTTC (SEQ ID NO: 8) |
| CS_Rev | CGA<u>CTCGAG</u>CGCATTATTCAAATTTTTTACTTATCTTCTC (SEQ ID NO: 11) |
| TS_Fwd | CGA<u>GGATCC</u>AAAAAGGCAAAATTTCCTTGC (SEQ ID NO: 12) |
| TS_Rev | CGA<u>CTCGAG</u>TAAGCATTTAACATTATTATTATTATCATATTTTATCAAAATCA (SEQ ID NO: 13) |
| DPAS_Fwd | CGA<u>GGATCC</u>GAGTTGCCACCTATTCCTTTATTATCAG (SEQ ID NO: 14) |
| DPAS_Rev | CGA<u>CTCGAG</u>CAGAGTACACACTTATGACTTTTATGTGC (SEQ ID NO: 15) |
| RO_Fwd | <u>GGCGCGAU</u>TCTCTTCCTCTGTTGGAATTGGC (SEQ ID NO: 16) |
| RO_Rev | <u>GGTTGCGAU</u>TCCAATTCATTTCTAAGCAATCTTCCTTTTTCA (SEQ ID NO: 6) |
| For full-length amplification | |
| CS_pOPINF_Fwd | <u>AAGTTCTGTTTCAGGGCCCG</u>GCTTCCCAAACTCCAACCTCAGATGA (SEQ ID NO: 17) |
| CS_pOPINF_Rev | <u>ATGGTCTAGAAAGCTTTA</u>CTCATGTTTGATGAAAGATGCTAAACG (SEQ ID NO: 18) |
| HID2_pOPINF_Fwd | <u>AAGTTCTGTTTCAGGGCCCG</u>GCTTCCCAAACTCCAACCTCAGATGA (SEQ ID NO: 19) |
| HID2_pOPINF_Rev | <u>ATGGTCTAGAAAGCTTTA</u>TTTGATGAAAGACGTTAAGCGTCTAATC (SEQ ID NO: 20) |
| TS_pOPINF_Fwd | <u>AAGTTCTGTTTCAGGGCCCG</u>GGTTCCTCAGATGAGACTATTTTTG (SEQ ID NO: 21) |
| TS_pOPINF_Rev | <u>ATGGTCTAGAAAGCTTTA</u>CTTGATGAAAGAAGCTAAACGTCTG (SEQ ID NO: 22) |
| PAS_pDONR207_Fwd | <u>GGGGACAAGTTTGTACAAAAAAGCAGGCTTA</u>ATGATAAAAAAAGTCCCA (SEQ ID NO: 23) |
| PAS_pDONR207_Rev | <u>GGGGACCACTTTGTACAAGAAAGCTGGGTA</u>AAGTTCGACTTGTAAATGG (SEQ ID NO: 24) |
| For cloning of PAS into pPink-HC | |
| PAS_Pichia_Fwd | <u>TCTCTCGAGAAAAGGT</u>CAATTCCTGAAGCTTTTCTCAATTGTATTTCC (SEQ ID NO: 26) |
| PAS_Pichia_Rev | <u>TTAAATGGCCGGCCG</u>AAGTTCGACTTGTAAATGGAGAGGGG (SEQ ID NO: 27) |
| For colony PCR | |
| T7_Fwd | TAATACGACTCACTATAGGG (SEQ ID NO: 28) |
| pOPIN_Rev | TAGCCAGAAGTCAGATGCT (SEQ ID NO: 29) |
| pDONR207_Fwd | TCGCGTTAACGCTAGCATGGATCTC (SEQ ID NO: 30) |
| pDONR207_Rev | GTAACATCAGAGATTTTGAGACAC (SEQ ID NO: 31) |
| pEAQ_Fwd | GGAGAAAGATTGTTAAGCTTCTGT (SEQ ID NO: 32) |
| pEAQ_Rev | AACATAGAAATGCACACCGAATAA (SEQ ID NO: 33) |
| pPINK_AOX1 | GACTGGTTCCAATTGACAAGC (SEQ ID NO: 34) |
| pPINK_CYC1 | GCGTGAATGTAAGCGTGAC (SEQ ID NO: 35) |

TABLE 1-continued

Primer sequences used in this study.
Cloning/restriction sites are underlined.

For qPCR

| | |
|---|---|
| CrEX_Fwd | ACAATACCATCGCCATCAC (SEQ ID NO: 36) |
| CrEX_Rev | AAGAGGACTGCTGGAAGG (SEQ ID NO: 37) |
| CrN2227_Fwd | TCCTTACGCCGCATTATCAG (SEQ ID NO: 38) |
| CrN2227_Rev | AGATGAGACAGTAACGCCTTG (SEQ ID NO: 39) |
| PAS_Fwd | CTTCACTCCCATGTCCAATCT (SEQ ID NO: 40) |
| PAS_Rev | CGATAGGATAAGCCCTCGTAATC (SEQ ID NO: 41) |
| DPAS_Fwd | GAAATAGCGGCATCGACAAAC (SEQ ID NO: 42) |
| DPAS_Rev | GCTGGGAGTGGTGCTAATAA (SEQ ID NO: 43) |
| CS_Fwd | CTCCTGGCGGGATGAATAAC (SEQ ID NO: 44) |
| CS_Rev | GGAAACCAGGGTAACCAACA (SEQ ID NO: 45) |
| TS_Fwd | AGATGCTCCTGGTGGAAATG (SEQ ID NO: 46) |
| TS_Rev | CAACCATGGAAATCAGCAACC (SEQ ID NO: 47) |

For localization

| | |
|---|---|
| PAS-YFPfor | CTGAGAACTAGTATGATAAAAAAAGTCCCAATAGTTCTTTCAA (SEQ ID NO: 48) |
| PAS40-YFPrev | CTGAGAACTAGTATCTAATGAAAATTTATTGGAAATACAATTG (SEQ ID NO: 49) |
| PAS60-YFPrev | CTGAGAACTAGTTTTGAGAACAGAATCATAGGAAGAATTGC (SEQ ID NO: 50) |
| DPAS-YFPfor | CTGAGAACTAGTATGGCCGGAAAATCAGCAGAAG (SEQ ID NO: 51) |
| DPAS-YFPrev | CTGAGAACTAGTTTATAACTCTGACGGAGGAGTCAAGGTATTT (SEQ ID NO: 52) |
| TSfor | CTGAGAACTAGTATGGGTTCCTCAGATGAGACTATTTTT (SEQ ID NO: 53) |
| TSrevstop | CTGAGAACTAGTTTACTTGATGAAAGAAGCTAAACGTCT (SEQ ID NO: 54) |
| TSrev | CTGAGAACTAGTCTTGATGAAAGAAGCTAAACGTCTGAG (SEQ ID NO: 55) |
| CSfor | CTGAGAACTAGTATGAATTCCTCAACTAATCCAACTTCAGAT (SEQ ID NO: 56) |
| CSrevstop | CTGAGAACTAGTTTACTCATGTTTGATGAAAGATGCTAAACG (SEQ ID NO: 57) |
| CSrev | CTGAGAACTAGTCTCATGTTTGATGAAAGATGCTAAACG (SEQ ID NO: 25) |

TABLE 2

Selected nucleotide and amino acid sequences of the enzymes used in this
investigation (see also accompanying SEQUENCE LISTING).

>PAS (SEQ ID NO: 5)
ATGATAAAAAAAGTCCCAATAGTTCTTTCAATTTTCTGCTTTCTTCTTCTACTCTCATCATCCCA
TGGCTCAATTCCTGAAGCTTTTCTCAATTGTATTTCCAATAAATTTTCATTAGATGTATCCATTT
TAAACATTCTTCATGTTCCCAGCAATTCTTCCTATGATTCTGTTCTCAAATCTACTATCCAAAT
CCAAGATTCCTCAAATCACCCAAGCCCTTAGCTATAATCACCCCAGTACTTCACTCCCATGTC
CAATCTGCTG TTATCTGTACCAAACAAGCCGGTTTACAAATTAGAATCCGAAGCGGAGGAGC
TGATTACGAGGGCTTATCCTATCGTTCTGAGGTTCCUTTATTCTGCTAGATCTCCAGAATCTT
CGATCAATTTCCGTTGATATTGAAGACAACAGCGCTTGGGTCGAATCAGGAGCAACAATTGG
TGAATTCTATCATGAGATAGCTCAGAACAGCCCTGTTCATGCGTTTCCAGCTGGGGTCTCTTC
CTCTGTTGGAATTGGCGGCCATTTGAGTAGCGGCGGTTTTGGTACATTGCTTCGGAAATATG
GATTAGCAGCCGATAATATAATCGATGCAAAAATTGTTGATGCCAGAGGCAGAATTCTTGATA
GGGAATCAATGGGAGAAGATCTATTTTGGGCTATTAGAGGAGGAGGAGGAGCTAGTTTTGGT
GTTATAGTTTCTTGGAAGGTTAAACTTGTAAAAGTCCCTCCGATGGTAACTGTTTTCATCTTGT
CCAAGACTTATGAAGAGGAGGTTTAGATCTTCTACACAAATGGCAATATATAGAACACAAAC
TCCCTGAAGATTTATTCCTTGCTGTAAGCATCATGGATGATTCATCAGTGGAAATAAAACACT
TATGGCAGGTTTTATGTCTCTGTTTCTTGGAAAAACAGAGGACCTTCTGAAAGTAATGGCGGA
AAATTTCCCACAACTTGGATTGAAAAAGGAAGATTGCTTAGAAATGAATTGGATTGATGCAGC

TABLE 2-continued

Selected nucleotide and amino acid sequences of the enzymes used in this investigation (see also accompanying SEQUENCE LISTING).

AATGTATTTTTCAGGACACCCAATTGGAGAATCCCGATCTGTGCTTAAAAACCGAGAATCTCA
TCTTCCAAAGACATGCGTTTCGATCAAATCAGACTTTATTCAAGAACCACAATCCATGGATGC
ATTGGAAAAGTTATGGAAGTTTTGTAGGGAAGAAGAAAATAGTCCCATAATACTGATGCTTCC
ACTGGGGGGAATGATGAGTAAAATATCAGAATCAGAAATCCCATTTCCTTACAGAAAAGATGT
GATTTACAGTATGATATACGAAATAGTTTGGAATTGTGAAGCAGTGAATCATCGGAAGAATA
TATCGATGGATTGGGAAGGCTTGAGGAATTAATGACTCCATATGTGAAACAACCAAGAGGTT
CTTGGTTCAGCACCAGAAACCTTTATACCGGTAAAAATAAAGGTCCAGGAACAACTTATTCCA
AAGCTAAAGAATGGGGATTTCGGTATTTTAATAATAATTTCAAAAAGTTGGCCCTTATCAAGG
ACAAGTTGATCCAGAAAACTTCTTCTACTATGAACAAAGCATTCCCCCTCTCCATTTACAAGTC
GAACTTTGA

>DPAS (SEQ ID NO: 7)
ATGGCCGGAAAATCAGCAGAAGAAGAACATCCCATTAAGGCTTACGGATGGGCTGTTAAAGA
TAGAACAACTGGGATTCTTTCTCCCTTCAAATTTTCCAGAAGGGCAACAGGTGATGATGATGT
CCGAATTAAGATACTCTACTGTGGAATTTGTCACACTGATCTTGCCTCAATCAAGAACGAATA
CGAGTTTCTTTCTTATCCTCTTGTGCCCGGGATGGAGATCGTTGGAATAGCAACGGAGGTTG
GAAAAGATGTCACAAAAGTGAAAGTTGGCGAAAAAGTAGCATTATCAGCCTATTTAGGATGTT
GTGGCAAATGCTATAGTTGTGTAAATGAACTCGAGAATTATTGTCCGGAAGTAATCATAGGTT
ATGGCACCCCATACCATGACGGAACAATTTGCTATGGGGGCCTTTCAAACGAAACTGTCGCA
AATCAAAGTTTTGTTCTTCGTTTTCCTGAAAGACTTTCTCCAGCTGGCGGAGCTCCTTTGCTTA
GCGCCGGAATTACTTCGTTTAGTGCAATGAGAAATAGCGGCATCGACAAACCTGGATTACAC
GTGGGAGTCGTCGGTCTCGGCGGATTAGGTCATCHGCTGTAAAATTTGCTAAGGCTTTTGG
TCTTAAAGTAACTGTTATTAGCACCACTCCCAGCAAGAAGGATGATGCTATAAATGGTGTTGG
TGCTGATGGATTCTTACTCAGCCGCGATGATGAACAAATGAAGGCTGCTATTGGAACCTTGG
ATGCAATTATTGATACACTGGCGGTTGTTCATCCCATAGCACCATTGCTTGATCTCCTGAGAA
GTCAAGGGAAATTTTTGTTACTTGGGGCGCCATCTCAATCACTTGAGTTGCCACCTATTCCTT
TATTATCAGGTGGGAAATCTATCATTGGAAGTGCGGCCGGAAATGTGAAGCAAACTCAAGAA
ATGCTTGATTTTGCAGCGGAGCATGATATAACTGCAAATGTTGAGATTATTCCAATAGAGTAC
ATAAATACTGCAATGGAACGTTTAGACAAGGGCGATGTTAGATACCGATTTGTAGTTGACATC
GAAAATACCTTGACTCCTCCGTCAGAGTTATAA

DPAS protein (SEQ ID NO: 2)
MAGKSAEEEHPIKAYGWAVKDRTTGILSPEKESRRATGDDDVIRIKILYCGICHTDLASIKNEYEFLS
YPLVPGMEIVGIATEVGKDVTKVKVGEKVALSAYLGCCGKCYSCVNELENYCPEVIIGYGTPYHD
GTICYGGLSNETVANQSFVLRFPERLSPAGGAPLLSAGITSFSAMRNSGIDKPGLHVGVVGLGGL
GHLAVKFAKAFGLKVTVISTTSKKDDAINGLGADGFLLSRDDEQMKAAIGTLDAIIDTLAVVHPIAPL
LDLLRSQGKELLLGAPSQSLELPPIPLLSGGKSIIGSAAGNVKQTQEMLDFAAEHDITANVEIIPIEYI
NTAMERLDKGDVRYREVVDIENTLTPPSEL >CS (SEQ ID NO: 9)
ATGGCTTCCCAAACTCCAACCTCAGATGAGACTATTTGGGATCTTTCTCCATATATTAAAATTT
TCAAAGATGGAAGAGTAGAAAGACTCCATAATAGTCCTTATGTTCCCCCATCACTTAATGATC
CAGAAACTGGCGTTTCTTGGAAAGATGTCCCGATTTCATCACAAGTTTCCGCTAGGGTATACA
TTCCAAAAATCAGCGACCATGAAAAACTCCCTATTTTTGTGTATGTGCATGGGGCTGGCTTTT
GTCTAGAATCTGCCTTCAGATCATTTTTCCACACTTTTGTCAAACACTTCGTAGCCGAAACCAA
AGTTATTGGGGTTTCGATTGAATATAGACTTGCCCCAGAGCACCTTTTACCCGCAGCTTATGA
AGATTGTTGGGAAGCCCTTCAATGGGTTGCTTCTCATGTGGGTCTCGACAATTCCGGCCTAA
AGACAGCTATTGATAAAGATCCATGGATAATAAACTATGGTGATTTCGATAGACTGTATTTGG
CGGGTGACAGTCCTGGTGCTAATATTGTTCACAACACACTTATCAGAGCTGGAAAAGAGAAA
CTGAAGGGCGGAGTGAAAATTTTGGGGCAATTCTTTACTACCCATATTTCATTATCCCAACC
AGCACGAAACTTAGTGATGATTTTGAGTATAACTACACATGTTACTGGAAATTGGCTTATCCAA
ATGCTCCTGGCGGGATGAATAACCCAATGATAAACCCCATAGCTGAAATGCTCCAGACTTG
GCTGGATACGGTTGCTCGAGGTTGTTGGTTACCCTGGTTTCATGATTTCAACGACTCCAGA
TGAGACTAAAGACATAAATGCGGTTTATATTGAGGCATTAGAAAAGAGTGGATGGAAAGGGG
AATTGGAAGTGGCTGATTTTGACGCAGATTATTTTGAACTCTTCACCTTGGAAACGGAGATGG
GCAAGAATATGTTCAGACGTTTAGCATCTTTCATCAAACATGAGTAA >TS (SEQ ID NO: 10)
ATGGGTTCCTCAGATGAGACTATTTTTGATCTTCCTCCATACATCAAAGTCTTCAAAGATGGAA
GAGTAGAAAGACTCCATTCTTCCCCATATGTTCCCCCATCTCTTAATGATCCAGAAACCGGTG
GAGTCTCTTGGAAAGACGTCCCAATTTCTTCAGTAGTTTCAGCTAGAATTTACCTTCCTAAAAT
CAACAACCATGATGAAAAACTCCCCATTATAGTCTATTTCCATGGAGCTGGTTTTTGTCTTGAA
TCGGCCTTCAAATCATTTTTCCACACTTATGTGAAACACTTTGTAGCAGAAGCCAAAGCTATT
GCGGTTTCTGTTGAGTTCAGGCTCGCCCCTGAAAACCATTTACCCGCAGCTTATGAAGATTG
CTGGGAAGCCCTTCAATGGGTTGCTTCTCATGTGGGTCTCGACATTTCCAGCTTGAAGACAT
GTATTGATAAAGATCCATGGATAATCAACTATGCCGATTTCGATAGACTCTATTTGTGGGGTG
ATAGCACCGGTGCCAATATTGTTCACAACACACTTATCAGATCTGGTAAAGAGAAATTGAACG
GCGGCAAAGTGAAGATTTTGGGGCAATTCTTTACTACCCATATTTCTTAATCAGGACGAGTT
CAAAACAGAGTGATTATATGGAGAATGAGTATAGATCTTACTGGAAATTGGCTTACCCAGATG
CTCCTGGTGGAAATGATAACCCAATGATAAACCCTACAGCTGAGAATGCTCCTGATCTGGCT
GGATATGGTTGCTCGAGGTTGCTGATTTCCATGGTTGCCGATGAAGCTAGAGATATAACTCTT
CTTTATATTGATGCATTGGAAAAGAGTGGATGGAAAGGTGAATTAGATGTGGCTGATTTTGAT
AtACAGTATTTTGAACTGTTTGAAATGGAAACAGAGGNTGCCAAGAACATGCTCTCAGACGTTTA
GCTTCTTTCATCAAGTAA

TABLE 2-continued

Selected nucleotide and amino acid sequences of the enzymes used in this investigation (see also accompanying SEQUENCE LISTING).

DPAS-2 (SEQ ID NO: 66; formerly identified as a "putative ADH" from Catharanthus roseus in GenBank accession KU865331)
MARKSPEDEHPVKAYGWAVKDGTTGILSPFKFSIRATGDNDVRIKILYCGVCRTDLAATKNAFGFL
SYPLVPGSREIVGIVSEIGKNVKKVKVGEKVGVAPHVGSCGKCKSCVNEVENFCPKLIIPYGTPYH
DGTICYGGFSNETVRDERFVERFPENLSLPGGAPLVSAGVTTYGALRNNGLDKPGLHVGVVGLG
GLGHLAVKFAKALGVKVTVISTNPSKEHDAINGFGADAFILTHHEEQMKAAMGTLDGILYTVPVVH
AIAPLLSLLGSQGKEVLIGAPSQLLEVPPIQLLEGGKSIIGSAAGNVKQUEMLEFAAKHDIIANVEIIQ
MDYINTAMERLDKGDVRYREVIDIENSLTLPSEV DPAS-2 (SEQ ID NO: 67; see note for SEQ ID NO: 66 above)
atggccagaa aatcaccaga agatgaacat cccgtgaagg cttacaaata ggccgtcaaa gatggaacaa
ctggaattct ttctcccttc aaattttcca tagggcaac aggtgataat gatgttcgaa tcaagatcct
ctattgtgga gtttgtcgta ccgatcttgc ggcaaccaag aacgcattcg ggtttctttc ttatcctctt
gtgcctggta gagagatcgt gggaatagtg agcgagatag ggaaaaatgt gaaaaagtt aaagttggag
aaaaagttgg agtagcccg catgtgggta gctgtggcaa atgcaagagt tgtgtgaatg aggtggagaa
tttctgtccg aaactaatca tcccttatgg cacccatac cacgatggta ctatttgcta cggtgatttc
tccaacgaga ctgtcaaaaa tgaacgcttt gttttttcgtt ttcctgaaaa tctttcgctg cctggcggag
ctcccttggt tagtgctagg gttaccacgt acggtgcatt gagaaataat ggcctcgaca agcccggatt
acacatagga gtcgtcggtc taggtggact aggtcatctg gctgttaaat ttgctaaggc tttaggcgtc
aaagtaactg ttattaatac caatcctagc aaggagcatg atgctataaa tgatttcgat gctgatgcct
tcatcctcac ccaccatgag gaacaaatga aggctgccat gggaactta gatggaattc tttatacagt
gcctattgtt catgccattg caccattact tagtctactg ggaagtcaaa ggaaatttgt gttgattgga
gcaccatctc aattacttga ggtgccacct attcaattat tatttggtgg aaaatctatt attggaagtg
cggctggaaa tgtgaaacaa atccaagaaa tgcttgaatt tgcagcaaaa catgatataa ttgcgaatgt
tgagattatc caaatggatt atataaatac tgcaatggaa cgtatagaca aaggtgatgt tagatatcga
tttgtaattg atatcgaaaa ctctctcact cttccatcag aggtgtga

TABLE 3

MRM transitions used for metabolites detection with UPLC/QqQ-MS method.

| Compound | Parent ion | Daughter ion | Collision Energy (V) |
|---|---|---|---|
| Catharanthine | 337.2 | 173.1 | 16 |
|  |  | 165.1 | 20 |
|  |  | 144.1 | 20 |
| Tabersonine | 337.2 | 305.2 | 22 |
|  |  | 228.2 | 22 |
|  |  | 168.1 | 36 |
| Stemmadenine acetate | 397.2 | 337.1 | 18 |
|  |  | 228.1 | 24 |
|  |  | 168.0 | 40 |
| Precondylocarpine acetate | 395.2 | 234.0 | 38 |
|  |  | 228.1 | 22 |
|  |  | 196.1 | 32 |

TABLE 4

NMR data for stemmadenine 1. HRMS, ESI positive: m/z calculated for $C_{21}H_{27}N_2O_3^+$ [M + H]$^+$: 355.2016, observed: 355.2021, Δ ppm = 1.4.

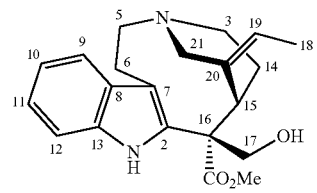

| | $^{13}$C (DMSO) | | | $^{1}$H (DMSO) | | |
|---|---|---|---|---|---|---|
| No | This report[a] | Grover et al. (2002)[b] | Feng et al. (2010)[c,d] | This report[a] | Grover et al. (2002)[b] | Feng et al. (59)[c,d] |
| 1 (NH) | n/a | n/a | n/a | 10.45 (s) | 10.47 (s) | 10.36 (s) |
| 2 | 133.9 | 133.8 | 133.8 | n/a | n/a | n/a |
| 3 | 45.5 | 45.2 | 45.6 | 3.30 (1H, m) | 3.30 (1H, m) | 3.3 (1H, m)[d] |
|  |  |  |  | 2.87 (1H, ddd, 13.3, 13.3, 6.8) | 2.83 (1H, m) | 2.8 (1H, m)[d] |
| 5 | 54.9 | 54.7 | 55.2 | 3.45 (1H, m) | 3.43 (1H, m) | unclear[d] |
|  |  |  |  | 3.17 (1H, m) | 3.14 (1H, m) | unclear[d] |
| 6 | 22.4 | 22.1 | 24.0 | 3.36 (2H, m) | 3.33 (2H, m) | unclear[d] |
| 7 | 109.0 | 108.8 | 110.2 | n/a | n/a | n/a |

TABLE 4-continued

NMR data for stemmadenine 1. HRMS, ESI positive: m/z calculated for $C_{21}H_{27}N_2O_3^+$ [M + H]$^+$: 355.2016, observed: 355.2021, Δ ppm = 1.4.

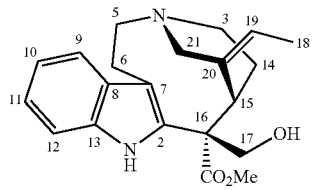

| | [13]C (DMSO) | | | [1]H (DMSO) | | |
|---|---|---|---|---|---|---|
| No | This report [a] | Grover et al. (2002)[b] | Feng et al. (2010)[c,d] | This report [a] | Grover et al. (2002)[b] | Feng et al. (59)[c,d] |
| 8 | 126.5 | 126.4 | unclear [d] | n/a | n/a | n/a |
| 9 | 117.9 | 117.4 | 117.9 | 7.59 (1H d, 7.9) | 7.60 (1H d, 7.8) | 7.54 (1H, d) [d] |
| 10 | 118.9 | 118.8 | 118.8 | 7.03 (1H, ddd, 8.0, 7.9, 1.0) | 7.02 (1H, d, 7.2) | 7.02 (1H, m) [d] |
| 11 | 121.4 | 121.3 | 121.2 | 7.10 (1H, ddd, 8.0, 7.9, 1.1) | 7.10 (1H, d, 7.0) | 7.05 (1H, m) [d] |
| 12 | 111.8 | 111.7 | 111.7 | 7.44 (1H, d, 8.0) | 7.45 (1H, d, 7.8) | 7.42 (1H, d) [d] |
| 13 | 135.1 | 135.0 | 135.1 | n/a | n/a | n/a |
| 14 | 23.9 | 23.8 | 25.8 | 2.48 (1H, m) 2.32 (1H, m) | 2.50 (1H, m?) 2.32 (1H, m?) | unclear [d] unclear [d] |
| 15 | 34.4 | 34.3 | 35.3 | 3.69 (1H, m) | 3.70 (1H, dd, 12.2, 3.1) | 3.65 (1H, m) [d] |
| 16 | 60.0 | 59.9 | 60.3 | n/a | n/a | n/a |
| 17 | 67.0 | 66.9 | 67.4 | 4.22 (1H, dd, 10.4, 4.8) 4.13 (1H, dd, 10.4, 5.2) | 4.25 (1H, dd, 10.5, 4.5) 4.22 (1H, dd, 10.5, 4.5) | 4.21 (1H, m) [d] 4.13 (1H, m) [d] |
| 18 | 13.9 | 13.8 | 14.0 | 1.70 (3H, dd, 6.9, 2.0) | 1.69 (3H, d, 6.0) | 1.68 (3H, d) [d] |
| 19 | 129.4 | 129.5 | unclear [d] | 5.56 (1H, q, 6.9) | 5.55 (1H, q, 6.0) | 5.45 (1H, m) [d] |
| 20 | 127.0 | 126.8 | 126.8 | n/a | n/a | n/a |
| 21 | 52.8 | 52.4 | 53.5 | 3.36 (1H, m) 2.51 (1H, m) | 3.35 (1H, m) 2.50 (1H, m) | unclear [d] 2.5 (1H, m) [d] |
| COOMe | 172.1 | 172.0 | 172.4 | n/a | n/a | n/a |
| COOMe | 52.4 | 52.0 | 52.3 | 3.70 (3H, s) | 3.70 (3H, s) | 3.69 (3H, s) [d] |
| OH | n/a | n/a | n/a | 5.76 (1H, t, 4.2) | 5.79 (1H, t, 5.0) | 5.73 (1H, br s) |

[a] recorded at 300 K, 400 MHz (100 MHz for $^{13}$C)
[b] recorded at 298 K, 300 MHz (75 MHz for 13C). Grover et al. (2002) Magn. Reson. Chem. 40: 474-476.
[c] temperature and frequency not reported. Feng et al., 2010, J. Nat. Prod. 73: 22-26.
[d] No assignments or numerical data reported, just images of spectra. Assignments here are based on comparison with Grover et al. and our data.

TABLE 5

NMR data for stemmadenine acetate 7 in comparison to the starting material stemmadenine 1. HRMS, ESI positive: m/z calculated for $C_{23}H_{29}N_2O_4^+$ [M + H]$^+$: 397.2122, observed: 397.2122, Δ ppm = 0.0.

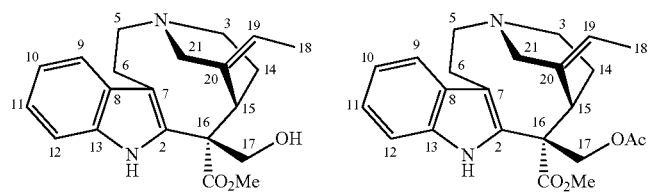

Stemmadenine 1     Stemmadenine acetate 7

| | [13]C | [1]H | [13]C | [1]H |
|---|---|---|---|---|
| No | MeOD [a] | MeOD [a] | MeOD [a] | MeOD [a] |
| 1 (NH) | n/a | not detected | n/a | not detected |
| 2 | 135.0 | n/a | 133.0 | n/a |
| 3 | 47.5 | 3.17 (1H, ddd, 13.8, 13.8, 6.6) 3.41 (1H, m) | 47.5 | 3.17 (1H, ddd, 13.6, 13.6, 7.0) 3.41 (1H, m) |
| 5 | 57.0 | 3.59 (1H, m) 3.47 (1H, m) | 57.1 | 3.59 (1H, m) 3.48 (1H, m) |
| 6 | 23.7 | 3.63 (1H, m) 3.47 (1H, m) | 23.8 | 3.61 (1H, m) 3.51 (1H, m) |

TABLE 5-continued

NMR data for stemmadenine acetate 7 in comparison to the starting material stemmadenine 1. HRMS, ESI positive: m/z calculated for $C_{23}H_{29}N_2O_4^+$ [M + H]$^+$: 397.2122, observed: 397.2122, Δ ppm = 0.0.

| No | $^{13}C$ MeOD [a] | $^{1}H$ MeOD [a] | $^{13}C$ MeOD [a] | $^{1}H$ MeOD [a] |
|---|---|---|---|---|
| 7 | 110.3 | n/a | 110.6 | n/a |
| 8 | 128.1 | n/a | 128.0 | n/a |
| 9 | 118.7 | 7.56 (1H, ddd, 8.0, 1.0, 1.0) | 118.9 | 7.58 (1H, ddd, 7.8, 0.9, 0.9) |
| 10 | 120.7 | 7.10 (1H, ddd, 8.0, 8.0, 1.2) | 120.9 | 7.12 (1H, ddd, 8.0, 7.1, 1.1) |
| 11 | 123.4 | 7.16 (1H, ddd, 8.3, 8.3, 1.2) | 123.6 | 7.18 (1H, ddd, 8.0, 7.1, 1.2) |
| 12 | 112.7 | 7.42 (1H, ddd, 8.0, 1.0, 1.0) | 112.7 | 7.43 (1H, ddd, 8.0, 0.9, 0.9) |
| 13 | 137.0 | n/a | 137.1 | n/a |
| 14 | 25.3 | 2.44 (1H, ddd, 16.6, 12.9, 6.5)<br>2.68 (1H, dddd, 16.6, 16.6, 6.6, 3.4) | 25.2 | 2.47 (1H, m)<br>2.70 (1H, m) |
| 15 | 36.1 | 3.86 (1H, dd, 12.9, 3.5) | 36.8 | 3.96 (1H, dd, 12.5, 3.3) |
| 16 | 61.6 | n/a | 59.4 | n/a |
| 17 | 69.2 | 4.35 (2H, s) | 69.7 | 4.71 (1H, d, 11.1)<br>4.92 (1H, d, 11.1) |
| 18 | 14.5 | 1.80 (3H, dd, 7.0, 2.2) | 14.5 | 1.84 (3H, dd, 7.0, 2.1) |
| 19 | 132.4 | 5.65 (1H, qd, 7.0, 1.7) | 132.4 | 5.68 (1H, q, 6.0) |
| 20 | 127.7 | n/a | 127.3 | n/a |
| 21 | 55.2 | 2.99 (1H, br d, 15.0)<br>3.44 (1H, br d, 15.0) | 54.8 | 2.74 (1H, m)<br>3.45 (1H, m) |
| COOMe | 174.1 | n/a | 172.9 | n/a |
| COOMe | 53.2 | 3.81 (3H, s) | 53.5 | 3.81 (3H, s) |
| OC(O)Me | n/a | n/a | 171.9 | n/a |
| OC(O)Me | n/a | n/a | 20.7 | 2.05 (3H, s) |

[a] recorded at 300 K, 400 MHz (100 MHz for $^{13}C$)

TABLE 6

NMR data and key correlations for precondylocarpine acetate 10. HRMS, ESI positive: m/z calculated for C23H27N2O4 [M + H]+: 395.1965, observed: 395.1967, Δ ppm = 0.5.

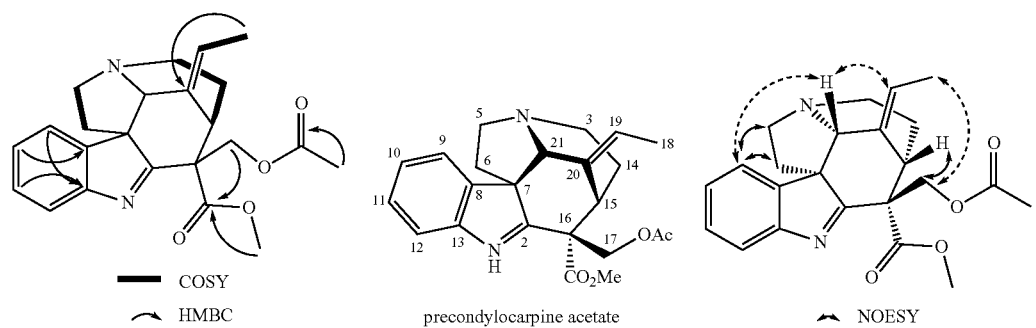

| No | $^{13}C$ CD$_3$CN [a] | $^{1}H$ CD$_3$CN [a] |
|---|---|---|
| 2 | n.d.[b] | n/a |
| 3 | 48.7 | 2.98 (1H, m)<br>2.65 (1H, m) |
| 5 | 58.7 | 3.46 (1H, m)<br>3.31 (1H, m) |
| 6 | 39.1 | 2.90 (1H, m)<br>1.84 (1H, m) |

TABLE 6-continued

NMR data and key correlations for precondylocarpine acetate 10. HRMS, ESI
positive: m/z calculated for C23H27N2O4 [M + H]+: 395.1965,
observed: 395.1967, Δ ppm = 0.5.

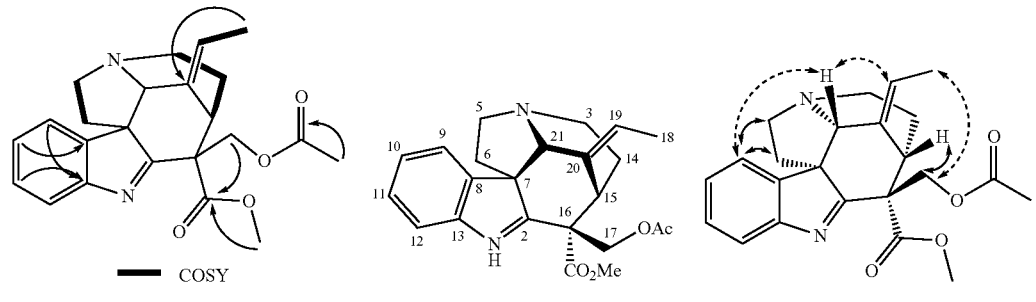

precondylocarpine acetate

— COSY
↷ HMBC
⤺ NOESY

| No | $^{13}C$ CD$_3$CN [a] | $^{1}H$ CD$_3$CN [a] |
|---|---|---|
| 7 | n.d.[b] | n/a |
| 8 | 147.5 | n/a |
| 9 | 112.2 | 7.44 (1H, m) |
| 10 | 127.3 | 7.25 (1H, ddd, 7.3, 7.3, 1.3) |
| 11 | 128.4 | 7.31 (1H, ddd, 7.5, 7.5, 1.4) |
| 12 | 121.3 | 7.45 (1H, m) |
| 13 | 154.4 | n/a |
| 14 | 31.5 | 2.13 (1H, m) |
|  |  | 2.05 (1H, m) |
| 15 | 34.6 | 3.52 (1H, m) |
| 16 | n.d.[b] | n/a |
| 17 | 67.8 | 5.01 (1H, d, 11.2) |
|  |  | 3.92 (1H, d, 11.2) |
| 18 | 13.3 | 1.57 (3H, d, 6.9) |
| 19 | 124.2 | 5.35 (1H, q, 6.9) |
| 20 | 134.8 | n/a |
| 21 | 76.1 | 3.89 (1H, d, 2.3) |
| COOMe | 172.5 | n/a |
| COOMe | 52.9 | 3.71 (3H, s) |
| OC(O)Me | 171.4 | n/a |
| OC(O)Me | 21.0 | 2.05 (3H, s) |

[a] recorded at 300 K, 400 MHz (100 MHz for $^{13}C$)
[b] Not identified by HMBC due to instability and low scale

TABLE 7

NMR data for tubotaiwine 12 obtained as the degradation product of
dihydroprecondylocarpine acetate 11 (580 μg crude mass, 179 μmol).

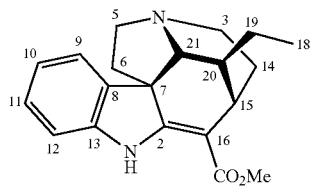

| | $^{13}C$ | | | $^{1}H$ | | |
|---|---|---|---|---|---|---|
| No | This report CDCl$_3$ [a] | Yamauchi et al. (60) CDCl$_3$ [b] | Martin et al. (61) CDCl$_3$ [c,d] | This report CDCl$_3$ [a] | Yamauchi et al. CDCl$_3$ [b] | Martin et al. CDCl$_3$ [c,d] |
| 1 (NH) | n/a | n/a | n/a | 8.84 (1H, s) | 8.85 [e] | 8.86 (1H, s) |
| 2 | 170.5 [e] | 168.8 | 179.9 | n/a | n/a | n/a |
| 3 | 45.0 | 46.2 | 45.5 | 2.49 (1H, m) | 2.46 (1H, m) | 2.46 (1H, ddd, 11.7, 9.6, 8.6) |
|  |  |  |  | 3.01 (1H, m) |  | 3.06-2.99 (1H, m) |
| 5 | 53.6 | 63.9 | 54.2 | 2.86 (2H, m) | 3.02-2.80 (2H) [e] | 2.96 (1H, dt, 11.8, 4.0) |
|  |  |  |  |  |  | 2.84 (1H, dd, 10.8, 7.1) |
| 6 | 43.8 | 44.0 | 44.3 | 1.80 (1H, m) | 1.81-1.76 (1H) [e] | 1.82-1.76 (1H, m) |
|  |  |  |  | 2.90 (1H, m) | 3.02-2.80 (1H) [e] | 2.94-2.87 (1H, m) |

TABLE 7-continued

NMR data for tubotaiwine 12 obtained as the degradation product of dihydroprecondylocarpine acetate 11 (580 μg crude mass, 179 μmol).

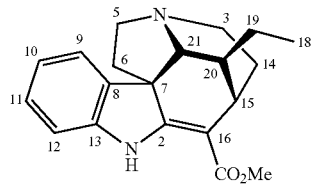

| | $^{13}C$ | | | $^{1}H$ | | |
|---|---|---|---|---|---|---|
| No | This report CDCl$_3$ [a] | Yamauchi et al. (60) CDCl$_3$ [b] | Martin et al. (61) CDCl$_3$ [c,d] | This report CDCl$_3$ [a] | Yamauchi et al. CDCl$_3$ [b] | Martin et al. CDCl$_3$ [c,d] |
| 7 | 55.1 | 55.1 | 55.4 | n/a | n/a | n/a |
| 8 | 137.0 | 137.2 | 137.5 | n/a | n/a | n/a |
| 9 | 119.6 | 119.5 | 119.9 | 7.16 (1H, d, 7.4) | 7.13 (1H, br d, 7) | 7.14 (1H, d, 7.3) |
| 10 | 121.2 | 121.0 | 121.2 | 6.88 (1H, ddd, 7.5, 7.5, 0.8) | 6.86 (1H, td, 7, 1) | 6.88 (1H, t, 7.5) |
| 11 | 127.3 | 127.1 | 127.3 | 7.11 (1H, ddd, 7.7, 7.7, 1.2) | 7.09 (1H, td, 7, 1) | 7.11 (1H, t, 7.7) |
| 12 | 109.7 | 109.6 | 109.8 | 6.80 (1H, d, 7.7) | 6.79 (1H, br d, 7) | 6.81 (1H, d, 7.7) |
| 13 | 143.7 | 143.7 | 143.9 | n/a | n/a | n/a |
| 14 | 28.3 | 28.5 | 28.7 | 1.80 (2H, m) | 1.81-1.75 (2H) [g] | 1.82-1.76 (2H, m) |
| 15 | 30.7 | 30.9 | 31.2 | 3.06 (1H, m) | 3.04 (1H, br s) | 3.06-2.99 (1H, m) |
| 16 | n.d. [f] | 96.7 | 95.8 | n/a | n/a | n/a |
| 18 | 11.5 | 11.5 | 11.8 | 0.70 (3H, t, 7.0) | 0.70 (3H, t, 7) | 0.70 (3H, t, 7.3) |
| 19 | 23.7 | 23.9 | 24.1 | 0.88-0.78 (2H, m) | 0.87-0.79 (2H) [g] | 0.86-0.78 (2H, m) |
| 20 | 41.0 | 41.2 | 41.5 | 1.98 (1H, m) | 1.97 (1H, m) | 2.00-1.95 (1H, m) |
| 21 | 65.3 | 65.5 | 65.8 | 3.88 (1H, br s) | 3.81 (1H, br s) | 3.81 (1H, s) |
| COOMe | 168.9 [e] | 170.5 | 169.1 | n/a | n/a | n/a |
| COOMe | 51.1 | 51.0 | 51.3 | 3.77 (3H, s) | 3.76 (3H) [g] | 3.77 (3H, s) |

[a] recorded at 300 K, 400 MHz (100 MHz for $^{13}C$)

[b] recorded at 400 MHz. (100 MHz for $^{13}C$); temperature not reported

[c] recorded at 298 K, 566 MHz (125 MHz for $^{13}C$)

[d] No assignments reported; signals assigned here based on similarity to Yamauchi et al. and our data

[e] Assignment supported by HMBC correlations (COOMe to COOMe, H-6 to C-2)

[f] Not detected by HMBC

[g] No multiplicity reported

---

The invention claimed is:

1. A method comprising:
contacting a terpene indole alkaloid with an enzyme under catalytic conditions to produce a terpene indole alkaloid derivative, wherein the enzyme comprises:
a first enzyme which is a precondylocarpine acetate synthase (PAS) comprising the amino acid sequence of SEQ ID NO: 1 or a functional variant or homologue thereof comprising an amino acid sequence having at least 90% sequence identity with and over a full length of SEQ ID NO: 1;
a second enzyme which is (i) a dehydroprecondylocarpine acetate synthase (DAS) comprising the amino acid sequence of SEQ ID NO: 2 or a functional variant or homologue thereof comprising an amino acid sequence having at least 90% sequence identity with and over a full length of SEQ ID NO: 2, or (ii) a dehydroprecondylocarpine acetate synthase (DAS) comprising the amino acid sequence of SEQ ID NO: 66 or a functional variant or homologue thereof having at least 90% sequence identity with and over a full length of SEQ ID NO: 66; or
both the first enzyme and the second enzyme.

2. The method of claim 1, wherein the enzyme further comprises:
a third enzyme which is a catharanthine synthase (CS) comprising the amino acid sequence of SEQ ID NO: 3 or a functional variant or homologue thereof comprising an amino acid sequence having at least 90% sequence identity with and over a full length of SEQ ID NO: 3;
a fourth enzyme which is a tabersonian synthase (TS) comprising the amino acid sequence of SEQ ID NO: 4 or a functional variant or homologue thereof having at least 90% sequence identity with and over a full length of SEQ ID NO: 4; or
both the third enzyme and the fourth enzyme.

3. The method of claim 2, wherein the terpene indole alkaloid is stemmadenine acetate.

4. The method of claim 3,
(a) wherein the stemmadenine acetate is contacted with the first enzyme and wherein the terpene indole alkaloid derivative is precondylocarpine acetate, or
(b) wherein the stemmadenine acetate is contacted with the first and second enzymes and wherein the terpene indole alkaloid derivative(s) are dihydroprecondylocarpine acetate, catharanthine, or both dihydroprecondylocarpine acetate and catharanthine, or
(c) wherein the stemmadenine acetate is contacted with the first, second and third enzymes and wherein the terpene indole alkaloid derivative is catharanthine, or
(d) wherein the stemmadenine acetate is contacted with the first, second and fourth enzymes and wherein the terpene indole alkaloid derivative is tabersonine.

5. The method of claim 2, wherein the terpene indole alkaloid is precondylocarpine acetate.

6. The method of claim 5,
(a) wherein the precondylocarpine acetate is contacted with the second enzyme and wherein the terpene indole alkaloid derivative(s) are dihydroprecondylocarpine acetate, catharanthine, or both dihydroprecondylocarpine acetate and catharanthine, or
(b) wherein the precondylocarpine acetate is contacted with the second and third enzymes and wherein the terpene indole alkaloid derivative is catharanthine, or
(c) wherein the precondylocarpine acetate is contacted with the first, second and fourth enzymes and wherein the terpene indole alkaloid derivative is tabersonine.

7. The method of claim 2, wherein the terpene indole alkaloid is dihydroprecondylocarpine acetate.

8. The method of claim 7,
   (a) wherein the dihydroprecondylocarpine acetate is contacted with the third enzyme and wherein the terpene indole alkaloid derivative is catharanthine, or
   (b) wherein the dihydroprecondylocarpine acetate is contacted with the fourth enzyme and wherein the terpene indole alkaloid derivative is tabersonine, or
   (c) wherein the dihydroprecondylocarpine acetate is contacted with the third and fourth enzymes and wherein the terpene indole alkaloid derivative is tabersonine and catharanthine.

9. The method of claim 1, wherein the contacting is performed in vivo.

10. The method of claim 9, wherein the contacting is performed in planta.

11. The method of claim 10, wherein the in planta comprises in *Nicotiana benthamiana*.

12. The method of claim 1, wherein the contacting is performed in vitro.

13. The method of claim 12, wherein the contacting is performed in an isolated plant cell, in yeast, or in a bacteria.

14. The method of claim 12, wherein the enzyme is provided by expression.

15. The method of claim 2, further comprising converting the terpene indole alkaloid derivative into a biologically active composition.

16. The method of claim 15, wherein the biologically active composition
   (a) has anti-cancer activity;
   (b) is vinblastine, wherein the terpene indole alkaloid derivative is tabersonine and wherein the method comprises converting the tabersonine to vindoline and coupling the vindoline with catharanthine to produce Vinblastine, wherein the coupling comprises synthetic coupling, enzymatic coupling, or synthetic coupling and enzymatic coupling;
   (c) is conophylline or a vasodilator;
   (d) is an anti-diabetic; or
   (e) is an anti-addictive.

17. An expression vector comprising
   (a) a nucleic acid encoding a first enzyme which is a precondylocarpine acetate synthase comprising the amino acid sequence of SEQ ID NO: 1 or a functional variant or homologue thereof comprising an amino acid sequence having at least 90% sequence identity with and over a full length of SEQ ID NO: 1;
   (b) a nucleic acid encoding a second enzyme which is (i) a dehydroprecondylocarpine acetate synthase comprising the amino acid sequence of SEQ ID NO: 2 or a functional variant or homologue thereof comprising an amino acid sequence having at least 90% sequence identity with and over a full length of SEQ ID NO: 2, or (ii) a dehydroprecondylocarpine acetate synthase comprising the amino acid sequence of SEQ ID NO: 66 or a functional variant or homologue thereof having at least 90% sequence identity with and over a full length of SEQ ID NO: 66;
   (c) a nucleic acid encoding a third enzyme which is a catharanthine synthase comprising the amino acid sequence of SEQ ID NO: 3 or a functional variant or homologue thereof comprising an amino acid sequence having at least 90% sequence identity with and over a full length of SEQ ID NO: 3;
   (d) a nucleic acid encoding a fourth enzyme which is a tabersonian synthase comprising the amino acid sequence of SEQ ID NO: 4 or a functional variant or homologue thereof having at least 90% sequence identity with and over a full length of SEQ ID NO: 4; or
   (e) a combination of (a), (b), (c) or (d).

18. A host cell comprising the expression vector of claim 17.

19. A host cell comprising
   (a) a nucleic acid encoding a first enzyme which is a precondylocarpine acetate synthase comprising the amino acid sequence of SEQ ID NO: 1 or a functional variant or homologue thereof comprising an amino acid sequence having at least 90% sequence identity with and over a full length of SEQ ID NO: 1;
   (b) a nucleic acid encoding a second enzyme which is (i) a dehydroprecondylocarpine acetate synthase comprising the amino acid sequence of SEQ ID NO: 2 or a functional variant or homologue thereof comprising an amino acid sequence having at least 90% sequence identity with and over a full length of SEQ ID NO: 2, or (ii) a dehydroprecondylocarpine acetate synthase comprising the amino acid sequence of SEQ ID NO: 66 or a functional variant or homologue thereof having at least 90% sequence identity with and over a full length of SEQ ID NO: 66;
   (c) a nucleic acid encoding a third enzyme which is a catharanthine synthase comprising the amino acid sequence of SEQ ID NO: 3 or a functional variant or homologue thereof comprising an amino acid sequence having at least 90% sequence identity with and over a full length of SEQ ID NO: 3;
   (d) a nucleic acid encoding a fourth enzyme which is a tabersonian synthase comprising the amino acid sequence of SEQ ID NO: 4 or a functional variant or homologue thereof having at least 90% sequence identity with and over a full length of SEQ ID NO: 4; or
   a combination of (a), (b), (c) or (d).

20. The host cell of claim 19, wherein the host cell comprises a plant cell, a yeast cell, or a bacterial cell.

21. The host cell of claim 19, wherein the host cell is a *Pichia pastoris* cell, a *Saccharomyces cerevisiae* cell, an *E. coli* cell, or a *Nicotiana benthamiana* cell.

22. A genetically modified plant comprising the expression vector of claim 17.

* * * * *